(12) United States Patent
Stanton, Jr.

(10) Patent No.: US 6,664,062 B1
(45) Date of Patent: Dec. 16, 2003

(54) THYMIDYLATE SYNTHASE GENE SEQUENCE VARIANCES HAVING UTILITY IN DETERMINING THE TREATMENT OF DISEASE

(75) Inventor: Vincent P. Stanton, Jr., Belmont, MA (US)

(73) Assignee: Nuvelo, Inc., Sunnyvale, CA (US)

( * ) Notice: Subject to any disclaimer, the term of this patent is extended or adjusted under 35 U.S.C. 154(b) by 0 days.

(21) Appl. No.: 09/963,333

(22) Filed: Sep. 24, 2001

Related U.S. Application Data

(60) Division of application No. 09/658,659, filed on Sep. 8, 2000, which is a continuation-in-part of application No. 09/596,033, filed on Jun. 15, 2000, now abandoned, which is a continuation-in-part of application No. 09/357,743, filed on Jul. 20, 1999, now abandoned, which is a continuation-in-part of application No. 09/357,024, filed on Jul. 19, 1999, now abandoned.

(60) Provisional application No. 60/093,484, filed on Jul. 20, 1998.

(51) Int. Cl.$^7$ .............................. C12Q 1/68; C12N 1/20; C12N 15/00; C07H 21/02; C07H 21/04
(52) U.S. Cl. ..................... 435/6; 435/252.3; 435/320.1; 536/23.1; 536/24.31; 536/24.33
(58) Field of Search ........................ 435/6, 252.3, 320.1; 536/23.1, 24.31, 24.33

(56) References Cited

U.S. PATENT DOCUMENTS

| | | | |
|---|---|---|---|
| 6,015,673 A | 1/2000 | Gonzalez et al. | 435/6 |
| 6,074,821 A | 6/2000 | Rozen et al. | 435/6 |
| 6,087,489 A | * 7/2000 | Dean | 536/24.5 |
| 6,130,043 A | * 10/2000 | Billing-Medel | 435/6 |
| 6,218,120 B1 | 4/2001 | Rozen et al. | 435/6 |

FOREIGN PATENT DOCUMENTS

| | | |
|---|---|---|
| WO | WO 95/33054 | 12/1995 |

OTHER PUBLICATIONS

Akar et al., "Effect of Metylenetetrahydrofolate Reductase 677 C–T, 1298 A–C, and 1317 T–C on Facotr V . . . " Thrombosis Research 97:163–167, 2000.

Engbersen et al., "Thermolabile 5,10–Methylenetetrahydrofolate Reductase as a Cause of Mild Hyperhomocysteinemia" Am. J. of Human Genet. 56:142–150, 1995.

Frosst et al., "A Candidate Genetic Risk Factor for Vascular Disease: a Common Mutation in Methylenetetrahydrofolate Reductase" Nature Genetics 10:111–113, 1995.

Goyette et al., "Human Methylenetetrahydrofolate Reductase: Isolation of cDNA, Mapping and Mutation Identification" Nature Genetics 7:195–200, 1994.

Goyette et al., "Gene Structure of Human and Mouse Methylenetetrahydrofolate Reductase (MTHFR)" Mammalian Genome 9:652–656, 1998.

Goyette et al., "Seven Novel Mutations in the Methylenetetrahydrofolate Reductase Gene and Genotype/Phenotype Correlations in Severe Methylenetetrahydrofolate Reductase Deficiency" Am. J. Hum. Genet. 56:1052–1059, 1995.

Goyette et al., GenBank Accession No. U09806, Dec. 6, 1999.

Kaneda et al., "Structural and Functional Analysis of the Human Thymidylate Synthase Gene" J. of Biol. Chem. 265:20277–20284, 1990.

Kang et al., "Thermolabile Methylenetetrahydrofolate Reductase: An Inherited Risk Factor for Coronary Artery Disease" Amer. J. Human. Genet. 48:536–545, 1991.

Van der Put et al., "A Second Common Mutation in the Methelenetetrahydrofolate Reductase Gene: As Additional Risk Factor for Neural–Tube Defects" Am. J. Hum. Genet. 62:1044–1051, 1998.

Van Ede et al., "Methotrexate in Rheumatoid Arthiritis: An Update with Focus on Mechanisms Involved in Toxicity" Seminars in Arthritis and Rheumatism 27:277–292, 1998.

Viel et al., "Loss of Heterozygosity at the 5,10–Methylenetetrahydrofolate Reductase Locus in Human Ovarian Carcinomas" British J. of Cancer 75:1105–1110, 1987.

Weisberg et al., "A second Genetic Polymorphism in Methylenetetrahydrofolate Reductase (MTHFR) Associate with Decreased Enzyme Activity" Mol. Genet. And Metabolism 64:169–172, 1998.

* cited by examiner

Primary Examiner—Carla J. Myers
Assistant Examiner—Arun Kr. Chakrabarti
(74) Attorney, Agent, or Firm—Fish & Richardson PC

(57) ABSTRACT

The present disclosure describes the use of genetic variance information for folate transport or metabolism genes or pyrimidine transport or metabolism genes in the selection of effective methods of treatment of a disease or condition. The variance information is indicative of the expected response of a patient to a method of treatment. Methods of determining relevant variance information and additional methods of using such variance information are also described.

3 Claims, 2 Drawing Sheets

THYMIDYLATE SYNTHASE GENE SEQUENCE VARIANCES HAVING UTILITY IN DETERMINING THE TREATMENT OF DISEASE

RELATED APPLICATIONS

This application is a divisional of U.S. application Ser. No. 09/658,659, filed Sep. 8, 2000, which is a CIP of Stanton, U.S. application Ser. No. 09/596,033, filed Jun. 15, 2000 now abandoned entitled GENE SEQUENCE VARIACNES IN GENES RELATED TO FOLATE METABOLISM HAVING UTILITY IN DETERMINING THE TREATMENT OF DISEASE which is a CIP of Stanton, U.S. application Ser. No. 09/357,743, filed Jul. 20, 1999 now abandoned, entitled GENE SEQUENCE VARIACNES IN GENES RELATED TO FOLATE METABOLISM HAVING UTILITY IN DETERMINING THE TREATMENT OF DISEASE which is a CIP of Stanton, U.S. application Ser. No. 9/357,024, filed Jul. 19, 1999 now abandoned, entitled GENE SEQUENCE VARIANCES IN GENES RELATED TO FOLATE METABOLISM HAVING UTILITY IN DETERMINING THE TREATMENT OF DISEASE, which claims the benefit of Stanton, U.S. Provisional Application No. 60/093,484, filed Jul. 20, 1998, entitled GENE SEQUENCE VARIACNES IN GENES RELATED TO FOLATE METABOLISM HAVING UTILITY IN DETERMINING THE TREATMENT OF DISEASE, which are all hereby incorporated by references in their entireties including drawings and tables.

BACKGROUND OF THE INVENTION

This application concerns the field of mammalian therapeutics and the selection of therapeutic regimens utilizing host genetic information, including gene sequence variances within the human genome in human populations.

The rate of approval of new drugs that enter human clinical trials is less than 20%, despite demonstrated efficacy of said new drugs in preclinical models of human disease. In some instances the low response rate in humans is due to genetic heterogeneity in the drug target or the pathway mediating the action of the drug. Identification of the genetic causes of variable drug response would allow more rational clinical development of drugs. Further, many drugs or other treatments approved for use in humans are known to have highly variable safety and efficacy in different individuals. A consequence of such variability is that a given drug or other treatment may be highly effective in one individual, and ineffective or not well tolerated in another individual. Thus, administration of such a drug to an individual in whom the drug would be ineffective would result in wasted cost and time during which the patient's condition may significantly worsen. Also, administration of a drug to an individual in whom the drug would not be tolerated could result in a direct worsening of the patient's condition and could even result in the patient's death.

For some drugs, up to 99% of the measurable variation in selected pharmacokinetic parameters has been shown to be inherited, or associated with genetic factors. Studies have also demonstrated a significant genetic component to pharmacodynamic variation. For a limited number of drugs, discrete gene sequence variances have been identified in specific genes that are involved in drug action, and these variances have been shown to account for the variable efficacy or safety of the drug in different individuals.

SUMMARY OF THE INVENTION

The present invention is concerned generally with the field of treatment of diseases and conditions in mammals, particularly in humans. It is concerned with the genetic basis of inter-patient variation in response to therapy, including drug therapy. Specifically, this invention describes the identification of gene sequence variances useful in the field of therapeutics for optimizing efficacy and safety of drug therapy for specific diseases or conditions and for establishing diagnostic tests useful for improving the development and use of pharmaceutical products in the clinic. Methods for identifying genetic variances and determining their utility in the selection of optimal therapy for specific patients are also described, along with probes and related materials which are useful, for example, in identifying the presence of a particular gene sequence variance in cells of an individual. The genes involved in the present invention are those listed in a pathway, gene table, list or example herein.

The inventors have determined that the identification of gene sequence variances within genes that may be involved in drug action is important for determining whether genetic variances account for variable drug efficacy and safety and for determining whether a given drug or other therapy may be safe and effective in an individual patient. Provided in this invention are identifications of genes and sequence variances which can be useful in connection with predicting differences in response to treatment and selection of appropriate treatment of a disease or condition. Such genes and variances have utility in pharmacogenetic association studies and diagnostic tests to improve the use of certain drugs or other therapies including, but not limited to, the drug classes and specific drugs identified in the 1999 Physicians' Desk Reference (53rd edition), Medical Economics Data, 1998, or the 1995 United States Pharmacopoeia XXIII National Formulary XVIII, Interpharm Press, 1994, or other sources as described below.

The terms "disease" or "condition" are commonly recognized in the art and designate the presence of signs and/or symptoms in an individual or patient that are generally recognized as abnormal. Diseases or conditions may be diagnosed and categorized based on pathological changes. Signs may include any objective evidence of a disease such as changes that are evident by physical examination of a patient or the results of diagnostic tests which may include, among others, laboratory tests to determine the presence of variances or variant forms of certain genes in a patient. Symptoms are subjective evidence of disease or a patients condition—i.e. the patients perception of an abnormal condition that differs from normal function, sensation, or appearance, which may include, without limitations, physical disabilities, morbidity, pain, and other changes from the normal condition experienced by an individual. Various diseases or conditions include, but are not limited to, those categorized in standard textbooks of medicine including, without limitation, textbooks of nutrition, allopathic, homeopathic, and osteopathic medicine. In certain aspects of this invention, the disease or condition is selected from the group consisting of the types of diseases listed in standard texts such as Harrison's Principles of Internal Medicine (14th Ed) by Anthony S. Fauci, Eugene Braunwald, Kurt J. Isselbacher, et al. (Editors), McGraw Hill, 1997, or Robbins Pathologic Basis of Disease (6th edition) by Ramzi S. Cotran, Vinay Kumar, Tucker Collins & Stanley L. Robbins, WB Saunders Co., 1998, or the Diagnostic and Statistical Manual of Mental Disorders: Dsm-IV (4th Ed), American Psychiatric Press, 1994 or other texts described below.

In connection with the methods of this invention, unless otherwise indicated, the term "suffering from a disease or condition" means that a person is either presently subject to the signs and symptoms, or is more likely to develop such signs and symptoms than a normal person in the population. Thus, for example, a person suffering from a condition can include a developing fetus, a person subject to a treatment or environmental condition which enhances the likelihood of developing the signs or symptoms of a condition, or a person who is being given or will be given a treatment which increase the likelihood of the person developing a particular condition. For example, tardive dyskinesia is associated with long-term use of anti-psychotics; gastrointestinal symptoms, alopecia and bone marrow suppression are associated with cancer chemotherapeutic regimens, and immunosuppression is associated with agents to limit graft rejection following transplantation. Thus, methods of the present invention which relate to treatments of patients (e.g., methods for selecting a treatment, selecting a patient for a treatment, and methods of treating a disease or condition in a patient) can include primary treatments directed to a presently active disease or condition, secondary treatments which are intended to cause a biological effect relevant to a primary treatment, and prophylactic treatments intended to delay, reduce, or prevent the development of a disease or condition, as well as treatments intended to cause the development of a condition different from that which would have been likely to develop in the absence of the treatment.

The term "therapy" refers to a process which is intended to produce a beneficial change in the condition of a mammal, e.g., a human, often referred to as a patient. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy can involve, for example, nutritional modifications, administration of radiation, administration of a drug, behavioral modifications and combinations of these, among others.

The term "drug" as used herein refers to a chemical entity or biological product, or combination of chemical entities or biological products, administered to a person to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, lipoproteins, and modifications and combinations thereof. A biological product is preferably a monoclonal or polyclonal antibody or fragment thereof such as a variable chain fragment cells; or an agent or product arising from recombinant technology, such as, without limitation, a recombinant protein, recombinant vaccine, or DNA construct developed for therapeutic, e.g., human therapeutic, use. The term "drug" may include, without limitation, compounds that are approved for sale as pharmaceutical products by government regulatory agencies (e.g., U.S. Food and Drug Administration (USFDA or FDA), European Medicines Evaluation Agency (EMEA), and a world regulatory body governing the Internation Conference of Harmonization (ICH) rules and guidelines), compounds that do not require approval by government regulatory agencies, food additives or supplements including compounds commonly characterized as vitamins, natural products, and completely or incompletely characterized mixtures of chemical entities including natural compounds or purified or partially purified natural products. The term "drug" as used herein is synonymous with the terms "medicine", "pharmaceutical" "product", or "product". Most preferably the drug is approved by a government agency for treatment of a specific disease or condition.

A "low molecular weight compound" has a molecular weight<5,000 Da, more preferably <2500 Da, still more preferably <1000 Da, and most preferably <700 Da.

Those familiar with drug use in medical practice will recognize that regulatory approval for drug use is commonly limited to approved indications, such as to those patients afflicted with a disease or condition for which the drug has been shown to be likely to produce a beneficial effect in a controlled clinical trial. Unfortunately, it has generally not been possible with current knowledge to predict which patients will have a beneficial response, with the exception of certain diseases such as bacterial infections where suitable laboratory methods have been developed. Likewise, it has generally not been possible to determine in advance whether a drug will be safe in a given patient. Regulatory approval for the use of most drugs is limited to the treatment of selected diseases and conditions. The descriptions of approved drug usage, including the suggested diagnostic studies or monitoring studies, and the allowable parameters of such studies, are commonly described in the "label" or "insert" which is distributed with the drug. Such labels or inserts are preferably required by government agencies as a condition for marketing the drug and are listed in common references such as the Physicians Desk Reference (PDR). These and other limitations or considerations on the use of a drug are also found in medical journals, publications such as pharmacology, pharmacy or medical textbooks including, without limitation, textbooks of nutrition, allopathic, homeopathic, and osteopathic medicine.

Many widely used drugs are effective in a minority of patients receiving the drug, particularly when one controls for the placebo effect. For example, the PDR shows that about 45% of patients receiving Cognex (tacrine hydrochloride) for Alzheimer's disease show no change or minimal worsening of their disease, as do about 68% of controls (including about 5% of controls who were much worse). About 58% of Alzheimer's patients receiving Cognex were minimally improved, compared to about 33% of controls, while about 2% of patients receiving Cognex were much improved compared to about 1% of controls. Thus a tiny fraction of patients had a significant benefit. Response to many cancer chemotherapy drugs is even worse. For example, 5-fluorouracil is standard therapy for advanced colorectal cancer, but only about 20–40% of patients have an objective response to the drug, and, of these, only 1–5% of patients have a complete response (complete tumor disappearance; the remaining patients have only partial tumor shrinkage). Conversely, up to 20–30% of patients receiving 5-FU suffer serious gastrointestinal or hematopoietic toxicity, depending on the regimen.

Thus, in a first aspect, the invention provides a method for selecting a treatment for a patient suffering from a disease or condition by determining whether or not a gene or genes in cells of the patient (in some cases including both normal and disease cells, such as cancer cells) contain at least one sequence variance which is indicative of the effectiveness of the treatment of the disease or condition. The gene is one specified herein, in particular one listed in a Table or list herein. Preferably the at least one variance includes a plurality of variances which may provide a haplotype or haplotypes. Preferably the joint presence of the plurality of variances is indicative of the potential effectiveness of the treatment in a patient having such plurality of variances. The plurality of variances may each be indicative of the potential effectiveness of the treatment, and the effects of the individual variances may be independent or additive, or the plurality of variances may be indicative of the potential effectiveness if at least 2, 3, 4, or more appear jointly. The plurality of variances may also be combinations of these relationships. The plurality of variances may include variances from one, two, three or more gene loci.

In a related aspect, the invention concerns a method for providing a correlation between a patient genotype and effectiveness of a treatment, by determining the presence or absence of a particular known variance or variances in cells of a patient for a gene of this invention, and providing a result indicating the expected effectiveness of a treatment for a disease or condition. The result may be formulated by comparing the genotype of the patient with a list of variances indicative of the effectiveness of a treatment, e.g., administration of a drug described herein. The determination may be by methods as described herein or other methods known to those skilled in the art.

In some cases, the selection of a method of treatment, i.e., a therapeutic regimen, may incorporate selection of one or more from a plurality of medical therapies. Thus, the selection may be the selection of a method or methods which is/are more effective or less effective than certain other therapeutic regimens (with either having varying safety parameters). Likewise or in combination with the preceding selection, the selection may be the selection of a method or methods which is safer than certain other methods of treatment in the patient.

The selection may involve either positive selection or negative selection or both, meaning that the selection can involve a choice that a particular method would be an appropriate method to use and/or a choice that a particular method would be an inappropriate method to use. Thus, in certain embodiments, the presence of the at least one variance is indicative that the treatment will be effective or otherwise beneficial (or more likely to be beneficial) in the patient. Stating that the treatment will be effective means that the probability of beneficial therapeutic effect is greater than in a person not having the appropriate presence or absence of particular variances. In other embodiments, the presence of the at least one variance is indicative that the treatment will be ineffective or contra-indicated for the patient. For example, a treatment may be contra-indicated if the treatment results, or is more likely to result, in undesirable side effects, or an excessive level of undesirable side effects. A determination of what constitutes excessive side-effects will vary, for example, depending on the disease or condition being treated, the availability of alternatives, the expected or experienced efficacy of the treatment, and the tolerance of the patient. As for an effective treatment, this means that it is more likely that a desired effect will result from the treatment administration in a patient with a particular variance or variances than in a patient who has a different variance or variances. Also in preferred embodiments, the presence of the at least one variance is indicative that the treatment is effective but results in undesirable effects or outcomes, e.g., has undesirable side-effects.

In reference to response to a treatment, the term "tolerance" refers to the ability of a patient to accept a treatment, based, e.g., on deleterious effects and/or effects on lifestyle. Frequently, the term principally concerns the patients perceived magnitude of deleterious effects such as nausea, weakness, dizziness, and diarrhea, among others. Such experienced effects can, for example, be due to general or cell-specific toxicity, activity on non-target cells, cross-reactivity on non-target cellular constituents (non-mechanism based), and/or side-effects of activity on the target cellular subsitutuent (mechanism based), or the cause of toxicity may not be understood. In any of these circumstances one may identify an association between the undesirable effects and variances in specific genes.

Adverse responses to drugs constitute a major medical problem, as shown in two recent meta-analyses (Lazarou, J. et al, Incidence of adverse drug reactions in hospitalized patients: a meta-analysis of prospective studies, JAMA 279:1200–1205, 1998; Bonn, Adverse drug reactions remain a major cause of death, Lancet 351:1183, 1998). An estimated 2.2 million hospitalized patients in the United Stated had serious adverse drug reactions in 1994, with an estimated 106,000 deaths (Lazarou et al.). To the extent that some of these adverse events are due to genetically encoded biochemical diversity among patients in pathways that effect drug action, the identification of variances that are predictive of such effects will allow for more effective and safer drug use.

In embodiments of this invention, the variance or variant form or forms of a gene is/are associated with a specific response to a drug. The frequency of a specific variance or variant form of the gene may correspond to the frequency of an efficacious response to administration of a drug. Alternatively, the frequency of a specific variance or variant form of the gene may correspond to the frequency of an adverse event resulting from administration of a drug. Alternatively the frequency of a specific variance or variant form of a gene may not correspond closely with the frequency of a beneficial or adverse response, yet the variance may still be useful for identifying a patient subset with high response or toxicity incidence because the variance may account for only a fraction of the patients with high response or toxicity. Preferably, the drug will be effective in more than 20% of individuals with one or more specific variances or variant forms of the gene, more preferably in 40% and most preferably in >60%. In other embodiments, the drug will be toxic or create clinically unacceptable side effects in more than 10% of individuals with one or more variances or variant forms of the gene, more preferably in >30%, more preferably in >50%, and most preferably in >70% or in more than 90%.

Also in other embodiments, the method of selecting a treatment includes eliminating a treatment, where the presence or absence of the at least one variance is indicative that the treatment will be ineffective or contra-indicated. In other preferred embodiments, in cases in which undesirable side-effects may occur or are expected to occur from a particular therapeutic treatment, the selection of a method of treatment can include identifying both a first and second treatment, where the first treatment is effective to treat the disease or condition, and the second treatment reduces a deleterious effect of the first treatment.

The phrase "eliminating a treatment" refers to removing a possible treatment from consideration, e.g., for use with a particular patient based on the presence or absence of a particular variance(s) in one or more genes in cells of that patient, or to stopping the administration of a treatment which was in the course of administration.

Usually, the treatment will involve the administration of a compound preferentially active in patients with a form or forms of a gene, where the gene is one identified herein. The administration may involve a combination of compounds. Thus, in preferred embodiments, the method involves identifying such an active compound or combination of compounds, where the compound is less active or is less safe or both when administered to a patient having a different form of the gene. In preferred embodiments, the compound is a compound in a drug class identified in the 1999 Physicians' Desk Reference (53rd edition), Medical Economics Data, 1998, the PharmaProjects database, the IMS database or identified herein, e.g., in an exemplary drug table herein (see, e.g., Examples 6, 8, and 9 and Tables 7 and 9 herein).

Also in preferred embodiments, the method of selecting a treatment involves selecting a method of administration of a compound, combination of compounds, or pharmaceutical composition, for example, selecting a suitable dosage level and/or frequency of administration, and/or mode of administration of a compound. The method of administration can be selected to provide better, preferably maximum therapeutic benefit. In this context, "maximum" refers to an approximate local maximum based on the parameters being considered, not an absolute maximum.

Also in this context, a "suitable dosage level" refers to a dosage level which provides a therapeutically reasonable balance between pharmacological effectiveness and deleterious effects. Often this dosage level is related to the peak or aveage serum levels resulting from administration of a drug at the particular dosage level.

Similarly, a "frequency of administration" refers to how often in a specified time period a treatment is administered, e.g., once, twice, or three times per day, every other day, once per week, etc. For a drug or drugs, the frequency of administration is generally selected to achieve a pharmacologically effective average or peak serum level without excessive deleterious effects (and preferably while still being able to have reasonable patient compliance for self-administered drugs). Thus, it is desirable to maintain the serum level of the drug within a therapeutic window of concentrations for the greatest percentage of time possible without such deleterious effects as would cause a prudent physician to reduce the frequency of administration for a particular dosage level.

A particular gene or genes can be relevant to more than one disease or condition, for example, the gene or genes can have a role in the initiation, development, course, treatment, treatment outcomes, or health-related quality of life outcomes of a number of different diseases, disorders, or conditions. Thus, in preferred embodiments, the disease or condition or treatment of the disease or condition is any which involves a particular gene. Preferably the gene is a gene identified herein.

Determining the presence of a particular variance or plurality of variances in a particular gene in a patient can be performed in a variety of ways. In preferred embodiments, the detection of the presence or absence of at least one variance involves amplifying a segment of nucleic acid including at least one of the at least one variances. Preferably a segment of nucleic acid to be amplified is 500 nucleotides or less in length, more preferably 100 nucleotides or less, and most preferably 45 nucleotides or less. Also, preferably the amplified segment or segments includes a plurality of variances, or a plurality of segments of a gene or of a plurality of genes.

In another aspect determining the presence of a set of variances in a specific gene may entail a haplotyping test that requires allele-specific amplification of a large DNA segment of no greater than 20,000 nucleotides, preferably no greater than 10,000 nucleotides and more preferably no greater than 5,000 nucleotides. Alternatively one allele may be enriched by methods other than amplification prior to determining genotypes at specific variant positions on the enriched allele as a way of determining haplotypes. Preferably the determination of the presence or absence of a variance involves determining the sequence of the variance site or sites by methods such as chain terminating DNA sequencing or minisequencing, or by oligonucleotide hybridization or by mass spectrometry.

The term "genotype" in the context of this invention refers to the particular alleleic form of a gene, which can be defined by the particular nucleotide(s) present in a nucleic acid sequence at a particular site(s).

In preferred embodiments, the detection of the presence or absence of the at least one variance involves contacting a nucleic acid sequence corresponding to one of the genes identified above or a product of such a gene with a probe. The probe is able to distinguish a particular form of the gene or gene product or the presence or a particular variance or variances, e.g., by differential binding or hybridization. Thus, exemplary probes include nucleic acid hybridization probes, peptide nucleic acid probes, nucleotide-containing probes which also contain at least one nucleotide analog, and antibodies, e.g., monoclonal antibodies, and other probes as discussed herein. Those skilled in the art are familiar with the preparation of probes with particular specificities. Those skilled in the art will recognize that a variety of variables can be adjusted to optimize the discrimination between two variant forms of a gene, including changes in salt concentration, temperature, pH and addition of various compounds that affect the differential affinity of GC vs. AT base pairs, such as tetramethyl ammonium chloride. (See Current Protocols in Molecular Biology by F. M. Ausubel, R. Brent, R. E. Kingston, D. D. Moore, J. G. Seidman, K. Struhl and V. B. Chanda (Editors), John Wiley & Sons.)

In other preferred embodiments, determining the presence or absence of the at least one variance involves sequencing at least one nucleic acid sequence. The sequencing involves sequencing of a portion or portions of a gene and/or portions of a plurality of genes which includes at least one variance site, and may include a plurality of such sites. Preferably, the portion is 500 nucleotides or less in length, more preferably 100 nucleotides or less, and most preferably 45 nucleotides or less in length. Such sequencing can be carried out by various methods recognized by those skilled in the art, including use of dideoxy termination methods (e.g., using dye-labeled dideoxy nucleotides) and the use of mass spectrometric methods. In addition, mass spectrometric methods may be used to determine the nucleotide present at a variance site. In preferred embodiments in which a plurality of variances is determined, the plurality of variances can constitute a haplotype or haplotypes.

The terms "variant form of a gene", "form of a gene", or "allele" refer to one specific form of a gene in a population, the specific form differing from other forms of the same gene in the sequence of at least one, and frequently more than one, variant sites within the sequence of the gene. The sequences at these variant sites that differ between different alleles of the gene are termed "gene sequence variances" or "variances" or "variants". The term "alternative form" refers to an allele that can be distinguished from other alleles by having distinct variances at at least one, and frequently more than one, variant sites within the gene sequence. Other terms known in the art to be equivalent include mutation and polymorphism, although mutation is often used to refer to an allele associated with a deleterious phenotype. In preferred aspects of this invention, the variances are selected from the group consisting of the variances listed in the variance tables herein or in a patent or patent application referenced and incorporated by reference in this disclosure. In the methods utilizing variance presence or absence, reference to the presence of a variance or variances means particular variances, i.e., particular nucleotides at particular polymorphic sites, rather than just the presence of any variance in the gene.

Variances occur in the human genome at approximately one in every 500–1,000 bases within the human genome when two alleles are compared. When multiple alleles from unrelated individuals are compared the frequency of variant sites increases. At most variant sites there are only two alternative nucleotides involving the substitution of one base for another or the insertion/deletion of one or more nucleotides. Within a gene there may be several variant sites. Variant forms of the gene or alternative alleles can be distinguished by the presence of alternative variances at a single variant site, or a combination of several different variances at different sites (haplotypes).

It is estimated that there are 3,300,000,000 bases in the sequence of a single haploid human genome. All human cells except germ cells are normally diploid. Each gene in the genome may span 100–10,000,000 bases of DNA sequence or 100–20,000 bases of mRNA. It is estimated that there are between 60,000 and 120,000 genes in the human genome. The "identification" of genetic variances or variant forms of a gene involves the discovery of variances that are present in a population. The identification of variances is required for development of a diagnostic test to determine whether a patient has a variant form of a gene that is known to be associated with a disease, condition, or predisposition or with the efficacy or safety of the drug. Identification of previously undiscovered genetic variances is distinct from the process of "determining" the status of known variances by a diagnostic test. The present invention provides exemplary variances in genes listed in the gene tables, as well as methods for discovering additional variances in those genes and a comprehensive written description of such additional possible variances. Also described are methods for DNA diagnostic tests to determine the DNA sequence at a particular variant site or sites.

The process of "identifying" or discovering new variances involves comparing the sequence of at least two alleles of a gene, more preferably at least 10 alleles and most preferably at least 50 alleles, (keeping in mind that each somatic cell has two alleles). The analysis of large numbers of individuals to discover variances in the gene sequence between individuals in a population will result in detection of a greater fraction of all the variances in the population. Preferably the process of identifying reveals whether there is a variance within the gene; more preferably identifying reveals the location of the variance within the gene; more preferably identifying provides knowledge of the sequence of the nucleic acid sequence of the variance, and most preferably identifying provides knowledge of the combination of different variances that comprise specific variant forms of the gene or alleles. In identifying new variances it is often useful to screen different population groups based on racial, ethnic, gender, and/or geographic origin because particular variances may differ in frequency between such groups. It may also be useful to screen DNA from individuals with a particular disease or condition of interest because they may have a higher frequency of certain variances than the general population.

The process of determining involves using diagnostic tests for specific variances or variant forms of the gene (or genes) that have been identified within the gene. It will be apparent that such diagnostic tests can only be performed after variances and variant forms of the gene have been identified. Identification of variances can be performed by a variety of methods, alone or in combination, including, for example, DNA sequencing, SSCP, heteroduplex analysis, denaturing gradient gel electrophoresis (DGGE), heteroduplex cleavage (either enzymatic as with T4 Endonuclease 7, or chemical as with osmium tetroxide and hydroxylamine), computational methods (described herein), and other methods described herein as well as others known to those skilled in the art. (See, for example: Cotton, R. G. H., Slowly but surely towards better scanning for mutations, Trends in Genetics 13(2):43–6, 1997, or Current Protocols in Human Genetics by N. C. Dracopoli, J. L. Haines, B. R. Korf, D. T. Moir, C. C. Morton, C. E. Seidman, J. G. Seidman, D. R. Smith and A. Boyle (Editors), John Wiley & Sons.)

In the context of this invention, the term "analyzing a sequence" refers to determining at least some sequence information about the sequence, e.g., determining the nucleotides present at particular sites in the sequence or determining the base sequence of all of a portion of the particular sequence.

In the context of this invention, the term "haplotype" refers to a cis arrangement of two or more polymorphic nucleotides, i.e., variances, on a particular chromosome, e.g., in a particular gene. The haplotype preserves the information of the phase of the polymorphic nucleotides—that is, which set of variances were inherited from one parent, and which from the other.

In preferred embodiments of this invention, the frequency of the variance or variant form of the gene in a population is known. Measures of frequency known in the art include "allele frequency", namely the fraction of genes in a population that have one specific variance or set of variances. The allele frequencies for any gene should sum to 1. Another measure of frequency known in the art is the "heterozygote frequency" namely, the fraction of individuals in a population who carry two alleles, or two forms of a particular variance or variant form of a gene, one inherited from each parent. Alternatively, the number of individuals who are homozygous for a particular form of a gene may be a useful measure. The relationship between allele frequency, heterozygote frequency, and homozygote frequency is described for many genes by the Hardy-Weinberg equation, which provides the relationship between allele frequency, heterozygote frequency and homozygote frequency in a freely breeding population at equilibrium. Most human variances are substantially in Hardy-Weinberg equilibrium. In a preferred aspect of this invention, the allele frequency, heterozygote frequency, or homozygote frequency are determined experimentally. Preferably a variance has an allele frequency of at least 0.01, more preferably at least 0.05, still more preferably at least 0.10. However, the allele may have a frequency as low as 0.001 if the associated phenotype is a rare form of toxic reaction to the treatment or drug.

In this regard, "population" refers to a geographically, ethnically, racially, gender, and/or culturally defined group of individuals or a group of individuals with a particular disease or condition or individuals that may be treated with a specific drug. In most cases a population will preferably encompass at least ten thousand, one hundred thousand, one million, ten million, or more individuals, with the larger numbers being more preferable. In a preferred aspect of this invention, the population refers to individuals with a specific disease or condition that may be treated with a specific drug. In an aspect of this invention, the allele frequency, heterozygote frequency, or homozygote frequency of a specific variance or variant form of a gene is known. In preferred embodiments of this invention, the frequency of one or more variances that may predict response to a treatment is determined in one or more populations using a diagnostic test.

It should be emphasized that it is currently not generally practical to study entire gene sequences in entire populations to establish the association between a specific disease or condition and a specific variance or variant form of the gene. Such studies are commonly performed in controlled clinical trials using a limited number of patients that are considered to be representative of the population with the disease.

In the context of this invention, the term "probe" refers to a molecule which can detectably distinguish between target molecules differing in structure. Detection can be accomplished in a variety of different ways depending on the type of probe used and the type of target molecule. Thus, for example, detection may be based on discrimination of activity levels of the target molecule, but preferably is based on detection of specific binding. Examples of such specific binding include antibody binding and nucleic acid probe hybridization. Thus, for example, probes can include enzyme substrates, antibodies and antibody fragments, and nucleic acid hybridization probes. Thus, in preferred embodiments, the detection of the presence or absence of the at least one variance involves contacting a nucleic acid sequence which includes a variance site with a probe, preferably a nucleic acid probe, where the probe preferentially hybridizes with a form of the nucleic acid sequence containing a complementary base at the variance site as compared to hybridization to a form of the nucleic acid sequence having a non-complementary base at the variance site, where the hybridization is carried out under selective hybridization conditions. Such a nucleic acid hybridization probe may span two or more variance sites. Unless otherwise specified, a nucleic acid probe can include one or more nucleic acid analogs, labels or other substituents or moieties so long as the base-pairing function is retained.

As is generally understood, administration of a particular treatment, e.g., administration of a therapeutic compound or combination of compounds, is chosen depending on the disease or condition which is to be treated. Thus, in certain preferred embodiments, the disease or condition is one for which administration of a treatment is expected to provide a therapeutic benefit; in certain embodiments, the compound is a compound identified herein, e.g., in a drug table such as Tables 7 and 9.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. On the other hand, the term "ineffective" indicates that a treatment does not provide sufficient pharmacological effect to be therapeutically useful, even in the absence of deleterious effects, at least in the total (unstratified) population. (Such a treatment may be effective in a subgroup that can be identified by the presence of one or more sequence variances or alleles.) "Less effective" means that the treatment results in a therapeutically significant lower level of pharmacological effectiveness and/or a therapeutically greater level of adverse physiological effects.

Thus, in connection with the administration of a drug, a drug which is "effective against" a disease or condition indicates that administration in a clinically appropriate manner results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

The term "deleterious effects" refers to physical effects in a patient caused by administration of a treatment which are regarded as medically undesirable. Thus, for example, deleterious effects can include a wide spectrum of toxic effects injurious to health such as death of normal cells when only death of diseased cells is desired, nausea, fever, inability to retain food, dehydration, damage to critical organs such as renal tubular necrosis, fatty liver or pulmonary fibrosis, among many others. In this regard, the term "contra-indicated" means that a treatment results in deleterious effects such that a prudent medical doctor treating such a patient would regard the treatment as unsuitable for administration. Major factors in such a determination can include, for example, availability and relative advantages of alternative treatments, consequences of non-treatment, and permanency of deleterious effects of the treatment.

It is recognized that many treatment methods, e.g., administration of certain compounds or combinations of compounds, produces side-effects or other deleterious effects in patients. Such effects can limit or even preclude use of the treatment method in particular patients, or may even result in irreversible injury, dysfunction, or death of the patient. Thus, in certain embodiments, the variance information is used to select both a first method of treatment and a second method of treatment. Usually the first treatment is a primary treatment which provides a physiological effect directed against the disease or condition or its symptoms. The second method is directed to reducing or eliminating one or more deleterious effects of the first treatment, e.g., to reduce a general toxicity or to reduce a side effect of the primary treatment. Thus, for example, the second method can be used to allow use of a greater dose or duration of the first treatment, or to allow use of the first treatment in patients for whom the first treatment would not be tolerated or would be contra-indicated in the absence of a second method to reduce deleterious effects.

In a related aspect, the invention provides a method for selecting a method of treatment for a patient suffering from a disease or condition by comparing at least one variance in at least one gene in the patient, with a list of variances in the gene or genes which are indicative of the effectiveness of at least one method of treatment. Preferably the comparison involves a plurality of variances or a haplotype indicative of the effectiveness of at least one method of treatment. Also, preferably the list of variances includes a plurality of variances.

Similar to the above aspect, in preferred embodiments the at least one method of treatment involves the administration of a compound effective in at least some patients with a disease or condition; the presence or absence of the at least one variance is indicative that the treatment will be effective in the patient; and/or the presence or absence of the at least one variance is indicative that the treatment will be ineffective or contra-indicated in the patient; and/or the treatment is a first treatment and the presence or absence of the at least one variance is indicative that a second treatment will be beneficial to reduce a deleterious effect of the first treatment; and/or the at least one treatment is a plurality of methods of treatment. For a plurality of treatments, preferably the selecting involves determining whether any of the methods of treatment will be more effective than at least one other of the plurality of methods of treatment. Yet other embodiments are provided as described for the preceding aspect in connection with methods of treatment using administration of a compound; treatment of various diseases, and variances in particular genes.

In the context of variance information in the methods of this invention, the term "list" refers to one or more variances which have been identified for a series or genes of potential importance in accounting for inter-individual variation in treatment response. Preferably there is a plurality of variances for the gene or genes, preferably a plurality of variances for a particular gene. Preferably the list is recorded in written or electronic form. For example, variances are recorded in Tables 3, 4, and 10 and additional gene variance identification tables herein in a form which allows comparison with other variance information.

In addition to the basic method of treatment, often the mode of administration of a given compound as a treatment for a disease or condition in a patient is significant in determining the course and/or outcome of the treatment for the patient. Thus, the invention also provides a method for selecting a method of administration of a compound to a patient suffering from a disease or condition, by determining the presence or absence of at least one variance in cells of the patient in a gene which is a gene selected from the genes identified in a gene table or list below, where such presence or absence is indicative of an appropriate method of administration of the compound. Preferably, the selection of a method of treatment (a treatment regimen) involves selecting a dosage level or frequency of administration or route of administration of the compound or combinations of those parameters. In preferred embodiments, two or more compounds are to be administered, and the selecting involves selecting a method of administration for one, two, or more than two of the compounds, jointly, concurrently, or separately. As understood by those skilled in the art, such plurality of compounds is often used in combination therapy, and thus may be formulated in a single drug, or may be separate drugs administered concurrently, serially, or separately. Other embodiments are as indicated above for selection of second treatment methods, methods of identifying variances, and methods of treatment as described for aspects above.

In another aspect, the invention provides a method for selecting a patient for administration of a method of treatment for a disease or condition, or of selecting a patient for a method of administration of a treatment, by comparing the presence or absence of at least one variance in a gene as identified above in cells of a patient, with a list of variances in the gene, where the presence or absence of the at least one variance is indicative that the treatment or method of administration will be effective in the patient. If the at least one variance is present in the patient's cells, then the patient is selected for administration of the treatment.

In preferred embodiments, the disease or the method of treatment is as described in aspects above, specifically including, for example, those described for selecting a method of treatment In another aspect, the invention provides a method for identifying a subset of patients with enhanced or diminished response or tolerance to a treatment method or a method of administration of a treatment where the treatment is for a disease or condition in the patient. The method involves correlating one or more variances in one or more genes in a plurality of patients with response to a treatment or a method of administration of a treatment. The correlation may be performed by determining the one or more variances in the one or more genes in the plurality of patients and correlating the presence or absence of each of the variances (alone or in various combinations) with the patient's response to treatment. The variances may be previously known to exist or may also be determined in the present method or combinations of prior information and newly determined information may be used. The enhanced or diminished response should be statistically significant, preferably such that p=0.10 or less, more preferably 0.05 or less, and most preferably 0.02 or less. A positive correlation between the presence of one or more variances and an enhanced response to treatment is indicative that the treatment is particularly effective in the group of patients having those variances. A positive correlation of the presence of the one or more variances with a diminished response to the treatment is indicative that the treatment will be less effective in the group of patients having those variances. Such information is useful, for example, for selecting or de-selecting patients for a particular treatment or method of administration of a treatment, or for demonstrating that a group of patients exists for which the treatment or method of treatment would be particularly beneficial or contra-indicated. Such demonstration can be beneficial, for example, for obtaining government regulatory approval for a new drug or a new use of a drug.

In preferred embodiments, the variances are in particular genes, or are particular variances described herein. Also, preferred embodiments include drugs, treatments, variance identification or determination, determination of effectiveness, lists, and/or diseases as described for aspects above or otherwise described herein.

In preferred embodiments, the correlation of patient responses to therapy according to patient genotype is carried out in a clinical trial, e.g., as described herein according to any of the variations described. Detailed description of methods for associating variances with clinical outcomes using clinical trials are provided below.

As indicated above, in aspects of this invention involving selection of a patient for a treatment, selection of a method or mode of administration of a treatment, and selection of a patient for a treatment or a method of treatment, the selection may be positive selection or negative selection. Thus, the methods can include eliminating a treatment for a patient, eliminating a method or mode of administration of a treatment to a patient, or elimination of a patient for a treatment or method of treatment.

Also, in methods involving identification and/or comparison of variances present in a gene of a patient, the methods can involve such identification or comparison for a plurality of genes. Preferably, the genes are functionally related to the same disease or condition, or to the aspect of disease pathophysiology that is being subjected to pharmacological manipulation by the treatment (e.g. a drug), or to the activation or inactivation of the drug, and more preferably the genes are involved in the same biochemical process or pathway.

In another aspect, the invention provides a method for identifying the forms of a gene in an individual, where the gene is one specified as for aspects above, by determining the presence or absence of at least one variance in the gene. In preferred embodiments, the at least one variance includes at least one variance selected from the group of variances identified in variance tables herein. Preferably, the presence or absence of the at least one variance is indicative of the effectiveness of a therapeutic treatment in a patient suffering from a disease or condition and having cells containing the at least one variance.

The presence or absence of the variances can be determined in any of a variety of ways as recognized by those skilled in the art. For example, the nucleotide sequence of at least one nucleic acid sequence which includes at least one variance site (or a complementary sequence) can be determined, such as by chain termination methods, hybridization methods or by mass spectrometric methods. Likewise, in preferred embodiments, the determining involves contacting a nucleic acid sequence or a gene product one of one of the genes with a probe which specifically identifies the presence or absence of a form of the gene. For example, a probe, e.g., a nucleic acid probe, can be used which specifically binds, e.g., hybridizes, to a nucleic acid sequence corresponding to a portion of the gene and which includes at least one variance site under selective binding conditions. As described for other aspects, determining the presence or absence of at least two variances can constitute determining a haplotype or haplotypes.

Other preferred embodiments involve variances related to types of treatment, drug responses, diseases, nucleic acid sequences, and other items related to variances and variance determination as described for aspects above.

In yet another aspect, the invention provides a pharmaceutical composition which includes a compound which has a differential effect in patients having at least one copy, or alternatively, two copies of a form of a gene as identified for aspects above and a pharmaceutically acceptable carrier, excipient, or diluent. The composition is adapted to be preferentially effective to treat a patient with cells containing the one, two, or more copies of the form of the gene.

In preferred embodiments of aspects involving pharmaceutical compositions, active compounds, or drugs, the material is subject to a regulatory limitation or restriction on approved uses or indications, e.g., by the U.S. Food and Drug Administration (FDA), limiting approved use of the composition to patients having at least one copy of the particular form of the gene which contains at least one variance. Alternatively, the composition is subject to a regulatory limitation or restriction on approved uses indicating that the composition is not approved for use or should not be used in patients having at least one copy of a form of the gene including at least one variance. Also in preferred embodiments, the composition is packaged, and the packaging includes a label or insert indicating or suggesting beneficial therapeutic approved use of the composition in patients having one or two copies of a form of the gene including at least one variance. Alternatively, the label or insert limits approved use of the composition to patients having zero or one or two copies of a form of the gene including at least one variance. The latter embodiment would be likely where the presence of the at least one variance in one or two copies in cells of a patient means that the composition would be ineffective or deleterious to the patient. Also in preferred embodiments, the composition is indicated for use in treatment of a disease or condition which is one of those identified for aspects above. Also in preferred embodiments, the at least one variance includes at least one variance from those identified herein.

The term "packaged" means that the drug, compound, or composition is prepared in a manner suitable for distribution or shipping with a box, vial, pouch, bubble pack, or other protective container, which may also be used in combination. The packaging may have printing on it and/or printed material may be included in the packaging.

In preferred embodiments, the drug is selected from the drug classes or specific exemplary drugs identified in an example, in a table or list herein, and is subject to a regulatory limitation or suggestion or warning as described above that limits or suggests limiting approved use to patients having specific variances or variant forms of a gene identified in Examples or in a gene list provided below in order to achieve maximal benefit and avoid toxicity or other deleterious effect.

A pharmaceutical composition can be adapted to be preferentially effective in a variety of ways. In some cases, an active compound is selected which was not previously known to be differentially active, or which was not previously recognized as a potential therapeutic compound. In some cases, the concentration of an active compound which has differential activity can be adjusted such that the composition is appropriate for administration to a patient with the specified variances. For example, the presence of a specified variance may allow or require the administration of a much larger dose, which would not be practical with a previously utilized composition. Conversely, a patient may require a much lower dose, such that administration of such a dose with a prior composition would be impractical or inaccurate. Thus, the composition may be prepared in a higher or lower unit dose form, or prepared in a higher or lower concentration of the active compound or compounds. In yet other cases, the composition can include additional compounds needed to enable administration of a particular active compound in a patient with the specified variances, which was not in previous compositions, e.g., because the majority of patients did not require or benefit from the added component.

The term "differential" or "differentially" generally refers to a statistically significant different level in the specified property or effect. Perferably, the difference is also functionally significant. Thus, "differential binding or hybridization" is sufficient difference in binding or hybridization to allow discrimination using an appropriate detection technique. Likewise, "differential effect" or "differentially active" in connection with a therapeutic treatment or drug refers to a difference in the level of the effect or activity which is distinguishable using relevant parameters and techniques for the effect or activity being considered. Preferably the difference in effect or activity is also sufficient to be clinically significant, such that a corresponding difference in the course of treatment or treatment outcome would be expected, at least on a probabilistic basis.

Also usefully provided in the present invention are probes which specifically recognize a nucleic acid sequence corresponding to a variance or variances in a gene or a product expressed from the gene, and are able to distinguish a variant form of the sequence or gene or gene product from one or more other variant forms of that sequence, gene, or gene product under selective conditions. Those skilled in the art recognize and understand the identification or determination of selective conditions for particular probes or types of probes. An exemplary type of probe is a nucleic acid hybridization probe, which will selectively bind under selective binding conditions to a nucleic acid sequence or a gene product corresponding to one or the genes identified for aspects above. Another type of probe is a peptide or protein, e.g., an antibody or antibody fragment which specifically or preferentially binds to a polypeptide expressed from a particular form of a gene as characterized by the presence or absence of at least one variance. Thus, in another aspect, the invention concerns such probes. In the context of this invention, a "probe" is a molecule, commonly a nucleic acid, though also potentially a protein, carbohydrate, polymer, or small molecule, that is capable of binding to one variance or variant form of the gene or gene product to a greater extent than to a form of the gene having a different base at one or more variance sites, such that the presence of the variance or variant form of the gene can be determined. Preferably the probe distinguishes at least one variance identified in Examples, tables or lists below. Preferably the probe also has specificity for the particular gene or gene product, at least to an extent such that binding to other genes or gene products does not prevent use of the assay to identify the presence or absence of the particular variance or variances of interest.

In preferred embodiments, the probe is an antibody or antibody fragment. Such antibodies may be polyclonal or monoclonal antibodies, and can be prepared by methods well-known in the art. In preferred embodiments, the probe is a nucleic acid probe at least 15, preferably at least 17 nucleotides in length, more preferably at least 20 or 22 or 25, preferably 500 or fewer nucleotides in length, more preferably 200 or 100 or fewer, still more preferably 50 or fewer, and most preferably 30 or fewer. In preferred embodiments, the probe has a length in a range from any one of the above lengths to any other of the above lengths (including endpoints). The probe specifically hybridizes under selective hybridization conditions to a nucleic acid sequence corresponding to a portion of one of the genes identified in connection with above aspects. The nucleic acid sequence includes at least one and preferably two or more variance sites. Also in preferred embodiments, the probe has a detectable label, preferably a fluorescent label. A variety of other detectable labels are known to those skilled in the art. Such a nucleic acid probe can also include one or more nucleic acid analogs.

In preferred embodiments, the probe is an antibody or antibody fragment which specifically binds to a gene product expressed from a form of one of the above genes, where the form of the gene has at least one specific variance with a particular base at the variance site, and preferably a plurality of such variances.

In connection with nucleic acid probe hybridization, the term "specifically hybridizes" indicates that the probe hybridizes to a sufficiently greater degree to the target sequence than to a sequence having a mismatched base at at least one variance site to allow distinguishing such hybridization. The term "specifically hybridizes" thus means that the probe hybridizes to the target sequence, and not to non-target sequences, at a level which allows ready identification of probe/target sequence hybridization under selective hybridization conditions. Thus, "selective hybridization conditions" refer to conditions which allow such differential binding. Similarly, the terms "specifically binds" and "selective binding conditions" refer to such differential binding of any type of probe, e.g., antibody probes, and to the conditions which allow such differential binding. Typically hybridization reactions to determine the status of variant sites in patient samples are carried out with two different probes, one specific for each of the (usually two) possible variant nucleotides. The complementary information derived from the two separate hybridization reactions is useful in corroborating the results.

Likewise, the invention provides an isolated, purified or enriched nucleic acid sequence of 15 to 500 nucleotides in length, preferably 15 to 100 nucleotides in length, more preferably 15 to 50 nucleotides in length, and most preferably 15 to 30 nucleotides in length, which has a sequence which corresponds to a portion of one of the genes identified for aspects above. Preferably the lower limit for the preceding ranges is 17, 20, 22, or 25 nucleotides in length. In other embodiments, the nucleic acid sequence is 30 to 300 nucleotides in length, or 45 to 200 nucleotides in length, or 45 to 100 nucleotides in length. The nucleic acid sequence includes at least one variance site. Such sequences can, for example, be amplification products of a sequence which spans or includes a variance site in a gene identified herein. Likewise, such a sequence can be a primer, or amplification oligonucleotide which is able to bind to or extend through a variance site in such a gene. Yet another example is a nucleic acid hybridization probe comprised of such a sequence. In such probes, primers, and amplification products, the nucleotide sequence can contain a sequence or site corresponding to a variance site or sites, for example, a variance site identified herein. Preferably the presence or absence of a particular variant form in the heterozygous or homozygous state is indicative of the effectiveness of a method of treatment in a patient.

Typically primers are utilized in pairs. Primers can be designed or selected by methods well-known to those skilled in the art based on nucleotide sequences corresponding to at least a portion or a gene identified herein. The primer or primers hybridizes to or allows amplification (e.g., using the polymerase chain reaction) through a nucleic acid sequence containing at least one sequence variance. Preferably such primers hybridize to a sequence not more than 300 nucleotides, more preferably not more than 200 nucleotides, still more preferably not more than 100 nucleotides, and most preferably not more than 50 nucleotides away from a variance site which is to be analyzed. Preferably, a primer is 100 nucleotides or fewer in length, more preferably 50 nucleotides or fewer, still more preferable 30 nucleotides or fewer, and most preferably 20 or fewer nucleotides in length.

Likewise, the invention provides a set of primers or amplification oligonucleutides (e.g., 2,3,4,6,8,10 or even more) adapted for binding to or extending through at least one gene identified herein. In preferred embodiments the set includes primers or amplification oligonucleotides adapted to bind to or extend through a plurality of sequence variances in a gene(s) identified herein. The plurality of variances preferably provides a haplotype. Those skilled in the art are familiar with the use of amplification oligonucleotides (e.g., PCR primers) and the appropriate location, testing and use of such oligonucleotides. In certain embodiments, the oligonucleotides are designed and selected to provide variance-specific amplification.

In reference to nucleic acid sequences which "correspond" to a gene, the term "correspond" refers to a nucleotide sequence relationship, such that the nucleotide sequence has a nucleotide sequence which is the same as the reference gene or an indicated portion thereof, or has a nucleotide sequence which is exactly complementary in normal Watson-Crick base pairing, or is an RNA equivalent of such a sequence, e.g., a mRNA, or is a cDNA derived from an mRNA of the gene.

In a related aspect, the invention provides a kit containing at least one probe or at least one primer or both (e.g., as described above) corresponding to a gene or genes of this invention. The kit is preferably adapted and configured to be suitable for identification of the presence or absence of a particular variance or variances, which can include or consist of sequence a nucleic acid sequence corresponding to a portion of a gene. The kit may also contain a plurality of either or both of such probes and/or primers, e.g., 2, 3, 4, 5, 6, or more of such probes and/or primers. Preferably the plurality of probes and/or primers are adapted to provide detection of a plurality of different sequence variances in a gene or plurality of genes, e.g., in 2, 3, 4, 5, or more genes or to sequence a nucleic acid sequence including at least one variance site in a gene or genes. Preferably one or more of the variance or variances to be detected are correlated with variability in a treatment response or tolerance, and are preferably indicative of an effective response to a treatment. In preferred embodiments, the kit contains components (e.g., probes and/or primers) adapted or useful for detection of a plurality of variances (which may be in one or more genes) indicative of the effectiveness of at least one treatment, preferably of a plurality of different treatments for a particular disease or condition. It may also be desirable to provide a kit containing components adapted or useful to allow detection of a plurality of variances indicative of the effectiveness of a treatment or treatment against a plurality of diseases. The kit may also optionally contain other components, preferably other components adapted for identifying the presence of a particular variance or variances. Such additional components can, for example, independently include a buffer or buffers, e.g., amplification buffers and hybridization buffers, which may be in liquid or dry form, a DNA polymerase, e.g., a polymerase suitable for carrying out PCR, and deoxy nucleotide triphosphases (dNTPs). Preferably a probe includes a detectable label, e.g., a fluorescent label, enzyme label, light scattering label, or other label. Preferably the kit includes a nucleic acid or polypeptide array. The array may, for example, include a plurality of different antibodies, a plurality of different nucleic acid sequences. Sites in the array can allow capture and/or detection of nucleic acid sequences or gene products corresponding to different variances in one or more different genes. Preferably the array is arranged to provide variance detection for a plurality of variances in one or more genes which correlate with the effectiveness of one or more treatments of one or more diseases.

The kit may also optionally contain instructions for use, which can include a listing of the variances correlating with a particular treatment or treatments for a disease of diseases.

Preferably the kit components are selected to allow detection of a variance described herein, and/or detection of a variance indicative of a treatment,e.g., administration of a drug, pointed out herein.

Additional configurations for kits of this invention will be apparent to those skilled in the art.

In another aspect, the invention provides a method for determining a genotype of an individual in relation to one or more variances in one or more of the genes identified in above aspects by using mass spectrometric determination of a nucleic acid sequence which is a portion of a gene identified for other aspects of this invention or a complementary sequence. Such mass spectrometric methods are known to those skilled in the art. In preferred embodiments, the method involves determining the presence or absence of a variance in a gene; determining the nucleotide sequence of the nucleic acid sequence; the nucleotide sequence is 100 nucleotides or less in length, preferably 50 or less, more preferably 30 or less, and still more preferably 20 nucleotides or less. In general, such a nucleotide sequence includes at least one variance site, preferably a variance site which is informative with respect to the expected response of a patient to a treatment as described for above aspects.

As indicated above, many therapeutic compounds or combinations of compounds or pharmaceutical compositions show variable efficacy and/or safety in various patients in whom the compound or compounds is administered. Thus, it is beneficial to identify variances in relevant genes, e.g., genes related to the action or toxicity of the compound or compounds. Thus, in a further aspect, the invention provides a method for determining whether a compound has a differential effect due to the presence or absence of at least one variance in a gene or a variant form of a gene, where the gene is a gene identified for aspects above.

The method involves identifying a first patient or set of patients suffering from a disease or condition whose response to a treatment differs from the response (to the same treatment) of a second patient or set of patients suffering from the same disease or condition, and then determining whether the frequency of at least one variance in at least one gene differs in frequency between the first patient or set of patients and the second patient or set of patients. A correlation between the presence or absence of the variance or variances and the response of the patient or patients to the treatment indicates that the variance provides information about variable patient response. In general, the method will involve identifying at least one variance in at least one gene. An alternative approach is to identify a first patient or set of patients suffering from a disease or condition and having a particular genotype, haplotype or combination of genotypes or haplotypes, and a second patient or set of patients suffering from the same disease or condition that have a genotype or haplotype or sets of genotypes or haplotypes that differ in a specific way from those of the first set of patients. Subsequently the extent and magnitude of clinical response can be compared between the first patient or set of patients and the second patient or set of patients. A correlation between the presence or absence of a variance or variances or haplotypes and the response of the patient or patients to the treatment indicates that the variance provides information about variable patient response and is useful for the present invention.

The method can utilize a variety of different informative comparisons to identify correlations. For example a plurality of pairwise comparisons of treatment response and the presence or absence of at least one variance can be performed for a plurality of patients. Likewise, the method can involve comparing the response of at least one patient homozygous for at least one variance with at least one patient homozygous for the alternative form of that variance or variances. The method can also involve comparing the response of at least one patient heterozygous for at least one variance with the response of at least one patient homozygous for the at least one variance. Preferably the heterozygous patient response is compared to both alternative homozygous forms, or the response of heterozygous patients is grouped with the response of one class of homozygous patients and said group is compared to the response of the alternative homozygous group.

Such methods can utilize either retrospective or prospective information concerning treatment response variability. Thus, in a preferred embodiment, it is previously known that patient response to the method of treatment is variable.

Also in preferred embodiments, the disease or condition is as for other aspects of this invention; for example, the treatment involves administration of a compound or pharmaceutical composition.

In preferred embodiments, the method involves a clinical trial, e.g., as described herein. Such a trial can be arranged, for example, in any of the ways described herein, e.g., in the Detailed Description.

The present invention also provides methods of treatment of a disease or condition. Such methods combine identification of the presence or absence of particular variances with the administration of a compound; identification of the presence of particular variances with selection of a method of treatment and administration of the treatment; and identification of the presence or absence of particular variances with elimination of a method of treatment based on the variance information indicating that the treatment is likely to be ineffective or contra-indicated, and thus selecting and administering an alternative treatment effective against the disease or condition. Thus, preferred embodiments of these methods incorporate preferred embodiments of such methods as described for such sub-aspects.

As used herein, a "gene" is a sequence of DNA present in a cell that directs the expression of a "biologically active" molecule or "gene product", most commonly by transcription to produce RNA and translation to produce protein. The "gene product" is most commonly a RNA molecule or protein or a RNA or protein that is subsequently modified by reacting with, or combining with, other constituents of the cell. Such modifications may include, without limitation, modification of proteins to form glycoproteins, lipoproteins, and phosphoproteins, or other modifications known in the art. RNA may be modified without limitation by complexing with proteins, polyadenylation, splicing, capping or export from the nucleus. The term "gene product" refers to any product directly resulting from transcription of a gene. In particular this includes partial, precursor, and mature transcription products (i.e, pre-mRNA and mRNA), and translation products with or without further processing including, without limitation, lipidation, phosphorylation, glycosylation, or combinations of such processing The term "gene involved in the origin or pathogenesis of a disease or condition" refers to a gene that harbors mutations that contribute to the cause of disease, or variances that affect the progression of the disease or expression of specific characteristic of the disease. The term also applies to genes involved in the synthesis, accumulation, or elimination of products that are involved in the origin or pathogenesis of a disease or condition including, without limitation, proteins, lipids, carbohydrates, hormones, or small molecules.

The term "gene involved in the action of a drug" refers to any gene whose gene product affects the efficacy or safety of the drug or affects the disease process being treated by the drug, and includes, without limitation, genes that encode gene products that are targets for drug action, gene products that are involved in the metabolism, activation or degradation of the drug, gene products that are involved in the bioavailability or elimination of the drug to the target, gene products that affect biological pathways that, in turn, affect the action of the drug such as the synthesis or degradation of competitive substrates or allosteric effectors or rate limiting reaction, or, alternatively, gene products that affect the pathophysiology of the disease process. (Particular variances in the latter category of genes may be associated with patient groups in whom disease etiology is more or less susceptible to amelioration by the drug. For example, there are several pathophysiological mechanisms in hypertension, and depending on the dominant mechanism in a given patient, that patient may be more or less likely than the average hypertensive patient to respond to a drug that primarily targets one pathophysiological mechanism. The relative importance of different pathophysiological mechanisms in individual patients is likely to be affected by variances in genes associated with the disease pathophysiology. The "action" of a drug refers to its effect on biological products within the body. The action of a drug also refers to its effects on the signs or symptoms of a disease or condition, or effects of the drug that are unrelated to the disease or condition leading to unanticipated effects on other processes. Such unanticipated processes often lead to adverse events or toxic effects. The terms "adverse event" or "toxic event" are known in the art and include, without limitation, those listed in the FDA reference system for adverse events.

In accordance with the aspects above and the Detailed Description below, there is also described for this invention an approach or method for developing drugs that are explicitly indicated for, and/or for which approved use is restricted to individuals in the population with specific variances or combinations of variances, as determined by diagnostic tests for variances or variant forms of certain genes involved in the disease or condition or involved in the action of the drug. Such drugs may provide more effective treatment for a disease or condition in a population identified or characterized with the use of a diagnostic test for a specific variance or variant form of the gene if the gene is involved in the action of the drug or in determining a characteristic of the disease or condition. Such drugs may be developed using the diagnostic tests for specific variances or variant forms of a gene to determine the inclusion of patients in a clinical trial.

Thus, the invention also provides a method for producing a pharmaceutical composition by identifying a compound which has differential activity against a disease or condition in patients having at least one variance in a gene, compounding the pharmaceutical composition by combining the compound with a pharmaceutically acceptable carrier, excipient, or diluent such that the composition is preferentially effective in patients who have at least one copy of the variance or variances. In some cases, the patient has two copies of the variance or variances. In preferred embodiments, the disease or condition, gene or genes, variances, methods of administration, or method of determining the presence or absence of variances is as described for other aspects of this invention.

Similarly, the invention provides a method for producing a pharmaceutical agent by identifying a compound which has differential activity against a disease or condition in patients having at least one copy of a form of a gene having at least one variance and synthesizing the compound in an amount sufficient to provide a pharmaceutical effect in a patient suffering from the disease or condition. The compound can be identified by conventional screening methods and its activity confirmed. For example, compound libraries can be screened to identify compounds which differentially bind to products of variant forms of a particular gene product, or which differentially affect expression of variant forms of the particular gene, or which differentially affect the activity of a product expressed from such gene. Preferred embodiments are as for the preceding aspect.

In another aspect, the invention provides a method of treating a disease or condition in a patient by selecting a patient whose cells have an allele of a gene selected from the genes listed herein, preferably in Tables 2, 6, or 8. The allele contains at least one variance correlated with more effective response to a treatment of the disease or condition, or tolerance of a treatment, e.g., a treatment with a drug or a drug of a class indicated herein.

Preferably the allele contains a variance as shown in Tables 2, 6, or 8 or other variance table herein. Also preferably, the altering involves administering to the patient a compound preferentially active on at least one but less than all alleles of the gene. Preferred embodiments include those as described above for other aspects of treating a disease or condition.

In a further aspect, the invention provides a method for determining a method of treatment effective to treat a disease or condition by altering the level of activity of a product of an allele of a gene selected from the genes listed in Table 2, 6, or 8, and determining whether that alteration provides a differential effect related to reducing or alleviating a disease or condition as compared to at least one alternative allele or an alteration in toxicity or tolerance of the treatment by a patient or patients. The presence of such a differential effect indicates that altering that level of activity provides at least part of an effective treatment for the disease or condition.

Preferably the determining is carried out in a clinical trial, e.g., as described above and/or in the Detailed Description below.

In still another aspect, the invention provides a method for evaluating differential efficacy of or tolerance to a treatment in a subset of patients who have a particular variance or variances in at least one gene by utilizing a clinical trial. In preferred embodiments, the clinical trial is a Phase I, II, III, or IV trial. Preferred embodiments include the stratifications and/or analyses as described below in the Detailed Description.

In yet another aspect, the invention provides a method for identifying at least one variance in at least one gene using computer-based sequence analysis or variance scanning as known to those skilled in the art.

Preferably the at least one gene is a plurality of genes, preferably at least 10, 20, 50, 100, 200, 500, 1000, 5000, 10,000, or even more. Preferably sequence and/or variance information on the plurality of genes is acumulated in one database or a set of commonly accessible databases within a single local computer network or on a single computer.

In yet another aspect, the invention provides experimental methods for finding additional variances in any of the genes provided in the table of Table 2, 6, or 8. In addition to the sequence analysis method, a number of experimental methods can also beneficially be used to identify variances. Thus the invention provides methods for producing cDNA (e.g., example 13) or genomic DNA and detecting additional variances in the genes provided in Table 2, 6, or 8 using the single strand conformation polymorphism (SSCP) method (Example 14), the T4 Endonuclease VII method (Example 15) or DNA sequencing (Example 16) or other methods pointed out below. The application of these methods to the identified genes will provide identification of additional variances that can affect inter-individual variation in drug or other treatment response. One skilled in the art will recognize that many methods for experimental variance detection have been described (in addition to the exemplary methods of examples 14, 15 and 16) which can be utilized. These additional methods include chemical cleavage of mismatches (see, e.g., Ellis T P, et al., Chemical cleavage of mismatch: a new look at an established method. *Human Mutation* 11(5):345–53, 1998),. denaturing gradient gel electrophoresis (see, e.g., Van Orsouw N J, et al., Design and application of 2-D DGGE-based gene mutational scanning tests. *Genet Anal.* 14(5–6):205–13, 1999) and heteroduplex analysis (see, e.g., Ganguly A, et al., Conformation-sensitive gel electrophoresis for rapid detection of single-base differences in double-stranded PCR products and DNA fragments: evidence for solvent-induced bends in DNA heteroduplexes. *Proc Natl Acad Sci USA*. 90 (21):10325–9, 1993).

In embodiments any of the above methods involving determination of the presence or absence of a particular variance or variances, the method preferably involves determining the presence or absence using a cell sample from an individual or individuals. Thus, the methods can also involve obtaining a cell sample from an individual. The cell sample can be any of a variety of different cells, e.g., blood cells skin cells, muscle cells, normal cells, or cancer cells.

By "comprising" is meant including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Other features and advantages of the invention will be apparent from the following description of the preferred embodiments thereof, and from the claims.

DETAILED DESCRIPTION OF THE PREFERRED EMBODIMENTS

Figure 1:
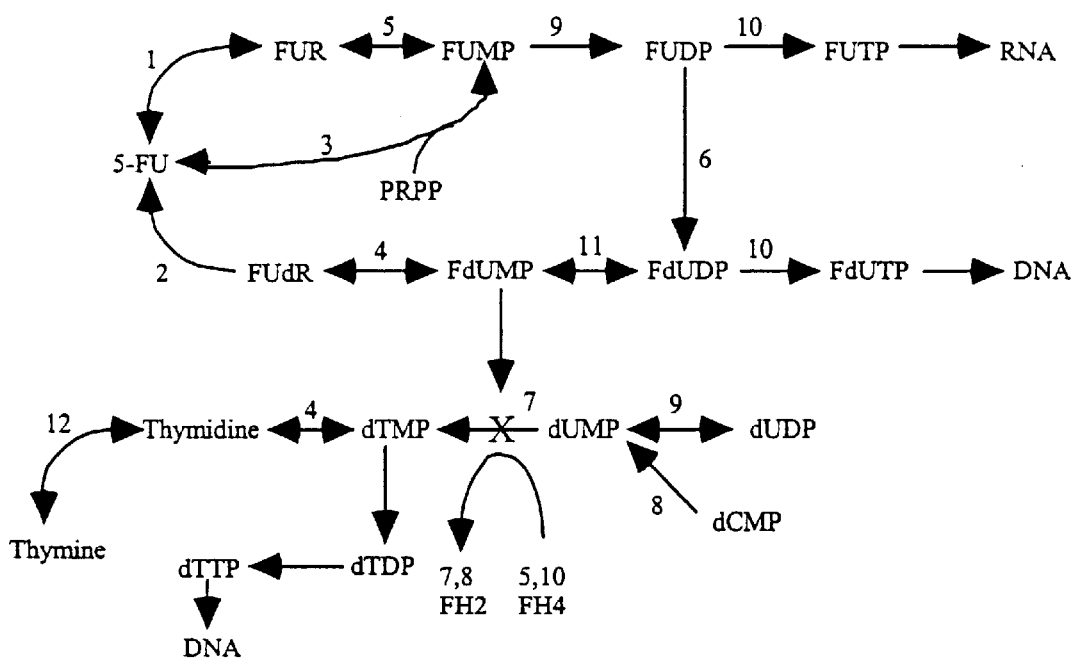
FIG. 1 is a diagram showing the relationships of enzymes involved in 5-FU metabolism and inhibition of thymidylate formation. Enzymes: 1. uridine phosphorylase; 2. thymidine phosphorylase; 3. orotate phosphoribosyl transferase; 4. thymidine kinase; 5. uridine kinase; 6. ribonucletide reductase; 7. thymidylate synthase; 8. dCMP deaminase; 9. nucleoside monophosphate kinase; 10. nucleoside diphosphate kinase; 11. nucleoside diphosphatase or cytidylate kinase; 12: thymine phosphorylase. FH2=dihydrofolate, FH4=tetrahydrofolate. The Figure is adapted from Goodman & Gilman's The Pharmacological Basis of Therapeutics, ninth edition, McGraw Hill, 1996, p. 1249.

Tables 10 will first be briefly described.

Table 10 is a partial list of DNA sequence variances in genes relevant to the methods described in the present invention. These variances were identified by the inventors in studies of selected genes, and are provided here as useful for the methods of the present invention. The variances in Table 10 were discovered by one or more of the methods described below in the Detailed Description or Examples. Table 10 has eight columns. Column 1, the "Name" column, contains the Human Genome Organization (HUGO) identifier for the gene. Column 2, the "GID" column provides the GenBank accession number of a genomic, cDNA, or partial sequence of a particular gene. Column 3, the "OMIM_ID"

column contains the record number corresponding to the Online Mendelian Inheritance in Man database for the gene provided in columns 1 and 2. This record number can be entered at the world wide web site http://www3.ncbi.nlm.nih.gov/Omim/searchomim.html to search the OMIM record on the gene. Column 4, the VGX_Symbol column, provides an internal identifier for the gene. Column 5, the "Description" column provides a descriptive name for the gene, when available. Column 6, the "Variance_Start" column provides the nucleotide location of a variance with respect to the first listed nucleotide in the GenBank accession number provided in column 2. That is, the first nucleotide of the GenBank accession is counted as nucleotide 1 and the variant nucleotide is numbered accordingly. Column 7, the "variance" column provides the nucleotide location of a variance with respect to an ATG codon believed to be the authentic ATG start codon of the gene, where the A of ATG is numbered as one (1) and the immediately preceding nucleotide is numbered as minus one (−1). This reading frame is important because it allows the potential consequence of the variant nucleotide to be interpreted in the context of the gene anatomy (5' untranslated region, protein coding sequence, 3' untranslated region). Column 7 also provides the identity of the two variant nucleotides at the indicated position. Column 8, the "CDS_Context" column indicates whether the variance is in a coding region but silent (S); in a coding region and results in an amino acid change (e.g., R347C, where the letters are one letter amino acid abbreviations and the number is the amino acid residue in the encoded amino acid sequence which is changed); in a sequence 5' to the coding region (5); or in a sequence 3' to the coding region (3). As indicated above, interpreting the location of the variance in the gene depends on the correct assignment of the initial ATG of the encoded protein (the translation start site). It should be recognized that assignment of the correct ATG may occasionally be incorrect in GenBank, but that one skilled in the art will know how to carry out experiments to definitively identify the correct translation initiation codon (which is not always an ATG). In the event of any potential question concerning the proper identification of a gene or part of a gene, due for example, to an error in recording an identifier or the absence of one or more of the identifiers, the priority for use to resolve the ambiguity is GenBank accession number, OMIM identification number, HUGO identifier, common name identifier. In this gene list, folate transporter (SLC19A1) and reduced folate carrier (RFC1) are the same gene and thymidylate synthetase and thymidylate synthase are the same gene.

The present invention is generally described below in connection with cancer chemotherapy. However, the described approach and techniques are applicable to a variety of other treatments and to genes associated with the efficacy and safety of such other treatments, for example, genes function in the pathways identified below, along with the specific genes listed. The present invention identifies a number of genes in certain treatment-related pathways, and further identifies a number of genetic sequence variances in those genes. The present description further describes how to identify variances which correlate with variable treatment efficacy and further how to identify additional variances in the identified genes and how to determine the treatment response correlation of those additional variances.

Chemotherapy of cancer currently involves use of highly toxic drugs with narrow therapeutic indices. Although progress has been made in the chemotherapeutic treatment of selected malignancies, most adult solid cancers remain highly refractory to treatment. Nonetheless, chemotherapy is the standard of care for most disseminated solid cancers. Chemotherapy often results in a significant fraction of treated patients suffering unpleasant or life-threatening side effects while receiving little or no clinical benefit; other patients may suffer few side effects and/or have complete remission or even cure. Any test that could predict response to chemotherapy, even partially, would allow more selective use of toxic drugs, and could thereby significantly improve efficacy of oncologic drug use, with the potential to both reduce side effects and increase the fraction of responders. Chemotherapy is also expensive, not just because the drugs are often costly, but also because administering highly toxic drugs requires close monitoring by carefully trained personnel, and because hospitalization is often required for treatment of (or monitoring for) toxic drug reactions. Information that would allow patients to be divided into likely responder vs. non-responder (or likely side effect) groups, with only the former to receive treatment, would therefore also have a significant impact on the economics of cancer drug use.

Predicting Response to Chemotherapy

Several methods for predicting response to chemotherapy in individual patients have been investigated over the years, ranging from the use of biochemical markers to testing drugs on a patient's cultured tumor cells. None of these methods has proven sufficiently informative and practical to gain wide acceptance. However, there are some specific examples of tests useful for predicting toxicity. For example, a diagnostic test to predict side effects associated with the antineoplastic drugs 6-mercaptopurine, 6-thioguanine and azathioprine has begun to gain wide acceptance, particularly among pediatric oncologists. Severe toxicity of thiopurine drugs is associated with deficiency of the enzyme thiopurine methyltransferase (TPMT). Currently most TPMT testing is done using an enzyme assay, however the TPMT gene has been cloned and mutations associated with low TPMT levels have been identified; genetic testing is beginning to supplant enzyme assays because genetic tests are more easily standardized and economical.

While there are no good tests that predict positive chemotherapeutic response, there is demonstrated utility to measuring estrogen and progesterone receptor levels in cancer tissue before selecting therapy directed at modulating hormonal state. Measuring genetic variation in proteins that mediate the effects, course, outcome, and/or development of adverse events in those patients potentially receiving chemotherapy drugs is, in some respects, analogous to measuring ER and PR levels, which mediate the effects of hormones.

I. Outline: Identification of Interpatient Variation in Response; Identification of Genes and Variances Relevant to Drug Action; Development of Diagnostic Tests; and Use of Variance Status to Determine Treatment Human therapeutic development follows a course from discovery and analysis in a laboratory (preclinical development) to testing the candidate therapeutic intervention in human subjects (clinical development). The preclinical development of candidate therapeutic interventions for use in the treatment of human disease, disorders, or conditions begins at the discovery stage whereby a candidate therapy is tested in vitro to achieve a desired biochemical alteration of a biochemical or physiological event. If successful, the candidate is generally tested in animals to determine toxicity, adsorption, distribution, and metabolism within a living species. Occasionally, there are available animal models that mimic human diseases, disorders, and conditions in which testing the candidate therapeutic intervention can provide supportive data to warrant proceeding to test the agent or compound in humans. When an agent or compound enters first in human studies, it is recognized that the prediction of whether the agent or product's preclinical success will be mimicked in humans is imperfect. Both safety and efficacy data will generally have to ultimately be determined in humans. Therefore, given economic constraints, and considering the complexities of human clinical trials, any technical advance to assist those skilled in the art of drug development will be welcomed. Advances can be implemented by aiding identification of genetic markers associated with interpatient variation in response during preclinical development (thereby allowing development of non-allele selective agents), or by identification or optimization of clinical trial design parameters in order to achieve successful development of therapeutic products at any stage of clinical development, or by identifying variables that will allow safe and efficacious use of a marketed product. Such advances will provide benefits in the form of therapeutic alternatives to those patients in need of medical care.

As indicated in the Summary above, certain aspects of the present invention typically involve the following process, which need not occur separately or in the order stated. Not all of these described processes must be present in a particular method, or need be performed by a single entity or organization or person. Additionally, if certain of the information is available from other sources, that information can be utilized in the present invention. The processes are as follows: a) variability between patients in the response to a particular treatment is observed; b) at least a portion of the variable response is correlated with the presence or absence of at least one variance in at least one gene; c) an analytical or diagnostic test is provided to determine the presence or absence of the at least one variance in individual patients; d) the presence or absence of the variance or variances is used to select a patient for a treatment or to select a treatment for a patient, or the variance information is used in other methods described herein.

A. Identification of Interpatient Variability in Response to a Treatment

Interpatient variability is the rule, not the exception, in clinical therapeutics. One of the best sources of information on interpatient variability is the nurses and physicians supervising the clinical trial who accumulate a body of first hand observations of physiological responses to the drug in different normal subjects or patients. Evidence of interpatient variation in response can also be measured statistically, and may be best described by statistical measures that examine magnitude of response (beneficial or adverse) across a large number of subjects.

In accord with the other portions of this description, the present invention concerns DNA sequence variances that can affect one or more of:

i. The susceptibility of individuals to a disease;
  ii. The course or natural history of a disease;
  iii. The response of a patient with a disease to a medical intervention, such as, for example, a drug, a biologic substance, physical energy such as radiation therapy, or a specific dietary regimen. The ability to predict either beneficial or detrimental responses is medically useful.

Thus variation in any of these three parameters may constitute the basis for initiating a pharmacogenetic study directed to the identification of the genetic sources of interpatient variation. The effect of a DNA sequence variance or variances on disease susceptibility or natural history (i and ii, above) are of particular interest as the variances can be used to define patient subsets which behave differently in response to medical interventions such as those described in (iii).

In other words, a variance can be useful for customizing medical therapy at least for either of two reasons. First, the variance may be associated with a specific disease subset that behaves differently with respect to one or more therapeutic interventions (i and ii above); second, the variance may affect response to a specific therapeutic intervention (iii above). Consider for exemplary purposes pharmacological therapeutic interventions. In the first case, there may be no effect of a particular gene sequence variance on the observable pharmacological action of a drug, yet the disease subsets defined by the variance or variances differ in their response to the drug because, for example, the drug acts on a pathway that is more relevant to disease pathophysiology in one variance-defined patient subset thanin another variance-defined patient subset. The second type of useful gene sequence variance affects the pharmacological action of a drug or other treatment. Effects on pharmacological responses fall generally into two categories; pharmacokinetic and pharmacodynamic effects. These effects have been defined as follows in Goodman and Gilman's Phamacologic Basis of Therapeutics (ninth edition, McGraw Hill, New York, 1986): "Pharmacokinetics" deals with the absorption, distribution, biotransformations and excretion of drugs. The study of the biochemical and physiological effects of drugs and their mechanisms of action is termed "pharmacodynamics."

Useful gene sequence variances for this invention can be described as variances which partition patients into two or more groups that respond differently to a therapy, regardless of the reason for the difference, and regardless of whether the reason for the difference is known.

B. Identification of Specific Genes and Correlation of Variances in Those Genes With Response to Treatment of Diseases or Conditions It is useful to identify particular genes which do or are likely to mediate the efficacy or safety of a treatment method for a disease or condition, particularly in view of the large number of genes which have been identified and which continue to be identified in humans. As is further discussed in section C below, this correlation can proceed by different paths. One exemplary method utilizes prior information on the pharmacology or pharmacokinetics or pharmacodynamics of a treatment method, e.g., the action of a drug, which indicates that a particular gene is, or is likely to be, involved in the action of the treatment method, and further suggests that variances in the gene may contribute to variable response to the treatment method.

Alternatively, if such information is not known, variances in a gene can be correlated empirically with treatment response. In this method, variances in a gene which exist in a population can be identified. The presence of the different variances or haplotypes in individuals of a study group, which is preferably representative of a population or populations, is determined. This variance information is then correlated with treatment response of the various individuals as an indication that genetic variability in the gene is at least partially responsible for differential treatment response. Statistical measures known to those skilled in the art are preferably used to measure the fraction of interpatient variation attributable to any one variance.

Useful methods for identifying genes relevant to the physiologic action of a drug or other treatment are known to those skilled in the art, and include large scale analysis of gene expression in cells treated with the drug compared to control cells, or large scale analysis of the protein expression pattern in treated vs. untreated cells, or the use of techniques for identification of interacting proteins or ligand-protein interactions.

C. Development of a Diagnostic Test to Determine Variance Status

In accordance with the description in the Summary above, the present invention generally concerns the identification of variances in genes which are indicative of the effectiveness of a treatment in a patient. The identification of specific variances, in effect, can be used as a diagnostic or prognostic test. Correlation of treatment efficacy and/or toxicity with particular genes and gene families or pathways is provided in Stanton et al., U.S. Provisional Application No. 60/093, 484, filed Jul. 20, 1998, entitled GENE SEQUENCE VARIANCES WITH UTILITY IN DETERMINING THE TREATMENT OF DISEASE (concerns the safety and efficacy of compounds active on folate or pyrimidine metabolism or action).

Genes identified in the examples below and the attached Tables and Figures can be used in the present invention.

Methods for diagnostic tests are well known in the art. Generally in this invention, the diagnostic test involves determining whether an individual has a variance or variant form of a gene that is involved in the disease or condition or the action of the drug or other treatment or effects of such treatment. Such a variance or variant form of the gene is preferably one of several different variances or forms of the gene that have been identified within the population and are known to be present at a certain frequency. In an exemplary method, the diagnostic test involves performed by amplifying a segment of DNA or RNA (generally after converting the RNA to cDNA) spanning one or more variances in the gene sequence. Preferably, the amplified segment is <500 bases in length, in an alternative embodiment the amplified segment is <100 bases in length, most preferably <45 bases in length. In many cases, the diagnostic test is performed by amplifying a segment of DNA or RNA (cDNA) spanning a variance, or even spanning more than one variance in the gene sequence and preferably maintaining the phase of the variances on each allele. The term "phase" means the association of variances on a single copy of the gene, such as the copy transmitted from the mother (maternal copy or maternal allele) or the father (paternal copy or paternal allele). It is apparent that such diagnostic tests are performed after initial identification of variances within the gene.

Diagnostic genetic tests useful for practicing this invention belong to two types: genotyping tests and haplotyping tests. A genotyping test simply provides the status of a variance or variances in a subject or patient. For example suppose nucleotide 150 of hypothetical gene X on an autosomal chromosome is an adenine (A) or a guanine (G) base. The possible genotypes in any individual are AA, AG or GG at nucleotide 150 of gene X.

In a haplotyping test there is at least one additional variance in gene X, say at nucleotide 810, which varies in the population as cytosine (C) or thymine (T). Thus a particular copy of gene X may have any of the following combinations of nucleotides at positions 150 and 810: 150A-810C, 150A-810T, 150G-810C or 150G-810T. Each of the four possibilities is a unique haplotype. If the two nucleotides interact in either RNA or protein, then knowing the haplotype can be important. The point of a haplotyping test is to determine the haplotypes present in a DNA or cDNA sample (e.g. from a patient). In the example provided there are only four possible haplotypes, but, depending on the number of variances in the gene and their distribution in human populations there may be three, four, five, six or more haplotypes at a given gene. The most useful haplotypes for this invention are those which occur commonly in the population being treated for a disease or condition. Preferably such haplotypes occur in at least 5% of the population, more preferably in at least 10%, still more preferably in at least 20% of the population and most preferably in at least 30% or more of the population. Conversely, when the goal of a pharmacogenetic program is to identify a relatively rare population that has an adverse reaction to a treatment, the most useful haplotypes may be rare haplotypes, which may occur in less than 5%, less than 2%, or even in less than 1% of the population. One skilled in the art will recognize that the frequency of the adverse reaction will provide a useful guide to the likely frequency of salient causative haplotypes.

Based on the identification of variances or variant forms of a gene, a diagnostic test utilizing methods known in the art can be used to determine whether a particular form of the gene, containing specific variances or haplotypes, or combinations of variances and haplotypes, is present in at least one copy, one copy, or more than one copy in an individual. Such tests are commonly performed using DNA or RNA collected from blood, cells, tissue scrapings or other cellular materials, and can be performed by a variety of methods including, but not limited to, hybridization with allele-specific probes, enzymatic mutation detection, chemical cleavage of mismatches, mass spectrometry or DNA sequencing, including minisequencing. Methods for haplotyping are provided in this application. In particular embodiments, hybridization with allele specific probes can be conducted in two formats: (1) allele specific oligonucleotides bound to a solid phase (glass, silicon, nylon membranes) and the labelled sample in solution, as in many DNA chip applications, or (2) bound sample (often cloned DNA or PCR amplified DNA) and labelled oligonucleotides in solution (either allele specific or short so as to allow sequencing by hybridization). The application of such diagnostic tests is possible after identification of variances that occur in the population. Diagnostic tests may involve a panel of variances from one or more genes, often on a solid support, which enables the simultaneous determination of more than one variance in one or more genes.

D. Use of Variance Status to Determine Treatment

The present disclosure describes exemplary gene sequence variances in genes identified in a gene table herein (e.g., Tables 2, 6, and 8), and variant forms of these gene that may be determined using diagnostic tests. As indicated in the Summary, such a variance-based diagnostic test can be used to determine whether or not to administer a specific drug or other treatment to a patient for treatment of a disease or condition. Preferably such diagnostic tests are incorporated in texts such as Clinical Diagnosis and Management by Laboratory Methods (19th Ed) by John B. Henry (Editor) WB Saunders Company, 1996; Clinical Laboratory Medicine: Clinical Application of Laboratory Data, (6th edition) by R. Ravel, Mosby-Year Book, 1995, or medical textbooks including, without limitation, textbooks of medicine, laboratory medicine, therapeutics, pharmacy, pharmacology, nutrition, allopathic, homeopathic, and osteopathic medicine; most preferably such a diagnostic test is specified by regulatory authorities, e.g., by the U.S. Food and Drug Administration, and is incorporated in the label or insert as well as the Physicians Desk Reference.

In such cases, the procedure for using the drug is restricted or limited on the basis of a diagnostic test for determining the presence of a variance or variant form of a gene. The procedure may include the route of administration of the drug, the dosage form, dosage, schedule of administration or use with other drugs; any or all of these may require selecting or determination consistent with the results of the diagnostic test or a plurality of such tests. Preferably the use of such diagnostic tests to determine the procedure for administration of a drug is incorporated in a text such as those listed above, or medical textbooks, for example, textbooks of medicine, laboratory medicine, therapeutics, pharmacy, pharmacology, nutrition, allopathic, homeopathic, and osteopathic medicine. As previously stated, preferably such a diagnostic test or tests are required by regulatory authorities and are incorporated in the label or insert as well as the Physicians Desk Reference.

Variances and variant forms of genes useful in conjunction with treatment methods may be associated with the origin or the pathogenesis of a disease or condition. In many useful cases, the variant form of the gene is associated with a specific characteristic of the disease or condition that is the target of a treatment, most preferably response to specific drugs or other treatments. Examples of diseases or conditions ameliorable by the methods of this invention are identified in the Examples and tables below; in general treatment of disease with current methods, particularly drug treatment, always involves some unknown element (involving efficacy or toxicity or both) that can be reduced by appropriate diagnostic methods.

Alternatively, the gene is involved in drug action, and the variant forms of the gene are associated with variability in the action of the drug. For example, in some cases, one variant form of the gene is associated with the action of the drug such that the drug will be effective in an individual who inherits one or two copies of that form of the gene. Alternatively, a variant form of the gene is associated with the action of the drug such that the drug will be toxic or otherwise contra-indicated in an individual who inherits one or two copies of that form of the gene.

In accord with this invention, diagnostic tests for variances and variant forms of genes as described above can be used in clinical trials to demonstrate the safety and efficacy of a drug in a specific population. As a result, in the case of drugs which show variability in patient response correlated with the presence or absence of a variance or variances, it is preferable that such drug is approved for sale or use by regulatory agencies with the recommendation or requirement that a diagnostic test be performed for a specific variance or variant form of a gene which identifies specific populations in which the drug will be safe and/or effective. For example, the drug may be approved for sale or use by regulatory agencies with the specification that a diagnostic test be performed for a specific variance or variant form of a gene which identifies specific populations in which the drug will be toxic. Thus, approved use of the drug, or the procedure for use of the drug, can be limited by a diagnostic test for such variances or variant forms of a gene; or such a diagnostic test may be considered good medical practice, but not absolutely required for use of the drug.

As indicated, diagnostic tests for variances as described in this invention may be used in clinical trials to establish the safety and efficacy of a drug. Methods for such clinical trials are described below and/or are known in the art and are described in standard textbooks. For example, diagnostic tests for a specific variance or variant form of a gene may be incorporated in the clinical trial protocol as inclusion or exclusion criteria for enrollment in the trial, to allocate certain patients to treatment or control groups within the clinical trial or to assign patients to different treatment cohorts. Alternatively, diagnostic tests for specific variances may be performed on all patients within a clinical trial, and statistical analysis performed comparing and contrasting the efficacy or safety of a drug between individuals with different variances or variant forms of the gene or genes. Preferred embodiments involving clinical trials include the genetic stratification strategies, phases, statistical analyses, sizes, and other parameters as described herein.

Similarly, diagnostic tests for variances can be performed on groups of patients known to have efficacious responses to the drug to identify differences in the frequency of variances between responders and non-responders. Likewise, in other cases, diagnostic tests for variance are performed on groups of patients known to have toxic responses to the drug to identify differences in the frequency of the variance between those having adverse events and those not having adverse events. Such outlier analyses may be particularly useful if a limited number of patient samples are available for analysis. It is apparent that such clinical trials can be or are performed after identifying specific variances or variant forms of the gene in the population.

The identification and confirmation of genetic variances is described in certain patents and patent applications. The description therein is useful in the identification of variances in the present invention. For example, a strategy for the development of anticancer agents having a high therapeutic index is described in Housman, International Application PCT/US/94 08473 and Housman, INHIBITORS OF ALTERNATIVE ALLELES OF GENES ENCODING PROTEINS VITAL FOR CELL VIABILITY OR CELL GROWTH AS A BASIS FOR CANCER THERAPEUTIC AGENTS, U.S. Pat. No. 5,702,890, issued Dec. 30, 1997, which are hereby incorporated by reference in their entireties. Also, a number of gene targets and associated variances are identified in Housman et al., U.S. patent application Ser. No. 09/045,053, entitled TARGET ALLELES FOR ALLELE-SPECIFIC DRUGS, filed Mar. 19, 1998, which is hereby incorporated by reference in its entirety, including drawings.

The described approach and techniques are applicable to a variety of other diseases, conditions, and/or treatments and to genes associated with the etiology and pathogenesis of such other diseases and conditions and the efficacy and safety of such other treatments.

Useful variances for this invention can be described generally as variances which partition patients into two or more groups that respond differently to a therapy (a therapeutic intervention), regardless of the reason for the difference, and regardless of whether the reason for the difference is known.

II. From Variance List to Clinical Trial: Identifying Genes and Gene Variances That Account for Variable Responses to Treatment There are a variety of useful methods for identifying a subset of genes from a large set that should be prioritized for further investigation with respect to their influence on inter-individual variation in disease predisposition or response to a particular drug. These methods include for example, (1) searching the relevant literature to identify genes relevant to a disease or the action of a drug; (2) screening the genes identified in step 1 for variances. A large set of exemplary variances are provided in Tables 3, 4, and 10; (3) using computational tools to predict the functional effects of variances in specific genes; (4) using in vitro or in vivo experiments to identify genes which may participate in the response to a drug or treatment, and to determine the variances which affect gene, RNA or protein function, and may therefore be important genetic variables affecting disease manifestations or drug response; and (5) retrospective or prospective clinical trials. Each of these methods is considered below in some detail.

(1) To begin, one preferably identifies, for a given treatment, a set of candidate genes that are likely to affect disease phenotype or drug response. This can be accomplished most efficiently by first assembling the relevant medical, pharmacological and biological data from available sources (e.g., public databases and publications). One skilled in the art can review the literature (textbooks, monographs, journal articles) and online sources (databases) to identify genes most relevant to the action of a specific drug or other treatment, particularly with respect to its utility for treating a specific disease, as this beneficially allows the set of genes to be analyzed ultimately in clinical trials to be reduced from an initial large set. Specific strategies for conducting such searches are described below. In some instances the literature may provide adequate information to select genes to be studied in a clinical trial, but in other cases additional experimental investigations of the sort described below will be preferable to maximize the likelihood that the salient genes and variances are moved forward into clinical studies. Experimental data are also useful in establishing a list of candidate genes, as described below.

(2) Having assembled a list of candidate genes generally the second step is to screen for variances in each candidate gene. Experimental and computational methods for variance detection are described in this invention, and a tables of exemplary variances is provided (e.g., Table 3, 4, and 10) as well as methods for identifying additional variances.

(3) Having identified variances in candidate genes the next step is to assess their likely contribution to clinical variation in patient response to therapy, preferably by using informatics-based approaches such as DNA and protein sequence analysis and protein modeling. The literature and informatics-based approaches provide the basis for prioritization of candidate genes, however it may in some cases be desirable to further narrow the list of candidate genes, or to measure experimentally the phenotype associated with specific variances or sets of variances (e.g. haplotypes).

(4) Thus, as a third step in candidate gene analysis, one skilled in the art may elect to perform in vitro or in vivo experiments to assess the functional importance of gene variances, using either biochemical or genetic tests. (Certain kinds of experiments—for example gene expression profiling and proteome analysis—may not only allow refinement of a candidate gene list but may also lead to identification of additional candidate genes.) Combination of two or all of the three above methods will provide sufficient information to narrow the set of candidate genes and variances to a number that can be studied in a clinical trial with adequate statistical power.

(5) The fourth step is to design retrospective or prospective human clinical trials to test whether the identified allelic variance, variances, or haplotypes or combination thereof influence the efficacy or toxicity profiles for a given drug or other therapeutic intervention. It should be recognized that this fourth step is the crucial step in producing the type of data that would justify introducing a diagnostic test for at least one variance into clinical use. Thus while each of the above four steps are useful in particular instances of the invention, this final step is indispensable. Further guidance and examples of how to perform these five steps is provided below.

1. Identification of Candidate Genes Relevant to the Action of a Drug

Practice of this invention will often begin with identification of a specific pharmaceutical product, for example a drug, that would benefit from improved efficacy or reduced toxicity or both, and the recognition that pharmacogenetic investigations as described herein provide a basis for achieving such improved characteristics. The question then becomes which of the genes and variances provided in this application, e.g., in Tables 3, 4, and 10, would be most relevant to interpatient variation in response to the drug. As discussed above, the set of relevant genes includes both genes involved in the disease process and genes involved in the interaction of the patient and the treatment—for example genes involved in pharmacokinetic and pharmacodynamic action of a drug. The biological and biomedical literature and online databases provide useful guidance in selecting such genes. Specific guidance in the use of these resources is provided below.

Review the Literature and Online Sources

One way to find genes that affect response to a drug in a particular disease setting is to review the published literature and available online databases regarding the pathophysiology of the disease and the pharmacology of the drug. Literature or online sources can provide specific genes involved in the disease process or drug response, or describe biochemical pathways involving multiple genes, each of which may affect the disease process or drug response.

Alternatively, biochemical or pathological changes characteristic of the disease may be described; such information can be used by one skilled in the art to infer a set of genes that can account for the biochemical or pathologic changes. For example, to understand variation in response to a drug that modulates serotonin levels in a central nervous system (CNS) disorder associated with altered levels of serotonin one would preferably study, at a minimum, variances in genes responsible for serotonin biosynthesis, release from the cell, receptor binding, presynaptic reuptake, and degradation or metabolism. Genes responsible for each of these functions should be examined for variation that may account for interpatient differences in drug response or disease manifestations. As recognized by those skilled in the art, a comprehensive list of such genes can be obtained from textbooks, monographs and the literature.

There are several types of scientific information, described in some detail below, that are valuable for identifying a set of candidate genes to be investigated with respect to a specific disease and therapeutic intervention. First there is the medical literature, which provides basic information on disease pathophysiology and therapeutic interventions. A subset of this literature is devoted to specific description of pathologic conditions. Second there is the pharmacology literature, which will provide additional information on the mechanism of action of a drug (pharmacodynamics) as well as its principal routes of metabolic transformation (pharmacokinetics) and the responsible proteins. Third there is the biomedical literature (principally genetics, physiology, biochemistry and molecular biology), which provides more detailed information on metabolic pathways, protein structure and function and gene structure.

Fourth, there are a variety of online databases that provide additional information on metabolic pathways, gene families, protein function and other subjects relevant to selecting a set of genes that are likely to affect the response to a treatment.

Medical Literature

A good starting place for information on molecular pathophysiology of a specific disease is a general medical textbook such as *Harrison's Principles of Internal Medicine*, 14th edition, (2 Vol Set) by A. S. Fauci, E. Braunwald, K. J. Isselbacher, et al. (editors), McGraw Hill, 1997, or *Cecil Textbook of Medicine* (20th Ed) by R. L. Cecil, F. Plum and J. C. Bennett (Editors) WB Saunders Co., 1996. For pediatric diseases texts such as *Nelson Textbook of Pediatrics* (15th edition) by R. E. Behrman, R. M. Kliegman, A. M. Arvin and W. E. Nelson (Editors), WB Saunders Co., 1995 or *Oski's Principles and Practice of Pediatrics* ($3^{rd}$ Edition) by J. A. Mamillan & F. A. Oski Lippincott-Raven, 1999 are useful introductions. For obstetrical and gynecological disorders texts such as *Williams Obstetrics* (20th Ed) by F. G. Cunningham, N. F. Gant, P. C. McDonald et al. (Editors), Appleton & Lange, 1997 provide general information on disease pathophysiology. For psychiatric disorders texts such as the *Comprehensive Textbook of Psychiatry*, VI (2 Vols) by H. I. Kaplan and B. J. Sadock (Editors), Lippincott, Williams & Wilkins, 1995, or *The American Psychiatric Press Textbook of Psychiatry* ($3^{rd}$ edition) by R. E. Hales, S. C. Yudofsky and J. A. Talbott (Editors) Amer Psychiatric Press, 1999 provide an overview of disease nosology, pathophysiological mechanisms and treatment regimens.

In addition to these general texts, there are a variety of more specialized medical texts that provide greater detail about specific disorders which can be utilized in developing a list of candidate genes and variances relevant to interpatient variation in response to a treatment. For example, within the field of medicine there are standard textbooks for each of the subspecialties. Some specific examples include:

*Heart Disease: A Textbook of Cardiovascular Medicine* (2 Volume set) by E. Braunwald (Editor), WB Saunders Co., 1996.

*Hurst's the Heart, Arteries and Veins* (9th Ed) (2 Vol Set) by R. W. Alexander, R. C. Schlant, V. Fuster, W. Alexander and E. H. Sonnenblick (Editors) McGraw Hill, 1998.

*Principles of Neurology* (6th edition) by R. D. Adams, M. Victor (editors), and A. H. Ropper (Contributor), McGraw Hill, 1996.

*Sleisenger & Fordtran's Gastrointestinal and Liver Disease: Pathophysiology, Diagnosis, Management* (6th edition) by M. Feldman, B. F. Scharschmidt and M. Sleisenger (Editors), WB Saunders Co., 1997.

*Textbook of Rheumatology* (5th edition) by W. N. Kelley, S. Ruddy, E. D. Harris Jr. and C. B. Sledge (Editors) (2 volume set) WB Saunders Co., 1997.

*Williams Textbook of Endocrinology* (9th edition) by J. D. Wilson, D. W. Foster, H. M. Kronenberg and Larsen (Editors), WB Saunders Co., 1998.

*Wintrobe's Clinical Hematology* (10th Ed) by G. R. Lee, J. Foerster (Editor) and J. Lukens (Editors) (2 Volumes) Lippincott, Williams & Wilkins, 1998.

*Cancer: Principles & Practice of Oncology* (5th edition) by V. T. Devita, S. A. Rosenberg and S. Heilman (editors), Lippincott-Raven Publishers, 1997.

*Principles of Pulmonary Medicine* (3rd edition) by S. E. Weinberger & J Fletcher (Editors), WB Saunders Co., 1998.

*Diagnosis and Management of Renal Disease and Hypertension* (2nd edition) by A. K. Mandal & J. C. Jennette (Editors), Carolina Academic Press, 1994. *Massry & Glassock's Textbook of Nephrology* (3rd edition) by S. G. Massry & R. J. Glassock (editors) Williams & Wilkins, 1995.

*The Management of Pain* by J. J. Bonica, Lea and Febiger, 1992

*Ophthalmology* by M. Yanoff & J. S. Duker, Mosby Year Book, 1998

*Clinical Ophthalmology: A Systemic Approach* by J. J. Kanski, Butterworth-Heineman, 1994. *Essential Otolaryngology* by J. K. Lee Appleton and Lange 1998.

In addition to these subspecialty texts there are many textbooks and monographs that concern more restricted disease areas, or specific diseases. Such books provide more extensive coverage of pathophysiologic mechanisms and therapeutic options. The number of such books is too great to provide examples for all but a few diseases, however one skilled in the art will be able to readily identify relevant texts. One simple way to search for relevant titles is to use the search engine of an online bookseller such as http:// www.amazon.com or http://www.barnesandnoble.com using the disease or drug (or the group of diseases or drugs to which they belong) as search terms. For example a search for asthma would turn up titles such as *Asthma: Basic Mechanisms and Clinical Management* (3rd edition) by P. J. Barnes, I. W. Rodger and N. C. Thomson (Editors), Academic Press, 1998 and Airways and Vascular Remodelling in Asthma and Cardiovascular Disease: Implications for Therapeutic Intervention: Based on the Scientific Program, by C. Page & J. Black (Editors), Academic Press, 1994.

Pathology Literature

In addition to medical texts there are texts that specifically address disease etiology and pathologic changes associated with disease. A good general pathology text is *Robbins Pathologic Basis of Disease* (6th edition) by R. S. Cotran, V. Kumar, T. Collins and S. L. Robbins, WB Saunders Co., 1998. Specialized pathology texts exist for each organ system and for specific diseases, similar to medical texts. These texts are useful sources of information for one skilled in the art for developing lists of genes that may account for some of the known pathologic changes in disease tissue. Exemplary texts are as follows:

*Bone Marrow Pathology* $2^{nd}$ edition, by B. J. Bain, I. Lampert. & D. Clark, Blackwell Science, 1996

*Atlas of Renal Pathology* by F. G. Silva, W.B. Saunders, 1999.

*Fundamentals of Toxicologic Pathology* by W. M. Haschek and C. G. Rousseaux, Academic Press, 1997.

*Gastrointestinal Pathology* by P. Chandrasoma, Appleton and Lange, 1998.

*Ophthalmic Pathology with Clinical Correlations* by J. Sassani, Lippincott-Raven, 1997.

*Pathology of Bone and Joint Disorders* by F. McCarthy, F. J. Frassica and A. Ross, W.B. Saunders, 1998.

*Pulmonary Pathology* by M. A. Grippi, Lippicott-Raven, 1995.

*Neuropathology* by D. Ellison, L. Chimelli, B. Harding, S. Love & J. Lowe, Mosby Year Book, 1997.

*Greenfield's Neuropatholgy* $6^{th}$ edition by J. G. Greenfield, P. L. Lantos & D. I. Graham, Edward Arnold, 1997.

Pharmacology, Pharmacogenetics and Pharmacy Literature

There are also both general and specialized texts and monographs on pharmacology that provide data on pharmacokinetics and pharmacodynamics of drugs. The discussion of pharmacodynamics (mechanism of action of the drug)in such texts is often supported by a review of the biochemical pathway or pathways that are affected by the drug. Also, proteins related to the target protein are often listed; it is important to account for variation in such proteins as the related proteins may be involved in drug pharmacology. For example, there are 14 known serotonin receptors. Various pharmacological serotonin agonists or antagonists have different affinities for these different receptors. Variation in a specific receptor may affect the pharmacology not only of drugs intentionally targeted to that receptor, but also drugs targeted to different receptors, that may have differential action on two allelic forms of the non-targeted receptor. Thus. genes encoding proteins structurally related to the target protein are useful for screening for variance in the present invention. A good general pharmacology text is *Goodman & Gilman's the Pharmacological Basis of Therapeutics* (9th Ed) by J. G. Hardman, L. E. Limbird, P. B. Molinoff, R. W. Ruddon and A. G. Gilman (Editors) McGraw Hill, 1996. There are also texts that focus on the pharmacology of drugs for specific disease areas, or specific classes of drugs (e.g. natural products) or adverse drug interactions, among other subjects. Specific examples include:

*The American Psychiatric Press Textbook of Psychopharmacology* (2nd edition) by A. F. Schatzberg & C. B. Nemeroff (Editors), Amer Psychiatric Press, 1998. ISBN: 0880488174.

*Essential Psychopharmacology: Neuroscientific Basis and Practical Applications* by N. Muntner and S. M. Stahl, Cambridge Univ Press, 1996.

There are also texts on pharmacogenetics which are particularly useful for identifying genes which may contribute to variable pharmacokinetic response. In addition there are texts on some of the major xenobiotic metabolizing proteins, such as the cytochrome P450 genes.

*Pharmacogenetics of Drug Metabolism* (International Encyclopedia of Pharmacology and Therapeutics) by Werner Kalow (Editor) Pergamon Press, 1992.

*Genetic Factors in Drug Therapy: Clinical and Molecular Pharmacogenetics* by D. A Price Evans, Cambridge Univ Press, 1993.

*Pharmacogenetics* (Oxford Monographs on Medical Genetics, 32) by W. W. Weber, Oxford Univ Press, 1997.

*Cytochrome P450: Structure, Mechanism, and Biochemistry* by P. R. Ortiz de Montellano (Editor), Plenum Publishing Corp, 1995.

*Appleton & Lange's Review of Pharmacy*, 6$^{th}$ edition, (Appleton & Lange's Review Series) by G. D. Hall & B. S. Reiss, Appleton & Lange, 1997.

Genetics, Biochemistry and Molecular Biology Literature

In addition to the medical, pathology, and pharmacology texts listed above there are several information sources that one skilled in the art will turn to for information on the genetic, physiologic, biochemical, and molecular biological aspects of the disease, disorder or condition or the effect of the therapeutic intervention on specific physiologic processes. The biomedical literature may include information on nonhuman organisms that is relevant to understanding the likely disease or pharmacological pathways in man.

Genetic texts may provide insight into the likely effect of an allelic variance, variances, or haplotypes on individual responses to a therapeutic intervention, particularly if there are genetic variances known to effect drug response. Example 1 describes variances in the dihydropyrimidine dehydrogenase (DPD) gene locus and their effects on fluoropyrimidine catabolism. DPD is an example of a gene that, in rare mutant forms, is associated with severe fluoropyrimidine poisoning. It is reasonable to expect that more common alleles may exist at the DPD locus and may affect fluoropyrimidine metabolism, thus accounting for interpatient variation. Thus the genetics of a rare allele or alleles may provide a basis for examining the effects of commonly occuring alleles on moderate phenotypes. The genetics of rare DPD deficiency is well described in medical genetics textbooks listed below, for example see Scriver et al (full citation below).

Also provided below are illustrative texts which will aid in the identification of a pathway or pathways, and a gene or genes that may be relevant to interindividual variation in response to a therapy. Textbooks of biochemistry, genetics and physiology are often useful sources for such pathway information. In order to ascertain the appropriate methods to analyze the effects of an alleleic variance, variances, or haplotypes in vitro, one skilled in the art will review existing information on molecular biology, cell biology, genetics, biochemistry; and physiology. Such texts are useful sources for general and specific information on the genetic and biochemical processes involved in disease and in drug action, as well as experimental procedures that may be useful in performing in vitro research on an allelic variance, variances, or haplotye.

Texts on gene structure and function and RNA biochemistry will be useful in evaluating the consequences of variances that do not change the coding sequence. Such variances may alter the interaction of RNA with proteins or other regulatory molecules affecting RNA processing, polyadenylation, and export.

Molecular and Cellular Biology

Molecular Cell Biology by H. Lodish, D. Baltimore, A. Berk, L. Zipursky & J. Darnell, WH Freeman & Co., 1995.

"Essentials of Molecular Biology", D. Freifelder and MalacinskiJones and Bartlett, 1993.

"Genes and Genomes: A Changing Perspective", M. Singer and P. Berg, 1991. University Science Books "Gene Structure and Expression", J. D. Hawkins, 1996. Cambridge University Press Molecular Biology of the Cell, 2nd edition, B. Alberts et alGarland Publishing, 1994.

Molecular Genetics

The Metabolic and Molecular Bases of Inherited Disease by C. R. Scriver, A. L. Beaudet, W. S. Sly (Editors), 7th edition, McGraw Hill, 1995

"Genetics and Molecular Biology", R. Schleif, 1994. 2nd edition, Johns Hopkins University Press "Genetics", P. J. Russell, 1996. 4th edition, Harper Collins "An Introduction to Genetic Analysis", Griffiths et al. 1993. 5th edition, W.H. Freeman and Company "Understanding Genetics: A molecular approach", Rothwell, 1993. Wiley-Liss General Biochemistry "Biochemistry", L. Stryer, 1995. W.H. Freeman and Company "Biochemistry", D. Voet and J. G. Voet, 1995. John Wiley and Sons "Principles of Biochemistry", A. L. Lehninger, D. L. Nelson, and M. M. Cox, 1993. Worth Publishers "Biochemistry", G. Zubay, 1998. Wm. C. Brown Communications "Biochemistry", C. K. Mathews and K. E. van Holde, 1990. Benjamin/Cummings Transcription "Eukaryotic Transcriptiuon Factors", D. S. Latchman, 1995. Academic Press "Eukaryotic Gene Transcription", S. Goodbourn (ed.), 1996. Oxford University Press.

"Transcription Factors and DNA Replication", D. S. Pederson and N. H. Heintz, 1994. CRC Press/R.G. Landes Company "Transcriptional Regulation", S. L. McKnight and K. Yamamoto (eds.), 1992. 2 volumes, Cold Spring Harbor Laboratory Press

RNA

"Control of Messenger RNA Stability", J. Belasco and G. Brawerman (eds.), 1993. Academic Press "RNA-Protein Interactions", Nagai and Mattaj (eds.), 1994. Oxford University Press "mRNA Metabolism and Post-transcriptional Gene Regulation", Harford and Morris (eds.), 1997. Wiley-Liss Translation "Translational Control", J. W.B. Hershey, M. B. Mathews, and N. Sonenberg (eds.), 1995. Cold Spring Harbor Laboratory Press General Physiology "Textbook of Medical Physiology" 9$^{th}$ Edition by A. C. Guyton and J. E. Hall W. B. Saunders, 1997

"Review of Medical Physiology", 18$^{th}$ Edition by W. F. Ganong, Appleton and Lange, 1997

Online Databases

Those skilled in the art are familiar with how to search the literature, such as, e.g., libraries, online pubmed, abstract listings, and online mutation databases. One particularly useful resource is maintained at the web site of the National Center for Biotechnology Information (ncbi): http://www.ncbi.nlm.nih.gov/. From the ncbi site one can access Online Mendelian Inheritance in Man (OMIM),. OMIM can be found at: httl://www3.ncbi.nlm.nih.gov/Omim/searchomim.html. OMIM is a medically oriented database of genetic information with entries for thousands of genes. The OMIM record number is provided for many of the genes in Table 10 (see column 3), and constitutes an excellent entry point for identification of references that point to the broader literature. Another useful site at NCBI is the Entrez browser, located at http://www3.ncbi.nlm.nih.gov/Entrez/. One can search genomes, polynucleotides, proteins, 3D structures, taxonomy or the biomedical literature (PubMed) via the Entrez site. More generally links to a number of useful sites with biomedical or genetic data are maintained at sites such as Med Web at the Emory University Health Sciences Center Library: http:/WWW.MedWeb.Emory.Edu/MedWeb/; Riken, a Japanese web site at: http://www.rtc.riken.go.ip/othersite.html with links to DNA sequence, structural, molecular biology, bioinformatics, and other databases; at the Oak Ridge National Laboratory web site: http://www.ornl.gov/hgmis/links.html; or at the Yahoo website of Diseases and Conditions: http://dir.yahoo.com/health/diseases and conditions/index.html. Each of the indicated web sites has additional useful links to other sites.

Another type of database with utility in selecting the genes on a biochemical pathway that may affect the response to a drug are databases that provide information on biochemical pathways. Examples of such databases include the Kyoto Encyclopedia of Genes and Genomes (KEGG), which can be found at: http://www.genome.ad.ip/kegg/kegg.html. This site has pictures of many biochemical pathways, as well as links to other metabolic databases such as the well known Boehringer Mannheim biochemical pathways charts: http://www.expasy.ch/cgi-bin/search-biochem-index. The metabolic charts at the latter site are comprehensive, and excellent starting points for working out the salient enzymes on any given pathway.

Each of the web sites mentioned above has links to other useful web sites, which in turn can lead to additional sites with useful information.

Research Libraries

Those skilled in the art will often require information found only at large libraries. The National Library of Medicine (http)://www.nlm.nih.gov/) is the largest medical library in the world and its catalogs can be searched online. Other libraries, such as university or medical school libraries are also useful to conduct searches. Biomedical books such as those referred to above can often be obtained from online bookstores as described above.

Biomedical Literature

To obtain up to date information on drugs and their mechanism of action and biotransformation; disease pathophysiology; biochemical pathways relevant to drug action and disease pathophysiology; and genes that encode proteins relevant to drug action and disease one skilled in the art will consult the biomedical literature. A widely used, publically accessible web site for searching published journal articles is PubMed (http://www.ncbi.nlm.nih.gov/PubMed/). At this site, one can search for the most recent articles (within the last 1–2 months) or for specific details on methods that are less recent (back to 1966). Many Journals also have their own sites on the world wide web and can be searched online. For example see the DEAL web site at: http://www.apnet.com/www/ap/aboutid.html. This site is an online library, featuring full text journals from Academic Press and selected journals from W.B. Saunders and Churchill Livingstone. The site provides access (for a fee) to nearly 2000 scientific, technical, and medical journals.

Experimental Methods for Identification of Genes Involved in the Action of a Drug There are a number of experimental methods for identifying genes and gene products that mediate or modulate the effects of a drug or other treatment. They encompass analyses of RNA and protein expression as well as methods for detecting protein—protein interactions and protein—ligand interactions. Two preferred-experimental methods for identification of genes that may be involved in the action of a drug are (1) methods for measuring the expression levels of many mRNA transcripts in cells or organisms treated with the drug (2) methods for measuring the expression levels of many proteins in cells or organisms treated with the drug.

RNA transcripts or proteins that are substantially increased or decreased in drug treated cells or tissues relative to control cells or tissues are candidates for mediating the action of the drug. Other useful experimental methods include protein interaction methods such as the yeast two hybrid system and variants thereof which facilitate the detection of protein—protein interactions.

The pool of RNAs expressed in a cell is sometimes referred to as the transcriptome. Methods for measuring the transcriptome, or some part of it, are known in the art. A recent collection of articles summarizing some current methods appeared as a supplement to the journal *Nature Genetics*. (The Chipping Forecast. Nature Genetics supplement, volume 21, January 1999.) Experiments have been described in model systems that demonstrate the utility of measuring changes in the transcriptome before before and after changing the growth conditions of cells, for example by changing the nutritional status. The changes in gene expression help reveal the network of genes that mediate physiological responses to the altered growth condition. Similarly, the addition of a drug to the cellular or in vivo environment, followed by monitoring the changes in gene expression can aid in identification of pharmacological gene networks.

The pool of proteins expressed in a cell is sometimes referred to as the proteome. Studies of the proteome may include not only protein abundance but also protein subcellular localization and protein-protein interaction. Methods for measuring the proteome, or some part of it, are known in the art. One widely used method is to extract total cellular protein and separate it in two dimensions, for example first by size and then by isoelectric point. The resulting protein spots can be stained and quantitated, and individual spots can be excised and analyzed by mass spectrometry to provide definitive identification. The results can be compared from two or more cell lines or tissues, at least one of which has been treated with a drug. The differential up or down modulation of specific proteins in response to drug treatment may indicate their role in mediating the pharmacologic actions of the drug. Another way to identify the network of proteins that mediate the actions of a drug is to exploit methods for identifying interacting proteins. By starting with a protein known to be involved in the action of a drug—for example the drug target—one can use systems such as the yeast two hybrid system and variants thereof (known to those skilled in the art) to identify additional proteins in the network of proteins that mediate drug action. The genes encoding such proteins would be useful for screening for DNA sequence variances, which in turn may be useful for analysis of interpatient variation in response to treatments. For example, the protein 5-lipoxygenase (5LO) s an enzyme which is a the beginning of the leukotriene biosynthetic pathway and is a target for anti-inflammatory drugs used to treat asthma and other diseases. In order to detect proteins that interact with 5-lipoxygenase the two-hybrid system was recently used to isolate three different proteins, none previously known to interact with 5LO. (Provost et al., Interaction of 5-lipoxygenase with cellular proteins. Proc. Natl. Acad. Sci. U.S.A. 96: 1881–1885, 1999.) A recent collection of articles summarizing some current methods in proteomics appeared in the August 1998 issue of the journal Electrophoresis (volume 19, number 11). Other useful articles include: Blackstock WP, et al. Proteomics: quantitative and physical mapping of cellular proteins. Trends Biotechnol. 17 (3): p. 121–7, 1999, and Patton W. F., Proteome analysis II. Protein subcellular redistribution: linking physiology to genomics via the proteome and separation technologies involved. *J. Chromatogr. B. Biomed. Sci. App.* 722(1–2):203–23. 1999.

Since many of these methods can also be used to assess whether specific polymorphisms are likely to have biological effects, they should also be considered as relevant in section 3, below, concerning methods for assessing the likely contribution of variances in candidate genes to clinical variation in patient responses to therapy.

2. Screen for Variances in Genes that may be Related to Therapeutic Response

Having identified a set of genes that may affect response to a drug the next step is to screen the genes for variances that may account for interindividual variation in response to the drug. There are a variety of levels at which a gene can be screened for variances, and a variety of methods for variance screening. The two main levels of variance screening are genomic DNA screening and cDNA screening. Genomic variance detection may include screening the entire genomic segment spanning the gene from the transcription start site to the polyadenylation site. Alternatively genomic variance detection may (for intron containing genes) include the exons and some region around them containing the splicing signals, for example, but not all of the intronic sequences. In addition to screening introns and exons for variances it is generally desirable to screen regulatory DNA sequences for variances. Promoter, enhancer, silencer and other regulatory elements have been described in human genes. The promoter is generally proximal to the transcription start site, although there may be several promoters and several transcription start sites. Enhancer, silencer and other regulatory elements may be intragenic or may lie outside the introns and exons, possibly at a considerable distance, such as 100 kb away. Variances in such sequences may affect basal gene expression or regulation of gene expression. In either case such variation may affect the response of an individual patient to a therapeutic intervention, for example a drug, as described in the examples. Thus in practicing the present invention it is useful to screen regulatory sequences as well as transcribed sequences, in order to identify variances that may affect gene transcription. Frequently information on the genomic sequence of a gene can be found in the sources above, particularly by searching GenBank or Medline (PubMed). The name of the gene can be entered at a site such as Entrez: http://www.ncbi.nlm.nih.gov/Entrez/nucleotide.html. Using the genomic sequence and information from the biomedical literature one skilled in the art can perform a variance detection procedure such as those described in examples 14, 15 and 16.

Variance detection is often first performed on the cDNA of a gene for several reasons. First, available data on functional sequence variances suggests that variances in the transcribed portion of a gene are most likely to have functional consequences as they can affect the interaction of the transcript with a wide variety of cellular factors during the complex processes of transcription, processing and translation. Second, as a practical matter the cDNA sequence of a gene is often available before the genomic structure is known, although the reverse may be true in the future as the sequence of the human genome is determined. If the genomic structure is not known then only the cDNA seqence can be scanned for variances. Methods for preparing cDNA are described in Example 13. Methods for variance detection on cDNA are described below and in the examples.

Methods for variance screening have been described, including DNA sequencing. See for example: U.S. Pat. No. 5,698,400: Detection of mutation by resolvase cleavage; U.S. Pat. No. 5,217,863: Detection of mutations in nucleic acids; and U.S. Pat. No. 5,750,335: Screening for genetic variation, as well as the examples and references cited therein for examples of useful variance detection procedures. Detailed variance detection procedures are also described in examples 14, 15 and 16. One skilled in the art will recognize that depending on the specific aims of a variance detection project (number of genes being screened, number of individuals being screened, total length of DNA being screened) one of the above cited methods may be preferable to the others, or yet another procedure may be optimal. A preferred method of variance detection is chain terminating DNA sequencing using dye labeled primers, cycle sequencing and software for assessing the quality of the DNA sequence as well as specialized software for calling heterozygotes. The use of such procedures has been described by Nickerson and colleagues. See for example: Rieder M. J., et al. Automating the identification of DNA variations using quality-based fluorescence re-sequencing: analysis of the human mitochondrial genome. *Nucleic Acids Res.* 26 (4):967–73, 1998, and: Nickerson D. A., et al. PolyPhred: automating the detection and genotyping of single nucleotide substitutions using fluorescence-based resequencing. *Nucleic Acids Res.* 25 (14):2745–51, 1997. Although the variances provided in tables 3, 4, and 10, consist principally of cDNA variances, it is a part of this invention that detection of genomic variances is also a useful method for identification of variances that may account for interpatient variation in response to a therapy.

3. Assess the Likely Contribution of Variances in Candidate Genes to Clinical Variation in Patient Responses to Therapy Once a set of genes likely to affect disease pathophysiology or drug action has been identified, and those genes have been screened for variances, said variances (e.g., provided in Tables 3, 4, and 10) can be assessed for their contribution to variation in the pharmacological or toxicological phenotypes of interest. There are several methods which can be used in the present invention for assessing the medical and pharmaceutical implications of a DNA sequence variance. They range from computational methods to in vitro and/or in vivo experimental methods (discussed below), to prospective human clinical trials (see below), and also include a variety of other laboratory and clinical measures that can provide evidence of the medical consequences of a variance. In general, human clinical trials constitute the highest standard of proof that a variance or set of variances is useful for selecting a method of treatment, however, computational and in vitro data, or retrospective analysis of human clinical data may provide strong evidence that a particular variance will affect response to a given therapy. Moreover, at an early stage in the analysis when there are many possible hypotheses to explain interpatient variation in treatment response, the use of informatics-based approaches to evaluate the likely functional effects of specific variances is an efficient way to proceed.

Informatics-based approaches to the prediction of the likely functional effects of variances include DNA and protein sequence analysis (phylogenetic approaches and motif searching) and protein modeling (based on coordinates in the protein database, or pdb; see http://www.rcsb.org/pdb/). Such analyses can be performed quickly and inexpensively, and the results allow selection of certain genes for more extensive in vitro or in vivo studies (see below) or for more variance detection (see above) or both.

More specifically, the structure of many medically and pharmaceutically important proteins, or homologs of such proteins in other species, or examples of domains present in such proteins, is known. Further, there are increasingly powerful tools for modeling the structure of proteins with unsolved structure, particularly if there is a related (e.g., a homologous) protein with known structure. (For reviews see: Rost et al., Protein fold recognition by prediction-based threading, *J. Mol. Biol.* 270:471–480, 1997; Firestine et al., Threading your way to protein function, *Chem. Biol.* 3:779–783, 1996) There are also powerful methods for identifying conserved domains and vital amino acid residues of proteins of unknown structure by analysis of phylogenetic relationships. (Deleage et al., Protein structure prediction: Implications for the biologist, *Biochimie* 79:681–686, 1997; Taylor et al., Multiple protein structure alignment, *Protein Sci.* 3:1858–1870, 1994) These methods can permit the prediction of functionally important variances, either on the basis of structure or evolutionary conservation. For example, a crystal structure can reveal which amino acids comprise a small molecule binding site. The identification of a polymorphic amino acid variance in the topological neighborhood of such a site, and in particular, the demonstration that at least one variant form of the protein has a variant amino acid which impinges on the known small molecule binding pocket differently from another variant form, provides strong evidence that the variance affects the function of the protein. From this it follows that the interaction of the protein with a treatment method, such an administered drug, will also likely be altered. One skilled in the art will recognize that the application of computational tools to the identification of functionally consequential variances involves applying the knowledge and tools of medicinal chemistry and physiology to the analysis.

Phylogenetic approaches to understanding sequence variation are also useful. Thus if a sequence variance occurs at a nucleotide or encoded amino acid residue where there is usually little or no variation in homologs of the protein of interest from non-human species, particularly evolutionarily remote species, then the variance is more likely to affect function of the RNA or protein.

4. Perform in vitro or in vivo Experiments to Assess the Functional Importance of Gene Variances The selection of an appropriate experimental program for testing the medical consequences of a variance may differ depending on the nature of the variance, the gene, and the disease. For example if there is already evidence that a protein is involved in the pharmacologic action of a drug, then the in vitro demonstration that an amino acid variance in the protein affects its biochemical activity is strong evidence that the variance will have an effect on the pharmacology of the drug in patients, and therefore that patients with different variant forms of the gene may have different responses to the same dose of drug. If the variance is silent with respect to protein coding information, or if it lies in a noncoding portion of the gene (e.g., a promoter, an intron, or a 5'- or 3'-untranslated region) then the appropriate biochemical assay may be to assess mRNA abundance, half life, or translational efficiency. If, on the other hand, there is no substantial evidence that the protein encoded by a particular gene is relevant to drug pharmacology, then the appropriate test is a clinical study addressing the responses to therapy of two patient groups distinguished on the basis of one or more variances. This approach reflects the current reality that biologists do not sufficiently understand gene regulation and gene expression to consistently make accurate inferences about the consequences of DNA sequence variances.

Thus, if there is a reasonable hypothesis regarding the effect of a protein on the action of a drug, then the in vitro and in vivo approaches described below will usefully predict whether a given variance is therapeutically consequential. If, on the other hand, there is no evidence of such an effect, then the most appropriate test is the empirical clinical measure of efficacy (which requires no evidence or assumptions regarding the mechanism by which the variance may exert an effect on a therapy). Clinical studies may be performed either prospectively or retrospectively.

Experimental Methods: Genomic DNA Analysis

Variances in DNA may affect the basal transcription or regulated transcription of a gene locus. Such variances may be located in any part of the gene but are most likely to be located in the promoter region, the first intron, or in 5' or 3' flanking DNA, where enhancer or silencer elements may be located. Methods for analyzing transcription are well known to those skilled in the art and exemplary methods are described in some of the texts cited below. Transcriptional run off assay is one useful method. Detailed protocols for useful methods can be found in texts such as: *Current Protocols in Molecular Biology* edited by: F. M. Ausubel, R. Brent, R. E. Kingston, D. D. Moore, J. G. Seidman, K. Struhl, John Wiley & Sons, Inc, 1999, or: Molecular Cloning: A Laboratory Manual by J. Sambrook, E. F. Fritsch and T Maniatis. 1989. 3 vols, 2nd edition, Cold Spring Harbor Laboratory Press Experimental Methods: RNA Analysis RNA variances may affect a wide range of processes including RNA splicing, polyadenylation, capping, export from the nucleus, interaction with translation intiation, elongation or termination factors, or the ribosome, or interaction with cellular factors including regulatory proteins, or factors that may affect mRNA half life. However, any effect of variances on RNA function should ultimately be measurable as an effect on RNA levels—either basal levels or regulated levels or levels in some abnormal cell state. Therefore one preferred method for assessing the effect of RNA variances on RNA function is to measure the levels of RNA produced by different alleles in one or more conditions of cell or tissue growth. Said measuring can be done by conventional methods such as Northern blots or RNAase protection assays (kits available from Ambion, Inc.), or by methods such as the Taqman assay (developed by the Applied Biosystems Division of the Perkin Elmer Corporation), or by using arrays of oligonucleotides or arrays of cDNAs attached to solid surfaces. Systems for arraying cDNAs are available commercially from companies such as Nanogen and General Scanning. Complete systems for gene expression analysis are available from companies such as Molecular Dynamics. For recent reviews of the technology see the supplement to volume 21 of Nature Genetics entitled "The Chipping Forecast", especially articles beginning on pages 9, 15, 20 and 25.

Additional methods for analyzing the effect of variances on RNA include secondary structure probing, and direct measurement of half life or turnover. Secondary structure can be determined by techniques such as enzymatic probing (using enzymes such as T1, T2 and S1 nuclease), chemical probing or RNAase H probing using oligonucleotides. Some RNA structural assays can be performed in vitro or on cell extracts or on Experimental Methods: Protein Analysis There are a variety of experimental methods for investigating the effect of a variance on response of a patient to a treatment. The preferred method will depend on the availability of cells expressing a particular protein, and the feasibility of a cell-based assay vs. assays on cell extracts, on proteins produced in a foreign host, or on proteins prepared by in vitro translation.

For example, the methods and systems listed below can be utilized to demonstrate differential expression and/or activity, or in model system phenotype/genotype correlations.

For the determination of protein levels or protein activity one could utilize a variety of techniques. The in vitro protein activity can be determined by transcription or translation in bacteria, yeast, baculovirus, COS cells (transient), CHO, or study directly in human cells. Further, one could perform pulse chase for experiments for the determination of changes in protein stability (half life).

One skilled in the art could manipulate the cell assay to address grouping the cells by genotypes or phenotypes. For example, identification of cells with different genotypes (possibly including families) and phenotype may be performed using standardized laboratory molecular biological protocols. After identification and grouping, one skilled in the art could determine whether there exists a correlation between cellular genotype and cellular phenotype.

Advancing an experimental preclinical program may include testing these in vitro hypotheses in vivo, e.g. an animal model. For example, one skilled in the art would readily have the ability to create gene knockouts. In this case, an embryonic stem cell is genetically manipulated to be deficient in a given gene. More specifically, a DNA construct is created that will undergo homologous recombination when inserted into the said embryonic stem cell nucleus. After the recombination event has occurred, the targeted gene is effectively inactivated due to the insertion of sequence (usually a translation stop or a marker gene sequence). This can be accomplished in worms, drosophila, or mice. The species chosen will be conducive to attain maximal experimental results for the particular gene and the particular variance, variances, or haplotype. Once the knockout species is created the candidate therapeutic intervention can be administered to the animal and tested for effects on gene expression or effects of various gene deficiencies. In the case whereby the chosen cell is a lower eukaryote, e.g. yeast, genetic manipulation occurs via introduction of a DNA construct that will undergo homologous recombination to disrupt the endogenous gene or genes.

The methods described above are reviewed and compiled in the following list of texts.

General Molecular Biology Methods

"Molecular Biology: A project approach", S. J. Karcher, Fall 1995. Academic Press "DNA Cloning: A Practical Approach", D. M. Glover and B. D. Hayes (eds). 1995. IRL/Oxford University Press. Vol. 1—Core Techniques; Vol 2—Expression Systems; Vol. 3—Complex Genomes; Vol. 4—Mammalian Systems.

"Short Protocols in Molecular Biology", Ausubel et al. October 1995. 3rd edition, John Wiley and Sons Current Protocols in Molecular Biology Edited by: F. M. Ausubel, R. Brent, R. E. Kingston, D. D. Moore, J. G. Seidman, K. Struhl, (Series Editior: V. B. Chanda), 1988

"Molecular Cloning: A laboratory manual", J. Sambrook, E. F. Fritsch. 1989. 3 vols, 2nd edition, Cold Spring Harbor Laboratory Press Polymerase Chain Reaction (PCR)

"PCR Primer: A laboratory manual", C. W. Diffenbach and G. S. Dveksler (eds.), 1995. Cold Spring Harbor Laboratory Press "The Polymerase Chain Reaction", K. B. Mullis et al. (eds.), 1994. Birkhauser "PCR Strategies", M. A. Innis, D. H. Gelf, and J. J. Sninsky (eds.), 1995. Academic Press General Procedures for Discipline Specific Studies Current Protocols in Neuroscience Edited by: J. Crawley, C. Gerfen, R. McKay, M. Rogawski, D. Sibley, P. Skolnick, (Series Editor: G. Taylor), 1997

Current Protocols in Pharmacology Edited by: S. J. Enna/M. Williams, J. W. Ferkany, T. Kenakin, R. E. Porsolt, J. P. Sullivan, (Series Editor: G. Taylor), 1998

Current Protocols in Protein Science Edited by: J. E. Coligan, B. M. Dunn, H. L. Ploegh, D. W. Speicher, P. T. Wingfield, (Series Editor: Virginia Benson Chanda), 1995

Current Protocols in Cell Biology Edited by: J. S. Bonifacino, M. Dasso, J. Lippincott-Schwartz, J. B. Harford, K. M. Yamada, (Series Editor: K. Morgan) 1999

Current Protocols in Cytometry Managing Editor: J. P. Robinson, Z. Darzynkiewicz (ed)/P. Dean (ed), A. Orfao (ed), P. Rabinovitch (ed), C. Stewart (ed), H. Tanke (ed), L. Wheeless (ed), (Series Editor: J. Paul Robinson), 1997

Current Protocols in Human Genetics Edited by: N. C. Dracopoli, J. L. Haines, B. R. Korf, D. T. Moir, C. C. Morton, C. E. Seidman, J. G. Seidman, D. R. Smith, (Series Editor: A. Boyle), 1994

Current Protocols in Immunology Edited by: J. E. Coligan, A. M. Kruisbeek, D. H. Margulies, E. M. Shevach, W. Strober, (Series Editor: R. Coico), 1991

III. Clinical Trials

A clinical trial is the definitive test of the utility of a variance or variances for the selection of optimal therapy.

Clinical trials require no knowledge of the biological function of the gene containing the variance or variances to be assessed, nor any knowledge of how the therapeutic intervention to be assessed works at a biochemical level; the question of the utility of a variance can be addressed at a purely phenomenological level. On the other hand, if there is information about either the biochemical basis of a therapeutic intervention or the biochemical effects of a variance, then a clinical trial can be designed to test a specific hypothesis.

Methods for performing clinical trials are well known in the art. (*Guide to Clinical Trials* by Bert Spilker, Raven Press, 1991; *The Randomized Clinical Trial and Therapeutic Decisions* by Niels Tygstrup (Editor), Marcel Dekker; *Recent Advances in Clinical Trial Design and Analysis* (Cancer Treatment and Research, Ctar 75) by Peter F. Thall (Editor) Kluwer Academic Pub, 1995. However, performing a clinical trial to test the genetic contribution to interpatient variation in drug response requires some additional design considerations, including defining what the genetic hypothesis is, how it is to be tested, how many patients will need to be enrolled to have adequate statistical power to measure an effect of a specified magnitude (power analysis), definition of primary and secondary endpoints, and methods of statistical analysis, as well as other aspects. In the outline below some of the major types of genetic hypothesis testing, power analysis, statistical analysis, etc. are summarized. One skilled in the art will recognize that certain of the methods will be best suited to specific clinical situations, and that additional methods are known and can be used in particular instances.

A. Performing a Clinical Trial

As used herein, a "clinical trial" is the testing of a therapeutic intervention in a volunteer human population for the purpose of determining whether a therapeutic intervention is safe and/or efficacious in the human volunteer or patient population for a given disease, disorder, or condition. The analysis of safety and efficacy in genetically defined subgroups differing by at least one variance is of particular interest.

A "clinical study" is that part of a clinical trial that involves determination of the effect a candidate therapeutic intervention on human subjects. It includes clinical evaluations of physiologic responses including pharmacokinetic (absorption, distribution, bioavailability, and excretion) as well as pharmacodynamic (physiologic response and efficacy) parameters. A pharmacogenetic clinical study is a clinical study that involves testing of one or more specific hypotheses regarding the effect of a genetic variance or variances (or set of variances, i.e. haplotype or haplotypes) in enrolled subjects or patients on response to a therapeutic intervention. These hypotheses are articulated before the study in the form of primary or secondary endpoints. For example the endpoint may be that in a particular genetic subgroup the rate of objectively defined responses exceeds some predefined threshold.

For each clinical study to commence enrollment and proceed to treat subjects at a given institution, an application that describes in detail the scientific premise for the therapeutic intervention and the procedures involved in the study, including the endpoints and analytical methods to be used in evaluating the data must be reviewed and accepted by regulatory authorities at the level of the institution and the federal government (in the U.S.). In the U.S., there are two regulatory bodies that oversee conduct of clinical trials: an Institutional Review Board (IRB) and the United States Food and Drug Administration (US FDA). The European counterpart of the US FDA is the European Medicines Evaluation Agency (EMEA). Similar agencies exist in other countries.

An Institutional Review Board accepts and reviews applications for clinical trials that are to be conducted at the institution and are to include healthy volunteers or human subjects from a defined patient population that seeks medical, surgical, rehabilitative, or social services at that institution. The application includes document sections that provide the rationale for and describe the scope of the clinical study. For example, an application to an IRB may include a clinical protocol, and informed consent forms.

It is also customary, but not required, to prepare an investigator's brochure which describes the scientific hypothesis for the proposed therapeutic intervention, the preclinical data, and the clinical protocol in concise language. The brochure is made available to any physician participating in the proposed or ongoing trial. The investigator's brochure for a pharmacogenetic clinical trial will include a full description of the genetic variance and/or variances believed or hypothesized to account for differential responses in the normal human subjects or patients, as well as a description of the genetic statistical analysis.

The supporting preclinical data is a report of all the in vitro, in vivo animal or previous human trial data that supports the safety and/or efficacy of a given therapeutic intervention. In a pharmacogenetic clinical trial the preclinical data may also include a description of the effect of a specific genetic variance or variances on biochemical or physiologic experimental variables, or on treatment outcomes, as determined by in vitro studies or by retrospective genetic analysis of clinical trial or other medical data (see below) used to first formulate or test a pharmacogenetic hypothesis.

The clinical protocol provides the relevant scientific and therapeutic introductory information, describes the inclusion and exclusion criteria for human subject enrollment, including genetic criteria if relevant, describes in detail the exact procedure or procedures for treatment using the candidate therapeutic intervention, describes laboratory analyses to be performed during the study period, and lastly describes the risks (both known and unknown) involving the use of the experimental candidate therapeutic intervention. In a clinical protocol for a pharmacogenetic clinical trial, the clinical protocol will further describe the gene or genes believed or hypothesized to affect differential patient responses and the variance or variances to be tested. Further, the clinical protocol for a pharmacogenetic clinical trial will include a description of the stratification of the treatment groups based on one or more gene sequence variances or combination of variances or haplotypes.

The informed consent document is a description of the therapeutic intervention and the clinical protocol in simple language (third grade level) for the patient to read, understand, and, if willing, agree to participate in the study by signing the document. In a pharmacogenetic clinical study the informed consent document will describe, in simple language, the use of a genetic test or a limited set of genetic tests to determine the subject or patients status at a particular gene variance or variances, and to further ascertain whether, in the study population, particular variances are associated with particular clinical or physiological responses.

The US FDA reviews proposed clinical trials through the process of an Investigational New Drug Application (IND). The IND is composed of the investigator's brochure, the supporting in vitro and in vivo animal or previous human data, the clinical protocol, and the informed consent documents or forms. In each of the sections of the IND, a specific description of a single allelic variance or a number of variances to be tested in the clinical study will be included. For example, in the investigator's brochure a description of the gene or genes believed or hypothesized to account, at least in part, for differential responses will be included as well as a description of genetic variance or variances of a particular candidate gene or genes. Further, the preclinical data may include a description of in vivo or in vitro studies of the biochemical or physiologic effects of a variance or variances (e.g., haplotype) in a candidate gene or genes, as well as the predicted effects of the variance or variances on efficacy or toxicology of the candidate therapeutic intervention. Alternatively the results of retrospective genetic analysis of response data in patients treated with the candidate therapy may be the basis for formulating the genetic hypotheses to be tested in the prospective trial. For first in man clinical studies, the focus of this section will be safety. The US FDA reviews the application with a particular emphasis on the safety data and whether toxicological data is supportive and sufficient to justify proceeding to human testing.

The established phases of clinical development are Phase I, II, III, and IV. The fundamental objectives for each phase become increasingly complex as the stages of clinical development progress. In Phase I, safety in humans is the primary focus. In these studies, dose-ranging designs establish whether the candidate therapeutic intervention is safe in the suspected therapeutic concentration range. In a pharmacogenetic clinical trial there may be an analysis of the effect of a variance or variances on Phase I safety or surrogate efficacy parameters. At the same time, pharmacokinetic parameters (e.g., adsorption, distribution, metabolism, and excretion) may be a secondary objective. In a pharmacogenetic clinical study, there may be additional analysis of the gene or genes and allelic variance or variances that are suspected to be involved in these pharmacokinetic parameters. As clinical development stages progress, trial objectives focus on the appropriate dose to elicit a therapeutically relevant response. In a pharmacogenetic clinical trial, the dose or doses selected may be different than those identified based upon preclinical safety and efficacy determinations. For example, phenotypic effects of an allele depends on its frequency and also its interaction with the environment, as described earlier. Therefore, once the frequency of an allele or haplotype has been established for selected human subjects or patients, the effect of the variance on the drug responses by performing both in vitro or in vivo analyses under controlled conditions. Under these conditions, drug dosage could be adjusted accordingly. In some instances, the chosen dose may be one that is sub-optimal or is significantly less toxic so that determination of the effect of allelic variance or variances for a given treatment or human volunteer population may be appropriately tested and analyzed. In other instances, the dose may be similar to or the same as that chosen based upon in vitro or in vivo data. In yet other instances, the dose may be greater than optimal because allelic differences or haplotypes may result in enhanced elimination, metabolic inactivation, or excretion.

Lastly, the objectives in the latter stages of clinical development center on the effect of the therapeutic intervention on the general population. In these trials, the numbers of individuals required for enrollment and the number of treatment conditions required to achieve the objectives of the trial is dictated by statistical power analysis. The number of patients required for a given pharmacogenetic clinical trial will be determined on the prior knowledge of but not exclusively limited to variance or haplotype frequency, actual disease, disorder, or condition causing allele or allele associated with the disease, disorder, or condition and their linkage relationships. For a large scale pharmacogenetic clinical study, the identified sample size will require an adequate analysis of the frequency of the allelic variance or variances within a given population, as described, for example, by Tu & Whitkemore (1999) and references therein.

Clinical trials can be designed to obscure the human subjects and/or the study coordinators from biasing that may occur during the testing of a candidate therapeutic invention. Often the candidate therapeutic intervention is compared to best medical treatment, or a placebo (a compound, agent, device, or procedure that appears identical to the candidate therapeutic intervention but is innocuous to the receiving subject). Thus, control with placebo limits efficacy perception by influencing factors such as prejudice on the part of the study participant or investigator, spontaneous alterations or variations that occur during treatment and are related to the disease studied, or are unrelated to the candidate therapeutic intervention. In pharmacogenetic clinical studies, a placebo arm or best medical therapy may be required in order to ascertain the effect of the allelic variance or variances on the efficacy or toxicology of the candidate therapeutic intervention.

Blinding refers to the lack of knowledge of the identity of the trial treatment and thus can be used to ascertain the real and not perceived effects of the candidate therapeutic intervention. Patients, trial subjects, investigators, data review committees, ancillary personnel, statisticians, and clinical trial monitors may be blinded or unblinded during the trial period. Open label trials refer to those that are unblinded; single blind is when the patient is kept unaware of the treatment groups; double blind is when both the patient and the investigator is kept unaware of the treatment groups; or a combination of these may be instituted during the trial period. Pharmacogenetic clinical trial design may include one or a combination of open label, single blind, or double blind clinical trial design because reduction of inherent biases due to the knowledge of the type of treatment the human subject or the patient is to receive will ensure detection of the accuracy of the benefits of the stratification based upon allelic variance or variances or haplotypes.

In the designed studies in all four phases, termination endpoints for trials including or excluding pharmacogenetic objectives are defined and include observation of adverse clinical events, voluntary lack of study participation either in the form of lack of adherence to the clinical protocol or sudden change in lifestyle of the participant, lack of adherence on the part of trial investigators to follow the trial protocol, death, or lack of efficacy or positive response within the test group.

Phase I of clinical development is a safety study performed in a limited (<15) number of normal, healthy volunteers usually at single institutions. The primary endpoints in these studies is to determine pharmacokinetic parameters (i.e. adsorption, distribution, and bioavailability), dose-related side effects that are either desirable or undesirable, and metabolites that corroborate preclinical animal studies. In a Phase I pharmacogenetic clinical trial, stratification based upon allelic variance or variances of a suspected gene or genes involving any or all of the pharmacokinetic parameters will be considered and incorporated in the objectives of the trial design.

In some cases, a pharmacogenetic Phase I study may enroll healthy human volunteers and stratify these individuals based upon their genotype. In this case, a study objective may include observation of the effect of the allele/haplotype (detectable or undetectable) which the candidate therapeutic intervention may exhibit within the allelic variance, allelic variances, or haplotype groupings which can be assessed in the absence of a disease, disorder, or condition.

In some cases (e.g. cancer or medically intractable, life threatening, for those in which no medical alternative exists, or seriously debilitating diseases, disorders, or conditions) Phase I studies can include a limited number of patients with a diagnosed disease, disorder, or condition for whom clinical parameters satisfy a specified inclusion criteria (see below). These safety/limited efficacy studies can be conducted at multiple institutions to ensure enrollment of these patients. In a pharmacogenetic Phase I study that will include patients to some degree, the gene or genes and allelic variance or variances suspected to be involved in the efficacy of the candidate therapeutic intervention will be considered in the design of the inclusion criteria, the objectives, and the primary endpoints.

Phase II studies include a limited number of patients (<100) that satisfy the required inclusion criteria and do not satisfy any of the exclusion criteria of the trial design. Phase II studies can be conducted at single or multiple institutions. Inclusion criteria for patient enrollment to a clinical trial is a list of qualities for a given patient population that includes pathophysiologic clinical parameters for a given disease, disorder, or condition that can be determined by clinical diagnosis or laboratory or diagnostic test; age; gender; fertility state (e.g. pre- or postmenopausal women); coexisting medical therapies; or psychological, emotional, or cognitive state. Inclusion criteria can also include defined psychological, emotional, or socioeconomic support by family or friends. Exclusion criteria for patient enrollment generally includes the listing of co-morbidities that may interfere with the observations of the medical or laboratory pathophysiological clinical parameters of the disease, disorder, or condition, age, gender, fertility state (e.g. pre- or postmenopausal women), or previous or concurrent medical, surgical, or diagnostic therapies. In Phase II, the primary endpoint of the study is generally limited efficacy and corroboration of the Phase I safety data in the specified patient population defined by the inclusion/exclusion criteria of the clinical protocol. Primary efficacy endpoints include observed improvements of pathophysiologic parameters that are determined medically, diagnostically (e.g. clinical laboratory values), or by surrogate measurements of the pathological state of the disease, disorder, or condition. Primary endpoints may also include limitation of pharmacologic therapies, reduction of time to death, or reduction in the progression of the disease, disorder, or condition. Surrogate markers are pathophysiologic parameters determined by medical or clinical laboratory diagnosis that are associated and have been correlated with the prognosis, progression, predisposition, or risk analysis with a disease, disorder, or condition that are not directly related to the primary diagnosed pathophysiologic condition, e.g. lowering blood pressure and coronary heart disease. Secondary endpoints are those that supplement the primary endpoint and can be used to support further clinical studies. For example, secondary endpoints include reduction in pharmacologic therapy, reduction in requirement of a medical device, or alteration of the progression of the disease disorder, or condition. Typically, in Phase II, treatment groups with varying doses are included in the study to identify the appropriate dosage and pharmacokinetic parameters to achieve maximum efficacy.

In a pharmacogenetic Phase II clinical trial, retrospective or prospective design will include the stratification of the patients based upon suspected gene or genes and allelic variance or variances involved in the pathway for pharmacodynamic or pharmacokinetic response demonstrated in the treatment groups of the candidate therapeutic intervention. These pharmacodynamic parameters may include surrogate endpoints, efficacy endpoints, or pathophysiologic thresholds. Pharmacokinetic parameters may include but are not exclusive of dosage, toxicological variables, metabolism, or excretion. Other parameters that may effect the outcome of a pharmacogenetic clinical trial may include gender, race, ethnic origins (population history), and combination of allelic variances of genes from multiple pathways, leading to but not exclusively efficacy or toxicology.

Phase III studies include multi-site, large, statistically significant, numbers of patients (<5,000) that fulfill the inclusion criteria for the study. The design of this type of trial includes power analysis to ensure the data will support the study objectives. In this large scale efficacy study, the primary endpoint is preferably defined as enhanced efficacy as compared to placebo or best medical care for said disease, disorder, or condition. The primary endpoint may include reduction of condition progression, improvement of a specific subset of symptoms, or in requirement or perceived need of medical therapy. In a pharmacogenetic Phase m clinical study, the endpoints will be the determination of the efficacy or toxicological differences that can be demonstrated to be dependent on the stratification based upon allelic variance or variances in a gene or genes that are suspected to be involved in the efficacy or toxicological population phenotype. Further in the Phase III pharnacogenetic clinical trial, the analysis of the impact of the allelic variance or variances will be broadened from the confirmatory Phase II pharmacogenetic clinical trial data that supports the notion that the phenotypic response differences can be identified as dependent on the allelic variance or variances of a gene or genes suspected to be involved in the efficacy or toxicological response.

After the completion of a Phase III study, the data and information from all of the trials are compiled into a New Drug Application for review by the US FDA for marketing approval in the US and its territories. The NDA includes the raw (unanalyzed) clinical data, i.e. the primary endpoints or secondary endpoints, a statistical analysis of all of the included data, a document describing in detail any adverse or observed side effects, tabulation of the participant dropouts and detailed reasons for the termination, and other specific data or details of ongoing in vitro or in vivo studies since the submission of the IND. If pharmacoeconomic objectives are a part of the clinical trial design data supporting cost or economic analyses are included in the NDA. In a pharmacogenetic clinical study, the pharmacoeconomic analyses may include demonstration or lack of benefit of the candidate therapeutic intervention in a cost benefit analysis, cost of illness study, cost minimization study, or cost utility analysis. In one or a combination of these studies, the effect of a diagnostic identification of the population and subsequent stratification based upon allelic variance or variances or haplotype of a suspected gene or genes involved in the efficacy or toxicological responses of the candidate therapeutic intervention will be used to support application for the approval for the marketing and sale of the candidate therapeutic intervention.

Phase IV studies occur after the therapeutic intervention has been approved for marketing. In these studies, retrospective data and data from a large patient population that do not necessarily fulfill the pathophysiologic requirements of the approved indication are included. In a Phase IV pharmacogenetic clinical trial, both retrospective and prospective design can be incorporated. In both cases, stratification based upon allelic variance or variances with adequate sample size in order to determine the statistical relevance of an outcome difference among the treatment groups.

Although the above listed phases of clinical development are well-established, there are cases whereby strict Phase I, II, III development does not occur, i.e. the clinical development of candidate therapeutic interventions for serious debilitating or life threatening diseases, or for those cases whereby no medical therapeutic alternative exists. In the cases whereby the target indication for cancer or medically intractable, life threatening or seriously debilitating diseases, disorders, or conditions the US FDA has regulatory procedural mechanisms that can expedite the availability of the therapeutic intervention for patients that fall into one or more of these categories. Such development incentives include Treatment IND, Fast-Track or Accelerated review, and Orphan Drug Status. In a pharmacogenetic clinical development program for candidate therapeutic interventions for this class of indications, consideration of sample size for adequate determination of the effect allelic variance or variances may have on the outcome response or endpoints is incorporated. Further consideration may include but is not limited to accrual rate for candidate patients, and number of institutions or clinical sites required to achieve an appropriate sample size.

In additional cases of diseases, disorders, or conditions where there are no therapeutic alternatives development, sponsors may choose to expedite the development of the candidate therapeutic intervention without making use of the above FDA regulatory clinical development incentives. In these cases, the sponsor proposes expedited clinical development of a candidate therapeutic intervention due to outstanding positive or unequivocal preclinical safety and/or efficacy data.

As used herein, "supplemental applications" are those in which a candidate therapeutic intervention is tested in a human clinical trial in order for the product to have an expanded label to include additional indications for therapeutic use. In these cases, the previous clinical studies of the therapeutic intervention, i.e. those involving the preclinical safety and Phase I human safety studies can be used to support the testing of the particular candidate therapeutic intervention in a patient population for a different disease, disorder, or condition than that previously approved in the US. In these cases, a limited Phase II study is performed in the proposed patient population. With adequate signs of efficacy, a Phase III study is designed. All other parameters of clinical development for this category of candidate therapeutic interventions proceeds as described above for interventions first tested in human candidates.

As used herein, "outcomes" or "therapeutic outcomes" are used to describe the results and value of healthcare intervention. Outcomes can be multi-dimensional, e.g., including one or more of the following: improvement of symptoms; regression of the disease, disorder, or condition; economic outcomes of healthcare decisions.

As used herein, "pharmacoeconomics" is the analysis of a therapeutic intervention in a population of patients diagnosed with a disease, disorder, or condition that includes at least one of the following studies: cost of illness study (COI); cost benefit analysis (CBA), cost minimization analysis (CMA), or cost utility analysis (CUA), or an analysis comparing the relative costs of a therapeutic intervention with one or a group of other therapeutic interventions. In each of these studies, the cost of the treatment of a disease, disorder, or condition is compared among treatment groups. As used herein, costs are those economic variables associated with a disease, disorder, or condition fall into two broad categories: direct and indirect. Direct costs are associated with the medical and non-medical resources used as therapeutic interventions, including medical, surgical, diagnostic, pharmacologic, devices, rehabilitation, home care, nursing home care, institutional care, and prosthesis. Indirect costs are associated with loss of productivity due to the disease, disorder, or condition suffered by the patient or relatives. A third category, the tangible and intangible losses due to pain and suffering of a patient or relatives often is included in indirect cost studies.

As used herein, "health-related quality of life" is a measure of the impact of the disease, disorder, or condition on an individual's or group of patient's activities of daily living. Preferably, included in pharmacoeconomic studies is an analysis of the health-related quality of life. Standardized surveys or questionnaires for general health-related quality of life or disease, disorder, or condition specific determine the impact the disease, disorder, or condition has on an individuals day to day life activities or specific activities that are affected by a particular disease, disorder, or condition.

As used herein, the term "stratification" refers to the creation of a distinction between patients on the basis of a characteristic or characteristics of the patient. Generally, in the context of clinical trials, the distinction is used to distinguish responses or effects in different sets of patients distinguished according to the stratification parameters. For the present invention, stratification preferably includes distinction of patient groups based on the presence or absence of particular variance or variances in one or more genes. The stratification may be performed only in the course of analysis or may be used in creation of distinct groups or in other ways.

A human clinical trial can result in data to support the utility of a gene variance or variances for the selection of optimal therapy. Clinical studies require no knowledge of the biological function of the gene containing the variance of the variances to be assessed, nor any knowledge of how the therapeutic invention to be assessed works at a biochemical level.

There are several important preclinical data sets that pose criteria to consider when designing a clinical study to assess the utility of a variance in a gene for selecting optimal therapy for a disease, disorder, or condition. Preferably, the data sets include one or a combination of at least of the following:

Mechanism of Action of the Therapeutic Intervention

If the candidate therapy (e.g. drug) has established mechanism of action, the target genes can be appropriately identified. In vitro data supporting altered physiologic activity of the variant forms of the gene in the presence of the therapy, assists the direction of the fundamental hypotheses and identifying the objectives for a human clinical trial.

Mechanism of Metabolic Transformation of the Therapeutic Intervention

If in vitro or in vivo animal studies have demonstrated metabolic biotransformation of the therapeutic intervention, correlation of the effects of a variance or variances on the metabolic biotransformation of the therapeutic intervention can further assist the direction of the fundamental hypotheses and identification of the objectives of the human clinical study.-

Effect of the Variance or Variances on Therapeutic Intervention

The combined preclinical data sets should point to the premise of a controlled clinical trial of the the therapeutic intervention. The design of the trial will preferably incorporate the preclinical data sets to determine the primary and secondary endpoints. Preferably, these endpoints will include whether the therapeutic intervention is efficacious, efficacious with undesirable side effects, ineffective, ineffective with undesirable side effects, or ineffective with deleterious effects. Pharmacoeconomic analyses may be incorporated in order to support the efficacious intervention, efficacious with undesirable side effects cases, whereby the clinical outcome is positive, and economic analyses are required for the support of overall benefit to the patient and to society.

The strategies for designing a clinical trial to test the effect of a genotypic variance or variances on a physiological response to therapeutic intervention for drugs with known mechanism of action, mechanism of biotransformation, and/or known physiologic response differentials correlated to genotypic variance or variances will be modified based upon the data and information from the preclinical studies and the patient symptomatic parameters unique to the target indication. However, the strategy (design) and the implementation (conduct) of the clinical study preferably consist of one or more of the following strategies.

A. Retrospective Clinical Trials.

In general the goal of retrospective clinical trials will be to test and refine hypotheses regarding genetic factors that are associated with drug responses. The best supported hypotheses can subsequently be tested in prospective clinical trials, and data from the prospective trials will likely comprise the main basis for an application to register the drug and predictive genetic test with the appropriate regulatory body. In some cases, however, it may become acceptable to use data from retrospective trials to support regulatory filings.

I. Clinical Trials to Study the Effect of One Gene Locus on Drug Response

A. Stratify patients by genotype at one candidate variance in the candidate gene locus.

1. Genetic stratification of patients can be accomplished in several ways, including the following (where 'A' is the more frequent form of the variance being assessed and 'a' is the less frequent form):

(a) AA vs. aa
(b) AA vs. Aa vs. aa
(c) AA vs. (Aa+aa)
(d) (AA+Aa) vs. aa.

2. The effect of genotype on drug response phenotype may be affected by a variety of nongenetic factors. Therefore it may be beneficial to measure the effect of genetic stratification in a subgroup of the overall clinical trial population. Subgroups can be defined in a number of ways including, for example, biological, clinical, pathological or environmental criteria. For example, the predictive value of genetic stratification can be assessed in a subgroup or subgroups defined by:

a. Biological criteria:
 i. gender (males vs. females)
 ii. age (for example above 60 years of age). Two, three or more age groups may be useful for defining subgroups for the genetic analysis.
 iii. hormonal status and reproductive history, including pre- vs. post-menopausal status of women, or multiparous vs. nulliparous women
 iv. ethnic, racial or geographic origin, or surrogate markers of ethnic, racial or geographic origin. (For a description of genetic markers that serve as surrogates of racial/thnic origin see, for example: Rannala, B. and J. L. Mountain, Detecting immigration by using multilocus genotypes. *Proc Natl Acad Sci USA*, 94 (17): 9197–9201, 1997. Other surrogate markers could be used, including biochemical markers.)

b. Clinical criteria:
 i. Disease status. There are clinical grading scales for many diseases. For example, the status of Alzheimer's Disease patients is often measured by cognitive assessment scales such as the mini-mental status exam (MMSE) or the Alzheimer's Disease Assessment Scale (ADAS), which includes a cognitive component (ADAS-COG). There are also clinical assessment scales for many other diseases, including cancer.
 ii. Disease manifestations (clinical presentation).

c. Pathological criteria:
 i. Histopathologic features of disease tissue, or pathological diagnosis. (For example there are many varieties of lung cancer: squamous cell carcinoma, adenocarcinoma, small cell carcinoma, bronchoalveolar carcinoma, etc., each of which may—which, in combination with genetic variation, may correlate with
 ii. Pathological stage. A variety of diseases have pathological staging schemes
 iii. Loss of heterozygosity (LOH)
 iv. Pathology studies such as measuring levels of a marker protein
 v. Laboratory studies such as hormone levels, protein levels, small molecule levels 3. Measure frequency of responders in each genetic subgroup. Subgroups may be defined in several ways.
 i. more than two age groups
 ii. age related status such as pre or post-menopausal
 Stratify by haplotype at one candidate locus where the haplotype is made up of two variances, three variances or greater than three variances.

4. Statistical Analysis of Clinical Trial Data

There are a variety of statistical methods for measuring the difference between two or more groups in a clinical trial. One skilled in the art will recognize that different methods are suited to different data sets. In general, there is a family of methods customarily used in clinical trials, and another family of methods customarily used in genetic epidemiological studies. Methods from either family may be suitable for performing statistical analysis of pharmacogenetic clinical trial data.

a. Conventional Clinical Trial Statistics

Conventional clinical trial statistics include hypothesis testing and descriptive methods, as elaborated below. Guidance in the selection of appropriate statistical tests for a particular data set can be obtained from texts such as: *Biostatistics: A Foundation for Analysis in the Health Sciences*, 7th edition (Wiley Series in Probability and Mathematical Statistics, Applied Probability and statistics) by Wayne W. Daniel, John Wiley & Sons, 1998; *Bayesian Methods and Ethics in a Clinical Trial Design* (Wiley Series in Probability and Mathematical Statistics. Applied Probability Section) by J. B. Kadane (Editor), John Wiley & Sons, 1996;

b. Hypothesis Testing Statistical Procedures
 (1) One-sample procedures (binomial confidence interval, Wilcoxon signed rank test, permutation test with general scores, generation of exact permutational distributions)

(2) Two-sample procedures (t-test, Wilcoxon-Mann-Whitney test, Normal score test, Median test, Van der Waerden test, Savage test, Logrank test for censored survival data, Wilcoxon-Gehan test for censored survival data, Cochran-Armitage trend test, permutation test with general scores, generation of exact permutational distributions)

(3) R×C contingency tables (Fisher's exact test, Pearson's chi-squared test, Likelihood ratio test, Kruskal-Wallis test, Jonckheere-Terpstra test, Linear-by linear association test, McNemar's test, marginal homogeneity test for matched pairs)

(4) Stratified 2×2 contingency tables (test of homogeneity for odds ratio, test of unity for the common odds ratio, confidence interval for the common odds ratio)

(5) Stratified 2×C contingency tables (all two-sample procedures listed above with stratification, confidence intervals for the odds ratios and trend, generation of exact permutational distributions)

(6) General linear models (simple regression, multiple regression, analysis of variance—ANOVA-, analysis of covariance, response-surface models, weighted regression, polynomial regression, partial correlation, multiple analysis of variance—MANOVA-, repeated measures analysis of variance).

(7) Analysis of variance and covariance with a nested (hierarchical) structure.

(8) Designs and randomized plans for nested and crossed experiments (completely randomized design for two treatment, split-splot design, hierarchical design, incomplete block design, latin square design)

(9) Nonlinear regression models

(10) Logistic regression for unstratified or stratified data, for binary or ordinal response data, using the logit link function, the normit function or the complementary log-log function.

(11) Probit, logit, ordinal logistic and gompit regression models.

(12) Fitting parametric models to failure time data that may be right-, left-, or interval-censored. Tested distributions can include extreme value, normal and logistic distributions, and, by using a log transformation, exponential, Weibull, lognormal, loglogistic and gamma distributions.

(13) Compute non-parametric estimates of survival distribution with right-censored data and compute rank tests for association of the response variable with other variables.

c. Descriptive Statistical Methods

Factor analysis with rotations

Canonical correlation

Principal component analysis for quantitative variables.

Principal component analysis for qualitative data.

Hierarchical and dynamic clustering methods to create tree structure, dendrogram or phenogram.

Simple and multiple correspondence analysis using a contingency table as input or raw categorical data.

Specific instructions and computer programs for performing the above calculations can be obtained from companies such as: SAS/STAT Software, SAS Institute Inc., Cary, N.C., USA; BMDP Statistical Software, BMDP Statistical Software Inc., Los Angeles, Calif., USA; SYSTAT software, SPSS Inc., Chicago, Ill., USA; StatXact & LogXact, CYTEL Software Corporation, Cambridge, Mass., USA.

d. Statistical Methods from Genetic Epidemiology

Genetic epidemiological methods can also be useful in carrying out statistical tests for the present invention.

Guidance in the selection of appropriate genetic statistical tests for analysis of a particular data set can be obtained from texts such as: *Fundamentals of Genetic Epidemiology* (Monographs in Epidemiology and Biostatistics, Vol 22) by M. J. Khoury, B. H. Cohen & T. H. Beaty, Oxford Univ Press, 1993; *Methods in Genetic Epidemiology* by Newton E. Morton, S. Karger Publishing, 1983; *Methods in Observational Epidemiology*, 2nd edition (Monographs in Epidemiology and Biostatistics, V. 26) by J. L. Kelsey (Editor), A. S. Whittemore & A. S. Evans, 1996; *Clinical Trials: Design, Conduct, and Analysis* (Monographs in Epidemiology and Biostatistics, Vol 8) by C. L. Meinert & S. Tonascia, 1986)

Strategy for the Implementation of a Clinical Study in the Case of a Therapeutic with Known Mechanism of Action:

1. Identify genes that encode proteins that perform functions related to drug absorption and/or, distribution, as well as genes related to the pharmacological action (pharmacodynamics) of the therapeutic intervention. Genes that encode proteins homologous to the proteins believed to carry out the above functions are also worth evaluation as they may carry out similar functions. Together the foregoing proteins constitute the candidate genes for affecting response of a patient to the therapeutic intervention.

2. Identify variances in the candidate genes. Initially, individual variances (and preferably their frequencies) will be identified by standard methods. Then, for genes with more than one variance, the commonly occurring patterns of variances occurring on a single chromosome (i.e. the haplotypes) may also be established using both computational and experimental approaches. For example, a computational approach might include one of, but not limited to, the following two methods a) expectation maximization (E-M) algorithm (Excoffier and Slatkin, Mol. Biol. Evol. 1995) and, b) a combination of Parsimonious and E-M methods.

If we have a large population, implementation of the E-M method will be performed first.

A given phenotype or a sequence could come from several genotypes. This is particularly true if the sequence is heterozygous at a number of nucleotide positions. Therefore, it is not practical to just count the phenotypes and make a conclusion on the underlying genotype, because it may lead to ambiguities. To avoid such ambiguities, an alternative iterative method called the EM (expectation-maximization) algorithm is used to derive the expected genotypes for a given phenotype or a sequence. This method assumes that the population under consideration is in Hardy-Weinberg equilibrium.

For example, consider the ABO locus in a population. Supposing, there are Na people of type A, Nb people of type B, Nab people of type AB, and No people of type O. Assuming N=Na+Nb+Nab+No in the random sample of people N, we cannot tell exactly how many of the Na people are homozygous for A/A and how many are heterozygotes for A/O.

In order to avoid this dilemma, we first assume that the expected number of genotypic frequencies in the population is in H-W equilibrium for any given (all) allele(s) frequency. This is followed by setting the allele frequencies and iteration n, and testing for its stability in a series of iterations, up to m. When the values of the initial allele frequencies stabilize at the end of series of iterations up to m, the resulting expected number of genotypes are assigned to phenotypes; for example, sequences or individuals.

The following steps are involved in the E-M algorithm:
1. Chose an allele or a haplotype in an expected class that occurs at the highest frequency
2. Use it as a base for the observed values and estimate the unobserved or the expected value
3. Use the second value as the true value and estimate the unobserved value from the second value
4. Continue this process (up to m) till you find values that do not change from one iteration to the next.

The final value is the maximum likelihood (highly likely) estimate of that allele or the haplotype As indicated above, also among the number of methods which are used for the purpose of classifying DNA sequences, haplotypes or phenotypic characters are the parsimony methods. Parsimony principle maintains that the best explanation for the observed differences among sequences, phenotypes (individuals, species) etc., is provided by the smallest number of evolutionary changes. Alternatively, simpler hypotheses are preferable to explain a set of data or patterns, than more complicated ones, and that ad hoc hypotheses should be avoided whenever possible (Molecular Systematics, Hillis et al., 1996). These methods for inferring relationship among sequences operate by minimizing the number of evolutionary steps or mutations (changes from one sequence/character) required to explain a given set of data.

For example, supposing we want to obtain relationships among a set of sequences and construct a structure (tree/topology), we first count the minimum number of mutations that are required for explaining the observed evolutionary changes among a set of sequences. A structure (topology) is constructed based on this number. When once this number is obtained, another structure is tried. This process is continued for all reasonable number of structures. Finally, the structure that required the smallest number of mutational steps is chosen as the likely structure/evolutionary tree for the sequences studied.

If the computed frequency of the haplotypes are equal to the number of individuals in the population, then there will be a consideration of utilizing additional methods. For these cases and if there is a small population, then the number of haplotypes will be considered relative to the number of entrants. In a method that is a modification of previously published work (Clark, Mol Biol and Evol. 1990) homozygotes will be assigned one unambiguous haplotype. If there is a single site variance (mutation) at one of the chromosomes then it will have two haplotypes. As the number of variances (mutations) increase in the diploid chromosomes, each of these variances will be compared with the haplotypes of the original population. Then a frequency will be assigned to the new variance based upon the Hardy-Weinberg expected frequencies. (See text below for why haplotypes are useful and how to determine them experimentally, if necessary.)

3. Retrospectively reanalyze data from already completed clinical trials. Since the questions are new, the data can be treated as if it were a prospective trial, with identified variances or haplotypes as stratification criteria and biological/clinical endpoints. Care should be taken to avoid studying a population in which there may be a link between drug-related genes and disease-related genes.
4. Select group of variances or haplotypes to differentiate: one control group including groups of variances with normal biological response one or a few case groups including groups of variances with significant biological impact
5. Establish phase III trials with selected variances as inclusion criteria and clinical/pharmacoeconomic endpoints. The number of patients required for adequate statistical power (approximately the same as in a usual phase III trial) will be determined from the phase II results and allele frequencies.

Strategy for the implementation of a clinical study in the case of a therapeutic intervention with known mechanism of biotransformation:
1. Identify genes that encode proteins that perform functions related to drug biotransformation or excretion, as well as genes related to the pharmacological action (pharmacodynamics) of the metabolized or biotransformed therapeutic intervention. Genes that encode proteins homologous to the proteins believed to carry out the above functions are also worth evaluation as they may carry out similar functions. Together the foregoing proteins constitute candidate genes for affecting response of a patient to the therapeutic intervention.
2. Identify variances in the candidate genes. Initially, individual variances will be identified by standard methods. Then, for genes with more than one variance, the commonly occurring patterns of variances occurring on a single chromosome (i.e. the haplotypes) may also be established. (See text below for why haplotypes are useful and how to determine them experimentally, if necessary.)
3. Retrospectively reanalyze data from already completed clinical trials. Since the questions are new, the data can be treated as if it were a prospective trial, with identified variances or haplotypes as stratification criteria and biological/clinical endpoints. Care should be taken to avoid studying a population in which there may be a link between drug-related genes and disease-related genes.
4. Select group of variances or haplotypes to differentiate: one control group including groups of variances with normal biological response one or a few case groups including groups of variances with significant biological impact.
5. Establish phase III trials with selected variances as inclusion criteria and clinical/pharmacoeconomic endpoints. The number of patients required for adequate statistical power (approximately the same as in a usual phase III trial) will be determined from the phase II results and allele frequencies.

Strategy for the Implementation of a Clinical Study in the Case of a Therapeutic Intervention where by the Effect of the Gene Variance or Variances on Therapeutic Intervention is Known:
1. Retrospectively reanalyze data from already completed clinical trials. In this case, since the questions are new, the data can be treated as if it were a prospective trial, with identified variances or haplotypes as stratification criteria and biological/clinical endpoints. Care should be taken to avoid studying a population in which there may be a link between drug-related genes and disease-related genes.
2. Select group of variances or haplotypes to differentiate: one control group including groups of variances with normal biological response and one or a few case groups including groups of variances with significant biological impact.
3. Establish phase III or phase IV (post marketing) trials with selected variances as inclusion criteria and clinical/pharmacoeconomic endpoints. The number of patients required for adequate statistical power (approximately the same as in a usual phase III trial) will be determined from the phase II results and allele frequencies.

A clinical trial in which pharmacogenetic related efficacy or toxicity endpoints are included in the primary or secondary endpoints will be part of a retrospective or prospective clinical trial. In the design of these trials, the allelic differences will be identified and stratification based upon these genotypic differences among patient or subject groups will be used to ascertain the significance of the impact a genotype has on the candidate therapeutic intervention. Retrospective pharmacogenetic trials can be conducted at each of the phases of clinical development, with the assumption that sufficient data is available for the correlation of the physiologic effect of the candidate therapeutic intervention and the allelic variance or variances within the treatment population. In the case of a retrospective trial, the data collected from the trial can be re-analyzed by imposing the additional stratification on groups of patients by specific allelic variances that may exist in the treatment groups. Retrospective trials can be useful to ascertain whether a hypothesis that a specific variance has a significant effect on the efficacy or toxicity profile for a candidate therapeutic intervention.

A prospective clinical trial has the advantage that the trial can be designed to ensure the trial objectives can be met with statistical certainty. In these cases, power analysis, which includes the parameters of allelic variance frequency, number of treatment groups, and ability to detect positive outcomes can ensure that the trial objectives are met.

In designing a pharmacogenetic trial, retrospective analysis of Phase II or Phase III clinical data can indicate trial variables for which further analysis is required. For example, surrogate endpoints, pharmacokinetic parameters, dosage, efficacy endpoints, ethnic and gender differences, and toxicological parameters may result in data that would require further analysis and re-examination through the design of an additional trial. In these cases, analysis involving statistics, genetics, clinical outcomes, and economic parameters may be considered prior to proceeding to the stage of designing any additional trials. Factors involved in the consideration of statistical significance may include Bonferroni analysis, permutation testing, with multiple testing correction resulting in a difference among the treatment groups that has occurred as a result of a chance of no greater than 20%, i.e. p<0.20. Factors included in determining clinical outcomes to be relevant for additional testing may include, for example, consideration of the target indication, the trial endpoints, progression of the disease, disorder, or condition during the trial study period, biochemical or pathophysiologic relevance of the candidate therapeutic intervention, and other variables that were not included or anticipated in the initial study design or clinical protocol. Factors to be included in the economic significance in determining additional testing parameters include sample size, accrual rate, number of clinical sites or institutions required, additional or other available medical or therapeutic interventions approved for human use, and additional or other available medical or therapeutic interventions concurrently or anticipated to enter human clinical testing. Further, there may be patients within the treatment categories that present data that fall outside of the average or mean values, or there may be an indication of multiple allelic loci that are involved in the responses to the candidate therapeutic intervention. In these cases, one could propose a prospective clinical trial having an objective to determine the significance of the variable or parameter and its effect on the outcome of the parent Phase II trial. In the case of a pharmacogenetic difference, i.e. a single or multiple allelic difference, a population could be selected based upon the distribution of genotypes. The candidate therapeutic intervention could then be tested in this group of volunteers to test for efficacy or toxicity. The repeat prospective study could be a Phase I limited study in which the subjects would be healthy human volunteers, or a Phase II limited efficacy study in which patients which satisfy the inclusion criteria could be enrolled. In either case, the second, confirmatory trial could then be used to systematically ensure an adequate number of patients with appropriate phenotype is enrolled in a Phase III trial.

A placebo controlled pharmacogenetics clinical trial design will be one in which target allelic variance or variances will be identified and a diagnostic test will be performed to stratify the patients based upon presence, absence, or combination thereof of these variances. In the Phase II or phase III stage of clinical development, determination of a specific sample size of a prospective trial will be described to include factors such as expected differences between a placebo and treatment on the primary or secondary endpoints and a consideration of the allelic frequencies.

The design of a pharmacogenetics clinical trial will include a description of the allelic variance impact on the observed efficacy between the treatment groups. Using this type of design, the type of genetic and phenotypic relationship display of the efficacy response to a candidate therapeutic intervention will be analyzed. For example, a genotypically dominant allelic variance or variances will be those in which both heterozygotes and homozygotes will demonstrate a specific phenotypic efficacy response different from the homozygous recessive genotypic group. A pharmacogenetic approach is useful for clinicians and public health professionals to include or eliminate small groups of responders or non-responders from treatment in order to avoid unjustified side-effects. Further, adjustment of dosages when clear clinical difference between heterozygous and homozygous individuals may be beneficial for therapy with the candidate therapeutic intervention In another example, a reccesive allelic variance or variances will be those in which only the homozygote recessive for that or those variances will demonstrate a specific phenotypic efficacy response different from the heterozygotes or homozygous dominants. An extension of these examples may include allelic variance or variances organized by haplotypes from additional gene or genes providing an explanation of clinical phenotypic outcome differences among the treatment groups. These types of clinical studies will point and address allelic variance and its role in the efficacy or toxicology pattern within the treatment population.

IV. Variance Identification and Use

A. Initial Identification of Variances in Genes

Selection of Population Size and Composition

Prior to testing to identify the presence of sequence variances in a particular gene or genes, it is useful to understand how many individuals should be screened to provide confidence that most or nearly all pharmacogenetically relevant variances will be found. The answer depends on the frequencies of the phenotypes of interest and what assumptions we make about heterogeneity and magnitude of genetic effects. At the beginning we only know phenotype frequencies (e.g. responders vs. nonresponders, frequency of various side effects, etc.). As an example, the occurrence of serious 5-FU/FA toxicity—e.g. toxicity requiring hospitalization is often >10%. The occurrence of life threatening toxicity is in the 1–3% range (Buroker et al. 1994). The occurrence of complete remissions is on the order of 2–8%. The lowest frequency phenotypes are thus on the order of ~2%. If we assume that (i) homogeneous genetic effects are responsible for half the phenotypes of interest and (ii) for the most part the extreme phenotypes represent recessive genotypes, then we need to detect alleles that will be present at ~10% frequency (0.1×0.1=0.01, or 1% frequency of homozygotes) if the population is at Hardy-Weinberg equilibrium. To have a ~99% chance of identifying such alleles would require searching a population of 22 individuals (see Table 1 below). If the major phenotypes are associated with heterozygous genotypes then we need to detect alleles present at ~0.5% frequency (2×0.005×0.995=0.00995, or ~1% frequency of heterozygotes). A 99% chance of detecting such alleles would require ~40 individuals (Table below). Given the heterogeneity of the North American population we cannot assume that all genotypes are present in Hardy-Weinberg proportions, therefore a substantial oversampling is done to increase the chances of detecting relevant variances: For our initial screening, usually, 62 individuals of known race/ethnicity are screened for variance. Variance detection studies can be extended to outliers for the phenotypes of interest to cover the possibility that important variances were missed in the normal population screening.

the Coriell Cell Repository (Camden, N.J.) maintains over 6,000 human cell cultures, mostly fibroblast and lymphoblast cell lines comprising the NIGMS Human Genetic Mutant Cell Repository. A catalog (http://locus.umdnj.edu/nigms) provides racial or ethnic identifiers for many of the cell lines. 55 of the 62 cell lines to be genotyped (as indicated above) are drawn from this collection; the remainder were obtained from the Beijing Cancer Institute. The cell lines are derived from 21 Caucasians (of Northern, Central and Southern European origin), 8 Afro-Americans, 9 Hispanics or Mexicans, 8 Chinese, 12 Japanese, 1 American Indian, 1 East Indian, 1 Iranian, and 1 Korean. These cell lines (plus ~75 other lymphoblastoid lines) are currently in use by the inventors for variance detection studies.

Source of Human DNA, RNA and cDNA Samples

PCR based screening for DNA polymorphism can be carried out using either genomic DNA or cDNA produced from mRNA. For many genes, only cDNA sequences have been published, therefore the analysis of those genes is, at

TABLE 1

| Allele frequencies | Number of subjects genotyped | | | | | | | |
|---|---|---|---|---|---|---|---|---|
| | n = 5 | n = 10 | n = 15 | n = 20 | n = 25 | n = 30 | n = 35 | n = 50 |
| p = .99, q = .01 | 9.56% | 18.21 | 26.03 | 33.10 | 39.50 | 45.28 | 50.52 | 63.40 |
| p = .97, q = .03 | 26.26 | 45.62 | 59.90 | 70.43 | 78.19 | 83.92 | 88.14 | 95.24 |
| p = .95, q = .05 | 40.13 | 64.15 | 78.53 | 87.15 | 92.30 | 95.39 | 97.24 | 99.65 |
| p = .93, q = .07 | 51.60 | 76.58 | 88.66 | 94.51 | 97.34 | 98.71 | 99.38 | 99.93 |
| p = .9, q = .1 | 65.13 | 87.84 | 95.76 | 98.52 | 99.48 | 99.82 | 99.94 | >99.99 |
| p = .8, q = .2 | 89.26 | 98.84 | 99.88 | 99.99 | >99.99 | >99.99 | >99.99 | >99.99 |
| p = .7, q = .3 | 97.17 | 99.92 | 99.99 | >99.99 | >99.99 | >99.99 | >99.99 | >99.99 |

Likelihood of Detecting Polymorphism in a Population as a Function of Allele Frequency & Number of Individuals Genotyped The table above shows the probability (expressed as percent) of detecting both alleles (i.e. detecting heterozygotes) at a biallelic locus as a function of (i) the allele frequencies and (ii) the number of individuals genotyped. The chances of detecting heterozygotes increases as the frequencies of the two alleles approach 0.5 (down a column), and as the number of individuals genotyped increases (to the right along a row). The numbers in the table are given by the formula: $1-(p)^{2n}-(q)^{2n}$. Allele frequencies are designated p and q and the number of individuals tested is designated n. (Since humans are diploid, the number of alleles tested is twice the number of individuals, or 2n.)

While it is preferable that numbers of individuals, or independent sequence samples, are screened to identify variances in a gene, it is also very beneficial to identify variances using smaller numbers of individuals or sequence samples. For example, even a comparison between the sequences of two samples or individuals can reveal sequence variances between them. Preferably, 5, 10, or more samples or individuals are screened.

Source of Nucleic Acid Samples

Nucleic acid samples, for example for use in variance identification, can be obtained from a variety of sources as known to those skilled in the art, or can be obtained from genomic or cDNA sources by known methods. For example, least initially, at the cDNA level since the determination of intron-exon boundaries and the isolation of flanking sequences is a laborious process. However, screening genomic DNA has the advantage that variances can be identified in promoter, intron and flanking regions. Such variances may be biologically relevant. Therefore preferably, when variance analysis of patients with outlier responses is performed, analysis of selected loci at the genomic level is also performed. Such analysis would be contingent on the availability of a genomic sequence or intron-exon boundary sequences, and would also depend on the anticipated biological importance of the gene in connection with the particular response.

When cDNA is to be analyzed it is very beneficial to establish a tissue source in which the genes of interest are expressed at sufficient levels that cDNA can be readily produced by RT-PCR. Preliminary PCR optimization efforts for 19 of the 29 genes in Table 2 reveal that all 19 can be amplified from lymphoblastoid cell mRNA. The 7 untested genes belong on the same pathways and are expected to also be PCR amplifiable.

PCR Optimization

Primers for amplifying a particular sequence can be designed by methods known to those skilled in the art, including by the use of computer programs such as the PRIMER software available from Whitehead Institute/MIT Genome Center. In some cases it is preferable to optimize the amplification process according to parameters and methods known to those skilled in the art; optimization of PCR reactions based on a limited array of temperature, buffer and primer concentration conditions is utilized. New primers are obtained if optimization fails with a particular primer set.

Variance Detection Using T4 Endonuclease VII Mismatch Cleavage Method

Any of a variety of different methods for detecting variances in a particular gene can be utilized, such as those described in the patents and applications cited in section A above. An exemplary method is a T4 Endo VII method. The enzyme T4 endonuclease VII (T4E7) is derived from the bacteriophage T4. T4E7 specifically cleaves heteroduplex DNA containing single base mismatches, deletions or insertions. The site of cleavage is 1 to 6 nucleotides 3' of the mismatch. This activity has been exploited to develop a general method for detecting DNA sequence variances (Youil et al. 1995; Mashal and Sklar, 1995). A quality controlled T4E7 variance detection procedure based on the T4E7 patent of R. G. H. Cotton and co-workers. (Del Tito et al., in press) is preferably utilized. T4E7 has the advantages of being rapid, inexpensive, sensitive and selective. Further, since the enzyme pinpoints the site of sequence variation, sequencing effort can be confined to a 25–30 nucleotide segment.

The major steps in identifying sequence variations in candidate genes using T4E7 are: (1) PCR amplify 400–600 bp segments from a panel of DNA samples; (2) mix a fluorescently-labeled probe DNA with the sample DNA; (3) heat and cool the samples to allow the formation of heteroduplexes; (4) add T4E7 enzyme to the samples and incubate for 30 minutes at 37° C., during which cleavage occurs at sequence variance mismatches; (5) run the samples on an ABI 377 sequencing apparatus to identify cleavage bands, which indicate the presence and location of variances in the sequence; (6) a subset of PCR fragments showing cleavage are sequenced to identify the exact location and identity of each variance.

The T4E7 Variance Imaging procedure has been used to screen particular genes. The efficiency of the T4E7 enzyme to recognize and cleave at all mismatches has been tested and reported in the literature. One group reported detection of 81 of 81 known mutations (Youil et al. 1995) while another group reported detection of 16 of 17 known mutations (Mashal and Sklar, 1995). Thus, the T4E7 method provides highly efficient variance detection.

DNA Sequencing

A subset of the samples containing each unique T4E7 cleavage site is selected for sequencing. DNA sequencing can, for example, be performed on ABI 377 automated DNA sequencers using BigDye chemistry and cycle sequencing. Analysis of the sequencing runs will be limited to the 30–40 bases pinpointed by the T4E7 procedure as containing the variance. This provides the rapid identification of the altered base or bases.

In some cases, the presence of variances can be inferred from published articles which describe Restriction Fragment Length Polymorphisms (RFLP). The sequence variances or polymorphisms creating those RFLPs can be readily determined using convention techniques, for example in the following manner. If the RFLP was initially discovered by the hybridization of a cDNA, then the molecular sequence of the RFLP can be determined by restricting the cDNA probe into fragments and separately hybridizing to a Southern blot consisting of the restriction digestion with the enzyme which reveals the polymorphic site, identifying the sub-fragment which hybridizes to the polymorphic restriction fragment, obtaining a genomic clone of the gene (e.g., from commercial services such as Genome Systems (Saint Louis, Mo.) or Research Genetics (Alabama) which will provide appropriate genomic clones on receipt of appropriate primer pairs). Using the genomic clone, restrict the genomic clone with the restriction enzyme which revealed the polymorphism and isolate the fragment which contains the polymorphism, e.g., identifying by hybridization to the cDNA which detected the polymorphism. The fragment is then sequenced across the polymorphic site. A copy of the other allele can be obtained by PCT from addition samples.

Variance Detection Using Sequence Scanning

In addition to the physical methods, e.g., those described above and others known to those skilled in the art (see, e.g., Housman, U.S. Pat. No. 5,702,890; Housman et al., U.S. patent application Ser. No. 09/045,053), variances can be detected using computational methods, involving computer comparison of sequences from two or more different biological sources, which can be obtained in various ways, for example from public sequence databases. The term "variance scanning" refers to a process of identifying sequence variances using computer-based comparison and analysis of multiple representations of at least a portion of one or more genes. Computational variance detection involves a process to distinguish true variances from sequencing errors or other artifacts, and thus does not require perfectly accurate sequences. Such scanning can be performed in a variety of ways as known to those skilled in the art, preferably, for example, as described in Stanton and Adams, U.S. Patent Application filed Apr. 26, 1999, Ser. No. 09/300,747.

While the utilization of complete cDNA sequences is highly preferred, it is also possible to utilize genomic sequences. Such analysis may be desired where the detection of variances in or near splice sites is sought. Such sequences may represent full or partial genomic DNA sequences for a gene or genes. Also, as previously indicated, partial cDNA sequences can also be utilized although this is less preferred. As described below, the variance scanning analysis can simply utilize sequence overlap regions, even from partial sequences. Also, while the present description is provided by reference to DNA, e.g., cDNA, some sequences may be provided as RNA sequences, e.g., mRNA sequences. Such RNA sequences may be converted to the corresponding DNA sequences, or the analysis may use the RNA sequences directly.

B. Determination of Presence or Absence of Known Variances

The identification of the presence of previously identified variances in cells of an individual, usually a particular patient, can be performed by a number of different techniques as indicated in the Summary above. Such methods include methods utilizing a probe which specifically recognizes the presence of a particular nucleic acid or amino acid sequence in a sample. Common types of probes include nucleic acid hybridization probes and antibodies, for example, monoclonal antibodies, which can differentially bind to nucleic acid sequences differing in one or more variance sites or to polypeptides which differ in one or more amino acid residues as a result of the nucleic acid sequence variance or variances. Generation and use of such probes is well-known in the art and so is not described in detail herein.

Preferably, however, the presence or absence of a variance is determined using nucleotide sequencing of a short sequence spanning a previously identified variance site. This will utilize validated genotyping assays for the polymorphisms previously identified. Since both normal and tumor cell genotypes can be measured, and since tumor material will frequently only be available as paraffin embedded sections (from which RNA cannot be isolated), it will be necessary to utilize genotyping assays that will work on genomic DNA. Thus PCR reactions will be designed, optimized, and validated to accommodate the intron exon structure of each of the genes. If the gene structure has been published (as it has for some of the listed genes), PCR primers can be designed directly. However, if the gene structure is unknown, the PCR primers may need to be moved around in order to both span the variance and avoid exon-intron boundaries. In some cases one-sided PCR methods such as bubble PCR (Ausubel et al. 1997) may be useful to obtain flanking intronic DNA for sequence analysis.

Using such amplification procedures, the standard method used to genotype normal and tumor tissues will be DNA sequencing. PCR fragments encompassing the variances will be cycle sequenced on ABI 377 automated sequencers using Big Dye chemistry

C. Correlation of the Presence or Absence of Specific Variances with Differential Treatment Response Prior to establishment of a diagnostic test for use in the selection of a treatment method or elimination of a treatment method, the presence or absence of one or more specific variances in a gene or in multiple genes is correlated with a differential treatment response. (As discussed above, usually the existence of a variable response and the correlation of such a response to a particular gene is performed first.) Such a differential response can be determined using prospective and/or retrospective data. Thus, in some cases, published reports will indicate that the course of treatment will vary depending on the presence or absence of particular variances. That information can be utilized to create a diagnostic test and/or incorporated in a treatment method as an efficacy or safety determination step.

Usually, however, the effect of one or more variances is separately determined. The determination can be performed by analyzing the presence or absence of particular variances in patients who have previously been treated with a particular treatment method, and correlating the variance presence or absence with the observed course, outcome, and/or development of adverse events in those patients. This approach is useful in cases where both the observation of treatment effects was clearly recorded and cell samples are available or can be obtained. Alternatively, the analysis can be performed prospectively, where the presence or absence of the variance or variances in an individual is determined and the course, outcome, and/or development of adverse events in those patients is subsequently or concurrently observed and then correlated with the variance determination.

Analysis of Haplotypes Increases Power of Genetic Analysis

Usually, variation in activity due to a single gene or a single genetic variance in a single gene is not sufficient to account for observed variation in patient response to a treatment, e.g., a drug, there are often other factors that account for some of the variation in patient response. This is to be expected as drug response phenotypes usually vary continuously, and such (quantitative) traits are typically influenced by a number of genes (Falconer and Mackay, 1997). Although it is impossible to determine a priori the number of genes influencing a quantitative trait, often only a few loci have large effects, where a large effect is 5–20% of total variation in the phenotype (Mackay, 1995).

Having identified genetic variation in enzymes that may affect action of a specific drug, it is useful to efficiently address its relation to phenotypic variation. The sequential testing for correlation between phenotypes of interest and single nucleotide polymorphisms may be adequate to detect associations if there are major effects associated with single nucleotide changes; certainly it is useful to this type of analysis. However there is no way to know in advance whether there are major phenotypic effects associated with single nucleotide changes and, even if there are, there is no way to be sure that the salient variance has been identified by screening cDNAs. A more powerful way to address the question of genotype-phenotype correlation is to assort genotypes into haplotypes. (A haplotype is the cis arrangement of polymorphic nucleotides on a particular chromosome.) Haplotype analysis has several advantages compared to the serial analysis of individual polymorphisms at a locus with multiple polymorphic sites.

(1) Of all the possible haplotypes at a locus ($2^n$ haplotypes are theoretically possible at a locus with n binary polymorphic sites) only a small fraction will generally occur at a significant frequency in human populations. Thus, association studies of haplotypes and phenotypes will involve testing fewer hypotheses. As a result there is a smaller probability of Type I errors, that is, false inferences that a particular variant is associated with a given phenotype.

(2) The biological effect of each variance at a locus may be different both in magnitude and direction. For example, a polymorphism in the 5' UTR may affect translational efficiency, a coding sequence polymorphism may affect protein activity, a polymorphism in the 3' UTR may affect mRNA folding and half life, and so on. Further, there may be interactions between variances: two neighboring polymorphic amino acids in the same domain—say cys/arg at residue 29 and met/val at residue 166—may, when combined in one sequence, for example, 29cys-166val, have a deleterious effect, whereas 29cys-166met, 29arg-166met and 29arg-166val proteins may be nearly equal in activity. Haplotype analysis is the best method for assessing the interaction of variances at a locus.

(3) Templeton and colleagues have developed powerful methods for assorting haplotypes and analyzing haplotype/phenotype associations (Templeton et al., 1987). Alleles which share common ancestry are arranged into a tree structure (cladogram) according to their time of origin in a population. Haplotypes that are evolutionarily ancient will be at the center of the branching structure and new ones (reflecting recent mutations) will be represented at the periphery, with the links representing intermediate steps in evolution. The cladogram defines which haplotype-phenotype association tests should be performed to most efficiently exploit the available degrees of freedom, focusing attention on those comparisons most likely to define functionally different haplotypes (Haviland et al., 1995). This type of analysis has been used to define interactions between heart disease and the apolipoprotein gene cluster (Haviland et al 1995) and Alzheimer's Disease and the Apo-E locus (Templeton 1995) among other studies, using populations as small as 50 to 100 individuals.

Methods for Determining Haplotypes

The goal of haplotyping will be to identify the common haplotypes at selected loci that have multiple sites of variance. Haplotypes will usually be determined at the cDNA level. Two general approaches to identification of haplotyes will be employed. First, haplotypes will be inferred from the pattern of allele segregation in families collected by the Centre d'Etude Polymorphisme Humaine. Cell lines from these families are available from the Coriell Repository. Cell lines for all members of families 884, 102, 104 and 1331 are currently utilized. Cell lines from six additional families will also be used to increase the likelihood of detecting common haplotypes. This approach will be useful for cataloging common haplotypes and for validating methods on samples with known haplotypes. Second, haplotypes will be determined directly from cDNA using the T4E7 procedure. T4E7 cleaves mismatched heteroduplex DNA at the site of the mismatch. If a heteroduplex contains only one mismatch, cleavage will result in the generation of two fragments. However, if a single heteroduplex (allele) contains two mismatches, cleavage will occur at two different sites resulting in the generation of three fragments. The appearance of a fragment whose size corresponds to the distance between the two cleavage sites is diagnostic of the two mismatches being present on the same strand (allele). Thus, T4E7 can be used to determine haplotypes in diploid cells.

An alternative method, allele specific PCR, may be used for haplotyping. The utility of allele specific PCR for haplotyping has already been established (Michalatos-Beloin et al., 1996; Chang et al. 1997). Opposing PCR primers are designed to cover two sites of variance (either adjacent sites or sites spanning one or more internal variances). Two versions of each primer are synthesized, identical to each other except for the 3' terminal nucleotide. The 3' terminal nucleotide is designed so that it will hybridize to one but not the other variant base. PCR amplification is then attempted with all four possible primer combinations in separate wells. Because Taq polymerase is very inefficient at extending 3' mismatches, the only samples which will be amplified will be the ones in which the two primers are perfectly matched for sequences on the same strand (allele). The presence or absence of PCR product allows haplotyping of diploid cell lines. At most two of four possible reactions should yield products. This procedure has been successfully applied, for example, to haplotype the DPD amino acid polymorphisms.

For haplotypes identified herein, haplotypes were identified by examining genotypes from each cell line. This list of genotypes was optimized to remove variance sites/individuals with incomplete information, and the genotype from each remaining cell line was examined in turn. The number of heterozygotes in the genotype were counted, and those genotypes containing more than one heterozygote were discarded, and the rest were gathered in a list for storage and display. For haplotypes identified herein, haplotypes were identified by examining genotypes from each cell line. This list of genotypes was optimized to remove variance sites/individuals with incomplete information, and the genotype from each remaining cell line was examined in turn. The number of heterozygotes in the genotype were counted, and those genotypes containing more than one heterozygote were discarded, and the rest were gathered in a list for storage and display.

D. Selection of Treatment Method Using Variance Information

1. General

Once the presence or absence of a variance or variances in a gene or genes is shown to correlate with the efficacy or safety of a treatment method, that information can be used to select an appropriate treatment method for a particular patient. In the case of a treatment which is more likely to be effective when administered to a patient who has at least one copy of a gene with a particular variance or variances (in some cases the correlation with effective treatment is for patients who are homozygous for variance or set of variances in a gene) than in patients with a different variance or set of variances, a method of treatment is selected (and/or a method of administration) which correlates positively with the particular variance presence or absence which provides the indication of effectiveness. As indicated in the Summary, such selection can involve a variety of different choices, and the correlation can involve a variety of different types of treatments, or choices of methods of treatment. In some cases, the selection may include choices between treatments or methods of administration where more than one method is likely to be effective, or where there is a range of expected effectiveness or different expected levels of contra-indication or deleterious effects. In such cases the selection is preferably performed to select a treatment which will be as effective or more effective than other methods, while having a comparatively low level of deleterious effects. Similarly, where the selection is between method with differing levels of deleterious effects, preferably a method is selected which has low such effects but which is expected to be effective in the patient.

Alternatively, in cases where the presence or absence of the particular variance or variances is indicative that a treatment or method of administration is more likely to be ineffective or contra-indicated in a patient with that variance or variances, then such treatment or method of administration is generally eliminated for use in that patient.

2. Diagnostic Methods

Once a correlation between the presence and absence of at least one variance in a gene or genes and an indication of the effectiveness of a treatment, the determination of the presence or absence of that at least one variance provides diagnostic methods, which can be used as indicated in the Summary above to select methods of treatment, methods of administration of a treatment, methods of selecting a patient or patients for a treatment and others aspects in which the determination of the presence or absence of those variances provides useful information for selecting or designing or preparing methods or materials for medical use in the aspects of this invention. As previously stated, such variance determination or diagnostic methods can be performed in various ways as understood by those skilled in the art.

In certain variance determination methods, it is necessary or advantageous to amplify one or more nucleotide sequences in one or more of the genes identified herein. Such amplification can be performed by conventional methods, e.g., using polymerase chain reaction (PCR) amplification. Such amplification methods are well-known to those skilled in the art and will not be specifically described herein. For most applications relevant to the present invention, a sequence to be amplified includes at least one variance site, which is preferably a site or sites which provide variance information indicative of the effectiveness of a method of treatment or method of administration of a treatment, or effectiveness of a second method of treatment which reduces a deleterious effect of a first treatment method, or which enhances the effectiveness of a first method of treatment. Thus, for PCR, such amplification generally utilizes primer oligonucleotides which bind to or extent through at least one such variance site under amplification conditions.

For convenient use of the amplified sequence, e.g., for sequencing, it is beneficial that the amplified sequence be of limited length, but still long enough to allow convenient and specific amplification. Thus, preferably the amplified sequence has a length as described in the Summary.

Also, in certain variance determination, it is useful to sequence one or more portions of a gene or genes, in particular, portions of the genes identified in this disclosure. As understood by persons familiar with nucleic acid sequencing. In particular, sequencing can utilize dye termination methods and mass spectrometric methods. The sequencing generally involves a nucleic acid sequence which includes a variance site as indicated above in connection with amplification. Such sequencing can directly provide determination of the presence or absence of a particular variance or set of variances, e.g., a haplotype, by inspection of the sequence (visually or by computer). Such sequencing is generally conducted on PCR amplified sequences in order to provide sufficient signal for practical or reliable sequence determination.

Likewise, in certain variance determinations, it is useful to utilize a probe or probes. As previously described, such probes can be of a variety of different types.

IV. Pharmaceutical Compositions, Including Pharmaceutical Compositions Adapted to be Preferentially Effective in Patients Having Particular Genetic Characteristics 1. General The methods of the present invention, in many cases will utilize conventional pharmaceutical compositions, but will allow more advantageous and beneficial use of those compositions due to the ability to identify patients who are likely to benefit from a particular treatment or to identify patients for whom a particular treatment is less likely to be effective or for whom a particular treatment is likely to produce undesirable or intolerable effects. However, in some cases, it is advantageous to utilize compositions which are adapted to be preferentially effective in patients who possess particular genetic characteristics, i.e., in whom a particular variance or variances in one or more genes is present or absent (depending on whether the presence or the absence of the variance or variances in a patient is correlated with an increased expectation of beneficial response). Thus, for example, the presence of a particular variance or variances may indicate that a patient can beneficially receive a significantly higher dosage of a drug than a patient having a different variance or variances.

2. Regulatory Indications and Restrictions

The sale and use of drugs and the use of other treatment methods usually are subject to certain restrictions by a government regulatory agency charged with ensuring the safety and efficacy of drugs and treatment methods for medical use, and approval is based on particular indications. In the present invention it is found that variability in patient response or patient tolerance of a drug or other treatment often correlates with the presence or absence of particular variances in particular genes. Thus, it is expected that such a regulatory agency may indicate that the approved indications for use of a drug with a variance-related variable response or toleration include use only in patients in whom the drug will be effective, and/or for whom the administration of the drug will not have intolerable deleterious effects, such as excessive toxicity or unacceptable side-effects. Conversely, the drug may be given for an indication that it may be used in the treatment of a particular disease or condition where the patient has at least one copy of a particular variance, variances, or variant form of a gene. Even if the approved indications are not narrowed to such groups, the regulatory agency may suggest use limited to particular groups or excluding particular groups or may state advantages of use or exclusion of such groups or may state a warning on the use of the drug in certain groups. Consistent with such suggestions and indications, such an agency may suggest or recommend the use of a diagnostic test to identify the presence or absence of the relevant variances in the prospective patient. Such diagnostic methods are described in this description. Generally, such regulatory suggestion or indication is provided in a product insert or label, and is generally reproduced in references such as the Physician's Desk Reference (PDR). Thus, this invention also includes drugs or pharmaceutical compositions which carry such a suggestion or statement of indication or warning or suggestion for a diagnostic test, and which may also be packaged with an insert or label stating the suggestion or indication or warning or suggestion for a diagnostic test.

In accord with the possible variable treatment responses, an indication or suggestion can specify that a patient be heterozygous, or alternatively, homozygous for a particular variance or variances or variant form of a gene. Alternatively, an indication or suggestion may specify that a patient have no more than one copy, or zero copies, of a particular variance, variances, or variant form of a gene.

A regulatory indication or suggestion may concern the variances or variant forms of a gene in normal cells of a patient and/or in cells involved in the disease or condition. For example, in the case of a cancer treatment, the response of the cancer cells can depend on the form of a gene remaining in cancer cells following loss of heterozygosity affecting that gene. Thus, even though normal cells of the patient may contain a form of the gene which correlates with effective treatment response, the absence of that form in cancer cells will mean that the treatment would be less likely to be effective in that patient than in another patient who retained in cancer cells the form of the gene which correlated with effective treatment response. Those skilled in the art will understand whether the variances or gene forms in normal or disease cells are most indicative of the expected treatment response, and will generally utilize a diagnostic test with respect to the appropriate cells. Such a cell type indication or suggestion may also be contained in a regulatory statement, e.g., on a label or in a product insert.

3. Preparation and Administration of Drugs and Pharmaceutical Compositions Including Pharmaceutical Compositions Adapted to be Preferentially Effective in Patients Having Particular Genetic Characteristics A particular compound useful in this invention can be administered to a patient either by itself, or in pharmaceutical compositions where it is mixed with suitable carriers or excipient(s). In treating a patient exhibiting a disorder of interest, a therapeutically effective amount of a agent or agents such as these is administered. A therapeutically effective dose refers to that amount of the compound that results in amelioration of one or more symptoms or a prolongation of survival in a patient.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized.

For any compound used in the method of the invention, the therapeutically effective dose can be estimated initially from cell culture assays. For example, a dose can be formulated in animal models to achieve a circulating plasma concentration range that includes the $IC_{50}$ as determined in cell culture. Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et. al., in *The Pharmacological Basis of Therapeutics*, 1975, Ch. 1 p.1). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of disorder of interest will vary with the severity of the condition to be treated and the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents of the invention may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions of the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

EXAMPLES

Example 1

Gene Identification

Metabolic Pathways that Affect 5-FU/FA Action

The biochemical pathways of 5-FU metabolism have been studied extensively. Likewise, folate metabolism has been well investigated and the enzymes that form and consume 5,10-methylenetetrahydrofolate are well known. The principal metabolic pathways that influence the pharmacologic action of 5-FU are summarized below.

De novo and Salvage Routes of Pyrimidine Nucleotide Formation (5-FU Anabolism) and Inhibition of Thymidylate Synthase 5-FU is a biologically inactive pyrimidine analog which must be phosphorylated and ribosylated to the nucleoside analog fluorodeoxyuridine monophosphate (FdUMP) to have clinical activity. FdUMP formation can occur via several routes, summarized in FIG. 1. 5-FU may be converted by uridine phosphorylase to fluorouridine (FUdR; the reverse reaction is catalyzed by uridine nucleosidase) and then to fluorouridine monophosphate (FUMP) by uridine kinase, or FUMP may be formed from 5-FU in one step via transfer of a phosphoribosyl group from 5-phosphoribosyl-1-pyrophosphate (PRPP), catalyzed by orotate phosphoribosyl transferase. FUMP can be converted to FUDP and subsequently FUTP by a nucleoside monophosphate kinase and nucleoside diphosphate kinase, respectively. FUTP is incorporated into RNA by RNA polymerases, which may account in part for 5-FU toxicity as a result of effects on processing or function (e.g. translation). Alternatively, FUDP may be reduced to the dinucleotide level, FdUDP (fluorodeoxyuridine diphosphate) by ribonucleotide diphosphate reductase, a heterodimeric enzyme. FdUDP can then be converted to FdUTP by nucleoside diphosphate kinase and incorporated into DNA by DNA polymerases which may account for some 5-FU toxicity. Fluoropyrimidine modified DNA may also be targeted by the nucleotide excision repair process. The more important path of FdUDP metabolism with respect to anticancer effects, however, is believed to be conversion to FdUMP by nucleoside diphosphatase (or cytidylate kinase, a bidirectional enzyme). dUMP is the precursor of dTMP in de novo pyrimidine biosynthesis, a reaction catalyzed by thymidylate synthase and which consumes 5,10-methylenetetrahydrofolate, producing 7,8 dihydrofolate. FdUMP, however, forms an inhibitory (probably covalent) complex with thymidylate synthase in the presence of 5,10-methylenetetrahydrofolate, thereby blocking formation of thymidylate (other than by the salvage pathway via thymidine kinase). The complex anabolism of FdUMP can be simplified by giving the deoxyribonucleoside of 5-FU, 5-fluorodeoxyuridine (also called floxuridine; FUdR), which can be converted to FdUMP in one step by thymidine kinase. However, FUdR is also rapidly converted back to 5-FU by the bidirectional enzyme thymidine phosphorylase.

5-FU Catabolism.

Metabolic elimination of 5-FU occurs via a three step pathway leading to alanine. The first and rate limiting enzyme in the elimination pathway is dihydropyrimidine dehydrogenase (DPD), which transforms more than 80% of a dose of 5-FU to the inactive dihydrofluorouracil form. Subsequently dihydropyrimidinase catalyzes opening of the pyrimidine ring to form 5-fluoro-ureidopropionate and then ureidopropionase (also called alanine synthase) catalyzes formation of 2-fluoro-alanine. The first two reactions are reversible.

The distribution of activity of these enzymes in human populations has not been established, however, a recent population survey of urinary pyrimidine levels in 1,133 adults revealed that levels of dihydrouracil range from 0–59 uM/g of creatinine, while uracil levels ranged from 0–130 uM/g creatinine (Hayashi et al., 1996), suggesting variation in the activity of enzymes of pyrimidine metabolism. It is worth noting that in animal studies catabolites of 5-FU apparently account for some fraction of 5-FU toxicity (Davis et al., 1994; Spector et al., 1995). This result is the rationale for current human trials of 5-FU combined with DPD inhibitors: if the 5-fluoro-metabolites are responsible for toxicity, then blocking their formation by inhibition of DPD, while simultaneously decreasing 5-FU dosage to compensate for the block in catabolism and excretion, should result in a better therapeutic index.

Folinic Acid Conversion to Tetrahydrofolate.

Figure 2:
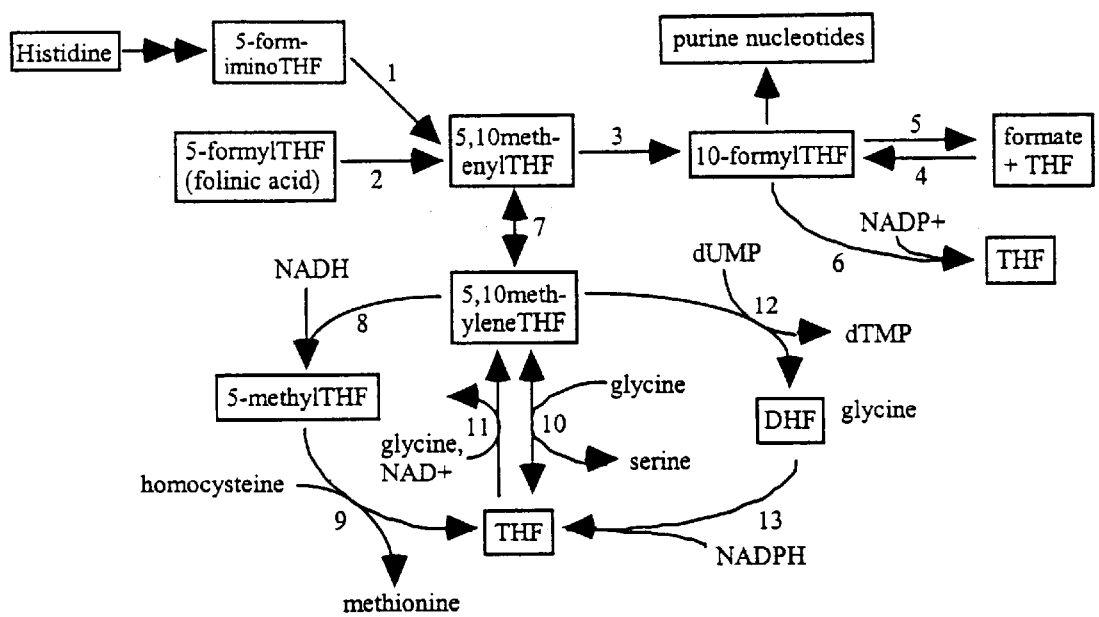
FIG. 2 is a diagram showing the relationship of enzymes related to folate metabolism and formation of 5,10-methylenetetrahydrofolate. Enzymes: 1. Formininotetrahydrofolate cyclodeaminase; 2. methenyltetrahydrofolate synthetase; 3. methenyltetra-hydrofolate cyclohydrolase; 4. formyltetrahydrofolate synthetase; 5. formyltetrahydrofolate hydrolase; 6. formyltetrahydrofolate dehydrogenase; 7. methyleneltetrahydrofolate dehydrogenase; 8. methyleneltetrahydrofolate reductase (MTHFR); 9. homocysteine methyltransferase (also called methionine synthetase); 10. serine transhydroxymethylase; 11. glycine cleavage system; 12. thymidylate synthase; 13. dihydrofolate reductase. Abbreviations: THF=tetrahydrofolate; DHF=dihydrofolate. Note that THF appears twice (i.e. the product of step 6 is also substrate for enzymes 10 and 11. Step 12 also appears in FIG. 1, above. This Figure is adapted from Mathews & van Holde, Biochemistry, The Benjamin/Cummings Publishing Co., Redwood City, Calif., 1990, page 697.

The conversion of FA to 5,10MTHF can occur via several routes, illustrated in FIG. 2.

Intracellular reduced folate levels can potentiate 5-FU action by increasing 5,10-methylenetetrahydrofolate levels (5,10-methyleneTHF; see center of FIG. 2), thereby stabilizing the ternary inhibitory complex formed with thymidylate synthase and FdUMP. This is the basis for therapeutic modulation of 5-FU with FA. As can be seen in FIG. 2, conversion of folinic acid (5-formylTHF) to 5,10-methenylTHF, the precursor of 5,10-methyleneTHF, requires methenyltetrahydrofolate synthetase (enzyme 2 in the Figure). Also, levels of 5,10-methyleneTHF may be affected directly by the activity of methyleneltetrahydrofolate dehydrogenase, methyleneltetrahydrofolate reductase, serine transhydroxymethylase and the glycine cleavage system enzymes (7, 8, 10 and 11 in FIG. 2), and indirectly by the other enzymes shown in the Figure.

Cell Uptake of Pyrimidine Nucleosides and Folinic Acid

Human cells have five concentrative nucleoside transporters with varying patterns of tissue distribution (see review by Wang et al., 1997). Two transporters, one with preference for purines and one for pyrimidines have been cloned recently (Felipe et al., 1998). 5-FU entry into cells may be modulated by activity of these transporters, particularly the pyrimidine transporter, although one prospective randomized clinical trial in which the nucleoside transport inhibitor dipyramidole was paired with 5-FU and FA failed to show a difference in outcome compared to 5-FU/FA alone (Kohne et al., 1995). Several folate transport systems have been identified in human cells. Folate receptor 1 (FR1) is a high affinity (nanomolar range) receptor for reduced folates. Three restriction fragment length polymorphisms (RFLPs) have been reported at the FR1 locus (Campbell et al., 1991). Reduced folates are also transported by folate receptor gamma and by a low affinity (1 uM) folate transporter. 15-fold variation in levels of folate transporter have been described in unselected tumor cell lines (Moscow et al., 1997).

Catalog Allelic Variation in Enzymes that Affect 5-FU and FA Action Select Genes for Analysis of Sequence Variation In accord with the pathway description above, variation in either expression levels or intrinsic activity of the proteins involved in (i) cellular uptake of pyrimidines or reduced folate, (ii) conversion of 5-FU to the nucleotide form FdUMP, FUTP or FdUTP, (iii) catabolism of 5-FU, (iv) conversion of folinic acid to 5,10-methylenetetrahydrofolate or (iv) depletion of cellular 5,10-methylenetetrahydrofolate may be causally related to variation in clinical effect of 5-FU/FA. Table 3 below lists exemplary genes that will be, or already have been screened for polymorphism.

TABLE 2

| Folate Transport | 5-FU Anabolism | 5-FU Catabolism | Conversion of Folinic Acid to 5,10-Methylene THF |
|---|---|---|---|
| Folate receptor 1 ( ) GenBank M28099 | Uridine phosphorylase GenBank X90858 | Dihydropyrimidine Dehydrogenase GenBank U09178 | Methylenetetrahydrofolate synthase GenBank L38298 |
| Folate receptor ( ) GenBank J02876 | Thymidine phosphorylase GenBank S72487 | Dihydropyrimidinase GenBank D78011 | Methenyltetrahydrofolate cyclohydrolase; formyltetrahydrofolate synthetase; Methenyltetrahydrofotate dehydrogenase (one locus) GenBank J04031 |
| Folate Transporter (SLC19AI) GenBank U19720 | Orotate phosphoribosyl-transferase GenBank J03626 | Inhibition of dTMP Synthesis | Methylenetetrahydrafolate reductase GenBank U09806 |
| Folate receptor ( ) GenBank Z32564 | Uridine Kinase GenBank D78335 Thymidine kinase 1 GenBank K02581; Thymidine Kinase 2 GenBank U77088 | Thymidylate synthase GenBank X02308 | Serine transhydroxymethylase 1 GenBank L11931 Methionine synthetase GenBank U50929 |
| Pyrimidine Transport | Ribonucleoside reductase: M1 subunit GenBank X59543 M2 subunit GenBank X59618 | Folate Polyglutamation | Glycine cleavage system, Protein H: GenBank M69175; Protein P: GenBank M64590; Protein T: GenBank D13811 |
| Nucleoside transporter 1 | Nucleoside diphosphate kinase, A subunit GenBank U29200 B subunit GenBank X58965 | Folylpolyglutamate synthetase GenBank M98045 Folylpolyglutamate hydrolase GenBank | Dihydrofolate reductase GenBank J00140 |

There are 27 genes in the above Table. Six genes which have already been surveyed for polymorphism are italicized. The following genes do not appear in the Table because there is no human cDNA in GenBank: 5-FU anabolism: Uridine monophosphate kinase; 5-FU catabolism: b-ureidopropionase; Folate metabolism: Glutamate formiminotransferase, Formiminotetrahydrofolate cyclodeaminase, Formyltetrahydrofolate hydrolase, Formyltetrahydrofolate dehydrogenase, and Protein L of the glycine cleavage system. Other genes not listed in the Table include DNA and RNA polymerases and DNA repair enzymes, some of which (e.g. DNA polymerase b and RNA polymerase II 220 and 33 kD subunits) have already been screened for polymorphism. Those additional genes are also useful in the present invention.

For several potential candidate genes there are mammalian cDNAs in GenBank but no human cDNA. For example, there is a 1,420 nucleotide full length rat β-ureidopropionase cDNA. Four overlapping human ESTs (F06711, H19181, R11806 and W55897) span 691 nucleotides of the rat coding sequence with >90% nucleotide identity. For selected candidate genes of likely importance, such as β-ureidopropionase, polymorphism analysis will be carried out on the available human sequence from dbEST.

Example 2

Variance Identification—Variances in Genes That Can Affect 5-FU/FA Action

Exemplary genes related to modulation of the action of 5-FU/FA have been analyzed for genetic variation; thymidylate synthase, ribonucleotide reductase (M1 subunit only), dihydrofolate reductase and dihydropyrimidine dehydrogenase cDNAs. 36 unrelated individuals were screened using 6 SSCP conditions and DNA sequencing. Other investigators have identified variances in MTHFR, methionine synthase and folate receptor. These findings are summarized in Table 3.

TABLE 3

Variation in Genes Which Modulate 5-FU/FA Pharmacology

| Gene Name (Genbank accession no.) | Variances | | | Heterozygote Frequency | Comments |
|---|---|---|---|---|---|
| | Base | RNA | Protein | | |
| Cytidine Deaminase (L27943) | 79 | T or G | lys27glu | >10% | |
| Dihydrofolate Reductase (J00140) | 721 | T or A | | 20% | |
| | 829 | C or T | | 14% | |
| | Rsal RFLP | | | 23, 33, 43% | 3 alleles |
| | ScrF1 | | | 26% | |
| | Rsal RFLP | | | 32% | unique Rsa1 RFLP |

TABLE 3-continued

Variation in Genes Which Modulate 5-FU/FA Pharmacology

| Gene Name (Genbank accession no.) | Variances Base | Variances RNA | Variances Protein | Heterozygote Frequency | Comments |
|---|---|---|---|---|---|
| Dihydropyrimidinase (D78011) | 1001 | A or G | gln334arg | rare | All found in patients with DHP deficiency |
| | 1303 | G or A | gly435arg | | |
| | 203 | G or C | thr68arg | | |
| | 1468 | G or C | arg490thr | | |
| | 1078 | T or C | trp360arg | rare | |
| | 812 to 814 | Insertion A | premat. term. | | |
| Dihydropyrimidine Dehydrogenase (U09178) | 166 | T or C | cys29arg | 11% | |
| | 577 | A or G | met166val | | |
| | 3925 | A or G | 3' UTR | 35% | |
| | 3937 | T or C | 3' UTR | 38% | |
| | 3432 | T or C | 3' UTR | 10% | |
| | | | arg21gln | rare | |
| | | | val1335leu | rare | |
| | 638 | A or G | tyr186cys | 2% | |
| | 784 | C or T | arg23Strp | rare | |
| | 296 to 299 | Delete TCAT | premat. term. | rare | |
| | 1682 | G or A | ser534asn | 0.5–3% | |
| | 1708 | A or G | ile543val | 7–35% | |
| | exon/intron 14 | G or A delete C | del. 581–635 premat. term. | 1% rare | 73% in DPD deficiency |
| | 1897 | G or A | val732ile | 1–7% | |
| | 2275 | G or A | arg886his | rare | |
| | 2738 | A or T | asp974trp | rare | |
| | 3002 | G or T | val995phe | rare | |
| | 2983 | | | | |
| Folate Receptor | | | | | One Msp I and 2 Pst I RFLPs |
| Folate receptor | 330–331 | 2 bp deletion | Premat. Term. | 75% | |
| Folate Transporter (SLC19A1) (U19720) | 341 | C or G | Silent | | |
| Folylpolyglutamate Synthetase (M98045) | 1747 | G or T | 3' UTR | 2% | |
| | 1900 | T or C | 3' UTR | 50% | |
| Glycine cleavage System: protein H (M69175) | 710 | C or G | 3' UTR | | |
| Glycine cleavage System: protein P (M64590) | | | ser564ile | rare | 70% in NKH patients |
| Glycine cleavage System: protein T (D13811) | 277 | G or T | Val50leu | 2% | |
| | 1073 | G or A | Arg315lys | 1% | |
| | 1083 | G or A | Silent | 2% | |
| | 1773 | C or T | 3' UTR | 3% | |
| Methenyltetrahydro-folate cyclohydrolase | 454 | G or A | Arg134lys | 22% | |
| | 969 | C or G | Gln306glu | 1% | |
| | 1614 | C or T | Silent | 1% | |
| | 2011 | G or A | Arg653gln | 35% | |
| | | | Arg293his | rare | |
| Methylenetetra-hydrofolate Reductase (U09806) | 129 | C or T | | Low | Both the amino acid changes affect MTHFR activity. |
| | 677 | C or T | Ala223val | 48% | |
| | 1068 | C or T | | low | |
| | 1298 | C or A | Ala430glu | high | |
| | 308 | T or C | silent | 5–39% | |
| | | | | rare | Rare mutations found in MTHFR deficiency |
| Methionine Synthase (U50929, U73338)) | 2756 | G or A | Asp919gly | 19–29% | Affects folate levels in colon cancer patients. |
| | 3970 | T or C | Silent | | |
| | 1158 | G or A | Cys225try | rare | |
| | 1004 | G or T | Ala to ser | | |
| | | | | rare | Rare mutations found in MS deficiency |
| Nucleoside Diphosphate kinase B (X58965) | | | BgII RFLP | | |
| Ribonucleotide Reductase, MI (X59543) | 1037 | C or A | | 33% | |
| | 2410 | A or G | | 40% | |
| | 2419 | A or G | | 20% | |
| | 2717 | T or A | | 19% | |
| | 2724 | Tin/del | | 19% | |
| | | | Sac1 RFLP | 47% | |
| Ribonucleotide | 524 | C or G | Silent | 1% | |

TABLE 3-continued

Variation in Genes Which Modulate 5-FU/FA Pharmacology

| Gene Name (Genbank accession no.) | Variances Base | Variances RNA | Variances Protein | Heterozygote Frequency | Comments |
|---|---|---|---|---|---|
| Reductase, M2 (X59618) | 1636 | C or T | 3' UTR | 1% | |
| | 2259 | T or C | 3' UTR | 1% | |
| Serine Hydroxy-methyltransferase (cytolic) (L11931) | 1444 | | Leu474phe | 23% | |
| | 1541 | C or T | 3' UTR | 26% | |
| Thymidine kinase 1 (K02581) | 90 | T or C | Silent | 50% | |
| | 279 | G or A | Silent | 13% | |
| | 282 | G or A | Silent | 30% | |
| | 772 | G or A | 3' UTR | 26% | |
| | 867 | G or A | 3' UTR | 50% | |
| | | Tac1 RFLP | | 40% | |
| | | BstEII RFLP | | 2, 34, 64% | 3 alleles |
| Thymidine kinase2 (U77088) | 1480 | T or C | 3' UTR | 9% | |
| Thymidine Phosphorylase (PD-ECGF) (S72487) | 601 | G or C | 3' UTR | 3% | |
| | 3673 | A or G | | | |
| | 3576 | T or C | silent | 54% | |
| | | | | rare | Rare mutations found in MNGIE patients |
| Thymidylate Synthase (X02308) | 276 | T or C | tyr33his | rare | |
| | 1140 | C or T | | 53% | |
| | 1210 | A or G | | 42% | |
| | 1571 | A or T | | 53% | |
| | | 28–34 nt repeats | 5' reg. Region | double: 19% | |
| Uridine mono-Phosphate synthetase (103626) | 742 | G or C | Gly213ala | 23% | |
| | 1575 | A or G | 3' UTR | 1% | |
| | | | | rare | Rare mutations found in Orotic aciduria patients |

A more complete catalog of genetic variances is shown in the following table for the dihydropyrimidine dehydrogenase (DPD) gene.

TABLE 4

Variances in Dihydropyrimidine Dehydrogenase Gene

| Variant nucleotlde (codon) | Variant base 1 (frequency) | Variant base 2 (frequency) | Effect on mRNA & protein | Comments |
|---|---|---|---|---|
| 166 (29) | T (62/70) | C (8/70) | cys29arg | Arg allele has no activity when expressed in *E. Coli* (Vreken, Human Genetics, 1997) |
| 577 (166) | A (69/72) | G (3/72) | met166val | Located in highly conserved domain; no functional studies |
| 784 (235) | C | T | arg235trp | Trp allele has no activity when expressed in *E. Coli* (Vreken, Human Genetics, 1997) |
| 1682 (534) | G (148/150) | A (2/150) | ser534asn | Apparently little or no functional effect in patient cells. |
| 1708 (543) | A (34/46) | G (12/46) | ile543val | Apparently little or no functional effect in patient cells. |
| intron 13 (destroys 5' GT splice site immediately after nt 1986) | G | A | no exon 14 | 55 missing amino acids result in unstable protein. Mutant allele may be present in ~1% of Finns; very rare in other groups, but detected in 8 of 11 patients with complete deficiency. |
| 1897 (606) | — | deletion of C | frameshift | Low/no activity allele; reported in only one patient so far. |
| 2738 (886) | G | A | arg886his | His allele has 25% of normal activity when expressed in Coli (Vreken, Human Genetics, '97) |
| 3002 (974) | A | T | asp974val | Val allele apparently has very low or no activity in patient sample. Very low frequency allele (<0.2% in Americans). |

TABLE 4-continued

Variances in Dihydropyrimidine Dehydrogenase Gene

| Variant nucleotide (codon) | Variant base 1 (frequency) | Variant base 2 (frequency) | Effect on mRNA & protein | Comments |
| --- | --- | --- | --- | --- |
| 3925 | A (41/62) | G (21/62) | 3' UTR | Two high frequency variances, 12 nt apart but not in complete linkage disequilibrium. |
| 3937 | C (40/64) | T (24/64) | 3' UTR | |

Variances in the exemplary genes above which affect the activity of the corresponding gene product have the potential to modulate the activity of 5-FU/FA and thereby provide predictive capability concerning the efficacy of such treatment in a particular patient. As discussed above, such predictive capability can further be provided by the joint determination of multiple variances, in one or a plurality of genes or both. Similarly, such variances can provide such predictive capability for other treatments, e.g., treatments with other compounds, which involve these genes.

Example 3

Relationship of Genes to Drug Response—5-Flurouracil 5-fluorouracil (5-FU) is a widely used chemotherapy drug. The effectiveness of 5-FU is potentiated by folinic acid (FA; generic name: leukovorin). The combination of 5-FU and FA is standard therapy for stage III/IV colon cancer. Patient responses to 5-FU and 5-FU/FA vary widely, ranging from complete remission of cancer to severe toxicity.

Clinical Use and Effectiveness of 5-FU and 5-FU/FA

5-FU is a pyrimidine analog in clinical use since 1957. 5-FU is used in the standard treatment of gastrointestinal, breast and head and neck cancers. Clinical trials have also shown responses in cancer of the bladder, ovary, cervix, prostate and pancreas. The remainder of this discussion will concern colorectal cancer. 5-FU is used both in the adjuvant therapy of Dukes Stage B and C cancer and in the treatment of disseminated cancer. 5-FU alone produces partial remissions in 10–30% of advanced colorectal cancers, however only a few percent of patients have complete remissions, and no benefit in survival has been demonstrated.

In the last 15 years a variety of biochemically motivated strategies for modulating 5-FU activity have been tested. For example, 5-FU has been used in combination with PALA, a pyrimidine synthesis inhibitor, to deplete cellular pools of UTP and thereby enhance formation of FUTP; in combination with methotrexate, to inhibit purine anabolism, leading to increased PRPP levels and consequent increased conversion of 5-FU to its active nucleotide metabolites; and in combination with folinic acid, which increases intracellular pools of reduced folate, driving formation of the ternary inhibitory complex formed by 5,10 methylenetetrahydrofolate, FdUMP and thymidylate synthase. Levamisole, interferon and alkylating agents have also been used in combination with 5-FU. 5-FU/Levamisole and 5-FU/FA are widely used in the adjuvant treatment of colon cancer, while 5-FU/FA is the most commonly used regimen for advanced colorectal cancer. Six of seven prospective randomized trials of 5-FU/FA vs. 5-FU alone in patients with advanced cancer have demonstrated up to two fold higher response rates to 5-FU/FA, while two of the studies also showed increased survival.

Two major dosing regimens are used: 5-FU plus low dose FA given for five consecutive days followed by a 23 day interval, or once weekly bolus iv 5-FU plus high dose FA. The higher FA dose results in plasma FA concentrations of 1 to 10 uM, comparable to those required for optimal 5-FU/FA synergy in tissue culture, however low dose FA (20 mg/m$^2$ vs. 500 mg/m$^2$) has produced comparable clinical benefit. Ongoing clinical trials are designed to further test new drug combinations. In summary, relatively few patients—in the single digits—live longer as a result of 5-FU/FA, although significantly more have partial disease remission. The factors that determine which patients respond or have side effects are not known.

5-FU Modulators

Leukovorin (folinic acid) is the most widely used 5-FU modulator, however a variety of other molecules have been used with 5-FU, including, for example, interferon-alpha, hydroxyurea, N-phosphonacetyl-L-aspartate, dipyridamole, levamisole, methotrexate, trimetrexate glucuronate, cisplatin and radiotherapy. S-1 is a novel oral anticancer drug, composed of the 5-FU prodrug tegafur plus gimestat (CDHP) and otastat potassium (Oxo) in a molar ratio of 1:0.4:1, with CDHP inhibiting dihydropyrimidine dehydrogenase in order to prolong 5-FU concentrations in blood and tumour and Oxo present as a gastrointestinal protectant. Some of these regimens show promising results, but no clear improvement over 5-FU/leukovorin. The clinical development and use of regimens containing 5-FU plus modulators may be facilitated by the methods of this invention.

Toxicity of 5-FU and Folinic Acid

5-FU toxicity has been well documented in randomized clinical trials. Patients receiving 5-FU/FA are at even greater risk of toxic reactions and must be monitored carefully during therapy. A variety of side effects have been observed, affecting the gastrointestinal tract, bone marrow, heart and CNS. The most common toxic reactions are nausea and anorexia, which can be followed by life threatening mucositis, enteritis and diarrhea. Leukopenia is also a problem in some patients, particularly with the weekly dosage regimen. In a recent randomized trial of weekly vs. monthly 5-FU/FA, there were 7 deaths related to drug toxicity among 372 treated patients (1.9%; Buroker et al. 1994). 31% of patients receiving the weekly regimen suffered diarrhea requiring hospitalization for a median of 10 days. Other severe toxicities, which occured at lower frequency, included leukopenia and stomatitis. In another example, 36% of patients receiving weekly bolus 5-FU plus FA (500 mg/m$^2$), in a NSABP trial suffered NCI grade 3 toxicity (Wolmark et al., 1996). Clearly, toxicity is a major cost of 5-FU/FA therapy, measured both in patient suffering and in financial terms (the cost of care for drug induced illness).

Other Factors

Many non-genetic factors can influence the response of cancers to drugs, including tumor location, vasculature, cell growth fraction and various drug resistance mechanisms. It is therefore not possible to explain all heterogeneity in response to 5-FU/FA administration by genetic variation. However, based on genetic studies of other quantitative traits it appears that a significant fraction of variation in drug response is due to genetic variation.

Example 4

Genetic Component of Drug Response Variability
Genetically Determined Variation in Response to 5-FU: Studies of Dihydropyrimidine Dehydrogenase Deficiency
Dihydropyrimidine Dehydrogenase Deficiency is Associated with 5-FU Toxicity 5-FU is inactivated by the same metabolic pathway as thymine and uracil (see above). DPD catalyzes the first, rate limiting step in pyrimidine catabolism and accounts for elimination of most 5-FU. Normal individuals eliminate 5-FU with a half life of ~10–15 minutes and excrete only 10% of a dose unchanged in the urine. In contrast, people genetically deficient in DPD eliminate 5-FU with a half life of ~2.5 hours and excrete 90% of a dose unchanged in the urine (Diasio et al., 1988). DPD deficiency has two clinical presentations: (i) an inborn error of metabolism causing some degree of neurologic dysfunction or (ii) asymtomatic until revealed by exposure to 5-FU or other pyrimidine analogs. With either presentation there is combined hyperuraciluria and hyperthyminuria. The vastly increased 5-FU half life in DPD deficient individuals causes severe toxicity and even death. Recently several mutations have been identified in DPD genes of deficient individuals (Wei et al., 1996), however none of these alleles appears to occur at appreciable frequency, so the cause of wide population variation in DPD levels is still not understood.

Dihydropyrimidine Dehydrogenase (DPD) Inhibitors

More than 85% of an injected dose of 5-FU is rapidly inactivated by dihydropyrimidine dehydrogenase (DPD) to therapeutically inactive catabolic products, however there is evidence that said catabolic products may be toxic to normal tissues. This has led to the development of DPD inhibitors with the aim to modify the therapeutic index of 5-FU. Several inhibitors in combination with 5-FU are under preclinical and clinical evaluation, including uracil and 5-chloro-2,4-dihydroxy pyridine, as modulators of 5-FU derived from its prodrug tegafur and 5-ethynyluracil as a modulator of 5-FU itself (Eniluracil, 776C85; Glaxo Wellcome Inc, Research Triangle Park, N.C.). Other compounds with DPD inhibitory activity include 5-propynyluracil. (For a review of DPD inhibitors see: Diasio, RB inproving 5-FU with a Novel Dihydropyrimidine Dehydrogenase Inactivator, Oncology, Mar. 12, 1998 (3 Suppl. 4):51–6.)

Population Studies of DPD Activity Show Wide Variation

Population surveys of DPD activity in normal individuals have been performed using blood and liver samples. These studies reveal a broad unimodal Gaussian distribution of DPD activity over a 7 to 14 fold range, with some individuals having very low or even undetectable levels. For example Etienne et al. (1994) report DPD activity ranging from 0.065 to 0.559 nM/min/mg protein in a study of 152 men and 33 women, while Fleming et al. (1993) found DPD activity in 66 cancer patients varied from 0.17 to 0.77 nM/min/mg protein. Lu et al (1995) found 18-fold variation in liver DPD assayed in 138 individuals. Milano and Etienne (1994) suggested that the frequency of heterozygous and homozygous deficiendy is 3% and 0.1%, respectively. The DNA sequence alterations responsible for null DPD alleles do not account for the high population variability (Ridge et al., 1997).

DPD Levels Correlate With Response to 5-FU

Intratumoral DPD levels have been measured in patients receiving 5-FU chemotherapy. When complete responders were compared to partial or nonresponders, DPD levels were lower in the compete responders (Etienne et al., 1995). Leukocyte DPD levels have also been measured in patients receiving 5-FU/FA chemotherapy. When patients were divided into 3 groups: high, medium and low DPD activity, the frequency of serious side effects was highest in the low DPD group and vice versa (Katona et al., 1997).

Biochemical Studies of Alternate Allelic Forms of DPD

The power of genetic analysis can be augmented by biochemical studies of alternate allelic forms of enzymes. Biochemical data on the distribution of activity of a series of enzymes in a biochemical pathway provides the basis for metabolic flux analysis (Keightly, 1996). It is beyond the scope of this proposal to exhaustively analyze biochemical variation in the enzymes of pyrimidine and folate metabolism. However, since we have identified new variances in DPD that may affect enzyme expression or activity, and because DPD is already proven to play a role in 5-FU response, we will determine the relationship between genotype and biochemistry for this enzyme.

DPD cDNAs have been cloned from a variety of higher eukaryotes and binding sites for its cofactors, prosthetic groups and substrate have been defined experimentally or by analogy with known consensus motifs (Yokata et al., 1994). The DPD polymorphisms that affect protein sequence occur at amino acids 29 (cys/arg) and 166 (met/val) in the amino-terminal one-third of the protein. Phylogenetic comparison of this region from boar, human, cow, fly, and bacteria (see below) shows that there are actually two highly conserved motifs that resemble either iron/sulfur or zinc binding motifs, the latter being more likely due to the spacing of the cysteine residues. The region around the met/val polymorphism at amino acid 166 is highly conserved. Even the spacing of the putative zinc-finger domains is maintained between distantly related species, hinting at their importance. Since amino acid 166 is close to a highly conserved (and probably functionally important) region and is itself conserved, being a methionine in all species, it seems likely that perturbations in this position would have consequence. The polymorphism substitutes a long amino acid side chain capable of hydrogen bonding (methionine) for a compact, hydrophobic amino acid (valine). The region around amino acid 29 is not as well conserved.

Common DPD Haplotypes

Eight haplotypes from 58 chromosomes (29 individuals) have been identified. Using methods described above, the DNA from these samples were analyzed by PCR. The single base pair substitutions at four locations were identified as allelic haplotypes, e.g. base pair number 166, 577, 3925, 3937. Base pair positions, 3925 and 3937 are located in the 3 prime untranslated regions of the cDNA and base pairs 166 and 577 are within the coding region.

TABLE 5

Identified DPD Haplotypes

| No. Chromosomes | Base Position | | | |
|---|---|---|---|---|
| | 166 | 577 | 3925 | 3937 |
| 14 (24%) | T (cys) | A (met) | G | C |
| 16 (28%) | T (cys) | A (met) | A | C |
| 16 (28%) | T (cys) | A (met) | A | T |
| 4 (7%) | C (arg) | A (met) | A | T |
| 3 (5%) | C (arg) | A (met) | G | C |
| 3 (5%) | C (arg) | A (met) | A | C |
| 1 (2%) | T (cys) | G (val) | G | C |
| 1 (2%) | T (cys) | G (val) | A | C |
| Total = 58(100%) | | | | |

Example 5

Exemplary Genes Involved in Folate Transport and Metabolism

While examples above concern 5-FU/FA action and genes which are expected to modulate such action, it is also useful to utilize genes involved in folate transport and metabolism generally. A number of these genes are also involved in 5-FU/FA action. Genes known to be involved in folate transport and metabolism are listed in the table below, along with available GenBank accession numbers for deposited sequences.

Example 6

Drugs Targeting Genes Involved in Folate Transport and Metabolism

In concert with the identification of useful genes involved in folate transport and metabolism, the table below identifies certain drug classes used for treatment of identified disorders, along with a brief characterization of the action of the drug. Exemplary drugs are identified within the individual classes. Variable response of patients to administra-

TABLE 6

Gene Field: Folate Transport & Metabolism

| Folate Transporters | Folate Polyglutamation | | Biosynthesis, Degradation and Interconversion of Folates |
|---|---|---|---|
| Folate receptor 1( ) (GenBank M28099) | Folylpolyglutamate synthetase (GenBank M98045) | Formiminotetrahydrofolate cyclodeaminase | Glutamate formiminotransferase |
| Folate receptor ( ) (GenBank J02876) | | Methenyltetrahydrofolate synthetase | Formyltetrahydrofolate hydrolase |
| Folate receptor ( ) (GenBank Z32564) | | Methylenetetrahydrofolate dehydrogenase | Methylenetetrahydrofolate synthase GenBank L38298 |
| Folate Transporter (SLC19A1) GenBank U19720 | | Methionine synthetase GenBank U50929 | Methylenetetrahydrofolate reductase GenBank U09806 |
| | | Dihydrofolate reductase GenBank J00140 | Serine transhydroxymethylase 1 GenBank L11931 |
| Folate Absorbtion Pteroyl-glutamyl carboxypeptidase | Inhibition of dTMP Synthesis Thymidylate synthase GenBank X02308 | Methenyltetrahydrofolate cyclohydrolase; formyltetrahydrofolate synthetase; Methenyltetrahydrofol-ate dehydrogenase (one locus) GenBank J04031 | Glycine cleavage system, Protein H: GenBank M69175; Protein P: GenBank M64590; Protein T: GenBank D13811; Protein L Formyltetrahydrofolate dehydrogenase |

Genes Affecting the Action of Drugs which Modulate Folate Metabolism.

There are 24 genes in the Table, four of which we have already surveyed for polymorphism (italicized genes). The genes with GenBank numbers are currently being screened for variances. Genes lacking GenBank numbers are not yet represented in GenBank as full length cDNAs; but will be scanned using relevant EST collections or using sequences from other publicly available sources.

tion of drugs of these classes, or administration of the specific drugs can be used in identifying variances responsible for such variable response. As described above, those variances can then be used in diagnostic tests, methods of selecting a treatment, methods of treating a patient, or other methods utilizing genetic variance information as otherwise described.

TABLE 7

Drug Field: Folate Transport & Metabolism

| Disease/Indication | Drug Class | Mechanism of Action | Exemplary Drugs |
|---|---|---|---|
| Cancer | Reduced folates | Block dTMP biosynthesis by inhibiting thymidylate synthase (TS) via formation of ternary complex involv-ing TS, 5-fluorodeoxyuridine and 5,10-methylenetetrahydrofolate | leukovorin, L-leukovorin, citrovor-um factor (used with 5-fluorouracil or related drugs) |
| Cancer | Reduced folates | Rescue bone marrow from lethal toxicity after high dose methotrexate | leukovorin, L-leukovorin, citrovor-um factor |
| Cancer | Folate analogs (antifolates) | Block de novo purine biosynthesis by inhibiting dihydrofolate reduc-tase, TS, azatetrahydrofolate | Methotrexate, aminopterin, dide- |

TABLE 7-continued

Drug Field: Folate Transport & Metabolism

| Disease/Indication | Drug Class | Mechanism of Action | Exemplary Drugs |
|---|---|---|---|
| Proliferative skin diseases (psoriasis) | Folate analogs (antifolates) | Block de novo purine biosynthesis by inhibiting dihydrofolate reduc-tase, TS, | Methotrexate, aminopterin, dide-azatetrahydrofolate |
| Immunosup-pression | Folate analogs (antifolates) | Block de novo purine biosynthesis by inhibiting dihydrofolate reduc-tase, TS, | Methotrexate, aminopterin, dide-azatetrahydrofolate |
| Autoimmune diseases, such as rheumatoid arthritis | Folate analogs (antifolates) | Block de novo purine biosynthesis by inhibiting dihydrofolate reduc-tase, TS, azatetrahydrofolate | Methotrexate, aminopterin, dide- |
| Folate deficiency | Folic acid | Increase folates for purine and pyrimidine biosynthesis | Folic acid |
| Cardiovascular disease (prevent atherosclerosis) | Folic acid | Reduce plasma homocysteine levels in patients with low MTHFR levels | Folic acid |
| Prevent spina bifida | Folic acid | Reduce plasma homocysteine levels in patients with low MTHFR levels | Folic acid |

Table 7. Drugs which affect or are affected by folate metabolism. A wide spectrum of diseases are treated with drugs that affect folate metabolism. Some drugs are used in the treatment of several diseases. All of the listed drugs are frequently used in combination with other drugs. For example methotrexate is used in cancer chemotherapy with cytoxan and fluoruracil to treat breast cancer, among other combinations.

Folate Analogs

Many novel antifolate compounds with unique pharmacologic properties are currently in clinical development. These newer antifolates differ from methotrexate, the most widely used and studied drug in this class, in terms of their lipophilicity, cellular transport mechanism, level of polyglutamation, and specificity for inhibiting folate-dependent enzymes, such as dihydrofolate reductase, thymidylate synthase, or glycinamide ribonucleotide formyltransferase. The clinical development and use of these new compounds can be affected by the methods of this invention. The new folate analogs include quinazoline derivatives such as ZD1694 (Tomudex, AstraZeneca) which requires Reduced Folate Carrier (RFC) mediated cell uptake and polyglutamation by Folylpolyglutamate Synthetase (FPGS); ZD9331 (AstraZeneca), which requires the RFC but is not polyglutamated by FPGS; LY231514 (Eli Lilly Research Labs, Indianapolis, Ind.) is a multitargeted pyrrolopyrimidine analogue antifolate which requires the RFC and polyglutamation; GW1843 (1843U89, GlaxoWellcome) is a benzoquinazoline compound with potent TS inhibitory activity, and which enters cells via the RFC but is polyglutamated only to the diglutamate, which leads to higher cellular retention without augmenting TS inhibitory activity; AG337 (p.o. and i.v. forms) and AG331 (both by Agouron, La Jolla, Calif., now part of Warner Lambert) are lipophilic TS inhibitors with action independent of the RFC and polyglutamation by FPGS; trimetrexate (US Bioscience) is a; Aminopterin is an older drug which has received renewed attention recently; edatrexate, piritrexim and lometrexol are other antifolate drugs. More generally, 5,8-dideazaisofolic acid (LAHQ), 5,10-dideazatetrahydrofolic acid (DDATHF), and 5-deazafolic acid are structures into which a variety of modifications have been introduced in the pteridine/quinazoline ring, the C9-N10 bridge, the benzoyl ring, and the glutamate side chain (see article below). Also Lilly have recently synthesized a new series of 2,4-diaminopyrido[2,3-d]pyrimidine based antifolates which are being evaluated both as antineoplastic and antiarthritic agents.

Other Therapeutic Categories in which Folate or Pyrimidine Pathwyas may be Relevant to Drug Development 1) Cardiovascular Drugs Homocysteine is a proven risk factor for cardiovascular disease. One important role of the folate cofactor 5-methyltetrahydrofolate is the provision of a methyl group for the remethylation of homocysteine to methionine by the enzyme methionine synthase. Variation in the enzymes of folate metabolism, for example methionine syntase or methylenetetrahydrofolate reductase (MTHFR), may affect the levels of 5-methyltetrahydrofolate or other folates that in turn influence homocysteine levels. The contribution of elevated homocysteine to atherosclerosis, thromboembolic disease and other forms of vascular and heart disease may vary from one patient to another. Such variation may be attributable, at least in part, to genetically determined variation in the levels or function of the enzymes of folate metabolism described in this application. Assistance of clinical development or use of drugs to treat said cardiovascular diseases might be afforded by an understanding of which patients are most likely to benefit. This is true whether the drugs are aimed at the modulation of folate levels (e.g. supplemental folate) or at other known causes of cardiovascular disease (e.g. lipid lowering drugs such as statins, or antithrombotic drugs such as salicylates, heparin or GPIIIa/IIb inhibitors). It may, for example, be desirable to exclude patients whose disease is significantly attributable to elevated homocysteine from treatment with agents aimed at the amelioration of other etiological causes, such as elevated cholesterol. Thus, the understanding of variation in the enzymes of folate transport and metabolism may be important in evaluating drugs used to treat atherosclerosis, thromboembolic diseases and other forms of vascular and heart disease.

2) CNS Drugs

The observation that phencyclidine, an NMDA receptor antagonist, induces a psychotic state closely resembling schizophrenia in normal individuals has led to attempts to modulate NMDA receptor function in schizophrenic patients. The amino acid glycine is an obligatory coagonist (with glutamate) at NMDA receptors (via its action at a strychnine-insensitive binding site on the NMDA receptor complex), and consequently glycine or glycinergic agents (e.g. glycine, the glycine receptor partial agonist, D-cycloserine, or the glycine prodrug milacemide) have been tried as an adjunct to conventional antipsychotics for the treatment of schizophrenia. Several trials have demonstrated a moderate improvement in negative symptoms of schizophrenia. Because the folate pathway modulates levels of serine and glycine, the endogenous levels of glycine in neurons may affect the response to glycine or glycinergic drugs. In particular, interpatient variation in glycine metabolism may affect drug efficacy.

Example 7

Genes Related to Pyrimidine Transport and Metabolism

Similar to the genes involved in folate transport and metabolism, genes involved in the related pathways of pyrimidine transport and metabolism are useful in the aspects of the present invention, e.g., for identifying variances responsible for variable treatment response, diagnostic methods, and methods of selecting a patient to receive a treatment. Exemplary genes are provided below and are further identified by cellular function. Genes involved in those functions are generally useful in the present invention.

are not yet represented in GenBank as full length cDNAs; but can be evaluated using relevant EST collections. Genes not listed in the Table but related to the mechanism of action of pyrimidine analogs include DNA and RNA polymerases and subunits and DNA repair enzymes, some of which (e.g. DNA polymerase and 220 kD and 33 kD subunits of RNA polymerase H) have already been screened for polymorphism. Such additional genes can also be used in the present invention.

Example 8

Drugs Targeting Genes Involved in Pyrimidine Transport & Metabolism

As was described above for drugs modulating genes involved in folate transport and metabolism, particular drug

TABLE 8

Gene Field: Pyrimidine Transport & Metabolism

| Pyrimidine Transport | Pyrimidine Biosynthesis - de novo and Salvage Pathways | | Pyrimidine Catabolism |
|---|---|---|---|
| Equilibrative nucleoside transporter 1 | Uridine phosphorylase GenBank X90858 | Ribonucleoside reductase: MI subunit GenBank X59543 M2 subunit GenBank X59618 | Dihydropyrimidine Dehydrogenase GenBank U09178 |
| Equilibrative nucleoside transporters 2, 3, 4 & 5 | Thymidine phosphorylase GenBank S72487 | Nucleoside diphosphate kinase, A subunit GenBank U29200 | Dihydropyrimidinase GenBank D78011 |
| Concentrative nucleoside transporters | Orotate phosphoribosyl-transferase GenBank J03626 | B subunit GenBank X58965 | -ureidopropionase |
| | Uridine Kinase GenBank D78335 | Unidine mono-phosphate kinase | Cytidine deaminase |
| | Thymidine kinase GenBank K02581; Thymidine Kinase 2 GenBank U77088 | Deoxycytidylate kinase | dCMP deaminase |
| Inhibition of dTMP Synthesis Thymidylate synthase GenBank X02308 | Deoxycytidine kinase | aminotransferase | β-alanine-pyruvate aminotransferase β-alanine-α-detoglutarate |

Table 8. Genes affecting the action of drugs which modulate pyrimidine metabolism. We have already surveyed three of the above genes for polymorphism (italicized genes). The genes with GenBank numbers are currently being screened for variances. Genes in the table lacking GenBank numbers classes and exemplary drugs are identified in the table below which modulate the action of pyrimidine transport and metabolism genes. These classes of drugs and exemplary drugs are similarly useful for identifying variances which affect the action

TABLE 9

Drug Field: Pyrimidine Transport & Metabolism

| Disease/Indication | Drug Class | Mechanism of Action | Exemplary Drugs |
|---|---|---|---|
| Cancer | Fluoropyrimidines | Block dTTP biosynthesis by inhib-iting thymidylate synthase; inhibit replication, transcription and/or repair by incorporation into DNA and RNA. | 5-FU, fluorode-oxyuridine, flu-orodeoxyuridine monophosphate, tegafur, ftorafur. |
| Cancer | Dihydropyrimidine dehydrogenase inhibitors | Potentiate fluoropyrimidines by blocking their catabolism, increasing half life. | 5-ethynyluracil; 5-propynyluracil; 2,6 dihydroxypy-ridine |
| Cancer | Cytidine analogs | Incorporation into DNA and conse-quent inhibition of DNA synthesis (replication, transcription, repair). | Cytosine arabino-side, gemcitabine, 5-azacytidine, 5-azacytosine ara-binoside, others. |

TABLE 9-continued

Drug Field: Pyrimidine Transport & Metabolism

| Disease/Indication | Drug Class | Mechanism of Action | Exemplary Drugs |
| --- | --- | --- | --- |
| Cancer | Other pyrimidine analogs | Inhibition of nucleic acid synthesis | |
| Cancer | Ribonucleotide reductase inhibitors | Inhibit reduction of ribonucleotides (e.g. CTP) to deoxyribonuc-leotides (dCTP) | Hydroxyurea |
| Cancer | Nucleotide/nucleoside uptake inhibitors | Block import of cytotoxic pyrimi-dine analogs (protective effect), or block import of normal pyrimidine nucleotides, thereby reducing salvage synthesis and increasing need for de novo synthesis, including dTMP synthesis. | dipyridamole, BIBW 22 (a dipyridamole analog), nitroben-zylthioinosine |

Table 9. Genes affecting the action of drugs which modulate pyrimidine metabolism. A variety of proliferative diseases, especially cancer, are treated with drugs that affect pyrimidine metabolism. All of the listed drugs are frequently used in combination with other drugs.

Other Pyrimidine Analogs

There are a large number of pyrimidine analogs in clinical development for a wide variety of indications. One of the most common indications is cancer and leukemia and lymphoma of various types. For example, 2',2'-difluorodeoxycytidine (gemcitabine; Gemzar) is a pyrimidine nucleoside drug with clinical efficacy in several common solid cancers; cytosine arabinoside (ARA-C) is another pyrimidine analog used in the treatment of leukemia; 2-chlorodeoxyadenosine and fludarabine (F-araA) are also used as antineoplastic drugs. 2'-deoxy-2'-(fluoromethylene) cytidine (MDL 101,731, Kyowa Hakko Kogyo Co.), 2',2'-difluorodeoxycytidine, 5-aza-2'deoxycytidine (decitabine), 5-azacytidine, 5-azadeoxycytidine, and are under development as antineoplastic drugs.

CNS Drugs—Pyrimidine Pathway

The pyrimidine nucleoside, uridine, has been proposed as a potential supplement in the treatment of psychosis based on its ability to reduce haloperidol-induced dopamine release. Thus, coadministration of uridine with haloperidol might enhance the antipsychotic action of standard neuroleptics, allowing for a reduction in dose and thereby a reduction in the frequency of side effects. The presumed mechanism is interaction with dopamine or GABA neurotransmission. The levels or function of pyrimidine transporters or pyrimidine de novo or salvage biosynthetic enzymes, or pyrimidine catabolic enzymes may affect the action of neuroleptics, or their modulation by pyrimidine nucleosides or pyrimidine analogs.

Other Therapeutics Relevant to the Pyrimidine Pathway

Another possible mode of pyrimidine nucleotide action is via stimulation of thromboxane A2 release from cultured glial cells. Uridine triphosphate, uridine diphosphate, cytidine triphosphate, and deoxythymidine triphosphate all induce concentration-dependent increases in the release of thromboxane A2 from cultured glial cells, indicating a possible role in brain response to damage in vivo.

Other cancers such as head and neck, breast, pancreas, other gastrointestinal cancers including stomach and intestinal may be directly targeted by therapeutic intervention that affects DNA methylation levels, pyrimidine synthesis, transport, and degradation pathways.

Many neurological diseases in both the CNS and the periphery may also be affected by therapeutic intervention of DNA methylation, pyrimidine synthesis, transport, and degradation pathways. Such intervention may be of therapeutic benefit to halt, retard, and or reduce symptoms of these often debilitating diseases.

Example 9

Drugs That Affect the Folate and Pyrimidine Pathways

There are many potential candidate therapeutic interventions or drugs that can affect the folate and pyrimidine pathways. Categories of these are 5-FU prodrugs, drugs that affect DNA methylation pathways, and other drugs that have been developed for similar indications as 5-FU.

5-FU Prodrugs

The clinical development and use of 5-FU prodrugs is further subject to improvement by the methods of this invention. These drugs are generally modified fluoropyrimidines that require one or more enzymatic activation steps for conversion into 5-FU. The activation steps may result in prolonged drug half-life and/or selective drug activation (i.e. conversion to 5-FU) in tumor cells.

Examples of such drugs include capecitabine (Xeloda, Roche), a drug that is converted to 5-FU by a three-step pathway involving Carboxylesterase 1, Cytidine Deaminase and Thymidine Phosphorylase. Another 5-FU prodrug is 5' deoxy 5-FU (Furtulon, Roche) which is converted to 5-FU by Thymidine Phosphorylase and/or Uridine Phosphorylase. Another 5-FU prodrug is 1-(tetrahydro-2-furanyl)-5-fluorouracil (FT, ftorafur, Tegafur, Taiho—Bristol Myers Squibb), a prodrug that is converted to 5-FU by cytochrome P450 enzyme, CYP3A4.

Drugs Acting on DNA Methyation Pathways

Antivirals

Herpes virus thymidine kinase phosphorylates many 5-substituted 2'-deoxyuridines, analogs of thymidine (e.g., idoxuridine, trifluridine, edoxudine, brivudine) and 5-substituted arabinofuranosyluracil derivatives (?5-Et-Ara-U, BV-Ara-U, Cl-Ara-U). The 5'-monophosphates are further phosphorylated by cellular enzymes to the 5'-triphosphates, which are usually competitive inhibitors of the viral-coded DNA polymerases.

Unlike herpes viruses, retroviruses including but not limited to human immunodeficiency viruses do not encode specific enzymes required for the metabolism of the purine or pyrimidine nucleotides to their corresponding 5'-triphosphates. Therefore, 2',3'-dideoxynucleosides and acyclic nucleoside phosphonates must be phosphorylated and metabolized by host cell kinases and other enzymes of purine and/or pyrimidine metabolism. In this way, affecting the pyrimidine synthetic, transport, or degradation pathways by candidate therapeutic intervention may be therapeutic beneficial in treating retroviral infections. Examples of candidate antivirals that may be affected by alteration of pyrimidine synthetic, transport, or degradation pathwyas are azidothymidine (AZT), acyclovir, and ganciclovir. These and other drugs have been used both as antivirals and antineoplastic agents.

Other Drugs Developed for Similar Indications as 5-FU

A variety of drugs are being developed for similar indications as 5-FU, and/or are being tested in combinations with 5-FU/leukovorin. These include the new platinum compound oxaliplatin (L-OHP) and the topoisomerase I inhibitors irinotecan (CPTI 1, Pharmacia-UpJohn) and topotecan. The effective clinical development or clinical use of these drugs may be enhanced by the methods of this invention. In particular, identification of patients likely to respond to 5-FU with or with our leukovorin, may be useful in selecting optimal responders to other drugs. Alternatively identification of patients likely to suffer toxic response to 5-FU containing regimens may allow identification of patients best treated with other drugs. Other drugs with activity against cancers usually treated with regimens containing 5-FU (e.g. metastatic colon cancer) include Suramin, a bis-hexasulfonated napthylurea; 6-hydroxymethylacylfulvene (HMAF; MGI 114); LY295501; bizelesin (U-7779; NSC615291), ONYX-015, monoclonal antibodies (e.g. 17-IA and MN-14), protein synthesis inhibitors such as RA 700, and angiogenesis inhibitors such as PF 4. Still other drugs may prevent colorectal cancer by preventing the formation of colorectal polyps (eg, cyclooxygenase inhibitors may induce apoptosis of polyps).

Example 10

Protocol for Clinical Trial for Determining the Relationship Between Toxicity of a Drug and Genetic Variances in Genes Related to the Action of the Drug THIS EXAMPLE PROVIDES AN EXEMPLARY CLINICAL TRIAL AS A CASE CONTROL STUDY WHICH INCLUDES EVALUATING THE EFFECTS OF SEQUENCE VARIANCES IN ENZYMES WHICH CAN MEDIATE THE EFFECTS OF A KNOWN DRUG, IN THIS CASE N AN ANTICANCER TREATMENT. THE INFORMATION IN THE BACKGROUND SECTION OF THIS PROTOCOL IS ALSO PROVIDED IN LARGE PART IN THE DETATILED DESCRIPTION, BUT IS REPEATED HERE FOR COMPLETENESS OF THE PROTOCOL DESCRIPTION.

PROTOCOL TITLE: Case-control study to determine the relationship between toxicity of 5-fluorouracil (5-FU) given with folinic acid (FA) to patients with solid tumors and DNA sequence variances in enzymes that mediate the action of 5-FU and FA.

II. SIGNATURE PAGE

Name, position, and address of individual approving protocol from study sponsor.

Name, position, and address of individual approving protocol from study sponsor.

III. TABLE OF CONTENTS

SIGNATURE PAGE 124
TABLE OF CONTENTS 125
ACRONYMS AND ABBREVIATIONS 127
STUDY FLOW CHART 128
1. SUMMARY 129
2. INTRODUCTION 131

-continued 2.1 Background 131
2.1.1 Potential for Improved Effectiveness of 5-FU and 5-FU/FA 131
2.1.2 Metabolic Pathways that Affect 5-FU/FA Action 133
2.1.3 Genetically Determined Variation in Response to 5-FU: 137 Studies of Dihydropyrimidine Dehydrogenase Deficiency
2.1.4 Variances in Genes That May Affect 5-FU/FA Action 138
2.1.5 Analysis of Haplotypes Increases Power of Genetic Analysis 138
2.1.6 Biochemical Studies of Alternate Allelic Forms of DPD 140
2.2 Study Rationale 140
3. OBJECTIVES 141
3.1 Primary Objective 141
3.2 Secondary Objectives 141
4. STUDY DESIGN 142
4.1 Study Outline 142
4.2 Subject Withdrawal from the Study 142
4.3 Discontinuation of the Study 142
5. STUDY POPULATION 142
5.1 Number of Subjects 142
5.2 Inclusion Criteria 143
5.3 Exclusion Criteria 143
5.4 Screening Log 144
6. ALLOCATION PROCEDURE 144
8. SCHEDULE OF EVENTS 144
11. STATISTICAL STATEMENT AND ANALYTICAL PLAN 145
11.1 Sample Size Considerations 145
11.2 Description of Objectives and EndpointS 145
11.2.1 Primary Objective and Endpoints 146
11.2.2 Secondary Objectives and Endpoints 146
11.3 CRiteria for the Endpoints 146
11.4 Statistical Methods To Be Used in Objective Analyses 147
12. ETHICAL REQUIREMENTS 147
12.1 Declaration of Helsinki 147
12.2 Subject Information and Consent 148
12.3 Subject Data Protection 148
13. FURTHER REQUIREMENTS AND GENERAL INFORMATION 148
13.1 Study Committee 148
13.2 Changes to Final Study Protocol 149
13.3 Record Retention 149
13.4 Reporting and Communication of Results 149
13.5 PROTOCOL COMPLETION 150
REFERENCES 151
SIGNED AGREEMENT OF THE STUDY PROTOCOL 152
APPENDIX II 154

IV. ACRONYMS AND ABBREVIATIONS

| | |
|---|---|
| 5-FU | 5-Fluorouracil |
| FA | Folinic acid |
| ° C. | Degree centigrade |
| CBC | Complete blood count |
| CRF | Case report form |
| DCC | Data Coordinating Center |
| DMC | Data Monitoring Committee |
| EC | Ethical Committee |
| ECG | Electrocardiogram |
| e.g. | For example |
| ° F. | Degrees Fahrenheit |
| FDA | Food and Drug Administration |
| i.e. | That is |
| IRB | Institutional Review Board |
| IV | Intravenous |
| mcg | Microgram |
| mg | Milligram |
| mL | Milliliter |
| mm$^3$ | Cubic millimeter |
| PD | Pharmacodynamic |
| PK | Pharmacokinetic |
| ® | Registered trade mark |
| REB | Research Ethics Board |
| USA | United States of America |
| USP | United States Pharmacopoeia |

V. STUDY FLOW CHART

|  | File Research | Medical Visit |
|---|---|---|
| Selection of patients from the file | X |  |
| Informed Consent Form signed |  | X |
| Inclusion/Exclusion criteria checking |  | X |
| Chart reporting |  | X |
| Demographic reporting |  | X |
| Blood sampling |  | X |

VI. 1. SUMMARY

Protocol

Title: Case-control study to determine the relationship between toxicity of 5-fluorouracil (5-FU) given with folinic acid (FA) to patients with solid tumors and DNA sequence variances in enzymes that mediate the action of 5-FU and FA.

| VII. VIII | Study Phase: | Phase IV |
|---|---|---|
| Study Design: |  | Single-center, case-control study. |

Study

Objectives: The primary objective of this study is to compare the variance frequency distribution in the dihydropyrimidine dehydrogenase (DPD) gene between two groups of patients with solid tumors, treated by weekly or monthly regimen of 5-FU+FA and defined by level of toxicity (graded according to the NCI common toxicity criteria) as:

Group 1: patients with high toxicity (grade III/IV on NCI criteria)

Group 2: patients with minimal toxicity (grade 0/I/II on NCI criteria)

The secondary objectives of the study are to determine the DPD gene haplotype frequency distribution and the variance and/or haplotype frequency distributions in selected genes (other than DPD gene) between two groups of patients with solid tumors, treated by weekly or monthly regimen of 5-FU+FA and defined by level of toxicity. Analyses will be done globally, then by regimen (monthly vs. weekly) and by type of toxicity (gastrointestinal vs. bone marrow).

Number of Subjects: Ninety (90) patients, 45 in each group, will be included.

Study Population: Patients treated with 5-FU+FA for solid tumors at the Massachusetts General Hospital, Dana-Farber Cancer Institute and Brigham and Women's Hospital.

StudyGroups: Patients will be divided into two groups depending on the degree of toxicity they experienced with treatment, if any:

patients with high toxicity (grade III/IV on NCI criteria), patients with minimal toxicity (grade 0/I/II on NCI criteria)

Visit Schedule: One visit to sign the informed consent form and to collect blood sample.

Evaluation Parameter: Frequency distribution of gene alleles and haplotypes.

IX. 2. INTRODUCTION

X. 2.1 Background

XI. 2.1.1 Potential for Improved Effectiveness of 5-FU and 5-FU/FA

Introduction

Chemotherapy of cancer involves use of highly toxic drugs with narrow therapeutic indices. Although progress has been made in the chemotherapeutic treatment of selected malignancies, most adult solid cancers remain highly refractory to treatment. Nonetheless, chemotherapy is the standard of care for most disseminated solid cancers. Chemotherapy often results in a significant fraction of treated patients suffering unpleasant or life-threatening side effects while receiving little or no clinical benefit; other patients may suffer few side effects and/or have complete remission or even cure. Any test that could predict response to chemotherapy, even partially, would allow more selective use of toxic drugs, and could thereby significantly improve efficacy of oncologic drug use, with the potential to both reduce side effects and increase the fraction of responders. Chemotherapy is also expensive, not just because the drugs are often costly, but also because administering highly toxic drugs requires close monitoring by carefully trained personnel, and because hospitalization is often required for treatment of (or monitoring for) toxic drug reactions. Information that would allow patients to be divided into likely responder vs. non-responder (or likely side effect) groups, only the former to receive treatment, would therefore also have a significant impact on the economics of cancer drug use.

Predicting Response to Chemotherapy

Several methods for predicting response to chemotherapy in individual patients have been investigated over the years, ranging from the use of biochemical markers to testing drugs on a patients cultured tumor cells. None of these methods has proven sufficiently informative and practical to gain wide acceptance. However, there are some specific examples of tests useful for predicting toxicity. For example, a diagnostic test to predict side effects associated with the antineoplastic drugs 6-mercaptopurine, 6-thioguanine and azathioprine has begun to gain wide acceptance, particularly among pediatric oncologists. Severe toxicity of thiopurine drugs is associated with deficiency of the enzyme thiopurine methyltransferase (TPMT). Currently most TPMT testing is done using an enzyme assay, however the TPMT gene has been cloned and mutations associated with low TPMT levels have been identified; genetic testing is beginning to supplant enzyme assays because genetic tests are more easily standardized and economical.

While there are no good tests that predict positive chemotherapeutic response, there is demonstrated utility to measuring estrogen and progesterone receptor levels in cancer tissue before selecting therapy directed at modulating hormonal state. Measuring genetic variation in proteins that mediate the effects of chemotherapy drugs is in some respects analogous to measuring ER and PR levels, which mediate the effects of hormones.

Clinical Use and Effectiveness of 5-FU and 5-FU/FA

5-FU is a pyrimidine analog in clinical use since 1957. 5-FU is used in the standard treatment of gastrointestinal, breast and head and neck cancers. Clinical trials have also shown responses in cancer of the bladder, ovary, cervix, prostate and pancreas. The remainder of this discussion will concern colorectal cancer. 5-FU is used both in the adjuvant therapy of Dukes Stage B and C cancer and in the treatment of disseminated cancer. 5-FU alone produces partial remissions in 10–30% of advanced colorectal cancers, however only a few percent of patients have complete remissions. In the last 15 years a variety of biochemically motivated strategies for modulating 5-FU activity have been tested. For example, 5-FU has been used in combination with PALA, a pyrimidine synthesis inhibitor, to deplete cellular pools of UTP and thereby enhance formation of FUTP; in combination with methotrexate, to inhibit purine anabolism, leading to increased PRPP levels and consequent increased conversion of 5-FU to its active nucleotide metabolites; and in combination with folinic acid, which increases intracellular pools of reduced folate, driving formation of the ternary inhibitory complex formed by 5,10 methylenetetrahydrofolate, FdUMP and thymidylate synthase. Levamisole, interferon and alkylating agents have also been used in combination with 5-FU. 5-FU/Levamisole and 5-FU/FA are widely used in the adjuvant treatment of colon cancer, while 5-FU/FA is the most commonly used regimen for advanced colorectal cancer. Several prospective randomized trials of 5-FU/FA vs. 5-FU alone in patients with advanced cancer have demonstrated up to two fold higher response rates to 5-FU/FA, while three of the studies also showed increased survival. Two major dosing regimens are used 5-FU plus low dose FA given for five consecutive days followed by a 23 day interval, or once weekly bolus IV 5-FU plus high dose FA. The higher FA dose results in plasma FA concentrations of 1 to 10 uM, comparable to those required for optimal 5-FU/FA synergy in tissue culture, however low dose FA (20 mg/m$^2$ vs. 500 mg/m$^2$) has produced comparable clinical benefit. Ongoing clinical trials are designed to further test new drug combinations. In summary, relatively few patients—in the single digits—live longer as a result of 5-FU/FA, although significantly more have partial disease remission. The factors that determine which patients respond or have side effects are not known.

Toxicity of 5-FU and Folinic Acid

5-FU toxicity has been well documented in randomized clinical trials. Patients receiving 5-FU/FA are at even greater risk of toxic reactions and must be monitored carefully during therapy. A variety of side effects have been observed, affecting the gastrointestinal tract, bone marrow, heart and CNS. The most common toxic reactions are nausea and anorexia, which can be followed by life threatening mucositis, enteritis and diarrhea. Leukopenia is also a problem in some patients, particularly with the weekly dosage regimen. In a recent randomized trial of weekly vs. monthly 5-FU/FA there were 7 deaths related to drug toxicity among 372 treated patients (1.9%; Buroker et al. 1994). 31% of patients receiving the weekly regimen suffered diarrhea-requiring hospitalization for a median of 10 days. Other severe toxicity, which occurred at lower frequency, included leukopenia and stomatitis. In another example, 36% of patients receiving weekly bolus 5-FU plus FA (500 mg/m$^2$), in a NSABP trial suffered NCI grade 3 toxicity (Wolmark et al., 1996). Clearly, toxicity is a major cost of 5-FU/FA therapy, measured both in patient suffering and in financial terms (the cost of care for drug induced illness).

Other Factors

Many non-genetic factors influence the response of cancers to drugs, including tumor location, vasculature, cell growth fraction and various drug resistance mechanisms. It will therefore not be possible to explain all heterogeneity in response to 5-FU/FA by genetic variation. However, based on genetic studies of other quantitative traits it seems likely that a significant fraction of variation in drug response can be explained (see below).

XII. 2.1.2 Metabolic Pathways that Affect 5-FU/FA Action

The biochemical pathways of 5-FU metabolism have been studied extensively. Likewise, folate metabolism has been well investigated and the enzymes that form and consume 5,10-methylenetetrahydrofolate are well known. The principal metabolic pathways that influence the pharmacologic action of 5-FU are summarized in FIG. 1.

FIG. 1. 5-FU metabolism and inhibition of thymidylate formation. Enzymes: 1. uridine phosphorylase; 2. thymidine phosphorylase; 3. orotate phosphoribosyl transferase; 4. thymidine kinase; 5. uridine kinase; 6. ribonucleotide reductase; 7. thymidylate synthase; 8. dCMP deaminase; 9. nucleoside monophosphate kinase; 10. nucleoside diphosphate kinase; 11. nucleoside diphosphatase or cytidylate kinase; 12: thymine phosphorylase. FH2=dihydrofolate, FH4=tetrahydrofolate. The Figure is adapted from Goodman & Gilman's The Pharmacological Basis of Therapeutics, ninth edition, McGraw Hill, 1996, p. 1249.

De novo and Salvage Routes of Pyrimidine Nucleotide Formation (5-FU Anabolism) and Inhibition of Thymidylate Synthase 5-FU is a biologically inactive pyrimidine analog, which must be phosphorylated, and ribosylated to the nucleoside analog fluorodeoxyuridine monophosphate (FdUMP) to have clinical activity. FdUMP formation can occur via several routes, summarized in FIG. 1. 5-FU may be converted by uridine phosphorylase to fluorouridine (FUdR; the reverse reaction is catalyzed by uridine nucleosidase) and then to fluorouridine monophosphate (FUMP) by uridine kinase, or FUMP may be formed from 5-FU in one step via transfer of a phosphoribosyl group from 5-phosphoribosyl-1-pyrophosphate (PRPP), catalyzed by orotate phosphoribosyl transferase. FUMP can be converted to FUDP and subsequently FUTP by a nucleoside monophosphate kinase and nucleoside diphosphate kinase, respectively. FUTP is incorporated into RNA by RNA polymerases, which may account in part for 5-FU toxicity as a result of effects on processing or function (e.g. translation). Alternatively, FUDP may be reduced to the dinucleotide level, FdUDP (fluorodeoxyuridine diphosphate) by ribonucleotide diphosphate reductase, a heterodimeric enzyme. FdUDP can then be converted to FdUTP by nucleoside diphosphate kinase and incorporated into DNA by DNA polymerases, which may account for some 5-FU toxicity. Fluoropyrimidine modified DNA may also be targeted by the nucleotide excision repair process. The more important path of FdUDP metabolism with respect to anticancer effects, however, is believed to be conversion to FdUMP by nucleoside diphosphatase/or cytidylate kinase, bi-directional enzyme). dUMP is the precursor of dTMP in de novo pyrimidine biosynthesis, a reaction catalyzed by thymidylate synthase and which consumes 5,10-methylenetetrahydrofolate, producing 7,8 dihydrofolate. FdUMP, however, forms an inhibitory (probably covalent) complex with thymidylate synthase in the presence of 5,10-methylenetetrahydrofolate, thereby blocking formation of thymidylate (other than by the salvage pathway via thymidine kinase). The complex anabolism of FdUMP can be simplified by giving the deoxyribonucleoside of 5-FU, 5-fluorodeoxyuridine (also called floxuridine; FUdR), which can be converted to FdUMP in one step by thymidine kinase. However, FUdR is also rapidly converted back to 5-FU by the bi-directional enzyme thymidine phosphorylase.

5-FU Catabolism.

Metabolic elimination of 5-FU occurs via a three-step pathway leading to -alanine. The first and rate limiting enzyme in the elimination pathway is dihydropyrimidine dehydrogenase (DPD), which transforms more than 80% of a dose of 5-FU to the inactive dihydrofluorouracil form. Subsequently dihydropyrimidinase catalyzes opening of the pyrimidine ring to form 5-fluoro-ureidopropionate and then -ureidopropionase (also called -alanine synthase) catalyzes formation of 2-fluoro-alanine. The first two reactions are reversible. The distribution of activity of these enzymes in human populations has not been established, however, a recent population survey of urinary pyrimidine levels in 1,133 adults revealed that levels of dihydrouracil range from 0–59 uM/g of creatinine, while uracil levels ranged from 0–130 uM/g creatinine (Hayashi et al., 1996), suggesting variation in the activity of enzymes of pyrimidine metabolism. It is worth noting that in animal studies catabolites of 5-FU apparently account for some fraction of 5-FU toxicity (Davis et al., 1994; Spector et al., 1995). This result is the rationale for current human trials of 5-FU combined with DPD inhibitors: if the 5-fluoro- metabolites are responsible for toxicity, then blocking their formation by inhibition of DPD, while simultaneously decreasing 5-FU dosage to compensate for the block in catabolism and excretion, should result in a better therapeutic index.

Folinic Acid Conversion to Tetrahydrofolate.

The conversion of FA to 5,10MTHF can occur via several routes, illustrated in FIG. 2

FIG. 2. Folate metabolism and formation of 5,10-methylenetetrahydrofolate.

Enzymes: 1. Formimino-tetrahydrofolate cyclodeaminase; 2. methenyltetrahydrofolate synthetase; 3. methenyltetrahydrofolate cyclohydrolase; 4. formyltetrahydrofolate synthetase; 5. formyltetrahydrofolate hydrolase; 6. formyltetrahydrofolate dehydrogenase; 7. methylenetetrahydrofolate dehydrogenase; 8. methylenetetrahydrofolate reductase (MTHFR); 9. homocysteine methyltransferase (also called methionine synthetase); 10. serine transhydroxymethylase; 11. glycine cleavage system; 12. thymidylate synthase; 13. dihydrofolate reductase. Abbreviations: THF=tetrahydrofolate; DHF=dihydrofolate. Note that THF appears twice (i.e. the product of step 6 is also substrate for enzymes 10 and 11. Step 12 also appears in FIG. 1, above. This Figure is adapted from Mathews & van Holde, Biochemistry, The Benjamin/Cummings Publishing Co., Redwood City Calif., 1990, page 697.

Intracellular reduced folate levels can potentiate 5-FU action by increasing 5,10-methylenetetrahydrofolate levels (5,10-methyleneTHF; see center of FIG. 2), thereby stabilizing the ternary inhibitory complex formed with thymidylate synthase and FdUMP. This is the basis for therapeutic modulation of 5-FU with FA. As can be seen in FIG. 2, conversion of folinic acid (5-formylTHF) to 5,10-methenylTHF, the precursor of 5,10-methyleneTHF, requires methenyltetrahydrofolate synthetase (enzyme 2 in the Figure). Also, levels of 5,1 0-methyleneTHF may be affected directly by the activity of methylenetetrahydrofolate dehydrogenase, methylenetetrahydrofolate reductase, serine transhydroxymethylase and the glycine cleavage system enzymes (7, 8, 10 and 11 in FIG. 2), and indirectly by the other enzymes shown in the Figure.

Cell Uptake of Pyrimidine Nucleosides and Folinic Acid

Human cells have five concentrative nucleoside transporters with varying patterns of tissue distribution (see review by Wang et al., 1997). Two transporters, one with preference for purines and one for pyrimidines have been cloned recently (Felipe et al., 1998). 5-FU entry into cells may be modulated by activity of these transporters, particularly the pyrimidine transporter, although one prospective randomized clinical trial in which the nucleoside transport inhibitor dipyridamole was paired with 5-FU and FA failed to show a difference in outcome compared to 5-FU/FA alone (Kohne et al., 1995). Several folate transport systems have been identified in human cells. Folate receptor 1 (FR1) is a high affinity (nanomolar range) receptor for reduced folates. Three restriction fragment length polymorphisms (RFLPs) have been reported at the FR1 locus (Campbell et al., 1991). Reduced folates are also transported by folate receptor gamma and by a low affinity (1 uM) folate transporter. 15-fold variations in levels of folate transporter have been described in unselected tumor cell lines (Moscow et al., 1997).

XIII. 2.1.3 Genetically Determined Variation in Response to 5-FU: Studies of Dihydropyrimidine Dehydrogenase Deficiency Dihydropyrimidine Dehydrogenase Deficiency is Associated with 5-FU Toxicity 5-FU is inactivated by the same metabolic pathway as thymine and uracil (see above). DPD catalyzes the first, rate-limiting step in pyrimidine catabolism and accounts for elimination of most 5-FU. Normal individuals eliminate 5-FU with a half-life of ~10-minutes and excrete only 10% of a dose unchanged in the urine. In contrast, people genetically deficient in DPD eliminate 5-FU with a half-life of ~2.5 hours and excrete 90% of a dose unchanged in the urine (Diasio et al., 1988). DPD deficiency has two clinical presentations: (i) an inborn error of metabolism causing some degree of neurologic dysfunction or (ii) asymptomatic until revealed by exposure to 5-FU or other pyrimidine analogs. With either presentation there is combined hyperuraciluria and hyperthyminuria. The vastly increased 5-FU half-life in DPD deficient individuals causes severe toxicity and even death. Recently several mutations have been identified in DPD genes of deficient individuals (Wei et al., 1996), however none of these alleles appears to occur at appreciable frequency, so the cause of wide population variation in DPD levels is still not understood.

Population Studies of DPD Activity Show Wide Variation

Population surveys of DPD activity in normal individuals have been performed using blood and liver samples. These studies reveal a broad unimodal Gaussian distribution of DPD activity over a 7 to 14 fold range, with some individuals having very low or even undetectable levels. For example Etienne et al. (1994) report DPD activity ranging from 0.065 to 0.559 nM/min/mg protein in a study of 152 men and 33 women, while Fleming et al. (1993) found DPD activity in 66 cancer patients varied from 0.17 to 0.77 nM/min/mg protein. Lu et al (1995) found 18-fold variation in liver DPD assayed in 138 individuals. Milano and Etienne (1994) suggested that the frequency of heterozygous and homozygous deficiency is 3% and 0.1%, respectively. The DNA sequence alterations responsible for null DPD alleles do not account for the high population variability (Ridge et al., 1997).

DPD Levels are Correlated with Response to 5-FU

Intratumoral DPD levels have been measured in patients receiving 5-FU chemotherapy. When complete responders were compared to partial or non-responders, DPD levels were lower in the compete responders (Etienne et al., 1995). Leukocyte DPD levels has also been measured in patients receiving 5-FU/FA chemotherapy. When patients were divided into 3 groups: high, medium and low DPD activity, the frequency of serious side effects was highest in the low DPD group and vice versa (Katona et al., 1997).

XIV. 2.1.4 Variances in Genes that may Affect 5-FU/FA Action

Variagenics has already surveyed thymidylate synthase, ribonucleotide reductase (M1 subunit only), and dihydrofolate reductase and dihydropyrimidine dehydrogenase cDNAs for genetic variation. 36 unrelated individuals were screened using 6 SSCP conditions and DNA sequencing. Other investigators have identified variances in MTHFR, methionine synthase and folate receptor. These findings are summarized in Appendix I.

XV

XVI. 2.1.5 Analysis of Haplotypes Increases Power of Genetic Analysis

It is evident from work to date that, while DPD activity is weakly predictive of 5-FU toxicity and drug response, there must be other factors that account for some of the variation in patient response. This is to be expected as drug response phenotypes usually vary continuously, and such (quantitative) traits are typically influenced by a number of genes (Falconer and Mackay, 1997). Although it is impossible to determine a priori the number of genes influencing a quantitative trait, often only a few loci have large effects, where a large effect is 5–20% of total variation in the phenotype (Mackay, 1995).

Having identified genetic variation in enzymes that may affect 5-FU action, how can we most efficiently address its relation to phenotypic variation? The sequential testing for correlation between phenotypes of interest and single nucleotide polymorphisms may be adequate to detect associations if there are major effects associated with single nucleotide changes; certainly it is worth performing this type of analysis. However there is no way to know in advance whether there are major phenotypic effects associated with single nucleotide changes and, even if there are, there is no way to be sure that the salient variance has been identified by screening cDNAs. A more powerful way to address the question of genotype-phenotype correlation is to assort genotypes into haplotypes. (A haplotype is the cis arrangement of polymorphic nucleotides on a particular chromosome.) Haplotype analysis has several advantages compared to the serial analysis of individual polymorphisms at a locus with multiple polymorphic sites.

(1) Of all the possible haplotypes at a locus ($2^n$ haplotypes are theoretically possible at a locus with n binary polymorphic sites) only a small fraction will generally occur at a significant frequency in human populations. Thus, association studies of haplotypes and phenotypes will involve testing fewer hypotheses. As a result there is a smaller probability of Type I errors, that is, false inferences that a particular variant is associated with a given phenotype.

(2) The biological effect of each variance at a locus may be different both in magnitude and direction. For example, a polymorphism in the 5' UTR may affect translational efficiency, a coding sequence polymorphism may affect protein activity, a polymorphism in the 3' UTR may affect mRNA folding and half life, and so on. Further, there may be interactions between variances: two neighboring polymorphic amino acids in the same domain—say cys/arg at residue 29 and met/val at residue 166-may, when combined in one sequence, for example, 29cys-166val, have a deleterious effect, whereas 29cys-166met, 29arg-166met and 29arg-166val proteins may be nearly equal in activity. Haplotype analysis is the best method for assessing the interaction of variances at a locus.

(3) Templeton and colleagues have developed powerful methods for assorting haplotypes and analyzing haplotype/phenotype associations (Templeton et al., 1987). Alleles, which share common ancestry, are arranged into a tree structure (cladogram) according to their time of origin in a population. Haplotypes that are evolutionarily ancient will be at the center of the branching structure and new ones (reflecting recent mutations) will be represented at the periphery, with the links representing intermediate steps in evolution. The cladogram defines which haplotype-phenotype association tests should be performed to most efficiently exploit the available degrees of freedom, focusing attention on those comparisons most likely to define functionally different haplotypes (Haviland et al., 1995). This type of analysis has been used to define interactions between heart disease and the apolipoprotein gene cluster (Haviland et al 1995) and Alzheimer's Disease and the Apo-E locus (Templeton 1995) among other studies, using population is small as 50 to 100 individuals.

XVII. 2.1.6 Biochemical Studies of Alternate Allelic Forms of DPD

The power of genetic analysis can be augmented by biochemical studies of alternate allelic forms of enzymes. Biochemical data on the distribution of activity of a series of enzymes in a biochemical pathway provides the basis for metabolic flux analysis (Keightly, 1996). It is beyond the scope of this clinical trial to analyze biochemical variation in the enzymes of pyrimidine and folate metabolism. However, since Variagenics has identified new variances in DPD that may plausibly affect enzyme expression or activity, and because DPD is already proven to play a role in 5-FU response, parallel studies will be conducted to investigate the relationship between genotype and biochemistry for this enzyme.

DPD cDNAs have been cloned from a variety of higher eukaryotes and binding sites for its cofactors, prosthetic groups and substrate have been defined experimentally or by analogy with known consensus motifs (Yokata et al., 1994). The DPD polymorphisms that affect protein sequence occur at amino acids 29 (cys/arg) and 166 (met/val) in the amino-terminal one-third of the protein. Phylogenetic comparison of this region from boar, human, cow, fly, and bacteria (see below) shows that there are actually two highly conserved motifs that resemble either iron/sulfur or zinc binding motifs, the latter being more likely due to the spacing of the cysteine residues. The region around the met/val polymorphism at amino acid 166 is highly conserved. Even the spacing of the putative zinc-finger domains is maintained between distantly related species, hinting at their importance. Since amino acid 166 is close to a highly conserved (and probably functionally important) region and is itself conserved, being a methionine in all species, it seems likely that perturbations in this position would have consequence. The polymorphism substitutes a long amino acid side chain capable of hydrogen bonding (methionine) for a compact, hydrophobic amino acid (valine). The region around amino acid 29 is not as well conserved.

XVIII. 2.2 Study Rationale 5-fluorouracil (5-FU) is a fluorinated pyrimidine analog that is widely used in chemotherapy. The effectiveness of 5-FU is potentiated by folinic acid (FA: generic name: leukovorin). The combination of 5-FU and FA is standard therapy for stage III/IV colon cancer. Patient responses to 5-FU and 5-FU/FA vary widely, ranging from complete remission of cancer to severe toxicity.

Pyrimidine base analogs are degraded by the same enzymes that degrade endogenous uracil and thymine. Dihydropyrimidine dehydrogenase (DPD) is the first degradative enzyme in this pathway, accounting for catabolism of more than 80% of an administered dose of 5-FU.

Total DPD deficiency (familial pyrimidinemia and pyridinuria) is a rare syndrome associated with 5-FU induced toxicity. A milder defect in DPD activity appears to account for the severe side effects that occur in 1%–3% of unselected cancer patients (Milano and Etienne, 1994).

The major toxic manifestations of 5-FU and FA depend on the schedule of administration and occur mainly in rapidly dividing tissues such as bone marrow and the mucosal lining of the gastrointestinal tract.

This study is designed to test whether genetically encoded biochemical variations in the enzymes of pyrimidine catabolism, nucleotide metabolism and folic acid metabolism, among patients treated with a weekly or monthly schedule of 5-FU+FA, account for some of the variation in drug toxicity. Applications of a successful pharmacogenetic study lie in the direction of safer, more efficacious, and hence more economical use of 5-FU, guided by genetic tests.

XIX. 3. OBJECTIVES

XX. 3.1 Primary Objective

The primary objective of this study is to compare the variance frequency distribution in the dihydropyrimidine dehydrogenase (DPD) gene between two groups of patients with solid tumors, treated by weekly or monthly regimen of 5-FU+FA and defined by level of toxicity (graded according to the NCI common toxicity criteria) as:

Group 1: patients with high toxicity (grade III/IV on NCI criteria)

Group 2: patients with minimal toxicity (grade 0/I/II on NCI criteria)

XXI. 3.2 Secondary Objectives

The secondary objectives of the study are to determine the DPD gene haplotype frequency distribution and the variance and/or haplotype frequency distributions in selected genes (other than DPD gene—see Appendix I-) between two groups of patients with solid tumors, treated by weekly or monthly regimen of 5-FU+FA and defined by level of toxicity. Analyses will be done globally, then by regimen (monthly vs. weekly) and by type of toxicity (gastrointestinal vs. bone marrow).

XXII. 4. STUDY DESIGN

XXIII. 4.1 Study Outline

The study will be done at selected medical institution.

The study is a single-center, case-control study. The duration of the study is expected to be not more than 8 months.

Genetic analysis of anonymized patient samples will take place at the study sponsor.

XXV. 4.2 Subject Withdrawal from the Study

Subjects who desire to discontinue participation in this study must be withdrawn from the study.

XXV. 4.3 Discontinuation of the Study

This study may be terminated by the study sponsor, after consultation with the Advisory Committee (see Section 11.2), at any time.

XI. 5. STUDY POPULATION

XXVII. 5.1 Number of Subjects

Ninety (90) subjects will be recruited for the study.

XXVIII. 5.2 Inclusion Criteria

To be eligible for entry into this study, candidates must meet the following eligibility criteria at the time of enrollment:

1. Above age of 18 years.
2. Diagnosis of solid tumor.
3. Treatment with a weekly or monthly regimen of 5-fluorouracil (5-FU) plus folinic acid (FA)
4. Classified according to the NCI common toxicity criteria as 0, I, II, III or IV grade.
5. Give written informed consent prior to any testing under this protocol, including screening tests and evaluations that are not considered part of the subject's routine care.

XXIX. 5.3 Exclusion Criteria

Candidates will be excluded from study entry if any of the following exclusion criteria exist at the time of enrollment:

Medical History
1. Diagnosis of cancer other than solid tumor.
2. Classified according to the NCI common toxicity criteria as grade II.
3. Known history of HIV, HBV or Hepatitis C virus infection (undesirable for making permanent cell line).

Treatment History
4. Treatment with 5-FU+FA but with other schedule than weekly or monthly.
5. Concomitant treatment with other cancer drugs than 5-FU+FA.

Miscellaneous
6. Unwillingness or inability to comply with the requirements of this protocol.

XXX. 5.4 Screening Log

For every patient initially considered for inclusion in this study, it is required to document and to specifically state the reason(s) for their exclusion.

XXXI. 6. ALLOCATION PROCEDURE

When the eligibility review screening has been completed and the subject has been found eligible for admission to the study, the subject will be assigned to one of the two following group, depending on the 5-FU+FA related toxicity he has experienced in the past:

Group 1: patients with high toxicity (grade III/IV on NCI criteria)

Group 2: patients with minimal toxicity (grade 0/I/II on NCI criteria)

7. SCHEDULE OF EVENTS

XXXII. Patients

Patients will only be required to come for giving informed consent, then having one blood drawing (17 ml total)—see Appendix II-.

Study Personnel

The following personnel will be involved in the conduct of this study.

A treating physician who will oversee subject assignment and discuss the protocol with the subject in order to obtain informed consent.

A treating nurse who will assist the treating physician in subject identification management and perform blood sampling.

A data manager who will collect and enter data in the clinical database.

Tests and Evaluations

The tests and evaluations described below must be performed by the required study personnel in order to determine subject eligibility.

Treating Physician
  Chart and demographic (sex, age, etc) reporting, inclusion/exclusion criteria checking.
Treating Nurse
  Blood sampling
Data Manager
  Clinical data entry.

11. STATISTICAL STATEMENT AND ANALYTICAL PLAN

11.1 Sample Size Considerations

The primary endpoint of this study is to measure and compare genotype distributions of the DPD gene in patients with and without 5-FU+FA toxicity. In order to be able to make a sample size calculation, we will ignore the complexities of the underlying genetic model and treat the data as n independent ordinary 2×2 contingency tables for the n variances in the cases and controls. So, using the 2 most frequent DPD variances listed in Appendix 1 and an odds-ratio of 4.00 for cases vs. controls, we can determine the sample size for every variance, with an equal number of subjects in each phenotypic (i.e. toxicity) group, required to detect, with 80% power at a two-sided significance level of 0.05, a statistically significant difference between distributions:

nucleotide 3925: 44 patients per group
nucleotide 3937: 43 patients per group.

A total of 90 patients (45 per group) will so be recruited.

11.2 Description of Objectives and EndpointS

11.2.1 Primary Objective and Endpoints

The primary objective of this study is to compare the variance frequency distributions in the dihydropyrimidine dehydrogenase (DPD) gene between two groups of patients with solid tumors, treated by weekly or monthly regimen of 5-FU+FA and defined by level of toxicity (grade 0/I/II vs. grade III/IV).

11.2.2 Secondary Objectives and Endpoints

The secondary objectives of the study are:
1. To determine which DPD gene variance(s) is(are) associated to 5-FU+FA toxicity
2. To determine which DPD haplotype(s) is(are) associated to 5-FU+FA toxicity.
3. To determine if one or more of the other gene variances (see Appendix 1) is(are) associated to 5-FU+FA toxicity
4. To determine if one or more of the other haplotypes is(are) associated to 5-FU+FA toxicity.

11.3 Criteria for the Endpoints

Since we do not know the mode of inheritance of a potential toxic susceptibility, we will ignore in a first step the complexities of the underlying genetic model and treat the data as an ordinary n×2 contingency table for the n variances in the cases and controls. Then, for every variance, we will compare genotype frequencies in order to detect a potential effect of homo- vs. heterozygosity.

We will also compare haplotype frequencies of r predetermined haplotypes. The method of cladograms (Templeton et al., 1987) will be used in an attempt to find out the smallest possible number r. In this method the evolutionary relationships between present day haplotypes are represented as a tree or cladogram.

11.4 Statistical Methods To Be Used in Objective Analyses

The statistical significance of the difference between variance frequencies will be assessed by a Pearson chi-squared test of homogeneity of proportions with n−1 degrees of freedom. Then, in order to determine which variance(s) is(are) responsible for an eventual significance, we will consider each variance individually against the rest, yielding up to n comparisons each based on a 2×2 table. This should result in chi-squared tests that are individually valid but taking the most significant of these tests is a form of multiple testing. A Bonferroni's adjustment for multiple testing will so be made to the P-values such as $p^*=1-(1-p)^n$.

The statistical significance of the difference between genotype frequencies associated to every variance will be assessed by a Pearson chi-squared test of homogeneity of proportions with 2 degrees of freedom, using the same Bonferroni's adjustment as above.

Testing for unequal haplotype frequencies between cases and controls can be considered in the same framework as testing for unequal variance frequencies since a single variance can be considered as a haplotype of a single locus. The relevant likelihood ratio test compares a model where two separate sets of haplotype frequencies apply to the cases and controls, to one where the entire sample is characterized by a single common set of haplotype frequencies. This can be performed by repeated use of a computer program (Terwilliger and Ott, 1994) to successively obtain the log-likelihood corresponding to the set of haplotype frequency estimates on the cases (ln $L_{case}$), on the controls (ln $L_{control}$) and on the overall (ln $L_{combined}$). The test statistic 2(ln $L_{case}$+ln $L_{control}$−ln $L_{combined}$) is then a chi-squared with r−1 degrees of freedom (where r is the number of haplotypes).

To test for potential confounding effects or effect-modifiers, such as sex, age, etc. logistic regression will be used with case-control status as the outcome variable, and genotypes and covariates (plus possible interactions) as predictor variables.

12. ETHICAL REQUIREMENTS

12.1 Declaration of Helsinki

See Appendix III.

12.2 Subject Information and Consent

Prior to any testing under this protocol, including screening tests and evaluations, written informed consent must be obtained from the subject in accordance with the Standards of the Partners Cancercare Human Protection Committee (HPC).

The background of the proposed study and the benefits and risks of the procedures and study will be explained to the subject. A copy of the informed consent document signed and dated by the subject must be given to the subject Confirmation of a subject's informed consent must also be documented in the subject's medical records prior to any testing under this protocol, including screening tests and evaluations.

12.3 Subject Data Protection

The subject will not be identified by name or other any identifying characteristic in any study reports, and these reports will be used for research purposes only the study sponsor, its designee(s), and various Government Health Agencies may inspect the records of this study. All relevant demographic and historical data regarding patient drug response will be recorded in an anonymized database.

13. FURTHER REQUIREMENTS AND GENERAL INFORMATION

13.1 Study Committee

Advisory Committee

An Advisory Committee will be formed to provide scientific and medical direction for the study and to oversee the administrative progress of the study. The Advisory Committee will meet at least once a month to monitor subjects. The Advisory Committee will determine whether the study should be stopped or amended for any reason.

The Advisory Committee will be comprised of the Director of Clinical Pharmacogenetics, Vice-President for Discovery Research from the study sponsor (and/or their designee) and participating investigators. The principal investigator will chair the Advisory Committee.

XLIV. 13.2 Changes to Final Study Protocol

All protocol amendments must be submitted to the IRB/REB/EC. Protocol modifications that impact on subject safety, the scope of the investigation, or affect the scientific quality of the study must be approved by the IRB/REB/EC and submitted to the appropriate regulatory authorities before initiation. However, Variagenics may, at any time, amend this protocol to eliminate an apparent immediate hazard to a subject. In this case, the appropriate regulatory authorities will be subsequently notified. In the event of a protocol modification, the subject consent form may require similar modifications.

XLV. 13.3 Record Retention

The Principal Investigator must maintain the records of signed consent forms, CRFs, all correspondences, dates of any monitoring visits, and records that support this information for a period of 15 years following notification by the study sponsor that the clinical investigations have been completed or discontinued. All local laws regarding retention of records must also be followed.

XLVI. 13.4 Reporting and Communication of Results

All information concerning the study sponsor's perations, such as patent applications, formulas, manufacturing processes, basic scientific data, and formulation information supplied by the study sponsor and not published previously, are considered confidential and shall remain the sole property of the study sponsor. The investigator agrees to use this information only in conducting this study and shall not use it for any other purposes without the study sponsor's written approval. The investigator agrees not to disclose the study sponsor's confidential information to anyone except to people involved in the study who need such information to assist in conducting the study and then only on like terms of confidentiality and nonuse.

It is understood by the investigator that the information developed from this clinical study will be used by the study sponsor and therefore may be disclosed as required to other clinical investigators, to the U.S. Food and Drug Administration, the Canadian Health and Welfare Health Protection Branch, the European Medicines Evaluation Agency, and to other government agencies. In order to allow for the use of the information derived from the clinical studies, it is understood that there is an obligation to provide the study sponsor with complete test results and all data developed in the study.

No publication or disclosure of study results will be permitted except as specified in a separate, written agreement between the study sponsor and the investigator.

XLVII. 13.5 Protocol Completion

The IRB/REB/EC must be notified of completion or termination of the protocol. Within 3 months of protocol completion or termination, the investigator must provide a final clinical summary report to the IRB/REB/EC. The Principal Investigator must maintain an accurate and complete record of all submissions made to the IRB/REB/EC, including a list of all reports and documents submitted. A copy of these reports should be sent to the study sponsor.

XLVIII. REFERENCES

Ausubel, F., et al. (1997) Current Protocols in Molecular Biology. Wiley and Sons, New York.

BritishMoscow, J. A., Connolly, T., Myers, T. G., et al. (1997) Reduced folate carrier gene (RFC1) expression and anti-folate resistance in transfected and non-slected cell lines. *Int. J Cancer* 72: 184–190.

Buroker et al., (1994) *Journal of Clinical Oncology* 12:14–20.

Campbell, I., Jones, T. Foulkes, W. and J. Trowsdale (1991) Folate binding protein is a marker for ovarian cancer. *Cancer Reearch* 51: 5329–38.

Chang, F.-M. and Kidd, K. K. (1997) *American Journal of Medical Genetics* 74:91–94.

Diasio R B, Beavers T L, Carpenter J T. (1988) Familial deficiency of dihydropyrimidine dehydrogenase. Biochemical basis for familial pyrimidinemia and severe 5-fluorouracil-induced toxicity. *J Clin Invest* 81:47–51.

Etienne, M. C., LaGrange, J. L., Dassonville, O., et al. (1994) Population study of dihydropyrimidine dehydrogenase in cancer patients. *J. Clin. Oncology* 12: 2248–2253.

Falconer, D. S. and T. F. C. Mackay (1997) Introduction to Quantitative Genetics. Longman, Essex.

Felipe, A., Valdes, R., Santo, B., et al. (1998) Na+ dependent nucleoside transport in liver: two different isoforms from the same gene family are expressed in liver cells. *Biochem. J.* 330: 997–1001.

HARRIS B E, CARPENTER J T, DIASIO R B. (1991) SEVERE 5-FLOUROURACIL TOXICITY SECONDARY TO DIHYDROPYRAMIDINE DEHYDROGENASE DEFICIENCY. A POTENTIAL MORE COMMON PHARMACOGENETIC SYNDROME. *CANCER* 68:499–501.

Haviland, M. B., Kessling, A. M., Davignon, J. and Sing, C. F. 1995. Cladistic analysis of the apolipoprotein AI-CIII-AIV gene cluster using a healthy French Canadian sample. I. Haploid analysis. *Ann. Hum. Genet.* 59: 211–231.

Keightley, P. D. (1996) Metabolic models of selection response. *J. Theoretical Biology* 182: 311–316.

Kohne, C. H., Hiddemann, W., Schuller, J., et al. (1995) Failure of orally administered dipyridamole to enhance the antineoplastic activity of fluorouracil in combination with leucovorin in patients with advanced colorectal cancer: a prospective reandomized trial. *J. Clin. Oncol.* 13: 1201–1208.

Krynetski, E. Y., Tai, H.-L., Yates, C. R., et al. (1996) Genetic polymorphism of thiopurine S-methyltransferase: clinical importance and molecular mechanisms. *Pharmacogenetics* 6: 272:290.

Lu, Z., Shang, R. and R. B. Diasio. (1993) Dihydropyrimidine dehydrogenase activity in human peripheral blood mononuclear cells and liver: population characteristics, newly identified deficient patients and clinical implications The genetic basis of quantitative variation. TIG 11: 464–470.

Michalatos-Beloin, S. Tishkoff, S. A., Bentley, et al. (1996) *Nucleic Acids Research* 24: 4841–4843

Milano, G. and M. C. Etienne. (1994) Potential importance of dihydropyrimidine dehydrogenase (DPD) in cancer chemotherappy. *Pharmacogenetics* 4: 301–306.

Ridge, S. A., Brown, O., McMurrough, Fernandez-Salguero, P., Evans, W. E., Gonzalez, F. J. and H. L. McLeod (1997) Mutations at codon 974 of the DPYD gene are a rare event. *British Journal of Cancer* 75: 178–179.

Ridge, S. A., Sludden, J., Wei, X., Sapone, A., Brown, O., Hardy, S., Canney, P., Fernandez-Salguero, P., Gonzalez, F. J., Cassidy, J. and H. L. McLeod (1997) Dihydropyrimidine dehydrogenase pharmacogenetics in patients with colorectal cancer. *British Journal of Cancer* 77: 497–500.

Templeton, A. R., Boerwinkle, E. and Sing, C. F. 1987. A cladistic analysis of phenotypic associations with haplotypes inferred from restriction endonuclease mapping. I. Basic theory and an analysis of Alcohol Dehydrogenase activity in Drosophila. *Genetics* 117: 343–351.

Terwilliger J., Ott J (1994) Handbook of Human Linkage Analysis. Baltimore: John Hopkins University Press.

Vreken P., Van Kuilenburg, A. B., Meinsma, R. and A. H. van Gennip (1997) Dihydropyrimidine dehydrogenase (DPD) deficiency: identification and expression of missense mutations C29R, R886H and R235W. *Human Genetics* 101: 333–338.

Wang, J., Schaner, M. E., Thomassen, S., et al. (1997) Functional and molecular characteristics of Na+ dependent nucleoside transporters. *Pharmaceutical Research* 14: 1524–32.

Wei, X., McLeod, H. L., McMurrough, J., et al. (1996) Molecular basis of the human dihydropyrimidine dehydrogenase deficiency and 5-fluorouracil toxicity. *J. Clin. Invest.* 98: 610–615.

Wolmark, et al. (1996) Proceedings *Am. Soc. Clin Oncol.* 15: 460.

Yokata, H., Fernandez-Salguero, P., Furuya, H., Lin, K., McBride, O. M., Podschum, B., Schnackerz, K. D., and Gonzalez, F. J. 1994. *JBC* 269:23192–23196

XLIX. SIGNED AGREEMENT OF THE STUDY PROTOCOL

I have read the foregoing protocol, VRG-9801, "Case-control study to determine the relationship between toxicity of 5-fluorouracil (5-FU given with folinic acid (FA) to patients with solid tumors and DNA sequence variances in enzymes that mediate the action of 5-FU and FA", Version 1, and agree to conduct the study as detailed herein and to inform all who assist me in the conduct of this study of their responsibilities and obligations.

Principal Investigator's Signature Date
Principal Investigator's Name (Print)
Investigational Site (Print)

APPENDIX II

L. Procedures for Handling Blood Samples for Cell Line Establishment

This document describes procedures for handling blood samples from cancer patients enrolled in trial for genetic studies at the study sponsor. The approach will be to first establish permanent lymphoblastoid cell lines. DNA and RNA will subsequently be extracted from these cell lines. This procedure will save the effort of purifying DNA and RNA directly from blood. Since the pharmacogenetic hypotheses to be investigated relate to the effect of genotype, not mRNA expression levels, lymphoblastoid cell lines should be satisfactory sources of nucleic acid for the genetic studies.

1. Cell line establishment will be done by the study site institutions (e.g., Genomics Core Facility of the Massachusetts General Hospital (MGH) Molecular Neurogenetics Unit).

2. From each patient collect two 8.5 ml yellow topped tubes (containing ACD solution A) for lymphoblastoid cell line development. All DNA and RNA will be produced from the cell lines at a later date; therefore there is no need for additional blood drawing.

3. Fill out a DNA/Cell Line Order Sheet. An example is attached. Please note that the patient's name should be anonymized at this point. (The Genomics Core Facility will accept anonymized order forms.) All samples (including those for PK studies) should be assigned the same arbitrary number to allow subsequent matching of clinical, pharmacokinetic and genetic data. Also, the date and time of blood drawing should be marker. DOB should be recorded as month and year only, and sex should be recorded. Record the number of tubes of blood drawn (2), date of draw and date of shipment. Under "Requisition" check off "Transformation only".

4. Arrange for the two ACD blood samples to be delivered to designated individual at the study site institution at the address given below:

Name and Address of Designated Individual at Study Site Institution.

Since the blood samples are typically aged at room temperature for a day or two before cell line establishment, it is not urgent that blood be delivered the same day it is drawn. Storage overnight, if necessary, should be at room temperature.

5. Please fax to the study sponsor a copy of the cell line order form so we are aware of accumulating cell lines. The fax number is 588-5399. Please fax to the attention of the designated individual for the study sponsor.

6. Once cell lines are established, vials will be archived at the study site institution, where they will be available to investigators.

7. Questions for the study sponsor should be addressed to the designated individual.

Example 11

Hardy-Weinberg Equilibrium

Evolution is the process of change and diversification of organisms through time, and evolutionary change affects morphology, physiology and reproduction of organisms, including humans. These evolutionary changes are the result of changes in the underlying genetic or hereditary material. Evolutionary changes in a group of interbreeding individuals or Mendelian population, or simply populations, are described in terms of changes in the frequency of genotypes and their constituent alleles. Genotype frequencies for any given generation is the result of the mating among members (genotypes) of their previous generation. Thus, the expected proportion of genotypes from a random union of individuals in a given population is essential for describing the total genetic variation for a population of any species. For example, the expected number of genotypes that could form from the random union of two alleles, A and a, of a gene are AA, Aa and aa. The expected frequency of genotypes in a large, random mating population was discovered to remain constant from generation to generation; or achieve Hardy-Weinberg equilibrium, named after its discoverers. The expected genotypic frequencies of alleles A and a (AA, 2Aa, aa) are conventionally described in terms of $p^2+2pq+q^2$ in which p and q are the allele frequencies of A and a. In this equation $(p^2+2pq+q^2=1)$, p is defined as the frequency of one allele and q as the frequency of another allele for a trait controlled by a pair of alleles (A and a). In other words, p equals all of the alleles in individuals who are homozygous dominant (AA) and half of the alleles in individuals who are heterozygous (Aa) for this trait. In mathematical terms, this is $$p=AA+\tfrac{1}{2}Aa$$

Likewise, q equals the other half of the alleles for the trait in the population, or $$q=aa+\tfrac{1}{2}Aa$$

Because there are only two alleles in this case, the frequency of one plus the frequency of the other must equal 100%, which is to say $$p+q=1$$

Alternatively, $$p=1-q \text{ OR } q=1-p$$

All possible combinations of two alleles can be expressed as:

$$(p+q)^2 1$$

or more simply, $$p^2+2pq+q^2=1$$

In this equation, if p is assumed to be dominant, then $p^2$ is the frequency of homozygous dominant (AA) individuals in a population, 2pq is the frequency of heterozygous (Aa) individuals, and $q^2$ is the frequency of homozygous recessive (aa) individuals.

From observations of phenotypes, it is usually only possible to know the frequency of homozygous dominant or recessive individuals, because both dominant and recessives will express the distinguishable traits. However, the Hardy-Weinberg equation allows us to determine the expected frequencies of all the genotypes, if only p or q is known. Knowing p and q, it is a simple matter to plug these values into the Hardy-Weinberg equation ($p^2+2pq+q^2=1$). This then provides the frequencies of all three genotypes for the selected trait within the population.

This illustration shows Hardy-Weinberg frequency distributions for the genotypes AA, Aa, and aa at all values for frequencies of the alleles, p and q. It should be noted that the proportion of heterozygotes increases as the values of p and q approach 0.5.

Linkage Disequilibirum

Linkage is the tendency of genes or DNA sequences (e.g. SNPs) to be inherited together as a consequence of their physical proximity on a single chromosome. The closer together the markers are, the lower the probability that they will be separated during DNA crossing over, and hence the greater the probability that they will be inherited together. Suppose a mutational event introduces a "new" allele in the close proximity of a gene or an allele. The new allele will tend to be inherited together with the alleles present on the "ancestral," chromosome or haplotype. However, the resulting association, called linkage disequilibrium, will decline over time due to recombination. Linkage disequilibrium has been used to map disease genes. In general, both allele and haplotype frequencies differ among populations. Linkage disequilibrium is varied among the populations, being absent in some and highly significant in others.5

Quantification of the Relative Risk of Observable Outcomes of a Pharmacogenetics Trial Let PlaR be the placebo response rate (0% (PlaR (100%) and TntR be the treatment response rate (0% (TntR (100%) of a classical clinical trial. ObsRR is defined as the relative risk between TntR and PlaR:

$$ObsRR=TntR/PlaR.$$

Suppose that in the treatment group there is a polymorphism in relation to drug metabolism such as the treatment response rate is different for each genotypic subgroup of patients. Let q be the allele a frequency of a recessive biallelic locus (e.g. SNP) and p=1−q the allele A frequency. Following Hardy-Weinberg equilibrium, the relative frequency of homozygous and heterozygous patients are as follow:

AA:p2Aa:2pq aa:q2 with $$(p2+2pq+q2)=1.$$

Let's define AAR, AaR, aaR as respectively the response rates of the AA, Aa and aa patients. We have the following relationship:

$$TntR=AAR*p2+AaR*2pq+aaR*q2.$$

Suppose that the aa genotypic group of patients has the lowest response rate, i.e. a response rate equal to the placebo response rate (which means that the polymorphism has no impact on natural disease evolution but only on drug activationed let's define ExpRR as the relative risk between AAR and aaR, as $$ExpRR=AAR/aaR.$$

From the previous equations, we have the following relationships:

$$ObsRR(ExpRR(1/PlaR$$

$$TntR/PlaR=(AAR*p2+AaR*2pq+aaR*q2)/PlaR$$

The maximum of the expected relative risk, max(ExpRR), corresponding to the case of heterozygous patients having the same response rate as the placebo rate, is such that:

$$ObsRR=ExpRR*p2+2pq+q2 \Leftrightarrow ExpRR=(ObsRR-2pq-q2)/p2 \text{ min-(ExpRR)},$$

corresponding to the case of heterozygous patients having the same response rate as the homozygous non-affected patients, is such that:

$$ObsRR=ExpRR*(p2+2pq)+q2 \Leftrightarrow ExpRR=(ObsRR-q2)/(p2+2pq)$$

For example, if q=0.4, PlaR=40% and ObsRR=1.5 (i.e. TntR=60%), then 1.6 (ExpRR (2.4. This means that the best treatment response rate we can expect in a genotypic subgroup of patients in these conditions would be 95.6% instead of 60%.

This can also be expressed in terms of maximum potential gain between the observed difference in response rates (TntR—PlaR) without any pharmacogenetic hypothesis and the maximum expected difference in response rates (max (ExpRR)*PlaR−TntR) with a strong pharmacogenetic hypothesis:

$$(\max(ExpRR)*PlaR-TntR)=[(ObsRR-2pq-q2)/p2]*PlaR-TntR$$

$$\Leftrightarrow (\max(ExpRR)*PlaR-TntR)=[TntR-PlaR*(2pq+q2)-TntR*p2]/p2$$

$$\Leftrightarrow (\max(ExpRR)*PlaR-TntR)=[TntR*(1-p2)-PlaR*(2pq+q2)]/p2$$

$$\Leftrightarrow (\max(ExpRR)*PlaR-TntR)=[(1-p2)/p2]*(TntR-PlaR)$$

that is for the previous example, (95.6%−60%)=[(1−0.62)/0.62]*(60%−40%)=35.6%

Suppose that, instead of one SNP, we have p loci of SNPs for one gene. This means that we have 2p possible haplotypes for this gene and (2p)(2p−1)/2 possible genotypes. And with 2 genes with p1 and p2 SNP loci, we have [(2p1)(2p1−1)/2]*[(2p2)(2p2−1)/2] possibilities; and so on. Examining haplotypes instead of combinations of SNPs is especially useful when there is linkage disequilibrium enough to reduce the number of combinations to test, but not complete since in this latest case one SNP would be sufficient. Yet the problem of frequency above still remains with haplotypes instead of SNPs since the frequency of a haplotype cannot be higher than the highest SNP frequency involved.

Statistical Methods to be Used in Objective Analyses

The statistical significance of the differences between variance frequencies can be assessed by a Pearson chi-squared test of homogeneity of proportions with n−1 degrees of freedom. Then, in order to determine whih variance(s) is(are) responsible for an eventual significance, we can consider. each variance individually against the rest, up to n comparisons, each based on a 2×2 table. This should result in chi-sequared tests that are individually valid, but taking the most significant of these tests is a form of multiple testing. A Bonferroni's adjustment for multiple testing will thus be made to the P-values, such as $p^*=1-(1-p)^n$.

The statistical significance of the difference between genotype frequencies associated to every variance can be assessed by a Pearson chi-squared test of homogeneity of proportions with 2 degrees of freedom, using the same Bonferroni's adjustment as above.

Testing for unequal haplotype frequencies between cases and controls can be considered in the same framework as testing for unequal variance frequencies since a single variance can be considered as a haplotype of a single locus. The relevant likelihood ratio test compares a model where two seqarate sets of haplotype frequencies apply to the cases and controls, to one where the entire sample is characterized by a single common set of haplotype frequencies. This can be performed by repeated use of a computer program (Terwilliger and Ott, 1994, Handbook of Human Linkage Analysis, Baltimore, John Hopkins University Press) to successively obtain the log-likelihood corresponding to the set of haplotpe frequency estimates on the cases ($lnL_{case}$), on the controls ($lnL_{control}$), and on the overall ($lnL_{combined}$). The test statistic $2((lnL_{case})+(lnL_{control})-(lnL_{combined}))$ is then chi-squared with degrees of freedom (where r is the number of haplotypes).

To test for potentially confounding effects or effect-modifiers, such as sex, age, etc., logistic regression can be used with case-control status as the outcome variable, and genotypes and covariates (plus possible interactions) as predictor variables.

Example 12

Exemplary Pharmacogenetic Analysis Steps

In accordance with the discussion of distribution frequencies for variances, alleles, and haplotypes, variance detection, and correlation of variances or haplotypes with treatment response variability, the points below list major items which will typically be performed in an analysis of the pharmacogenetic determination of the effects of variances in the treatment of a disease and the selection/optimization of treatment.

List candidate gene/genes for a known genetic disease, and assign them to the respective metabolic pathways.

Determine their alleles, observed and expected frequencies, and their relative distributions among various ethnic groups, gender, both in the control and in the study (case) groups Measure the relevant clinical/phenotypic (biochemical/physiological) variables of the disease If the causal variance/allele in the candidate gene is unknown, then determine linkage disequilibria among variances of the candidate gene(s)

Divide the regions of the candidate genes into regions of high linkage disequilibrium and low disequilibrium Develop haplotypes among variances that show strong linkage disequilibrium using the computation methods.

Determine the presence of rare haplotypes experimentally. Confirm if the computationally determined rare haplotypes agree with the experimentally determined haplotypes. If there is a disagreement between the experimentally determined haplotypes and the computationally derived haplotypes, drop the computationally derived rare haplotypes, Construct cladograms from these haplotypes using the Templeton (1987) algorithm.

Note regions of high recombination. Divide regions of high recombination further to see patterns of linkage disequilibria.

Establish association between cladograms and clinical variables using the nested analysis of variance as presented by Templeton (1995), and assign causal variance to a specific haplotype For variances in the regions of high recombination, use permutation tests for establishing associations between variances and the phenotypic variables If two or more genes are found to affect a clinical variable determine the relative contribution of each of the genes or variances in relation to the clinical variable, using step-wise regression or discriminant function or principal component analysis.

Determine the relative magnitudes of the effects of any of the two variances on the clinical variable due to their genetic (additive, dominant or epistasis) interaction.

Using the frequency of an allele or haplotypes, as well as biochemical/clinical variables determined in the in vitro or in vivo studies, determine the effect of that gene or allele on the expression of the clinical variable, according to the measured genotype approach of Boerwinkle et al (Ann. Hum. Genet 1986).

Stratify ethnic/clinical populations based on the presence or absence of a given allele or a haplotype Optimize drug dosages based on the frequency of alleles and haplotypes as well as their effects using the measured genotype approach as a guide Example 13

Method for Producing cDNA

In order to identify sequence variances in a gene by laboratory methods it is in some instances useful to produce cDNA(s) from multiple human subjects. (In other instances it may be preferable to study genomic DNA.). Methods for producing cDNA are known to those skilled in the art, as are methods for amplifying and sequencing the cDNA or portions thereof. An example of a useful cDNA production protocol is provided below. As recognized by those skilled in the art, other specific protocols can also be used.

cDNA Production

** Make sure that all tubes and pipette tips are RNase-free. (Bake them overnight at 100° C. in a vaccum oven to make them RNase-free.)

1 Add the following to a RNase-free 0.2 ml micro-amp tube and mix gently:
   24 ul water (DEPC treated)
   12 ul RNA (1 ug/ul)
   12 ul random hexamers (50 ng/ul)
2 Heat the mixture to 70° C. for ten minutes.
3 Incubate on ice for 1 minute.
4 Add the following:
   16 ul 5×Synthesis Buffer
   8 ul 0.1 M DTT
   4 ul 10 mM dNTP mix (10 mM each dNTP)
   4 ul SuperScript RT II enzyme
   Pipette gently to mix.
5 Incubate at 42° C. for 50 minutes.
6 Heat to 70° C. for ten minutes to kill the enzyme, then place it on ice.
7 Add 160 ul of water to the reaction so that the final volume is 240 ul.
8 Use PCR to check the quality of the cDNA. Use primer pairs that will give a ~800 base pair long piece. See "PCR Optimization" for the PCR protocol.

The following chart shows the reagent amounts for a 20 ul reaction, a 80 ul reaction, and a batch of 39 (which makes enough mix for 36) reactions:

|  | 20 ul X | 80 ul X | 80 ul X |  |
|---|---|---|---|---|
|  | 1 tube | 1 tube | 39 tubes |  |
| water | 6 ul | 24 ul | 936 | water |
| RNA | 3 ul | 12 ul |  | RNA |
| random hexamers | 3 ul | 12 ul | 468 | random hexamers |
| synthesis buffer | 4 ul | 16 ul | 624 | synthesis buffer |
| 0.1 M DTT | 2 ul | 8 ul |  | 0.1 M DTT |
| 10 mM dNTP | 1 ul | 4 ul | 156 | 10 mM dNTP |
| SSRT | 1 ul | 4 ul | 156 | SSRT |

Example 14

Method for Detecting Variances by Single Strand Conformation Polymorphism (SSCP) Analysis This example describes the SSCP technique for identification of sequence variances of genes. SSCP is usually paired with a DNA sequencing method, since the SSCP method does not provide the nucleotide identity of variances. One useful sequencing method, for example, is DNA cycle sequencing of $^{32}$p labeled PCR products using the Femtomole DNA cycle sequencing kit from Promega (WI) and the instructions provided with the kit. Fragments are selected for DNA sequencing based on their behavior in the SSCP assay.

Single strand conformation polymorphism screening is a widely used technique for identifying an discriminating DNA fragments which differ from each other by as little as a single nucleotide. As originally developed by Orita et al. (Detection of polymorphisms of human DNA by gel electrophoresis as single-strand conformation polymorphisms. *Proc Natl Acad Sci USA.* 86(8):2766–70, 1989), the technique was used on genomic DNA, however the same group showed that the technique works very well on PCR amplified DNA as well. In the last 10 years the technique has been used in hundreds of published papers, and modifications of the technique have been described in dozens of papers. The enduring popularity of the technique is due to (1) a high degree of sensitivity to single base differences (>90%) (2) a high degree of selectivity, measured as a low frequency of false positives, and (3) technical ease. SSCP is almost always used together with DNA sequencing because SSCP does not directly provide the sequence basis of differential fragment mobility. The basic steps of the SSCP procdure are described below.

When the intent of SSCP screening is to identify a large number of gene variances it is useful to screen a relatively large number of individuals of different racial, ethnic and/or geographic origins. For example, 32 or 48 or 96 individuals is a convenient number to screen because gel electrophoresis apparatus are available with 96 wells (Applied Biosystems Division of Perkin Elmer Corporation), allowing 3×32, 2×48 or 96 samples to be loaded per gel.

The 32 (or more) individuals screened should be representative of most of the worlds major populations. For example, an equal distribution of Africans, Europeans and Asians constitutes a reasonable screening set. One useful source of cell lines from different populations is the Coriell Cell Repository (Camden, N.J.), which sells EBV immortalized lyphoblastoid cells obtained from several thousand subjects, and includes the racial/ethnic/geographic background of cell line donors in its catalog. Alternatively, a panel of cDNAs can be isolated from any specific target population.

SSCP can be used to analyze cDNAs or genomic DNAs. For many genes cDNA analysis is preferable because for many genes the full genomic sequence of the target gene is not available, however, this circumstance will change over the next few years. To produce cDNA requires RNA. Therefore each cell lines is grown to mass culture and RNA is isolated using an acid/phenol protocol, sold in kit form as Trizol by Life Technologies (Gaithersberg, Md.). The unfractionated RNA is used to produce cDNA by the action of a modified Maloney Murine Leukemia Virus Reverse Transcriptase, purchased in kit form from Life Technologies (Superscript II kit). The reverse transcriptase is primed with random hexamer primers to initiate cDNA synthesis along the whole length of the RNAs. This proved useful later in obtaining good PCR products from the 5' ends of some genes. Alternatively, oligodT can be used to prime cDNA synthesis.

Material for SSCP analysis can be prepared by PCR amplification of the cDNA in the presence of one $\alpha^{32}P$ labeled dNTP (usually $\alpha^{32}P$ dCTP). Usually the concentration of nonradioactive dCTP is dropped from 200 uM (the standard concentration for each of the four dNTPs) to about 100 uM, and $^{32}P$ dCTP is added to a concentration of about 0.1–0.3 uM. This involves adding a 0.3–1 ul (3–10 uCi) of $^{32}P$ cCTP to a 10 ul PCR reaction. Radioactive nucleotides can be purchased from DuPont/New England Nuclear.

The customary practice is to amplify about 200 base pair PCR products for SSCP, however, an alternative approach is to amplify about 0.8–1.4 kb fragments and then use several cocktails of restriction endonucleases to digest those into smaller fragments of about 0.1–0.3 kb, aiming to have as many fragments possible between 0.15 and 0.3 kb. The digestion strategy has the advantage that less PCR is required, reducing both time and costs. Also, several different restriction enzyme digests can be performed on each set of samples (for example 96 cDNAs), and then each of the digests can be run separately on SSCP gels. This redundant method (where each nucleotide is surveyed in three different fragments) reduces both the false negative and false positive rates. For example: a site of variance might lie within 2 bases of the end of a fragment in one digest, and as a result not affect the conformation of that strand; the same variance, in a second or third digest, would likely lie in a location more prone to affect strand folding, and therefore be detected by SSCP.

After digestion, the radiolabelled PCR products are diluted 1:5 by adding formamide load buffer (80% formamide, 1×SSCP gel buffer) and then denatured by heating to 90%C for 10 minutes, and then allowed to renature by quickly chilling on ice. This procedure (both the dilution and the quick chilling) promotes intra- (rather than inter-) strand association and secondary structure formation. The secondary structure of the single strands influences their mobility on nondenaturing gels, presumably by influencing the number of collisions between the molecule and the gel matrix (i.e., gel sieving). Even single base differences consistently produce changes in intrastrand folding sufficient to register as mobility differences on SSCP.

The single strands were then resolved on two gels, one a 5.5% acrylamide, 0.5×TBE gel, the other an 8% acrylamide, 10% glycerol, 1×TTE gel. (Other gel recipes are known to those skilled in the art.) The use of two gels provides a greater opportunity to recognize mobility differences. Both glycerol and acrylamide concentration have been shown to influence SSCP performance. By routinely analyzing three different digests under two gel conditions (effectively 6 conditions), and by looking at both strands under all 6 conditions, one can achieve a 12-fold sampling of each base pair of cDNA. However, if the goal is to rapidly survey many genes or cDNAs then a less redundant procedure would be optimal.

Example 15

Method for Detecting Variances by T4 Endonuclease VII (T4E7) Mismatch Cleavage Method The enzyme T4 endonuclease VII is derived from the bacteriophage T4. T4 endonuclease VII is used by the bacteriophage to cleave branched DNA intermediates which form during replication so the DNA can be processed and packaged. T4 endonuclease can also recognize and cleave heteroduplex DNA containing single base mismatches as well as deletions and insertions. This activity of the T4 endonuclease VII enzyme can be exploited to detect sequence variances present in the general population.

The following are the major steps involved in identifying sequence variations in a candidate gene by T4 endonuclease VII mismatch cleavage:

1. Amplification by the polymerase chain reaction (PCR) of 400–600 bp regions of the candidate gene from a panel of DNA samples The DNA samples can either be cDNA or genomic DNA and will represent some cross section of the world population.
2. Mixing of a fluorescently labeled probe DNA with the sample DNA. Heating and cooling the mixtures causing heteroduplex formation between the probe DNA and the sample DNA.
3. Addition of T4 endonuclease VII to the heteroduplex DNA samples. T4 endonuclease will recognize and cleave at sequence variance mismatches formed in the heteroduplex DNA.
4. Electrophoresis of the cleaved fragments on an ABI sequencer to determine the site of cleavage.
5. Sequencing of a subset of PCR fragments identified by T4 endonuclease VI to contain variances to establish the specific base variation at that location.

A more detailed description of the procedure is as follows:

A candidate gene sequence is downloaded from an appropriate database. Primers for PCR amplification are designed which will result in the target sequence being divided into amplification products of between 400 and 600 bp. There will be a minimum of a 50 bp of overlap not including the primer sequences between the 5' and 3' ends of adjacent fragments to ensure the detection of variances which are located close to one of the primers.

Optimal PCR conditions for each of the primer pairs is determined experimentally. Parameters including but not limited to annealing temperature, pH, $MgCl_2$ concentration, and KCl concentration will be varied until conditions for optimal PCR amplification are established. The PCR conditions derived for each primer pair is then used to amplify a panel of DNA samples (cDNA or genomic DNA) which is chosen to best represent the various ethnic backgrounds of the world population or some designated subset of that population.

One of the DNA samples is chosen to be used as a probe. The same PCR conditions used to amplify the panel are used to amplify the probe DNA. However, a flourescently labeled nucleotide is included in the deoxy-nucleotide mix so that a percentage of the incorporated nucleotides will be fluorescently labeled.

The labeled probe is mixed with the corresponding PCR products from each of the DNA samples and then heated and cooled rapidly. This allows the formation of heteroduplexes between the probe and the PCR fragments from each of the DNA samples. T4 endonuclease VII is added directly to these reactions and allowed to incubate for 30 min. at 37 C. 10 ul of the Formamide loading buffer is added directly to each of the samples and then denatured by heating and cooling. A portion of each of these samples is electrophoresed on an ABI 377 sequencer. If there is a sequence variance between the probe DNA and the sample DNA a mismatch will be present in the heteroduplex fragment formed. The enzyme T4 endonuclease VII will recognize the mismatch and cleave at the site of the mismatch. This will result in the appearance of two peaks corresponding to the two cleavage products when run on the ABI 377 sequencer.

Fragments identified as containing sequencing variances are subsequently sequenced using conventional methods to establish the exact location and sequence variance.

Example 16

Method for Detecting Variances by DNA Sequencing

Sequencing by the Sanger dideoxy method or the Maxim Gilbert chemical cleavage method is widely used to determine the nucleotide sequence of genes. Presently, a worldwide effort is being put forward to sequence the entire human genome. The Human Genome Project as it is called has already resulted in the identification and sequencing of many new human genes. Sequencing can not only be used to identify new genes, but can also be used to identify variations between individuals in the sequence of those genes.

The following are the major steps involved in identifying sequence variations in a candidate gene by sequencing:

1. Amplification by the polymerase chain reaction (PCR) of 400–700 bp regions of the candidate gene from a panel of DNA samples The DNA samples can either be cDNA or genomic DNA and will represent some cross section of the world population.

2. Sequencing of the resulting PCR fragments using the Sanger dideoxy method. Sequencing reactions are performed using flourescently labeled dideoxy terminators and electrophoresed on an ABI 377 sequencer or its equivalent.
3. Analysis of the resulting data from the ABI 377 sequencer using software programs designed to identify sequence variations between the different samples analyzed.

A more detailed description of the procedure is as follows:

A candidate gene sequence is downloaded from an appropriate database. Primers for PCR amplification are designed which will result in the target sequence being divided into amplification products of between 400 and 700 bp. There will be a minimum of a 50 bp of overlap not including the primer sequences between the 5' and 3' ends of adjacent fragments to ensure the detection of variances which are located close to one of the primers.

Optimal PCR conditions for each of the primer pairs is determined experimentally. Parameters including but not limited to annealing temperature, pH, $MgCl_2$ concentration, and KCl concentration will be varied until conditions for optimal PCR amplification are established. The PCR conditions derive from each primer pair is then used to amplify a panel of DNA samples (cDNA or genomic DNA) which is chosen to best represent the various ethnic backgrounds of the world population or some designated subset of that population.

PCR reactions are purified using the QIAquick 8 PCR purification kit (Qiagen cat #28142) to remove nucleotides, proteins and buffers. The PCR reactions are mixed with 5 volumes of Buffer PB and applied to the wells of the QIAquick strips. The liquid is pulled through the strips by applying a vacuum. The wells are then washed two times with 1 ml of buffer PE and allowed to dry for 5 minutes under vacuum. The PCR products are eluted from the strips using 60 ul of elution buffer.

The purified PCR fragments are sequenced in both directions using the Perkin Elmer ABI Prism™ Big Dye™ terminator Cycle Sequencing Ready Reaction Kit (Cat #4303150). The following sequencing reaction is set up: 8.0 ul Terminator Ready Reaction Mix, 6.0 ul of purified PCR fragment, 20 picomoles of primer, deionized water to 20 ul. The reactions are run through the following cycles 25 times: 96° C. for 10 second, annealing temperature for that particular PCR product for 5 seconds, 60° C. for 4 minutes.

The above sequencing reactions are ethanol precipitated directly in the PCR plate, washed with 70% ethanol, and brought up in a volume of 6 ul of formamide dye. The reactions are heated to 90° C. for 2 minutes and then quickly cooled to 4° C. 1 ul of each sequencing reaction is then loaded and run on an ABI 377 sequencer.

The output for the ABI sequencer appears as a series of peaks where each of the different nucleotides, A, C, G, and T appear as a different color. The nucleotide at each position in the sequence is determined by the most prominent peak at each location. Comparison of each of the sequencing outputs for each sample can be examined using software programs to determine the presence of a variance in the sequence. One example of heterozygote detection using sequencing with dye labeled terminators is described by Kwok et. al. (Kwok, P.-Y.; Carlson, C.; Yager, T. D., Ankener, W., and D. A. Nickerson, *Genomics* 23, 138–144, 1994). The software compares each of the normalized peaks between all the samples base by base and looks for a 40% decrease in peak height and the concomitant appearance of a new peak underneath. Possible variances flagged by the software are further analyzed visually to confirm their validity.

In connection with the provision and description of nucleic acid sequences, the references herein to gene names and to GenBank and OMIM reference numbers provides the relevant sequences, recognizing that the described sequences will, in most cases, also have other corresponding allelic variants. Also, it is recognized that the referenced sequences may contain sequencing error. Such error does not interfere with identification of a relevant gene or portion of a gene, and can be readily corrected by redundant sequencing of the relevant sequence (preferably using both strands of DNA). Nucleic acid molecules or sequences can be readily obtained or determined utilizing the reference sequences. In general, molecules such as nucleic acid hybridization probes and amplification primers can be provided and are described by the selected portion of the reference sequence, corrected if necessary. Thus, nucleic acid hybridization probes and/or primers are thus described by a portion of a reference sequence or a sequence complementary thereto (sequence corrected if necessary), or an allelic variant of such a sequence, which preferably includes at least one variance site, preferably a variance site indicative of the effectiveness of a treatment for a disease or condition, and preferably include at least 12,13,14,15,16,17, 18,19,20,23,25,27,30,35,40,45, or 50 nucleotides.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, using other compounds, and/or methods of administration are all within the scope of the present invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the following claims.

| Hugo | GID | Variance Table OMIM ID | VGX Symbol | Description |
|---|---|---|---|---|
| | Variance Start | Variance | | |
| U73338 | U73338 | 156570 | GEN-69 | Methionine Synthase |
| | 194 | (−201) C >G | 5' | |
| | 284 | (−111) C >T | 5' | |
| | 1136 | 742G >A | V248M | |
| | 1252 | 858C >T | Silent | |
| | 1334 | 940G >A | D314N | |
| | 1699 | 1305T >C | Silent | |
| | 3150 | 2756A >G | D919G | |
| | 3207 | 2813G >T | S938I | |
| | 3209 | 2815G >C | G939R | |
| | 5444 | 5050C >A | 3' | |
| | 5551 | 5157G >A | 3' | |
| | 5573 | 5179C >T | 3' | |
| | 5659 | 5265T >C | 3' | |
| | 5678 | 5284T >C | 3' | |
| | 5874 | 5480C >T | 3' | |
| | 5934 | 5540A >G | 3' | |
| D78586 | D78586 | 114010 | GEN-BR | CAD PROTEIN |
| | 3434 | 3408C >T | Silent | |
| | 4313 | 4287T >C | Silent | |
| | 4799 | 4773A >G | Silent | |
| | 5255 | 5229C >T | Silent | |
| | 5455 | 5429G >A | R1810Q | |
| | 5507 | 5481T >C | Silent | |
| | 5810 | 5784C >T | Silent | |
| | 6128 | 6102C >T | Silent | |
| | 6626 | 6600C >T | Silent | |
| | 6686 | 6660C >T | Silent | |
| U09178 | U09178 | 274270 | GEN-HA | |
| | Dihydropyrimidine Dehydrogenase | | | |
| | 166 | 85T >C | C29R | |
| | 577 | 496A >G | M166V | |
| | 638 | 557A >G | Y186C | |
| | 1708 | 1627A >G | I543V | |
| | 3432 | 3351T >C | 3' | |
| | 3682 | 3601C >T | 3' | |
| | 3730 | 3649G >A | 3' | |
| | 3925 | 3844A >G | 3' | |
| | 3937 | 3856T >C | 3' | |
| U19720 | U19720 | 600424 | GEN-I1 | Folate Transporter (SLC19A1) |
| | 175 | 80G >A | R27H | |
| | 341 | 246C >G | Silent | |
| | 791 | 696C >T | Silent | |
| | 1067 | 972G >A | Silent | |
| | 1337 | 1242G >A | Silent | |
| | 1997 | 1902T >C | 3' | |
| | 2100 | 2005^2006insG | 3' | |
| | 2582 | 2487T >G | 3' | |
| | 2617 | 2522G >T | 3' | |
| | 2652 | 2557T >C | 3' | |
| U92868 | U92868 | 600424 | GEN-LUK | Homo sapiens reduced |

-continued

| Hugo | GID | Variance Table OMIM ID | VGX Symbol | Description |
|---|---|---|---|---|
| | Variance Start | Variance | | |
| | folate carrier (RFC1) gene, exons, 1a, 1c and 1b | | | |
| | 431 | 431A >G | Intron | |
| | 441 | 441A >G | Intron | |
| | 498 | 498C >T | Intron | |
| | 579 | 579G >C | Intron | |
| | 599 | 599G >C | Intron | |
| x02308 | x02308 | 188350 | GEN-KL | Thymidylate synthetase (SEQIDNO:1) |
| | 1066 | 961T >C | 3' | |
| | 1136 | 1031A >G | 3' | |
| | 1497 | 1392T >A | 3' | |
| D00517 | D00517 | 188350 | GEN-LUC | Thymidylate synthase, promoter (SEQIDNO:2) |
| | 276 | 276C >T | Intron | |
| | 321 | 321T >C | Intron | |
| | 452 | 452G >A | Intron | |
| | 457 | 457^insC | Intron | |
| | 491 | 491C >A | Intron | |
| | 533 | 533T >C | Intron | |
| | 624 | 624A >C | Intron | |
| | 639 | 639A >G | Intron | |
| | 655 | 655T >C | Intron | |
| D00596 | D00596 | 188350 | GEN-LUD | Homo sapiens |
| | gene for thymidylate synthase, exons 1, 2, 3, 4, 5, 6, 7, complete cds (SEQIDNO:3) | | | |
| | 701 | 701A >C | Intron | |
| | 716 | 716A >G | Intron | |
| | 732 | 732T >C | Intron | |
| | 1293 | 1293A >G | Intron | |
| | 1322 | 1322C >G | Intron | |
| | 1379 | 1379T >C | Intron | |
| | 1590 | 1590C >T | Intron | |
| | 1688 | 1688C >A | Intron | |
| | 2401 | 2401A >G | Intron | |
| | 2429 | 2429G >A | Intron | |
| | 2488 | 2488C >T | Intron | |
| | 2594 | 2594G >T | Intron | |
| | 2618 | 2618G >A | Intron | |
| | 3083 | 3083G >A | Intron | |
| | 3125 | 3125G >A | Intron | |
| | 3212 | 3212C >T | Intron | |
| | 3619 | 3619T >A | Intron | |
| | 3635 | 3635G >A | Intron | |
| | 4256 | 4256G >A | Intron | |
| | 4898 | 4898A >G | Intron | |
| | 5006 | 5006C >T | Intron | |
| | 5062 | 5062G >A | Intron | |
| | 5167 | 5167G >A | Intron | |
| | 11069 | 11069A >G | Intron | |
| | 11238 | 11238C >T | Intron | |
| | 11293 | 11293T >G | Intron | |
| | 11422 | 11422T >C | Intron | |
| | 11686 | 11686C >T | Intron | |
| | 12598 | 12598T >C | Intron | |
| | 13171 | 13171T >C | Intron | |
| | 13298 | 13298G >A | Intron | |
| | 13645 | 13645T >C | Intron | |
| | 13751 | 13751C >A | Intron | |
| | 13782 | 13782T >C | Intron | |
| | 13806 | 13806T >C | Intron | |
| | 13813 | 13813T >C | Intron | |
| | 14479 | 14479A >G | Intron | |
| | 14546 | 14546^insT | Intron | |
| | 14585 | 14585C >T | Intron | |
| | 14729 | 14729G >A | Intron | |
| | 14787 | 14787C >T | Intron | |
| | 14795 | 14795G >A | Intron | |
| | 15041 | 15041T >C | Intron | |
| | 15343 | 15343G >A | Intron | |
| | 15449 | 15449G >A | Intron | |
| | 15502 | 15502G >A | Intron | |
| | 15545 | 15545C >T | Intron | |

| Hugo | GID Variance Start | Variance Table OMIM ID Variance | VGX Symbol | Description |
|---|---|---|---|---|
| | 15589 | 15589A >G | Intron | |
| | 15769 | 15769C >T | 3' | |
| | 15839 | 15839A >G | 3' | |
| | 16148 | 16148G >A | 3' | |
| | 16198 | 16198T >G | 3' | |
| | 16202 | 16202G >T | Intron | |
| X59618 | X59618 | 180390 | GEN-M3 | Ribonucleotide reductase M2 polypeptide |
| | 128 | (−67)G >A | 5' | |
| | 189 | (−6)T >G | 5' | |
| | 524 | 330C >G | Silent | |
| | 1399 | 1205T >A | 3' | |
| | 1464 | 1270G >A | 3' | |
| | 1636 | 1442C >T | 3' | |
| | 1738 | 1544C >T | 3' | |
| | 2259 | 2065T >C | 3' | |
| S72487 | S72487 | 131222 | GEN-3LD | Thymidine phosphorylase, partial |
| | 183 | 19G >A | D7N | |
| | 483 | 319C >T | 3' | |
| | 601 | 437G >C | 3' | |
| | 1299 | 1135G >A | 3' | |
| M58602 | M58602 | 131222 | GEN-LUB | Thymidine phosphorylase, promoter and genomic |
| | 124 | 124C >T | 3' | |
| | 439 | 439G >A | 3' | |
| | 1044 | 1044^insCT | 3' | |
| | 1331 | 1331G >A | 3' | |
| | 1977 | 1977G >A | Intron | |
| | 2149 | 2149G >A | Intron | |
| | 2467 | 2467A >G | Intron | |
| | 2634 | 2634C >G | Intron | |
| | 2975 | 2975G >A | Intron | |
| | 3116 | 3116G >T | Intron | |
| | 3255 | 3255A >C | Intron | |
| | 3344 | 3344T >C | Intron | |
| | 4051 | 4051C >T | Intron | |
| | 4782 | 4782G >A | Intron | |
| | 5022 | 5022T >C | Intron | |
| | 5266 | 5266G >A | Intron | |
| | 5285 | 5285G >C | Intron | |
| | 5438 | 5438T >A | Intron | |
| | 5482 | 5482C >T | Intron | |
| | 5629 | 5629G >A | Intron | |
| | 5648 | 5648G >T | Intron | |
| | 5731 | 5731G >A | Intron | |
| M98045 | M98045 | 136510 | GEN-4C3 | Homo sapiens folylpolyglutamate synthetase mRNA, complete cds |
| | 802 | 732C >T | Silent | |
| | 1747 | 1677G >T | 3' | |
| | 1900 | 1830T >C | 3' | |
| U24253 | U24253 | 136510 | GEN-LUE | Human folylpolyglutamate synthetase (FPGS) gene, exons 5–11, and partial cds |
| | 1424 | 1424C >A | Intron | |
| | 1649 | 1649G >A | Intron | |
| | 2554 | 2554A >G | Intron | |
| U24252 | U24252 | 136510 | GEN-LUF | Folylpolyglutamate synthetase, promoter and exons 1–4 |
| | 263 | 263A >G | Intron | |
| | 266 | 266G >T | Intron | |
| | 527 | 527C >G | Intron | |
| | 1037 | 1037A >G | 5' | |
| | 1139 | 1139G >A | Intron | |
| | 1217 | 1217C >T | Intron | |
| | 1647 | 1647C >T | Intron | |
| | 1955 | 1955G >A | Intron | |
| | 2017 | 2017G >A | Intron | |
| | 2037 | 2037G >A | Intron | |
| | 2189 | 2189A >G | Intron | |
| | 2282 | 2282C >T | Intron | |
| | 2309 | 2309A >G | Intron | |
| U09806 | U09806 | 236250 | GEN-4FZ | Human methylenetetrahydrofolate reductase mRNA, partial cds |
| | 120 | 120T >C | Silent | |
| | 464 | 464T >G | M155R | |
| | 519 | 519C >T | Silent | |
| | 668 | 668C >T | A223V | |
| | 1059 | 1059T >C | Silent | |
| | 1289 | 1289C >A | 3' | |
| | 1308 | 1308T >C | 3' | |
| | 1784 | 1784G >A | 3' | |
| AF061655 | AF061655 | 123920 | GEN-LUJ | Cytidine deaminase, promoter |
| | 575 | 575T >C | Intron | |
| | 648 | 645T >C | Intron | |
| | 771 | 771G >C | Intron | |
| | 883 | 883G >A | Intron | |
| | 941 | 941^insC | 5' | |
| | 1051 | 1051A >C | K27Q | |

What is claimed is:

1. A method comprising:

(a) providing a sample comprising nucleic acid molecules present in a biological sample obtained from a patient;

(b) contacting the sample with either a probe comprising at least 15 contiguous nucleotides of the nucleotide sequence of SEQ ID NO:1, the probe comprising at least one of:
      (i) nucleotide 1066 wherein N is C;
      (ii) nucleotide 1136 wherein N is G;
      (iii) nucleotide 1497 wherein N is A;
   or the complement thereof; and (c) determining if the sample comprises a nucleic acid molecule that hybridizes to the probe.

2. A method comprising:

(a) providing a sample comprising nucleic acid molecules present in a biological sample obtained from a patient;

(b) contacting the sample with either a probe comprising at least 15 contiguous nucleotides of the nucleotide sequence of SEQ ID NO:2, the probe comprising at least one of:
      (i) nucleotide 276 wherein N is T;
      (ii) nucleotide 321 wherein N is C;
      (iii) nucleotide 452 wherein N is A;
      (iv) C is inserted after nucleotide 457;
      (v) nucleotide 491 wherein N is A;
      (vi) nucleotide 533 wherein N is C;
      (vii) nucleotide 624 wherein N is C;
      (viii) nucleotide 639 wherein N is G;
      (ixi) nucleotide 655 wherein N is C;
   or the complement thereof; and (c) determining if the sample comprises a nucleic acid molecule that hybridizes to the probe.

3. A method comprising:

(a) providing a sample comprising nucleic acid molecules present in a biological sample obtained from a patient;

(b) contacting the sample with either a probe comprising at least 15 contiguous nucleotides of the nucleotide sequence of SEQ ID NO:3, the probe comprising at least one of:
(i) nucleotide 701 wherein N is C;
(ii) nucleotide 716 wherein N is G;
(iii) nucleotide 732 wherein N is C;
(iv) nucleotide 1293 wherein N is G;
(v) nucleotide 1322 wherein N is G;
(vi) nucleotide 1379 wherein N is C;
(vii) nucleotide 1590 wherein N is T;
(viii) nucleotide 1688 wherein N is G;
(ixi) nucleotide 2401 wherein N is G;
(x) nucleotide 2429 wherein N is A;
(xi) nucleotide 2488 wherein N is T;
(xii) nucleotide 2594 wherein N is T;
(xiii) nucleotide 2618 wherein N is A;
(xiv) nucleotide 3083 wherein N is A;
(xv) nucleotide 3125 wherein N is A;
(xvi) nucleotide 3212 wherein N is T
(xvii) nucleotide 3619 wherein N is A;
(xviii) nucleotide 3635 wherein N is A;
(xix) nucleotide 4256 wherein N is A;
(xx) nucleotide 4898 wherein N is G;
(xxi) nucleotide 5006 wherein N is T;
(xxii) nucleotide 5062 wherein N is A;
(xxiii) nucleotide 5167 wherein N is A;
(xxiv) nucleotide 11069 wherein N is G;
(xxv) nucleotide 11238 wherein N is T;
(xxvi) nucleotide 11293 wherein N is G;
(xxvii) nucleotide 11422 wherein N is C;
(xxviii) nucleotide 11686 wherein N is T;
(xxix) nucleotide 12598 wherein N is C;
(xxx) nucleotide 13171 wherein N is C;
(xxxi) nucleotide 13298 wherein N is A;
(xxxii) nucleotide 13645 wherein N is C;
(xxxiii) nucleotide 13751 wherein N is A;
(xxxiv) nucleotide 13782 wherein N is C;
(xxxv) nucleotide 13806 wherein N is C;
(xxxvi) nucleotide 13813 wherein N is C;
(xxxvii) nucleotide 14479 wherein N is G;
(xxxviii) T is inserted after nucleotide 14546;
(xxxix) nucleotide 14585 wherein N is T;
(xl) nucleotide 14729 wherein N is A;
(xli) nucleotide 14787 wherein N is T;
(xlii) nucleotide 14795 wherein N is A;
(xliii) nucleotide 15041 wherein N is C;
(xliv) nucleotide 15343 wherein N is A;
(xlv) nucleotide 15449 wherein N is A;
(xlvi) nucleotide 15502 wherein N is A;
(xlvii) nucleotide 15545 wherein N is T;
(xlvii) nucleotide 15589 wherein N is G;
(xlix) nucleotide 15769 wherein N is T;
(l) nucleotide 15839 wherein N is G;
(li) nucleotide 16148 wherein N is A;
(lii) nucleotide 16198 wherein N is G; and
(liii) nucleotide 16202 wherein N is T
or the complement thereof; and
(c) determining if the sample comprises a nucleic acid molecule that hybridizes to the probe.

* * * * *

SEQUENCE LISTING

<160> NUMBER OF SEQ ID NOS: 16

<210> SEQ ID NO 1
<211> LENGTH: 7224
<212> TYPE: DNA
<213> ORGANISM: Homo sapiens
<220> FEATURE:
<221> NAME/KEY: misc_feature
<222> LOCATION: 194, 3209
<223> OTHER INFORMATION: n = c or g
<221> NAME/KEY: misc_feature
<222> LOCATION: 1136, 1334, 3150, 5551, 5934
<223> OTHER INFORMATION: n = a or g
<221> NAME/KEY: misc_feature
<222> LOCATION: 284, 1252, 1699, 5573, 5659, 5678, 5874
<223> OTHER INFORMATION: n = c or t
<221> NAME/KEY: misc_feature
<222> LOCATION: 3207
<223> OTHER INFORMATION: n = g or t
<221> NAME/KEY: misc_feature
<222> LOCATION: 5444
<223> OTHER INFORMATION: n = c or a

<400> SEQUENCE: 1

```
aaaggttcta aatgtctgcg gggctcagag ccggatgtca cgtcgtcctc ctctgccggt       60
tttctcttgg gtccttttcc gtgccgtccc gcgactccgc ctctgccgc gcgtgtctgg       120
ctgctaggcc gacaccaagg actggccggg tacccgggaa gaaagcacgt gctccagcag      180
ttgccgcgcc cagncccgag agaggcccta gggcgctgcg ggctttcggg gtccgcagtc      240
cccccgcgac gcgagccaac gggaggcgtc aaaagacccg ggcnttgtgt ggcaggctcg      300
cctggcgctg gctggcgtgg cccttggccg tcgtcacctg tggagagcac gtcttctctg      360
ccgcgccctc tgcgcaagga ggagactcga caacatgtca cccgcgctcc aagacctgtc      420
gcaacccgaa ggtctgaaga aaccctgcg ggatgagatc aatgccattc tgcagaagag       480
gattatggtg ctggatggag ggatgggac catgatccag cgggagaagc taaacgaaga      540
acacttccga ggtcaggaat ttaaagatca tgccaggccg ctgaaaggca acaatgacat      600
tttaagtata actcagcctg atgtcattta ccaaatccat aaggaatact gctggctgg       660
ggcagatatc attgaaacaa atacttttag cagcactagt attgcccaag ctgactatgg      720
ccttgaacac ttgcctacc ggatgaacat gtgctctgca ggagtggcca gaaaagctgc       780
cgaggaggta actctccaga caggaattaa gaggtttgtg gcagggctc tgggtccgac       840
taataagaca ctctctgtgt ccccatctgt ggaaaggccg gattatagga acatcacatt      900
tgatgagctt gttgaagcat accaagagca ggccaaagga cttctggatg gcggggttga      960
tatcttactc attgaaacta tttttgatac tgccaatgcc aaggcagcct tgtttgcact     1020
ccaaaatctt tttgaggaga atatgctcc ccggcctatc tttatttcag ggacgatcgt      1080
tgataaaagt gggcggactc tttccggaca gacaggagag ggatttgtca tcagcntgtc     1140
tcatggagaa ccactctgca ttggattaaa ttgtgctttg ggtgcagctg aaatgagacc     1200
ttttattgaa ataattggaa aatgtacaac agcctatgtc ctctgttatc cnaatgcagg     1260
tcttcccaac acctttggtg actatgatga aacgccttct atgatggcca agcacctaaa     1320
ggattttgct atgnatggct tggtcaatat agttggagga tgctgtgggt caacaccaga     1380
tcatatcagg gaaattgctg aagctgtgaa aaattgtaag cctagagttc cacctgccac     1440
tgcttttgaa ggacatatgt tactgtctgg tctagagccc ttcaggattg gaccgtacac     1500
caactttgtt aacattggag agcgctgtaa tgttgcagga tcaaggaagt ttgctaaact     1560
catcatggca ggaaactatg aagaagcctt gtgtgttgcc aaagtgcagg tggaaatggg     1620
agcccaggtg ttggatgtca acatggatga tggcatgcta gatggtccaa gtgcaatgac     1680
cagattttgc aacttaatng cttccgagcc agacatcgca aagtaccctt tgtgcatcga     1740
ctcctccaat tttgctgtga ttgaagctgg gttaaagtgc tgccaaggga agtgcattgt     1800
caatagcatt agtctgaagg aaggagagga cgacttcttg gagaaggcca ggaagattaa     1860
aaagtatgga gctgctatgg tggtcatggc ttttgatgaa gaaggacagg caacagaaac     1920
agacacaaaa atcagagtgt gcaccccgggc ctaccatctg cttgtgaaaa aactgggctt     1980
```

```
taatccaaat gacattattt ttgaccctaa tatcctaacc attgggactg gaatggagga    2040
acacaacttg tatgccatta attttatcca tgcaacaaaa gtcattaaag aaacattacc    2100
tggagccaga ataagtggag gtctttccaa cttgtccttc tccttccgag aatggaagc    2160 cattcgagaa gcaatgcatg gggttttcct ttaccatgca atcaagtctg catggacat    2220 ggggatagtg aatgctggaa acctccctgt gtatgatgat atccataagg aacttctgca    2280
gctctgtgaa gatctcatct ggaataaaga ccctgaggcc actgagaagc tcttacgtta    2340
tgcccagact caaggcacag gagggaagaa agtcattcag actgatgagt ggagaaatgg    2400
ccctgtcgaa gaacgccttg agtatgccct tgtgaagggc attgaaaaac atattattga    2460
ggatactgag gaagccaggt taaaccaaaa aaaatatccc cgacctctca atataattga    2520
aggacccctg atgaatggaa tgaaaattgt tggtgatctt tttggagctg aaaaatgtt    2580 tctacctcag gttataaagt cagcccgggt tatgaagaag gctgttggcc accttatccc    2640
tttcatggaa aagaaagag aagaaaccag agtgcttaac ggcacagtag aagaagagga    2700
cccttaccag ggcaccatcg tgctggccac tgttaaaggc gacgtgcacg acataggcaa    2760
gaacatagtt ggagtagtcc ttggctgcaa taatttccga gttattgatt taggagtcat    2820
gactccatgt gataagatac tgaaagctgc tcttgaccac aaagcagata taattggcct    2880
gtcaggactc atcactcctt ccctggatga aatgattttt gttgccaagg aaatggagag    2940
attagctata aggattccat tgttgattgg aggagcaacc acttcaaaaa cccacacagc    3000
agttaaaata gctccgagat acagtgcacc tgtaatccat gtcctggacg cgtccaagag    3060
tgtggtggtg tgttcccagc tgttagatga aaatctaaag gatgaatact ttgaggaaat    3120
catggaagaa tatgaagata ttagacaggn ccattatgag tctctcaagg agaggagata    3180
cttaccctta agtcaagcca gaaaaantng tttccaaatg gattggctgt ctgaacctca    3240
cccagtgaag cccacgttta ttgggaccca ggtctttgaa gactatgacc tgcagaagct    3300
ggtggactac attgactgga agccttcctt tgatgtctgg cagctccggg gcaagtaccc    3360
gaatcgaggc tttcccaaga tatttaacga caaaacagta ggtggagagg ccaggaaggt    3420
ctacgatgat gcccacaata tgctgaacac actgattagt caaaagaaac tccgggcccg    3480
gggtgtggtt gggttctggc cagcacagag tatccaagac gacattcacc tgtacgcgga    3540
ggctgctgtg ccccaggctg cagagcccat agccaccttc tatgggttaa ggcaacaggc    3600
tgagaaggac tctgccagca cggagccata ctactgcctc tcagacttca tcgctccctt    3660
gcattctggc atccgtgact acctgggcct gtttgccgtt gcctgctttg ggtagaaga    3720 gctgagcaag gcctatgagg atgatggtga cgactacagc agcatcatgg tcaaggcgct    3780
gggggaccgg ctggcagagg cctttgcaga agagctccat gaaagagttc gccgagaact    3840
gtgggcctac tgtggcagtg agcagctgga cgtcgcagac ctgcgcaggc tgcggtacaa    3900
gggcatccgc ccggctcctg gctaccccag ccagcccgac cacaccgaga agctcaccat    3960
gtggagactt gcagacatcg agcagtctac aggcattagg ttaacagaat cattagcaat    4020
ggcacctgct tcagcagtct caggcctcta cttctccaat ttgaagtcca aatattttgc    4080
tgtggggaag atttccaagg atcaggttga ggattatgca ttgaggaaga acatatctgt    4140
ggctgaggtt gagaaatggc ttggacccat tttgggatat gatacagact aactttttt    4200 ttttttgcct tttttattct tgatgatcct caaggaaata caacctaggg tgccttaaaa    4260
ataacaacaa caaaaaacct gtgtgcatct ggctgacact tccctgcttc tggttttcga    4320
```

```
agactattta gtggaacctt gtagaggagc agggtcttcc tgcagtgcct ggaaaacagg      4380
cgctgttttt ttgggacctt gcgtgaagag cagtgagcag ggttcctgtg gtttccctgg      4440
tccctctgag atggggacag actgaagaca gaggtcgttt gatttcaaag caagtcaacc      4500
tgcttttttc tgtttttaca gtggaatcta ggaggccact tagtcgtctt tttttcctct      4560
tagaagaaaa gcctgaaact gagttgaata gagaagtgtg accctgtgac aaaatgatac      4620
tgtgagaaat ggggcatttt aatctaagtg gttataacag tggattctga cggggaaggt      4680
gtagctctgt tctcttcgga agacctcgtt ttctaaaggc tggactaaat ggctgcagaa      4740 ctcccttttgg caaaaggcat gcgctcactg cttgcttgtc agaaacactg aagccatttg      4800
ccccagtgtg gtcaagcagc catgctttct gggcattttc gtcctcccat aatttcatat      4860
ttccgtaccc ctgaggaaac aaaaaggaaa tgaggagaga aagttactgt taagggtggt      4920
taacattttt tttgttttgt tttgttttgg tttttttttt tttgagacag agtctggctc      4980
tgtcgcccag gctggagtgc agggggcgcaa tctcggctca tagcaagctc cgcctcctgg      5040
gttcatgcca ttctcctgcc tcagcctcca gagtagctgg gactacaggt gcccgccacc      5100
acacccggct aatttttttgt gttttttacaa aatacaaaaa agtagagaca ggatttcact      5160
gtgttagcca ggatggtctt gatctcccga cctcgtgatc tgcccacctc agcctcccaa      5220
aatgctggga ttacaggcgt gagccaccga gcctggccgg ttaacatctt ttaattgttt      5280
ccaggattga gcaggttctc agctgggctc tgatatcccg tgcggagttg acaagtggg      5340 cagcataaag tcactcattt cttaccattt tattcccctc aattctcaat atattcagta      5400
atgaagaatg gtgccaccac tcaagcaaca agcctcaaac tcanccatgt catctttttc      5460
ttggatgatt gcagttattt caaaaatttg catgcaaaat atacactcat cctacttcaa      5520
gatggtggtg gcaatagtca ggagaaggta ncattggagt cctggtttga ttngaaggat      5580
gaagacgaag aagcaaggga ggaacaaatg aagaaccatc tttgttcatg aataggaata      5640
ttcaagatta taaaggtanc aggtctccta aaattganct atggatttaa taccatttt      5700 aatggaaatt ccaacagatt ttattgaatg aaacaagcag gtgtttatat ggagtagcaa      5760
aggacttaaa attaccaaat gcttctaaat atgaaggaga ggttggggac acgcaccta      5820 tgtgatacca agttttattg tcaagacagt gtcatggtgc agaggtaggc attntgagca      5880
ggggaacaaa ataagggcct agaaactcac ccgtgcatat gttgaccttt gcanaatgac      5940
ctggtgacat ggcaagtcag tggggacagg aaggaccact ccctaagtaa tcccagaaca      6000
atggctattc atgtgggaaa aaaagaaatt ttactttctc tcaccttacc tggtgataag      6060
ttccaaatat gttaagggct ttaatacaaa agcaaaaat tgtcagtgtt tggatgaaaa      6120
aagccttagg gcaggaaaga atctcttgag acataaagta gtaatcataa aggacaagat      6180
ggttaagtca attctgttaa aactcaaggc ttatattaag caaacacttg aagtgagaag      6240
atgatccaca acttgagaag acatttataa tacaaataac tgatgaagga ttcataatca      6300
caaatataga gaattcctat ttaaaaaaat agaaaaatag tgaagactac acaagaggaa      6360 ataggcttt taaataaata gatgttctgt agcattggtc agggaaatat gaattaggac      6420
cacaatgaga ttccatttta tatccataag atttgcaaag gttgggtctg acagtaccag      6480
ttgttagatc tgtagggact tgtacaacat tgtggatgtg taaacaggca ccactgcttt      6540
aaaaaacaat tatcccttac agacttgaac atttgcagac cttatgatct tgcttccaac      6600
tcccacctgt atgtccagca aactcttgca tgtggccact aggaggaatg tgtaagaatg      6660
ttcatagtta catattata atagttaata actggaaaaa gtgaaatgta tgtctgtcta      6720
```

-continued

```
caggaaaata ggtgaataat tagatatatg tattcattct acgggatatt attcagtagt    6780
ggaaatgagt gaactacagc tatacctcac aataagaatg aatctcagaa aatattaagg    6840
aaaaaagcaa gtttgaagag accacatggg gcgtactatt tttattgagc ccaaaaacaa    6900
gcaaaaccaa agaatatgta gtctaagcat acgtatacaa taaaactatg ctattaaaaa    6960
aaaaggtaac tgataaaacca aaattgagca tagtaattac ccacagaagg aggaagtgga    7020
agggacagga gcacataggt agatgccaag ttatgcagct gttctggttc ctcctggtag    7080
gcttacaagt gtttactata tgctattaat acattatact ttataactaa tagataacag    7140 tttttttacat attaaatatg ttctacttaa atatattata aaaaataaag gcaaagtgga    7200
atgataacct aaaaaaaaaa aaaa                                            7224
```

<210> SEQ ID NO 2
<211> LENGTH: 6972
<212> TYPE: DNA
<213> ORGANISM: Homo sapiens
<220> FEATURE:
<221> NAME/KEY: misc_feature
<222> LOCATION: 3434, 4313, 5255, 5507, 5810, 6128, 6626, 6686
<223> OTHER INFORMATION: n = c or t
<221> NAME/KEY: misc_feature
<222> LOCATION: 4799, 5455
<223> OTHER INFORMATION: n = a or g

<400> SEQUENCE: 2

```
cgcccccgcc tctgagctcc cttcccatgg cggccctagt gttggaggac gggtcggtcc      60
tgcggggcca gcccttggg gccgccgtgt cgactgccgg ggaagtggtg tttcaaaccg      120
gcatggtcgg ctaccccgag gccctcactg atccctccta caaggcacag atcttagtgc      180
tcacctatcc tctgatcggc aactatggca tccccccaga tgaaatggat gagttcggtc      240
tctgcaagtg gtttgaatcc tcgggcatcc acgtagcagc actggtagtg ggagagtgct      300
gtcctactcc cagccactgg agtgccaccc gcaccctgca tgagtggctg cagcagcatg      360
gcatccctgg cttgcaagga gtagacactc gggagctgac caagaagttg cgggaacagg      420
ggtctctgct ggggaagctg gtccagaatg aacagaacc ttcatccctg ccattcttgg      480 acccccaatgc ccgcccctg gtaccagagg tctccattaa gactccacgg gtattcaata      540 caggggggtgc ccctcggatc cttgctttgg actgtggcct caagtataat cagatccgat      600
gcctctgcca gcgtggggct gaggtcactg tggtaccctg gaccatgca ctagacagcc      660 aagagtatga gggtctcttc ttaagtaatg ggcctggtga ccctgcctcc tatcccagtg      720
tcgtatccac actgagccgt gtttttatctg agcctaatcc ccgacctgtc tttgggatct      780
gcctgggaca ccagctattg gccttagcca ttggggccaa gacttacaag atgagatatg      840
ggaaccgagg ccataaccag ccctgcttgt tggtgggctc tgggcgctgc tttctgacat      900
cccagaacca tgggtttgct gtggagacag actcactgcc agcagactgg gctcctctct      960
tcaccaacgc caatgatggt tccaatgaag gcattgtgca caacagcttg cctttcttca     1020
gtgtccagtt tcacccagag caccaagctg gcccttcaga tatggaactg cttttcgata     1080
tctttctgga aactgtgaaa gaggccacac tgggaaccc tggggccag acagttagag     1140 agcggctgac tgagcgcctc tgtccccctg ggattccac tcccggctct ggacttccac     1200
caccacgaaa ggttctgatc ctgggctcag gggcctctc cattggccaa gctggagaat     1260
ttgactactc gggctctcag gcaattaagg ccctgaagga ggaaaacatc cagacgttgc     1320
tgatcaaccc caatattgcc acagtgcaga cctcccaggg gctggccgac aaggtctatt     1380
```

-continued

```
ttcttcccat aacacctcat tatgtaaccc aggtgatacg taatgaacgc cccgatggtg    1440
tgttactgac ttttgggggc cagactgctc tgaactgtgg tgtggagctg accaaggccg    1500
gggtgctggc tcggtatggg gtccgggtcc tgggcacaac agtggagacc attgagctga    1560
ccgaggatcg acgggccttt gctgccagaa tggcagagat cggagagcat gtggccccga    1620
gcgaggcagg aaattctctt gaacaggccc aggcagccgc tgaacggctg ggtacccctg    1680
tgctagtgcg tgcagccttt gccgtgggtg gcctgggctc tggctttgcc tctaacaggg    1740
aggagctctc tgctctcgtg gccccagctt ttgcccatac cagccaagtg ctagtagaca    1800
agtctctgaa gggatggaag gagattgagt acgaggtggt gagagacgcc tatggcaact    1860
gtgtcacggt gtgtaacatg gagaacttgg acccactggg catccacact ggtgagtcca    1920
tagtggtggc ccctagccag acactgaatg acagggagta tcagctcctg aggcagacag    1980
ctatcaaggt gacccagcac ctgggaattg ttggggagtg caatgtgcag tatgccttga    2040
accctgagtc tgagcagtat tacatcattg aagtgaatgc caggctctct cgcagctctg    2100
ccctggccag taaggccaca ggttatccac tggcttatgt ggcagccaag ctagcattgg    2160
gcatcccttt gcctgagctc aggaactctg tgacaggggg tacagcagcc tttgaaccca    2220
gcgtggatta ttgtgtggtg aagattcctc gatgggaccc tagcaagttc ctgcgagtca    2280
gcacaaagat tgggagctgc atgaagagcg ttggtgaagt catgggcatt gggcgttcat    2340
ttgaggaggc cttccagaag gccctgcgca tggtggatga aactgtgtg ggctttgatc    2400 acacagtgaa accagtcagc gatatggagt tggagactcc aacagataag cggatttttg    2460
tggtggcagc tgctttgtgg gctggttatt cagtggaccg cctgtatgag ctcacacgca    2520
tcgaccgctg gttcctgcac cgaatgaagc gtatcatcgc acatgcccag ctgctagaac    2580
aacaccgtgg acagccttt g ccgccagacc tgctgcaaca ggccaagtgt cttggcttct    2640
cagacaaaca gattgccctt gcagttctga gcacagagct ggctgttcgc aagctgcgtc    2700
aggaactggg gatctgtcca gcagtgaaac agattgacac agttgcagct gagtggccag    2760
cccagacaaa ttacctatac ctaacgtatt ggggcaccac ccatgacctc accttcgaa    2820 cacctcatgt cctagtcctt ggctctggcg tctaccgtat tggctccagt gttgagtttg    2880
actggtgtgc tgtaggctgc atccagcagc tccgaaagat gggatataag accatcatgg    2940
tgaactataa cccagagaca gtcagcaccg actatgacat gtgtgatcga ctctactttg    3000
atgagatctc ttttgaggtg gtgatggaca tctatgagct cgagaaccct gaaggtgtga    3060
tcctatccat gggtggacag ctgcccaaca catggccat ggcgttgcat cggcagcagt    3120
gccgggtgct gggcacctcc cctgaagcca ttgactcggc tgaaaccgt ttcaagtttt    3180 cccggctcct tgacaccatt ggtatcagcc agcctcagtg gagggagctc agtgaccgcg    3240
agtctgctcg ccaattctgc cagaccgtgg ggtaccctg tgtggtgcgc ccctcctatg    3300
tgctgagcgg tgctgctatg aatgtggcct acgcggatgg agacctggag cgcttcctga    3360
gcagcgcagc agccgtctcc aaagagcatc ccgtggtcat ctccaagttc atccaggagg    3420
ctaaggagat tgangtggat gccgtggcct ctgatggtgt ggtggcagcc atcgccatct    3480
ctgagcatgt ggagaatgca ggtgtgcatt caggtgatgc gacgctggtg accccccac    3540 aagatatcac tgccaaaacc ctggagcgga tcaaagccat tgtgcatgct gtgggccagg    3600
agctacaggt cacaggaccc ttcaatctgc agctcattgc caaggatgac cagctgaaag    3660
ttattgaatg caacgtacgt gtctctcgct ccttccccct cgtttccaag acactgggtg    3720
```

```
tggacctagt agccttggcc acgcgggtca tcatggggga agaagtggaa cctgtggggc    3780
taatgactgg ttctggagtc gtgggagtaa aggtgcctca gttctccttc tcccgcttgg    3840
cgggtgctga cgtggtgttg ggtgtggaaa tgaccagtac tggggaggtg gccggctttg    3900
gggagagccg ctgtgaggca tacctcaagg ccatgctaag cactggcttt aagatcccca    3960
agaagaatat cctgctgacc attggcagct ataagaacaa aagcgagctg ctcccaactg    4020
tgcggctact ggagagcctg ggctacagcc tctatgccag tctcggcaca gctgacttct    4080
acactgagca tggcgtcaag gtaacagctg tggactggca cttttgaggag gctgtggatg    4140 gtgagtgccc accacagcgg agcatcctgg agcagctagc tgagaaaaac tttgagctgg    4200
tgattaacct gtcaatgcgt ggagctgggg ccggcgtct ctcctccttt gtcaccaagg    4260
gctaccgcac ccgacgcttg ccgctgact tctccgtgcc cctaatcatc ganatcaagt    4320
gcaccaaact ctttgtggag gccctaggcc agatcgggcc agcccctcct ttgaaggtgc    4380
atgttgactg tatgacctcc caaaagcttg tgcgactgcc gggattgatt gatgtccatg    4440
tgcacctgcg ggaaccaggt gggacacata aggaggactt tgcttcaggc acagccgctg    4500
ccctggctgg gggtatcacc atggtgtgtg ccatgcctaa tacccggccc cccatcattg    4560
acggccctgc tctggccctg gcccagaagc tggcagaggc tggcgcccgg tgcgactttg    4620
cgctattcct tggggcctcg tctgaaaatg caggaacctt gggcaccgtg gccgggtctg    4680
cagccgggct gaagctttac ctcaatgaga ccttctctga gctgcggctg gacagcgtgg    4740
tccagtggat ggagcatttc gagacatggc cctcccacct ccccattgtg gctcacgcng    4800
agcagcaaac cgtggctgct gtcctcatgg tggctcagct cactcagcgc tcagtgcaca    4860
tatgtcacgt ggcacggaag gaggagatcc tgctaattaa agctgcaaag gcacggggct    4920
tgccagtgac ctgcgaggtg gctccccacc acctgttcct aagccatgat gacctggagc    4980
gcctggggcc tgggaagggg gaggtccggc ctgagcttgg ctcccgccag gatgtggaag    5040
ccctgtggga ggacatggct gtcatcgact gctttgcctc agaccatgct ccccatacct    5100
tggaggagaa gtgtgggtcc aggcccccac ctgggttccc agggttagag accatgctgc    5160
cactactcct gacggctgta agcgagggcc ggctcagcct ggacgacctg ctgcagcgat    5220
tgcaccacaa tcctcggcgc atctttcacc tgccnccgca ggaggacacc tatgtggagg    5280
tggatctgga gcatgagtgg acaattccca gccacatgcc cttctccaag gcccactgga    5340
caccttttga agggcagaaa gtgaagggca ccgtccgccg tgtggtcctg cgaggggagg    5400
ttgcctatat cgatgggcag gttctggtac ccccgggcta tggacaggat gtacngaagt    5460
ggccacaggg ggctgttcct cagctcccac cctcagcccc tgccacnagt gagatgacca    5520
cgacacctga agacccccgc cgtggcatcc agggcttcc tgatggccgc ttccatctgc    5580
cgccccgaat ccatcgagcc tccgaccag gtttgccagc tgaggagcca aggagaagt    5640 cctctcggaa ggtagccgag ccagagctga tgggaacccc tgatggcacc tgctaccctc    5700
caccaccagt accgagacag gcatctcccc agaacctggg gaccctggc ttgctgcacc    5760 cccagacctc accctgctg cactcattag tgggccaaca tatcctgtcn gtccagcagt    5820
tcaccaagga tcagatgtct cacctgttca atgtggcaca cacactgcgt atgatggtgc    5880
agaaggagcg gagcctcgac atcctgaagg ggaaggtcat ggcctccatg ttctatgaag    5940
tgagcacacg gaccagcagc tcctttgcag cagccatggc ccggctggga ggtgctgtgc    6000
tcagcttctc ggaagccaca tcgtccgtcc agaagggcga atcctggct gactccgtgg    6060 agaccatgag ctgctatgcc gacgtcgtcg tgctccggca ccccccagcct ggagcagtgg    6120
```

```
agctggcngc caagcactgc cggaggccag tgatcaatgc tggggatggg gtcggagagc    6180
accccaccca ggccctgctg gacatcttca ccatccgtga ggagctggga actgtcaatg    6240
gcatgacgat cacgatggtg ggtgacctga agcacggacg cacagtacat tccctggcct    6300
gcctgctcac ccagtatcgt gtcagcctgc gctacgtggc acctcccagc ctgcgcatgc    6360
cacccactgt gcgggccttc gtggcctccc gcggcaccaa gcaggaggaa ttcgagagca    6420
ttgaggaggc gctgcctgac actgatgtgc tctacatgac tcgaatccag aaggaacgat    6480
ttggctctac ccaggagtac gaagcttgct ttggtcagtt catcctcact ccccacatca    6540
tgacccgggc caagaagaag atggtggtga tgcacccgat gccccgtgtc aacgagataa    6600
gcgtggaagt ggactcggat ccccgngcag cctacttccg ccaggctgag aacggcatgt    6660
acatccgcat ggctctgtta gccacngtgc tgggccgttt ctaggggcct ggcttcctca    6720
gcctcttctc tttaggccca gctgctgggc aaggaattcc agtgcctcct acggggcag    6780
cacacttaga tattcctgga catccagatt gctcacatgt gctgaccaca cttcaggctc    6840
tggactggag ctctctggca tggggtggg gcctcagatg ctgggcccca gtctgcccca    6900
tcttcattcc tgcaccttaa acctgtacag tcattttct actgacttaa taaacagccg    6960
agctgtccct tg                                                       6972

<210> SEQ ID NO 3
<211> LENGTH: 3951
<212> TYPE: DNA
<213> ORGANISM: Homo sapiens
<220> FEATURE:
<221> NAME/KEY: misc_feature
<222> LOCATION: 166, 3432, 3682, 3937
<223> OTHER INFORMATION: n = t or c
<221> NAME/KEY: misc_feature
<222> LOCATION: 577, 638, 1708, 3730, 3925
<223> OTHER INFORMATION: n = a or g

<400> SEQUENCE: 3
gctgtcactt ggctctctgg ctggagcttg aggacgcaag gagggtttgt cactggcaga     60
ctcgagactg taggcactgc catggcccct gtgctcagta aggactcggc ggacatcgag    120
agtatcctgg ctttaaatcc tcgaacacaa actcatgcaa ctctgngttc cacttcggcc    180
aagaaattag acaagaaaca ttggaaaaga atcctgata agaactgctt taattgtgag    240
aagctggaga ataattttga tgacatcaag cacacgactc ttggtgagcg aggagctctc    300
cgagaagcaa tgagatgcct gaaatgtgca gatgccccgt gtcagaagag ctgtccaact    360
aatcttgata ttaaatcatt catcacaagt attgcaaaca gaactatta tggagctgct    420
aagatgatat tttctgacaa cccacttggt ctgacttgtg aatggtatg tccaacctct    480
gatctatgtg taggtggatg caatttatat gccactgaag agggacccat taatattggt    540
ggattgcagc aatttgctac tgaggtattc aaagcantga gtatcccaca gatcagaaat    600
ccttcgctgc ctcccccaga aaaatgtct gaagcctntt ctgcaaagat tgctctttt    660
ggtgctgggc ctgcaagtat aagttgtgct tccttttgg ctcgattggg gtactctgac    720
atcactatat ttgaaaaaca agaatatgtt ggtggtttaa gtacttctga aattcctcag    780
ttccggctgc cgtatgatgt agtgaatttt gagattgagc taatgaagga ccttggtgta    840
aagataattt gcggtaaaag cctttcagtg aatgaaatga ctcttagcac tttgaaagaa    900
aaaggctaca agctgcttt cattggaata ggtttgccag aacccaataa agatgccatc    960
ttccaaggcc tgacgcagga ccaggggttt tatacatcca agactttttt gccacttgta   1020
```

```
gccaaaggca gtaaagcagg aatgtgcgcc tgtcactctc cattgccatc gatacgggga    1080
gtcgtgattg tacttggagc tggagacact gccttcgact gtgcaacatc tgctctacgt    1140
tgtggagctc gccgagtgtt catcgtcttc agaaaaggct ttgttaatat aagagctgtc    1200
cctgaggaga tggagcttgc taaggaagaa aagtgtgaat ttctgccatt cctgtcccca    1260
cggaaggtta tagtaaaagg tgggagaatt gttgctatgc agtttgttcg acagagcaa    1320 gatgaaactg gaaaatggaa tgaagatgaa gatcagatgg tccatctgaa agccgatgtg    1380
gtcatcagtg cctttggttc agttctgagt gatcctaaag taaagaagc cttgagccct    1440 ataaaattta acagatgggg tctcccagaa gtagatccag aaactatgca aactagtgaa    1500
gcatgggtat ttgcaggtgg tgatgtcgtt ggtttggcta acactacagt ggaatcggtg    1560
aatgatggaa agcaagcttc ttggtacatt cacaaatacg tacagtcaca atatggagct    1620
tccgtttctg ccaagcctga actaccctc ttttacactc ctattgatct ggtggacatt    1680
agtgtagaaa tggccggatt gaagtttnta aatccttttg gtcttgctag cgcaactcca    1740
gccaccagca catcaatgat tcgaagagct tttgaagctg gatggggttt tgcccctcacc    1800 aaaactttct ctcttgataa ggacattgtg acaaatgttt cccccagaat catccgggga    1860
accacctctg gccccatgta tggccctgga caaagctcct ttctgaatat tgagctcatc    1920
agtgagaaaa cggctgcata ttggtgtcaa agtgtcactg aactaaaggc tgacttccca    1980
gacaacattg tgattgctag cattatgtgc agttacaata aaaatgactg gacggaactt    2040
gccaagaagt ctgaggattc tggagcagat gccctggagt taaatttatc atgtccacat    2100
ggcatgggag aaagaggaat gggcctggcc tgtgggcagg atccagagct ggtgcggaac    2160
atctgccgct gggttaggca agctgttcag attccttttt ttgccaagct gaccccaaat    2220
gtcactgata ttgtgagcat cgcaagagct gcaaaggaag gtggtgccaa tggcgttaca    2280
gccaccaaca ctgtctcagg tctgatggga ttaaaatctg atggcacacc ttggccagca    2340
gtggggattg caaagcgaac tacatatgga ggagtgtctg ggacagcaat cagacctatt    2400
gctttgagag ctgtgacctc cattgctcgt gctctgcctg gatttcccat tttggctact    2460 ggtgaattg actctgctga aagtggtctt cagtttctcc atagtggtgc ttccgtcctc    2520
caggtatgca gtgccattca gaatcaggat ttcactgtga tcgaagacta ctgcactggc    2580
ctcaaagccc tgctttatct gaaaagcatt gaagaactac aagactggga tggacagagt    2640
ccagctactg tgagtcacca gaaagggaaa ccagttccac gtatagctga actcatggac    2700
aagaaactgc caagttttgg accttatctg gaacagcgca agaaaatcat agcagaaaac    2760
aagattagac tgaaagaaca aaatgtagct ttttcaccac ttaagagaag ctgttttatc    2820
cccaaaaggc ctattcctac catcaaggat gtaataggaa aagcactgca gtaccttgga    2880
acatttggtg aattgagcaa cgtagagcaa gttgtggcta tgattgatga agaaatgtgt    2940
atcaactgtg gtaaatgcta catgacctgt aatgattctg gctaccaggc tatacagttt    3000
gatccagaaa cccacctgcc caccataacc gacacttgta caggctgtac tctgtgtctc    3060
agtgtttgcc ctattgtcga ctgcatcaaa atggtttcca ggacaacacc ttatgaacca    3120
aagagaggcg taccttatc tgtgaatccg gtgtgttaag gtgatttgtg aaacagttgc    3180
tgtgaacttt catgtcacct acatatgctg atctcttaaa atcatgatcc ttgtgttcag    3240 ctcttttccaa attaaaacaa atatacattt tctaaataaa aatatgtaat ttcaaaatac    3300
atttgtaagt gtaaaaaatg tctcatgtca atgaccattc aattagtggc ataaaataga    3360
```

-continued

| | |
|---|---|
| ataattctttt tctgaggata gtagttaaat aactgtgtgg cagttaattg gatgttcact | 3420 |
| gccagttgtc tnatgtgaaa aattaacttt ttgtgtggca attagtgtga cagtttccaa | 3480 |
| attgccctat gctgtgctcc atatttgatt tctaattgta agtgaaatta agcattttga | 3540 |
| aacaaagtac tctttaacat acaagaaaat gtatccaagg aaacatttta tcaataaaaa | 3600 |
| ttacctttaa ttttaatgct gtttctaaga aaatgtagtt agctccataa agtacaaatg | 3660 |
| aagaaagtca aaaattattt gntatggcag ataagaaag cctaaaattg agtttgtgga | 3720 |
| ctttattaan taaaatcccc ttcgctgaaa ttgcttattt ttggtgttgg atagaggata | 3780 |
| gggagaatat ttactaacta aataccattc actactcatg cgtgagatgg gtgtacaaac | 3840 |
| tcatcctctt ttaatggcat ttctctttaa actatgttcc taaccaaatg agatgatagg | 3900 |
| atagatcctg gttaccactc ttttnctgtg cacatanggg ccccggaatt c | 3951 |

<210> SEQ ID NO 4
<211> LENGTH: 2816
<212> TYPE: DNA
<213> ORGANISM: Homo sapiens
<220> FEATURE:
<221> NAME/KEY: misc_feature
<222> LOCATION: 175, 1067
<223> OTHER INFORMATION: n = g or a
<221> NAME/KEY: misc_feature
<222> LOCATION: 341
<223> OTHER INFORMATION: n = c or g
<221> NAME/KEY: misc_feature
<222> LOCATION: 791, 1997, 2618, 2653
<223> OTHER INFORMATION: n = t or c
<221> NAME/KEY: misc_feature
<222> LOCATION: 1337
<223> OTHER INFORMATION: n = c or a
<221> NAME/KEY: misc_feature
<222> LOCATION: 2107
<223> OTHER INFORMATION: nucleotide in position 2107 is g, or absent
<221> NAME/KEY: misc_feature
<222> LOCATION: 2583
<223> OTHER INFORMATION: n = t or g

<400> SEQUENCE: 4

| | |
|---|---|
| gggccgggtc cgggagcccc agggcagccg ccccgccgag tcgcaggcac agtgtcacct | 60 |
| tcgtcccctc cggagctgca cgtggcctga gcaggatggt gccctccagc ccagcggtgg | 120 |
| agaagcaggt gcccgtggaa cctgggcctg accccgagct ccggtcctgg cggcncctcg | 180 |
| tgtgctacct ttgcttctac ggcttcatgg cgcagatacg gccaggggag agcttcatca | 240 |
| cccccctacct cctgggcccc gacaagaact tcacgcggga gcaggtcacg aacgagatca | 300 |
| cgccggtgct gtcgtactcc tacctggccg tgctggtgcc ngtgttcctg ctcaccgact | 360 |
| acctgcgcta cacgccggtg ctgctgctgc agggctcag cttcgtgtcg gtgtggctgc | 420 |
| tgctgctgct gggccactcg gtggcgcaca tgcagctcat ggagctcttc tacagcgtca | 480 |
| ccatggccgc gcgcatcgcc tattcctcct acatcttctc tctcgtgcgg cccgcgcgct | 540 |
| accagcgtgt ggccggctac tcgcgcgctg cggtgctgct gggcgtgttc accagctccg | 600 |
| tgctgggcca gctgctggtc actgtgggcc gagtctcctt ctccacgctc aactacatct | 660 |
| cgctggcctt cctcaccttc agcgtggtcc tcgccctctt cctgaagcgc cccaagcgca | 720 |
| gcctcttctt caaccgcgac gaccggggc ggtgcgaaac ctcggcttcg gagctggagc | 780 |
| gcatgaatcc nggcccaggc gggaagctgg gacacgccct gcgggtggcc tgtgggggact | 840 |
| cagtgctggc gcggatgctg cgggagctgg gggacagcct gcgcggccg cagctgcgcc | 900 |
| tgtggtccct ctggtgggtc ttcaactcgg ccggctacta cctggtggtc tactacgtgc | 960 |

-continued

```
acatcctgtg gaacgaggtg gaccccacca ccaacagtgc gcgggtctac aacggcgcgg    1020
cagatgctgc ctccacgctg ctgggcgcca tcacgtcctt cgccgcngc ttcgtgaaga    1080 tccgctgggc gcgctggtcc aagctgctca tcgcgggcgt cacggccacg caggcggggc    1140
tggtcttcct tctggcgcac acgcgccacc cgagcagcat ctggctgtgc tatgcggcct    1200
tcgtgctgtt ccgcggctcc taccagttcc tcgtgcccat cgccaccttt cagattgcat    1260
cttctctgtc taaagagctc tgtgccctgg tcttcggggt caacacgttc tttgccacca    1320
tcgtcaagac catcatnact ttcattgtct cggacgtgcg gggcctgggc ctcccggtcc    1380
gcaagcagtt ccagttatac tccgtgtact tcctgatcct gtccatcatc tacttcttgg    1440
gggccatgct ggatggcctg cggcactgcc agcggggcca ccaccgcgg cagccccgg    1500 cccagggcct gaggagtgcc gcggaggaga aggcagcaca ggcactgagc gtgcaggaca    1560
agggcctcgg aggcctgcag ccagcccaga gcccgccgct ttccccagaa gacagcctgg    1620
gggctgtggg gccagcctcc ctggagcaga gacagagcga cccataccctg gcccaggccc    1680 cggccccgca ggcagctgaa ttcctgagcc cagtgacaac cccttccccc tgcactctgt    1740
gctccgccca agcctcaggc cctgaggctg cagatgagac ttgtcccag ctggctgtcc    1800 atcctcctgg tgtcagcaag ctgggtttgc agtgtcttcc aagcgacggt gttcagaatg    1860
tgaaccagtg actctcgggc gccctgtgg taactttgca ggcggcctc agtgcatccc    1920 cacgacccct gcctcgaggg ccgcctgcct tagcaatggg ggcctccgct tatcctgcta    1980 gcaggcccc taggatnccc cctgccctgt gccgcactct ggcggtggcc acagcgtgct    2040
ggcgacactc agggcagctg cctggccatg ctgtccctgc actgtgcccc gcgggctttg    2100
ttgctgngaa gaggtgggtg gtgggcttct gcgtccacca ggcctcactg gctcatgccc    2160 cttgggggc ttgagacaaa tcctttctgc ccccagggc tagtgaagtg gcctcttgga    2220
taccagctca ggggacactg gccccacagg agttgtgagc cctctagggc agggtgggag    2280
ccgggaccct caggtgtagc tgagctgtga cattgctggt catccttggt gctcttgctt    2340
ttttgaaaga tgcttttttt tttttaact gacgtagaat gaagaactgc atgtggcttc    2400
tctgtctctg tggaaaagcc atctcaggtt ggcggcagac acattgtcat cagaggggag    2460
cagcggctct ggtcctcgga gctggttcct ctctcccacc ctaagggcag ccctccatgg    2520
tcctgtctgt ccttctgaag tgtgtccatc ctgacctgcg ggtcctcagc tgctcccaca    2580
ctngtgccag cccggagggg actggtcccg gtcaccgngg acgtgctggc cttggtatgt    2640
gccaggcttg ccngggctgg gcagccttgg gggggctgcc tttgtggtgg gcgctgggga    2700
agtacgtccc agcggcctca gggtctaagg agcgctagtg ccttgcccac aggtgcggga    2760
ccatctgatg tgatgtgaat actcttccca catacattaa acacacttaa gtgaga        2816
```

<210> SEQ ID NO 5
<211> LENGTH: 3772
<212> TYPE: DNA
<213> ORGANISM: Homo sapiens
<220> FEATURE:
<221> NAME/KEY: misc_feature
<222> LOCATION: 431, 441
<223> OTHER INFORMATION: n = a or g
<221> NAME/KEY: misc_feature
<222> LOCATION: 498
<223> OTHER INFORMATION: n = c or t
<221> NAME/KEY: misc_feature
<222> LOCATION: 579, 599
<223> OTHER INFORMATION: n = g or c

<400> SEQUENCE: 5

-continued

```
gatcccccat ttccagccaa caaatccttt ttaagttcct ttgagatttg ttacgtgtgc      60
ttgctacact caggactctg gaaagaagcc caggccagag ctttgggcag gcggccattt     120
aggcaagggc cctgtgttgg cttcctggtg gggttgccct gctggtgggc gggagaccaa     180
gagcaccccc gcaacaccag gaggcaggtc gcggattgtg ctgtctacac tccggaaggg     240
gtacattcca ggctgctgcc ccagactcac ccctcgcctg gacccgcac tcttgagctg      300
tgggtaccac ggtggccgtc cccttctgtt ctgtgcagtg gacttcctgg ctcctcctta     360
gccttggggc cccacagccc tcggcttggc ttccctcccc atagccaggc cctgggtaac     420
tccaggggaa ngtgaccctg nggcccccca cttctccccg tgctcctgca caggccttgg     480
gctttcggcg gtgctgtntg ccgcagcccc acgccttcct gggagagtgg cccaggcccc     540
ccttcctgag tgtgactgcg ctgccgtctg cgaggcctnc gcggtctcc cccgggctnt      600
cctgctggga tggggactgg tggccccggg ccacgtcctg gatccggctt gctccttggt     660
acaagccgta cgggtcacgg tcaggcagga gggcgggcgg cggggtcccg ggggcgccga     720
gttcggggcg tgcggtcccc aagagcaggc tgtgcgtgtc cctgttggag ccccacgaag     780
gcggcccagg gcacccctga gggcgcgtgg gccgacccgc gtcccggatc cagcttgcgc     840
caggaatgca ggtgttccag ggtgccaaaa ggaaaacgca caaggcctcg tcgaggaggg     900
ggggtcagga gggaccgggg ggtgggaaga acgcggggga gagggatggc aggtgcccg      960
cccgagggac cgacacctcc gcgagtggca ccccaggatg ctgacgccgg cggggtgggg    1020
ggcccgaggg gcggtcgggg tcaggggggcg gccccagggg tagggccgca gcacgagggg    1080
ccgcgtgacc cggcggtgac cggtggggga gaggccggcg ccggggctgg gagacggccg    1140
tgggtgggag ggtgccccgt ggggacgctc ctgccgcagc gcccggccac gcgcgaggcc    1200
ccgcccctcag gacgcgttcg cggacggac ccgcccaccc gcagccgcc ggcccgccgc     1260
gcgccttgtg ggcgctgtag tcccggagtc cgcgtgcgcg gggccgggtc cgggagcccc    1320
agggcagccg ccccgccgag tcgcaggtac cggtggggaa cggggccacg gggcgcgtgt    1380
cgggggctgc ggggtgtctc ggggccctgg ggtgagtgcg gggcgcgggc cgaggtttgc    1440
agggccctgt gaggtgagtg tggggctgg cgctggggtc cgcggggccc tggggagggt     1500
gcgggcgtg ggccggggtc tgcggtctgc agcctggggt ccgcggggcc tggggagggt     1560
gcggggcgtg gccggggtct gcggtctgca gcctggggtc tgggggccc tggggagggt     1620
gcggggcgtg gccggggtc tcgcggggt cgcggtggcc cggggcctg gcagaaccgt       1680
tgctgtgcac ggggtttccc gccgctcgct ttccgccgca gcctgcgaat ggggtgggga    1740
gtcccgggcc ccagcctgcc ctccgcgtca tcctggggcg ccaagtccca ccccggtc      1800
tggaggaaag cgtggatccg cgttcgcgcc caggcacgtg ttgcttcggg acgggccagc    1860
cggtgggtga accctgccag ccacgcgtgg ggcgggccc tggcacatct ccagaccatt     1920
gtctcctgtg ccagaagctt tgtaggtgca acttccccct ggagcagctg tgggtgcgga    1980
tccagcggac gaatcccgag gcgtctcaga gagagcctgg acagccgctg gagcctttcc    2040
cgagtgggtc cttccaacac cgctacagca ggaaagccat cccctaggg tcctgtccat     2100
cggaaactcc tgtcctgggg agtctgcctg cctggcctca ggacacaggc caactaagct    2160
ggccccgaaa tccagaatgc atccagaggg aaggtgggat aaagtccttg gagcgcctgt    2220
tggccgccct gtaaagaggt ggcctccccc tacgagacc cgaggatccc cgcacagccc     2280
agattcaatc agcagagccg aggtgcctct ggcccagtgc acctgcctgc cctgtccagg    2340
```

-continued

```
cctgggagcc aggctgcatc tcactggccg cctttgcctg ggtgccacct gtgcactgct    2400
tgttgcaatt gctaattgct ttctttccga agggctttgg aggattttta taattccaga    2460
tagtacagtt atctctgctg gacacagatg agaaagagtg cttctcgggt gtttgggcct    2520
gcagcagtga tagccggagg tctaattatg ctgttaggaa ccctgaactt ggtcatctga    2580
acaggggtgg gagggtgtgc aatgctttct tcttcttctt cttcttttta aactagcagg    2640
cgttctaaaa aacataacga acattcttgg ttagccttcc agagtaggag ctggtttaaa    2700
cacggaatga taggtggcgt ttgcttgtgt tttgattgcg ggtctctggc cttctctggt    2760
gcttggaagg acagggcctg ggtggggctg gtcactgtgg acagtggggc cggggatttg    2820 cagggggctgt tacaaccttc tcctgaaggc agggattctc tctgcttccc cgtggccctc    2880
ctgtctggtc ggggacttcc ttcagatgcc gggaagaggc ctcaagctgt atgggactgg    2940 gctgggtggct ggacacttgg agtctaggcg tccctggct tggggctgcg tttctatgat    3000
ggtgaccaag ttccctatct ttcctcttgg aggtggtctg ggccgtgatg gccaagcctc    3060
tgtcagtggg ctacgttcac ggcacataag ttgagtatgc tggcagcaga ggctgactgt    3120
taagaccagc agcagcccct tgctggcgga gactctggct gtctctccaa ggaaggaatg    3180
ttctggtcgc ttctggaggt ggcaccttc agaacagggg gcccaagtac ccagggctcc    3240
cgggcccctg ggggtcctgt gggtgggatc tgactcctgc ggccatggac tgtgggcgca    3300
gaccctgggc ttagttcagc tcctgatggc tccccgttgt ctgcggcgat ctggttgctc    3360
tggttgtctg gggatcggtg cgcctgtcta aacctgctga caggtgggaa agtgaacttg    3420
acagggagtc ccagggccaa atgggtctcc cagtggggag gagtgggtgc ggtctgaggt    3480
atgtccagct ctaccgtgg cctctctggg catcaggtc cctggtgatg gagcccaacc    3540
tttgtgcact gatcttccca gctgttgaca ggccctgagg aggcgtggaa ggtgaggccg    3600
aggcaggcga ccgtcagatc tgcctcggcc tggcagtggc ccctgcctgc gcttcctcct    3660
gcctggccgg ctgttttcat cctggcccctt tgagaacttc tagggtcctg gctgcctcca    3720
atggagggtg ctggtcccat cttcttccca gctgtgccct gccgtggagc tc            3772
```

<210> SEQ ID NO 6
<211> LENGTH: 1536
<212> TYPE: DNA
<213> ORGANISM: Homo sapiens
<220> FEATURE:
<221> NAME/KEY: misc_feature
<222> LOCATION: 1066
<223> OTHER INFORMATION: n = t or c
<221> NAME/KEY: misc_feature
<222> LOCATION: 1136
<223> OTHER INFORMATION: n = a or g
<221> NAME/KEY: misc_feature
<222> LOCATION: 1497
<223> OTHER INFORMATION: n = t or a

<400> SEQUENCE: 6

```
gggggggggg ggaccacttg gcctgcctcc gtcccgccgc gccacttggc ctgcctccgt     60
cccgccgcgc cacttcgcct gcctccgtcc cccgcccgcc gcgccatgcc tgtggccggc    120
tcggagctgc cgcgccggcc cttgcccccc gccgcacagg agcgggacgc cgagccgcgt    180
ccgccgcacg gggagctgca gtacctgggg cagatccaac acatcctccg ctgcggcgtc    240
aggaaggacg accgcacggg caccggcacc ctgtcggtat tcggcatgca ggcgcgctac    300
agcctgagag atgaattccc tctgctgaca accaaacgtg tgttctggaa gggtgttttg    360
gaggagttgc tgtggtttat caagggatcc acaaatgcta aagagctgtc ttccaaggga    420
```

```
gtgaaaatct gggatgccaa tggatcccga gacttttttgg acagcctggg attctccacc    480
agagaagaag gggacttggg cccagtttat ggcttccagt ggaggcattt tggggcagaa    540
tacagagata tggaatcaga ttattcagga cagggagttg accaactgca aagagtgatt    600
gacaccatca aaaccaaccc tgacgacaga agaatcatca tgtgcgcttg aatccaaga    660 gatcttcctc tgatggcgct gcctccatgc catgccctct gccagttcta tgtggtgaac    720
agtgagctgt cctgccagct gtaccagaga tcgggagaca tgggcctcgg tgtgcctttc    780
aacatcgcca gctacgccct gctcacgtac atgattgcgc acatcacggg cctgaagcca    840 ggtgactttta tacacacttt gggagatgca catatttacc tgaatcacat cgagccactg    900
aaaattcagc ttcagcgaga acccagacct ttcccaaagc tcaggattct tcgaaaagtt    960
gagaaaattg atgacttcaa agctgaagac tttcagattg aagggtacaa tccgcatcca   1020
actattaaaa tggaaatggc tgtttagggt gctttcaaag gagctngaag gatattgtca   1080
gtctttaggg gttgggctgg atgccgaggt aaaagttctt tttgctctaa aagaanaagg   1140
aactaggtca aaaatctgtc cgtgacctat cagttattaa tttttaagga tgttgccact   1200
ggcaaatgta actgtgccag ttctttccat aataaaaggc tttgagttaa ctcactgagg   1260
gtatctgaca atgctgaggt tatgaacaaa gtgaggagaa tgaaatgtat gtgctcttag   1320
caaaaacatg tatgtgcatt tcaatcccac gtacttataa agaaggttgg tgaatttcac   1380
aagctatttt tggaatattt ttagaatatt ttaagaattt cacaagctat tccctcaaat   1440
ctgagggagc tgagtaacac catcgatcat gatgtagagt gtggttatga actttanagt   1500
tgttttatat gttgctataa taaagaagtg ttctgc                             1536

<210> SEQ ID NO 7
<211> LENGTH: 1187
<212> TYPE: DNA
<213> ORGANISM: Homo sapiens
<220> FEATURE:
<221> NAME/KEY: misc_feature
<222> LOCATION: 276, 321, 534, 656
<223> OTHER INFORMATION: n = c or t
<221> NAME/KEY: misc_feature
<222> LOCATION: 452, 640
<223> OTHER INFORMATION: n = a or g
<221> NAME/KEY: misc_feature
<222> LOCATION: 492, 625
<223> OTHER INFORMATION: n = c or a
<221> NAME/KEY: misc_feature
<222> LOCATION: 458
<223> OTHER INFORMATION: nucleotide in position 458 is c, or absent

<400> SEQUENCE: 7
gatcgcgcca ctgcactcca gcctgggtga gagagcgaga ctctgtctca aaaaaaaaa     60 aaaaagaccg ccagggctca acaaaaaaac ctcggaaaag ccctggcggt cttttttttt   120
tttttttttt tttttttttg gacagtctt gctctgtcgc ccaggctgga gtacaatggt   180
cggatcttgg ctcactgcaa cctctgcctc ccaggttcaa gcaattcttc tgcctcagcc   240
tcccaagtag ccaccacgcc cagctaattt ttgtantttt agtagagacg ggggtttcac   300
catgttgtcc aggctggtct ngaactcctg acctcaggtg atccacccgc ctcggccccc   360
caaagtacta ggattacagg cgtgagccac cgcgtccagc gccctggcgg tttttaatca   420
agtagaaaag ctgcattata ccacttgctt cngttgcntt cagtgagaac gaagaaatgg   480
aaatgcaaat cncttattag ttgtaggaaa cagatctcaa acagcagttt tgtngacaag   540
accgcaggaa aacgtgggaa ctgtgctgct ggcttagaga aggcgcggtc gaccagacgg   600
```

-continued

```
ttcccaaagg gcgcagtcct tcccngccac cgcacctgcn tccaggttcc cgggtntcct      660
aagactctca gctgtggccc tgggctccgt tctgtgccac accgtgact  ctgcgtttc      720 cccctggcgc acgctctcta gagcggggc cgccgcgacc ccgccgagca ggaagaggcg      780
gagcgcggga cggccgcggg aaaaggcgcg cggaagggt cctgccaccg cgccacttgg      840
cctgcctccg tcccgccgcg ccacttggcc tgcctccgtc ccgccgcgcc acttcgcctg      900
cctccgtccc ccgcccgccg cgccatgcct gtggccggct cggagctgcc gcgccggccc      960 ttgcccccg ccgcacagga gcgggacgcc gagccgcgtc cgccgcacgg ggagctgcag     1020
tacctggggc agatccaaca catcctccgc tgcggcgtca ggaaggacga ccgcacgggc     1080
accggcaccc tgtcggtatt cggcatgcag gcgcgctaca gcctgagagg tgacgccgcg     1140 ggccctgcg ggacgggtgg cgggaaggag ggaggcgcgg ctgggga                  1187
```

<210> SEQ ID NO 8
<211> LENGTH: 18597
<212> TYPE: DNA
<213> ORGANISM: Homo sapiens
<220> FEATURE:
<221> NAME/KEY: misc_feature
<222> LOCATION: 701, 13751
<223> OTHER INFORMATION: n = c or a
<221> NAME/KEY: misc_feature
<222> LOCATION: 716, 1293, 2401, 2429, 2618, 3083, 3125, 3635, 4256,
      4898, 5062, 5167, 11069, 13298, 14479, 14730, 14796,15344, 15450,
      15503, 15590,15840, 16149
<223> OTHER INFORMATION: n = a or g
<221> NAME/KEY: misc_feature
<222> LOCATION: 732, 1379, 1590, 2488, 3212, 5006, 11238, 11422, 11686,
      12598, 13171, 13645, 13782, 13806, 13813, 14586, 14788,
      15042, 15546, 15770
<223> OTHER INFORMATION: n = c or t
<221> NAME/KEY: misc_feature
<222> LOCATION: 1322, 1688
<223> OTHER INFORMATION: n = c or g
<221> NAME/KEY: misc_feature
<222> LOCATION: 2594, 11293, 16199, 16203
<223> OTHER INFORMATION: n = g or t
<221> NAME/KEY: misc_feature
<222> LOCATION: 3619
<223> OTHER INFORMATION: n = a or t
<221> NAME/KEY: misc_feature
<222> LOCATION: 14547
<223> OTHER INFORMATION: nucleotide in position 14547 is t, or absent

<400> SEQUENCE: 8

```
cctgtagtcc cagctacgcg agaggctgag gcagcagaat tacttgaacc caggaggcgg       60
aggttgcagt gagccgagat cgcgccactg cactccagcc tgggtgagag agcgagactc      120
tgtctcaaaa aaaaaaaaaa aagaccgcca gggctcaaac aaaaaacctc ggaaaagccc      180
tggcggtctt tttttttttt tttttttttt tttttggga cagtcttgct ctgtcgccca      240
ggctggagta caatggtcgg atcttggctc actgcaacct ctgcctccca ggttcaagca      300
attcttctgc ctcagcctcc caagtagcca ccacgcccag ctaattttg tactttagt      360 agagacgggg gtttcaccat gttgtccagg ctggtcttga actcctgacc tcaggtgatc      420
cacccgcctc ggccccccaa agtactagga ttacaggcgt gagccaccgc gtccagcgcc      480
ctggcggttt taatcaagt agaaaagctg cattatacca cttgcttcgg ttgcttcagt      540
gagaacgaag aaatggaaat gcaaatccct tattagttgt aggaaacaga tctcaaacag      600
cagttttgtt gacaagaccg caggaaaacg tgggaactgt gctgctggct tagagaaggc      660
gcggtcgacc agacggttcc caaagggcgc agtccttccc ngccaccgca cctgcntcca      720
```

-continued

| | |
|---|---|
| ggttcccggg tntcctaaga ctctcagctg tggccctggg ctccgttctg tgccacaccc | 780 |
| gtggctcctg cgtttccccc tggcgcacgc tctctagagc gggggccgcc gcgaccccgc | 840 |
| cgagcaggaa gaggcggagc gcgggacggc cgcgggaaaa ggcgcgcgga agggtcctg | 900 |
| ccaccgcgcc acttggcctg cctccgtccc gccgcgccac ttggcctgcc tccgtcccgc | 960 |
| cgcgccactt cgcctgcctc cgtccccgc ccgccgcgcc atgcctgtgg ccggctcgga | 1020 |
| gctgccgcgc cggcccttgc ccccgccgc acaggagcgg gacgccgagc gcgtccgcc | 1080 |
| gcacggggag ctgcagtacc tggggcagat ccaacacatc ctccgctgcg gcgtcaggaa | 1140 |
| ggacgaccgc acgggcaccg gcaccctgtc ggtattcggc atgcaggcgc gctacagcct | 1200 |
| gagaggtgac gccgcgggcc cctgcgggac gggtggcggg aaggagggag gcgcggctgg | 1260 |
| ggagagcgct cgggagctgc cgggcgctgc ggnccccgtt tagtcctaac ctcaatcctg | 1320 |
| cnagggaggg gacgcatcgt cctcctcgcc ttacagacgc cgaaacggag ggtcccatna | 1380 |
| gggacgtgac tggcgcgggc aacacacaca gcagcgacag ccgggaggta agccgcgtcc | 1440 |
| cagcggctcc gcgccgggc tcgcagtcgc cccagtgatg ccgtggcccc cgaggcgggc | 1500 |
| gtcatcgggc agcgtttgcc cagtgctgga gggttaggga gagctgcctg ggcttgaccg | 1560 |
| cgcgccggtc tcaaagtcct ggctttggcn cctcctccgt tttccctgt ggaccattcc | 1620 |
| gcttcgcagc gttttcaaaa actggagcga aagtgatgtg ggcggggcaa aggcggcggg | 1680 |
| aagaggganag cactgaagct ggcgcgggaa cttggttttcc tggtggcctc ccatccaatc | 1740 |
| cccacgaacc agctttcctc ttaaaccttg aaaagagaaa ttcgggagtt cgagttctta | 1800 |
| gtcgtccttt cctctttcct ttccgacagg agcaccccag gcaaaaaatg tctcgcgggt | 1860 |
| cattggcgcc aggctttcag gggacagtgg ggcggggcgg ggtgggcaca ggacgttagg | 1920 |
| cagccgttgg ccctccctaa ggccacaccg tcctgccgtc ctggatcctg cgccagctgc | 1980 |
| gcggggagg ggactcgaag gtgtgtgagc caggggctga ccttgaccgc tcagataaat | 2040 |
| ggagcgcagc cttgacacag gggtggaggt ggttttgaat ggggaaaccc attcgtggtg | 2100 |
| aagcagattc actgtagcta gcggaaaagc cctccggccc acggaccat ctagagacga | 2160 |
| atacatagca gctgctgtgg ctgattggcg tgggacagcg tggggagttt tgtctgagga | 2220 |
| gagggatcca cttttctgca gctccaagcc caggggcctt tgatgagcca tagacctcat | 2280 |
| tttaacccca cctttctgct tagacattga gcaagttact tctcatatag cttccctata | 2340 |
| tgttaaaaat ggagaaaata atgcttagta ggcaattctg ataaaagcag gtgcttgcaa | 2400 |
| naatctctct gttgtctgaa tataaactnt accacaagcg agtgcggatg aacgaggact | 2460 |
| gcatttaaag ataagttttt cactttnat ttctctgtgg ctcgacactt ctgatgcctc | 2520 |
| ccttttttgtt cctgggacac atgcttggtg ttgtcttcac acctttgtga caggattagc | 2580 |
| actagtgggc agtngatgat agctcctcct cccttttncc acatgttcat ccctgccctc | 2640 |
| gccaccatct cactgtgtgg aattcctgtg tccactggtc accgggcac agaagtgctg | 2700 |
| tctcagcctg aatcgggcca ctgatgggac ttgcagcctg ggagctccac cgtgatctct | 2760 |
| ggcccacttt gcgggagtct aggctttctg gatgctccag gcctcacgtc ccagggcagt | 2820 |
| tttcttccct gaagaaagtt ggatggcatg atctgtcttc ccatcttgaa accgtatggc | 2880 |
| aaattgtttt tcagatgaat tccctctgct gacaaccaaa cgtgtgttct ggaagggtgt | 2940 |
| tttggaggag ttgctgtggt ttatcaaggt aaagaagtcg ctgctattag aagtcagtag | 3000 |
| tctgttctca acacagcagc cagtgagatc ctttcaaaac tcaaagcagc caggtgtggt | 3060 |
| ggctcacgcc tgtaatccca ccnctttggg aggctgagtc agatcacctg aggttaggaa | 3120 |

```
tttgngacca gcctggccaa catggcgaca ccccagtctc tactaataac acaaaaaatt    3180
agccaggtgt gctggtgcat gtctgtaatc cnagctactc aggaggctga ggcatgagaa    3240
ttgctcacga ggcggaggtt gtagtgagct gagatcgtgg cactgtactc cagcctggcg    3300
acagagggag aacccatgtc aaaaacaaaa aagacacca ccaaaggtca aagcatatca     3360
ttcctcaccc tcaagccctt agtggctcca tttcactcag taagagccac ggtccttatg    3420
gtgtccgttt ttcagctctg accttagctg ctgctctctg caccaccctg ctgttcttgt    3480 gagttttga gcacaccggg acatccccac tccctggaac cttcttcccc cacacttggc     3540
ttcttccttt gagtctctac tccactcggg caagccttcc tagacctcct gatttaaaac    3600
tgtgactctc ccccaaccnc cttggtgttt ctccntagac gaacatcacc atctgatgta    3660
tgtcagcctt tcccttcccc tgttagaagg gggacagcag gtagtaaaag tgaaatgtgc    3720
tgtaagcttt atgagggcag aggatttgtt tctcgtgttc actgttgtat cgccagggcc    3780
tcaaacacag cctgccacat agtaggagtc aacatatatt gatcactaaa tgtagatacc    3840
acctgtgttc ccatgttcat ataaattcta gaagagtctc ttcagtaaca aggtgaaccc    3900
cttccagagg gctgagtagg tacctcaggc cggggccaga gtgctgtgaa gacagcagca    3960
gcccagacca agcttctctg tgttccgtgt cctggtctag aaccagcgat gttctttctg    4020
accagtgctt tttggaaggt ggctgaggtc tgggctcagg tctgggccat actagaagct    4080
gggatccctt ctatagagca cttggtatgg cttgtatggt cttggggcaa gccagaccca    4140
agccctctta tcccatttta gaaagggctt caatttggat ccagccccag gtctgcctta    4200
gctctgtatt cttggggtat tttgttctgt attggcctat cttgactaac aatgancctt    4260
ggatttgaaa catatcatca gaaacctcag aagacaacat tcttaaactg gctagagcct    4320
ggtctgaatg gatgaaaagg agagactttt gaagcaatat gtaaaagatt gagaaatgat    4380
ttgttggaaa tttctcaatt ggagaaattt ctttgatttg ttggaaattt ctttgattct    4440
ttctcaatca aagaaaatcg ggacaaactc aacaatagaa agggaggaag caagatactc    4500
agaaataaaa tgcattcccc tgtttcaact taatgcttca attcaggatt ctaaggaatc    4560
cttgccagga atgtcagact caccttgata gttggagtta ctccattggt gactcgatca    4620
aatacaggag ttgaggcacc tgcactgtaa aatactgatt agtctgatca ttaggaatat    4680
cctgtatgcc aggtagaaga tacattgaac agattgcatg taggcattaa attcattttg    4740
gggtattaca tatagacaac acatttcatt aagaaacata aaactgtcag atcggtggaa    4800
tacttaaaag cacttggagg tgtttagcct aaaaagctta gttgagggga atggaagaaa    4860
agatctggga gggtggttcc aaagaaggga tcagactntc ctaaagccct caggaatctg    4920
ggctgggacc acctacttaa agataggatg ggcagctggg tgtggtggct cacgcctgta    4980
atcccagcac ttcgggaggc cgaagngggc ggatcacctg aggtcaggag ttcgaggcca    5040
gcctgaccaa catggagaaa cnctgtctct actaaaaata caaaattagc tgggtgtagt    5100
ggcgcatgcc tgtaatccca gctactcggg aggctgaggc aggggaatcg cttgaacctg    5160
ggaggtngag ggtgccgtga gccacgatcg cgccattgca ctccagcctg gcaacaaga    5220 gcgaaactct caaaaacaa aaaaaggat gggttccata tggtggtgt caagtgccca      5280 cctcctagca agtcagcagg ggccagaggc ccttgtaagt ggtgtctcgg gggatcaac    5340 tgagatggct taagatttac ctggatgcct gctctgctct cccatctct tccagggatc     5400 cacaaatgct aaagagctgt cttccaaggg agtgaaaatc tgggatgcca atggatcccg    5460
```

```
agactttttg gacagcctgg gattctccac cagagaagaa ggggacttgg gcccagttta    5520
tggcttccag tggaggcatt ttggggcaga atacagagat atggaatcag gtgaggagat    5580
agaacaatgc cttccatttc cggtgccct tcctagcacg tgtttgctcc gttgttttag     5640
ataaggtctg ggggatgagt caatgtcaca ggagctgatg tatagctttg accttgtgag    5700
gggtggtgcc aggttgaagc cacaattaac gcctactgaa ggccgtttca catcttttt     5760
tttttttttt ttttaattat tatactttaa gttttagggt acatgtgcac aatgtgcagg    5820
ttagttacat atgtatacat gtgccatgct ggtgcgctgc accactaact caccatctag    5880
catcaggtat atctcccaat gctatcctc cccctcctc ccaccccaca acatccccag      5940
agtgtgatgt tccccttcct gtgtccatat gttctcgttg ttcgattccc actatgagtg    6000
agaatatgcg gtgtttggtt ttttgttctt gcgatagttt actgagaatg atgatttcca    6060
tttcaccacg tccctacaga ggacatgaac tcatcatttt ttatggctgc atagtattcc    6120
atggtgtata tgtgccacat tttcttaatc cagtctatca tgttggacat ttgggttggt    6180
tccaagtctt tgcctattgt gaatagtgcc acaataaaca tacgtgtgca tgtgtcttta    6240
tagcagcatg atttaatagt cctttgggta tacccagt aatgggatgg ctgggtcaaa      6300
tggtatttct agttctagat ccccgaggaa tcgccacact gacttccaca atggttgaac    6360
tagtttacag tcccaccaac agtgtcaaag tgtcctattt ctccacatcc tctccagcac    6420
ctgttgtttc ctgactttt aatgattgcc attctaactg gtgtgagatg gtatctcatt    6480
gtggttttga tttgcgtttc tctgatgcc agtgatggtg agcattttt catgtgtttt     6540
ttggctgcat aaatgtcttc ttttgagaag tgtctgttca tgtccttcgc ccactttttg    6600
atggggttgt ttttttctta taaatttgtt tgagttcatt gtagattctg gatattagcc    6660
ctttgtcaga tgagtaggtt gcaaaaatgt tctcccattt tgtgggttgc ctgttcactc    6720
tgatggtagt ttcttttgct gtgcagaagc tctttagttt aattagatcc catttgtcaa    6780
ttttggcttt tgttgccatt gcttttggca taggcatgaa gtccttgccc atgcctatgt    6840
cctgaatggt aatgcctagg ttttcttcta ggttttttat ggttttaggt ctaacgttta    6900
agtctttaat ccatcttgaa ttgattttg tataaggtgt aaggaaggga tccagtttca    6960
gcttttaca tatggctagc cagttttccc agcaccattt attacatagg gaatcctttc     7020
cccattgctt gtttttctca ggtttgtcaa agatcagata gttgtagata tgcggcgtta    7080
tttctgaggg ctctgttctg ttccattgat ctatgtgtct gttttggtac cagtaccata    7140
ctgtttggt tactgtagcc ttgtagtata gtttgaagtc aggtagcgtg atgcctccag    7200
ctttgttctt ttggcttagg attgacttgg cgatgcgggc tctttttggg ttccatatga    7260
actttaaagt agttttttcc aattctgtga agaaagtcat tggtagcttg atggggatgg    7320
cattgaatct ataaattacc ttgggcagta tggccatttt cacgatattg attcttccta    7380
cccatgagca tggaatggtc ttccatttct ttgtatcctc ttttatttca ttgagcagtg    7440
gtttgtagtt ctccttgaag aggtccttca catccctttt aaggtggatt cctaggtatt    7500
ttattctctt tgaagcaatt gtgagtggaa gttcactcat gatttggctc tctgtttgtc    7560
tgttattggt gtataagaat gcttgtgatt tttgcagatt gatttatat cctgagactt      7620
tgctgaagct gcttatcagc ttaaggagat tttgggctga dacaatgggg ttttctagat    7680
atacaatcat gtcgtctgca aacagggaca atttgacttc ctcttttcct aattgaatac    7740
cctttatttc cttctcctgc ctaattgccc tggccagaac ttccaacact atgttgaata    7800
ggagtggtga gagagggcat ccctgtcttg tgccagtttt caaagggaat gcttccagtt    7860
```

-continued

```
tttgcccatt cactatgata ttggctgtgg ctttgtcata gatagctctt attattttga    7920
aatatgttcc atcaatacct aatttattga gagtttttag catgatgtgt tgttgaattt    7980
tgtcaaaggc ttttctgca tctattgaga taatcatgtg gtttttgtct ttggatctgt    8040
ttatatgctg gattacattt attgatttgc gtatattgaa ccagccttgc atcctaggga    8100
tgaagcccac atgatcatgg tggataagct ttttgatgtg ctgctggatt cggtttgcca    8160 gtatttatt gaggattttt gcatcaatgt tcatcaagga tattggtcta aaattctctt    8220
ttttggtgtg tctctgccca gctttggtat caggatgatg ttggcttcat aaaatgagtt    8280
agggaggatt ccctcttttt ctattgattg aatagtttc agaaggaatg gtaccagttc    8340
ctctttgtac ctctggagaa ttcggctgtg aatccatctg gtcctggact ctctttggtt    8400
ggtaagctat tgattattgc cacaatttca gctcctgtta ttggtctatt cagagattca    8460
acttcttcct ggtttagtct tgggagagtg tatgtgtcaa ggaatttatc catttcttct    8520
agattttcta gtttatttgc gtagaggtgt ttgtagtaat ctctgatggt agtttgtatt    8580
tctgtgggat cggtggtgat atccccttta tcatttttta ttgcgtctat ttgattcttc    8640 tcttttctt tattagtctt gctagcggtc tataaattt gttgatcctt tcaaaaaacc    8700
agctcctgga ttcattaatt ttttgaaggg ttttttgtgt ctctatttcc ttcagttctg    8760
ctctgatttt agttatttct tgccttctgc tagcttttga atatgtttgc tcttgctttt    8820
ctagttcttt taattgtgat gttagggtgt caattttgga tctttcctgc tttctcttgt    8880
gggcatttag tgctataaat ttccctctac acactgcttt gaatgtgtcc cagaggttct    8940
ggtatgttgt gtcttttgttc ttgttggttt caaagaacat ctttatttct gccttcattt    9000
cgttatgtac ccagtagtca ttcaggagca ggttgttcag tttccatgta gttgagcagt    9060
tttgagtgag attcttaatc ctgagttcta gtttgattgc actgtggtct gagagatagt    9120
ttgttataat ttctgttctt ttacatttgc tgaggagagc tttacttcca actatgtggt    9180
cggttttgga ataggtgtgg tgtggtgctg aaaaaaatgt atattctgtt gatttgggat    9240
ggagttctgt agatgtctat taggtctgct tggtgcagag ctgagttcaa ttcctgggta    9300
tccttgttga ctttctgtct cgttgatctg tgtactgttg acagtgggtg ttaaagtctc    9360
ccattattaa tgtgtggagt ctaagtctct ttgtaggtca ctcagatgat tggcacttac    9420
tgggcgcttg gcactttcca tactgtgtca tcggcagata gctgcatggt tggtgttcgt    9480
gctggggaat gggaagttca tcggtgggac aaggacaaaa tgcccccatt gctttgttgt    9540
ggctttaatc tcccttttcga ggctgagcca cagcgtgctg taggtggcgc tgctgtgaag    9600
cgcagtacca gggtcacact ccactcccag ctctgcagag gtggagaaag aatgaaacat    9660
ctcactcctg gacttccact ttcctgtcac tgttggtgtc acctcttact ggatgtcaca    9720
gagcccagcc cctcccacct gtgcctagga aaagcagatg ccaccttgga atgtggggtt    9780
tgtgtgtgca atttactagc tgggcagaga ccagcaacct ggagagcagg tgtctcgtct    9840
aaggggacag tcacatttca cctccagcca cctggaggaa tttgggcctg gtgatgtcag    9900
aattcttcaa taaaagccta aaatctatat tttatgtgcg gtcatgagat ctgttaaatg    9960
ttagcaactt caggaagttt aaaaatgctg tgtggaccta gaataggcaa gttcttaaag   10020
gcagaaagtg gaatgctagt ttccagggac tggggaacag ggaggaatgg ggagttcatg   10080
tttaatgggc acagagggtt tgttagggat gacgaaaaag ttcgggagat ggtgatggtg   10140
atggagatgg tgatggtgat ggagatggtg atggtgatgg tgatggtgat gggtgatggt   10200
```

```
gatggtgatg gtgatggtga tggagatggt gatggtgatg gtgatggaga tggtgatggt    10260
gatggtgatg gtgatggaga tggtgatggt gatggagatg gtgatggtga tggtgatgga    10320
gatggtgatg gtgatggtga tggtgatggt gatggtgatg gtgatggaga tggagatggt    10380
gatggtgatg gttgcctaac atcaggaacg tgcttaatgc ttctgaattg cacacaaaaa    10440
tggcaagttt aatattatgt gtactttatc acaatgaaaa aagctgctgc gtgggccaag    10500
ttacttgtgc aggtaatgtt ctgcaggtgg ttgcctgcac ctcagttgta gggtgtccgt    10560
aggatgtgag gccagtcccc gggcttaatg atgctttaaa tcctgcctag tattcaatta    10620
tttcttgtcg cttaaaaggc ctaataaaat tatggtctta gtttacagtg gtatgaatgc    10680
ttagctgttg gatttagta ggaaagttcg tcccttttg tttttaattt tgttttacag      10740
attcacagga attttttttt tttttttttt tttttttttt taatgcacag aaagtttccc    10800
tggactctct acccagtttc cccagtgata atatcttggg taacatcctg tatacattca    10860
cattggtgca ttcctcagag ttgtcagatt ttgctagttt tacgtgcact tgtgtatgtg    10920
tgtatttgca atttagcac gtgtagactc ttgtaaccac tacaatcaag ttacagaact     10980
acactaccaa ggttcatctt tttaaaatct ttgatgttac cttttttgga acagtgacca    11040
tgagaggact ttcctcccaa aattttgana actactgaac cagaatatag tctgacacta    11100
ataggtagaa atttaaccaa aggagattat gaagctctgc acttgagtta acaaaatcac    11160
ttctcagctt ccagttccat ctcagaagga aggaaaaggg attaaaaatc cagagaccag    11220
aaaatgggag caaagtanaa ggtggtgtaa tcattacaga ggtttcctga tgtttccaag    11280
tcagtcgtgt gtngagctgc taaactctaa agtaattta ggtggaatgt tggaaacatg     11340
ctgctgaggt gatagaaagg aatccatggt cctctgttag ttggaaagta tatggaatac    11400
tatattctac ataagataca anctctctg tgagacaagg ataaagtaga ttttgtcagt     11460
gaaattgtga caagaatcgc tgatgggttt agagcctaag tttgcgagga gcactggaag    11520
aaattaagat tgttgagatt ggaaaggggtt agctatgggg gaacaggagg aggtgactcc   11580
atgacagacc aaatattcaa aggactgtgt agaagaggaa aaagactttg ttagggctcc    11640
agaggacaga gccaggagtc agacagggcc ttgaactcaa cccacngaga tctgcaaact    11700
ttgcaggatg caccagatgt cttgtagcca tgggtcaagg ggggaccctg ggtaagagac    11760
tgtaatagat gacctctaag gccatctcat gacatgtgtg attaatgtat gtacctgtcc    11820 tctcttttg acaattctac agattattca ggacagggag ttgaccaact gcaaagagtg     11880
attgacacca tcaaaaccaa ccctgacgac agaagaatca tcatgtgcgc ttggaatcca    11940
agaggttgaa agaaccccgt cgtcttcatt tatactaacc atactcttag agggaagcaa    12000
tctggttttg tgcagaggca ctgagggagg caggaccctg ggcaacttcc cccagccaca    12060
tggttgtgtg acgttgggca agtcacattt tgctgcactt tcaccttcag atcatgaggt    12120
tgggcccaga ggattttttt tttttttttt ttttttgaga cagagttttg ctctgttgcc    12180
caggctggaa tgcaacggcg tgatcttggc tcactgtaac ctctgcctcc tgggttcgag    12240
tgattctcct gcctcagcct ccaagtagct gggattacag catgtgccac catgcctggc    12300
taattttgta tttttagtag agacgggttc acatgttggt caggctggtc ttgactcctg    12360
accctcagat gatctgcctt gcctcagcct cccaaccgag tgatcttaag ttgtgtatta    12420
tactcattct tacacaaaaa gggctttaaa tgcctagaaa ctacatgaag atgttaacat    12480
tttaaatgga agcagatgaa gttccagctc gctgccacct cactaacatt tttaacaatt    12540
atattgtaaa attcaactct accagggtgt agagccaggt gtggtggctc acacctgnaa    12600
```

```
ttccaacaac tccagaggcc aaggcgagag gatcatttga acccacggaa tttgaggctg   12660
tagtgagtca tgatcacgcc attgcactcc atcctgggca acagagtgag accctgaata   12720
tttaaaaaca acaacaacaa caaaactcta tcaggatatc ataagtactt agagtgaaat   12780
acttgcatct gtaatagaga cttatttttt ttttttttga gacacagtct caccctgttg   12840
cccaggctgg agtgcagtgg tttgatctcc gctcacggca acctccatct cccaggttca   12900
agtgagttcc cattcctcag ccccagagct gggaccacag gcgcgcgaat ttttgtattt   12960
ttagcagaga cggggtttca ctatgttggc caggctagtc tcaaactcaa gttggcctca   13020
agtgatctgc ccaccctggc gtcccagtgt tgggatttca ggcatgagcc actgtgcctg   13080
gccatgtaat agagactttt aatataggag ggtgtaccag aagcaccagt ttcctgtggc   13140
aaacagaatt attcctgctg tatttgtaat ntggtgccac gaggtagccc agatcccttc   13200
agctctgatg gaagagcatt gcttcagccg taaatggaca cctgcagaaa ccttgcaccg   13260
atggatagtc tccctcagct ccgtgccatc gctgcagngg ctgttatgga catcactgca   13320
gcccagtggc tctctctcct ggtctccacc atatgagttg gcttctgttt ctctcctgtt   13380
ttactttgcc tttagctgtg gtctttcaaa ccaccatccc tccttatctt cctctgctgg   13440
ttcctcagat cttcctctga tggcgctgcc tccatgccat gccctctgcc agttctatgt   13500
ggtgaacagt gagctgtcct gccagctgta ccagagatcg ggagacatgg gcctcggtgt   13560
gcctttcaac atcgccagct acgccctgct cacgtacatg attgcgcaca tcacgggcct   13620
gaaggtgggc tgtctcggga agggngactt gccagcctac cacatgagct cttcagttct   13680
ttaatatggg aaaacaaatt gcagagttta gtctctgatt agcttttaaa tttgatatgt   13740
gtaagtaaga natgaaccag cttttacttt gaaaccttcc tnttctggaa ggttttctgg   13800
ccctgnggta tangcactaa cagatctata caggttgttt gtgatacagc ttctatggat   13860
cttctcaaaa gctatgctga ggttgggtat ggtggctcat gcctgtaatc ccagcacttt   13920
ggaagactga gacaggagca attgcttgag gtctggagtt caataccagc ctgggcaaca   13980
taacaagatg ctgttgctac aaaaaaatgg aaaagctaca ctaaattatt ttttttaaaa   14040
aagccttgcg gtgtctgcat attctaatgt ttttaaatga tgttttaaag aattgaaact   14100
aacatactgt tctgctttct cccggtttat agccaggtga ctttatacac actttgggag   14160
atgcacatat ttacctgaat cacatcgagc cactgaaaat tcaggtaaga attagatgtt   14220
atacttttgg gtttggtacc ttctcttgat aaaaggttga ctgtggaaca ggtatctgct   14280
caatgctgtg tccaagataa agatgactgc tccaaatgtg gggcttcagt ttagggagaa   14340
gtggtgggca ggtgggcagg acaaggcagg catctgcctc agcaaccatg gcacttaact   14400
tgtcaggtgc tgtgaggtac taagcaccag taccagagag ggaagagcca cattcaagcc   14460 agggattgt ccaaaaggng gcattttaac tcattttaac ttgaaggaga attgaagtgc   14520
aaatgttttt cctttctttt tttttgnag atggagtctt tctctgtcgg ccaggctgga   14580
gtgtgncgtg gtgcgatctc agctcactgc aacctccacc tcccgggttc aagcaattct   14640
tctgcctcag cctcccaggt agctgggatt acaggcacat gccaccacac ccagctaatt   14700
ttttgtatta ttagtagaga tggggtttcn tcatgttggc caggctgatc tcaaactcct   14760
gacttcaagt gtaccacctg cctcagcntc cgaaanttct ggaattacag gcataagcca   14820
ccaccctggc cataaatatt ttttgttaat tttacattaa gtacaatatt taggtccaaa   14880
cttcaaaagt ctgttgaaat ccctgaagtt atagcagcca acaattgata tgaaatggca   14940
```

```
ataaaaatgt aagttcatct gcttcatgag ccttaaggaa aaaaactcag aaccagacac  15000
tttttagccc cttccaggtt agatccaggt tttaaaagtt antcctttga gggagtttgg  15060
ctgcttttga gtggaggtga cttcaggctt attctctctg gctctctgct ctggtcattt  15120
ttagacatag taataggttg tgacctgtct tcacatccta attgccactg tctgttcatc  15180
ccaggaatcc tggctttcat ccctttctgt tcactgtcca tgcatgtcat ctttccttct  15240
ttctgccagg gaccagatgg gttagggatt gtgaattcaa gtaaacgtag agctactatg  15300
agttacagat tgactgtgtt cctgtcttta ataaatttgc caanagtggt tataagaact  15360
tacacctgat gaggcaccag gctcctgatg ctgtgtaatg tcacaaaata cccctcactc  15420
tcgatctgtg caagagaaca gctggttgcn ctccaatcat gttacataac ctacgcgaag  15480
gtatcgacag gatcatactc ctntaaaata gaactttgtt gatcacatcc tgtgtacttg  15540
tttcanggac atgaggagca attacaacag gtcgtacaat tatggcaaan taatggcctt  15600
attttgtttt tagcttcagc gagaacccag acctttccca aagctcagga ttcttcgaaa  15660
agttgagaaa attgatgact tcaaagctga agactttcag attgaagggt acaatccgca  15720
tccaactatt aaaatggaaa tggctgtttta gggtgctttc aaaggagctn gaaggatatt  15780
gtcagtcttt aggggttggg ctggatgccg aggtaaaagt tcttttttgct ctaaaagaan  15840 aaggaactag gtcaaaaatc tgtccgtgac ctatcagtta ttaatttttta aggatgttgc  15900 cactggcaaa tgtaactgtg ccagttcttt ccataataaa aggctttgag ttaactcact  15960
gagggtatct gacaatgctg aggttatgaa caaagtgagg agaatgaaat gtatgtgctc  16020
ttagcaaaaa catgtatgtg catttcaatc ccacgtactt ataaagaagg ttggtgaatt  16080
tcacaagcta ttttttggaat attttttagaa tattttaaga atttcacaag ctattccctc  16140
aaatctgang gagctgagta acaccatcga tcatgatgta gagtgtggtt atgaacttna  16200
aanttatagt tgttttatat gttgctataa taaagaagtg ttctgcattc gtccacgctt  16260
tgttcattct gtactgccac ttatctgctc agttccttcc taaaatagat taaagaactc  16320
tccttaagta aacatgtgct gtattctggt ttggatgcta cttaaaagag tatattttag  16380
aaataatagt gaatatattt tgccctattt ttctcatttt aactgcatct tatcctcaaa  16440
atataatgac catttaggat agagtttttt tttttttttt ttaaactttt ataaccttaa  16500
agggttattt taaaataatc tatggactac catttttgccc tcattagctt cagcatggtg  16560
tgacttctct aataatatgc ttagattaag caaggaaaag atgcaaaacc acttcggggt  16620
taatcagtga aatatttttc ccttcgttgc ataccagata cccccggtgt tgcacgacta  16680
tttttattct gctaatttat gacaagtgtt aaacagaaca aggaattatt ccaacaagtt  16740
atgcaacatg ttgcttatt tcaaattaca gtttaatgtc taggtgccag cccttgatat  16800
agctattttt gtaagaacat cctcctggac tttgggttag ttaaatctaa acttatttaa  16860
ggattaagta ggataacgtg cattgatttg ctaaaagaat caagtaataa ttacttagct  16920
gattcctgag ggtggtatga cttctagctg aactcatctt gatcggtagg attttttaaa  16980
tccatttttg taaaactatt tccaagaaat tttaagccct ttcacttcag aaagaaaaaa  17040
gttgttgggg ctgagcactt aattttcttg agcaggaagg agtttcttcc aaacttcacc  17100
atctggagac tggtgtttct ttacagattc ctccttcatt tctgttgagt agccgggatc  17160
ctatcaaaga ccaaaaaaat gagtcctgtt aacaaccacc tggaacaaaa acagatttta  17220
tgcatttatg ctgctccaag aaatgctttt acgtctaagc cagaggcaat taattaattt  17280
tttttttttt gacatggagt cactgtccgt tgcccaggct gcagtgcagt ggcgcaatct  17340
```

-continued

```
tggctcactg caacctccac ctcccaggtt caagtgattc tcctgcctca gcctcccatg    17400
tagctgggat cacaggcacc tgccaccatg cccggctaat ttttgtatt ttttgtagag    17460 acagggtttc accatgttgg ccaggctggt ctcaaacacc tgacctcaaa tgatccacct    17520
gcctcagcct cccaaagtgt tgggattaca ggcgtaagcc accatgccca gcctgaatt    17580 aatatttta aaataagttt ggagactgtt ggaaataata gggcagagga acatatttta    17640
ctggctactt gccagagtta gttaactcat caaactcttt gataatagtt tgacctctgt    17700
tggtgaaaat gagccatgat ctcttgaaca tgatcagaat aaatgcccca gccacacaat    17760
tgtagtccaa acttttagg tcactaactt gctagatggt gccaggtttt tttgcacaag    17820
gagtgcaaat gttaagatct ccactagtga ggaaaggcta gtattacaga agccttgtca    17880
gaggcaattg aacctccaag ccctggccct caggcctgag gattttgata cagacaaact    17940
gaagaaccgt ttgttagtgg atattgcaaa caaacaggag tcaaagcttg gtgctccaca    18000
gtctagttca cgagacaggc gtggcagtgg ctggcagcat ctcttctcac aggggccctc    18060
aggcacagct taccttggga ggcatgtagg aagcccgctg gatcatcacg ggatacttga    18120
aatgctcatg caggtggtca acatactcac acaccctagg aggagggaat cagatcgggg    18180
caatgatgcc tgaagtcaga ttattcacgt ggtgctaact taaagcagaa ggagcgagta    18240
ccactcaatt gacagtgttg gccaaggctt agctgtgtta ccatgcgttt ctaggcaagt    18300
ccctaaacct ctgtgcctca ggtccttttc ttctaaaata tagcaatgtg aggtggggac    18360
tttgatgaca tgaacacacg aagtccctct gagaggtttt gtggtgccct ttaaaaggga    18420
tcaattcaga ctctgtaaat atccagaatt atttgggttc ctctggtcaa aagtcagatg    18480
aatagattaa aatcaccaca ttttgtgatc tatttttcaa gaagcgtttg tatttttca    18540 tatggctgca gcagctgcca ggggcttggg gtttttttgg caggtagggt tgggagg      18597
```

<210> SEQ ID NO 9
<211> LENGTH: 2500
<212> TYPE: DNA
<213> ORGANISM: Homo sapiens
<220> FEATURE:
<221> NAME/KEY: misc_feature
<222> LOCATION: 128, 1464
<223> OTHER INFORMATION: n = g or a
<221> NAME/KEY: misc_feature
<222> LOCATION: 189
<223> OTHER INFORMATION: n = t or g
<221> NAME/KEY: misc_feature
<222> LOCATION: 524
<223> OTHER INFORMATION: n = c or g
<221> NAME/KEY: misc_feature
<222> LOCATION: 1399
<223> OTHER INFORMATION: n = t or a
<221> NAME/KEY: misc_feature
<222> LOCATION: 1636, 1738, 2259
<223> OTHER INFORMATION: n = c or t

<400> SEQUENCE: 9

```
cccaggcgca gccaatggga agggtcggag gcatggcaca gccaatggga agggccgggg     60
caccaaagcc aatgggaagg gccgggagcg cgcggcgcgg gagatttaaa ggctgctgga    120
gtgagggntc gcccgtgcac cctgtcccag ccgtcctgtc ctggctgctc gctctgcttc    180
gctgcgccnc cactatgctc tccctccgtg tcccgctcgc gcccatcacg gacccgcagc    240
agctgcagct ctcgccgctg aagggggctca gcttggtcga caaggagaac acgccgccgg    300
ccctgagcgg gacccgcgtc ctggccagca agaccgcgag gaggatcttc caggagccca    360
```

```
cggagccgaa aactaaagca gctgccccg gcgtggagga tgagccgctg ctgagagaaa      420
accccgccg ctttgtcatc ttccccatcg agtaccatga tatctggcag atgtataaga      480
aggcagaggc ttccttttgg accgccgagg aggttgacct ctcnaaggac attcagcact      540
gggaatccct gaaacccgag gagagatatt ttatatccca tgttctggct ttctttgcag      600
caagcgatgg catagtaaat gaaaacttgg tggagcgatt tagccaagaa gttcagatta      660
cagaagcccg ctgtttctat ggcttccaaa ttgccatgga aaacatacat tctgaaatgt      720
atagtcttct tattgacact tacataaaag atcccaaaga aagggaattt ctcttcaatg      780
ccattgaaac gatgccttgt gtcaagaaga aggcagactg ggccttgcgc tggattgggg      840
acaaagaggc tacctatggt gaacgtgttg tagcctttgc tgcagtggaa ggcatttttct      900
tttccggttc ttttgcgtcg atattctggc tcaagaaacg aggactgatg cctggcctca      960
cattttctaa tgaacttatt agcagagatg agggtttaca ctgtgatttt gcttgcctga     1020
tgttcaaaca cctggtacac aaaccatcgg aggagagagt aagagaaata attatcaatg     1080
ctgttcggat agaacaggag ttcctcactg aggccttgcc tgtgaagctc attgggatga     1140
attgcactct aatgaagcaa tacattgagt ttgtggcaga cagacttatg ctggaactgg     1200
gtttagcaa ggttttcaga gtagagaacc catttgactt tatggagaat atttcactgg     1260
aaggaaagac taacttcttt gagaagagag taggcgagta tcagaggatg ggagtgatgt     1320
caagtccaac agagaattct tttaccttgg atgctgactt ctaaatgaac tgaagatgtg     1380
cccttacttg gctgatttnt tttttccatc tcataagaaa aatcagctga agtgttacca     1440
actagccaca ccatgaattg tccntaatgt tcattaacag catctttaaa actgtgtagc     1500
tacctcacaa ccagtcctgt ctgtttatag tgctggtagt atcacctttt gccagaaggc     1560
ctggctggct gtgacttacc atagcagtga caatggcagt cttggcttta aagtgagggg     1620
tgacccttta gtgagnttag cacagcggga ttaaacagtc cttaaccag cacagccagt      1680
taaagatgc agcctcactg cttcaacgca gattttaatg tttacttaaa tataaacntg     1740
gcactttaca aacaaataaa cattgttttg tactcacggc ggcgataata gcttgattta     1800
tttggtttct acaccaaata cattctcctg accactaatg ggagccaatt cacaattcac     1860
taagtgacta aagtaagtta aacttgtgta gactaagcat gtaattttta agttttattt     1920
taatgaatta aaatatttgt taaccaactt taaagtcagt cctgtgtata cctagatatt     1980
agtcagttgg tgccagatag aagacaggtt gtgttttat cctgtggctt gtgtagtgtc      2040
ctgggattct ctgcccccctc tgagtagagt gttgtgggat aaaggaatct ctcagggcaa     2100
ggagcttctt aagttaaatc actagaaatt tagggtgat ctgggccttc atatgtgtga      2160
gaagccgttt catttattt ctcactgtat tttcctcaac gtctggttga tgagaaaaaa      2220
ttcttgaaga gttttcatat gtgggagcta aggtagtant gtaaaatttc aagtcatcct     2280
taaacaaaat gatccaccta agatcttgcc cctgttaagt ggtgaaatca actagaggtg     2340
gttcctacaa gttgttcatt ctagttttgt ttggtgtaag taggttgtgt gagttaattc     2400
atttatattt actatgtctg ttaaatcaga aattttttat tatctatgtt cttctagatt     2460
ttacctgtag ttcataaaaa aaaaaaaaaa aaaaaaaaa                             2500
```

<210> SEQ ID NO 10
<211> LENGTH: 1718
<212> TYPE: DNA
<213> ORGANISM: Homo sapiens
<220> FEATURE:
<221> NAME/KEY: misc_feature
<222> LOCATION: 183, 1299
<223> OTHER INFORMATION: n = g or a
<221> NAME/KEY: misc_feature
<222> LOCATION: 483
<223> OTHER INFORMATION: n = c or t
<221> NAME/KEY: misc_feature
<222> LOCATION: 601
<223> OTHER INFORMATION: n = g or c

<400> SEQUENCE: 10

```
atgggcttg gggctgggcg gccagacgct aactcggatg ctcccaggct acgccttggc      60
catgacccgt gcgccgcgc gcccccgcct tcaccttcgg cgcgcgcttc cccacgcagc     120
agacgacgtg cggccccggg ccaggccacc tggtgcccgc tcgcatgacc gtgcgcggca     180
ccnacggcgc ccccgcctac tccatctacg gccgcccacg ccgctcagcg cccttcctca     240
ctccgggacc tggtcaggac ccccgggccc ctggccaccc caacgccgaa ctgcgtccag     300
ggaggcccac ctgggaaccc ccgacctgaa ccccgagtcc ccctcggata ccctaacacg     360
atattcggta cccccatatc cggatctcaa atcccaaacc ccgaaccccac ggggctttga    420
taaatcgtgg ctcagactcc ccactagtcc caggacccca tctcgggtac ccaccaggct     480
ccnacgcagt tctagccccc cacacccttg atccgcccg caggcaggta cttcccggag      540
cgagcgggga acgcgacgta ccccagtgcg cctcggcaca ccattgctcc ccgaaactgg     600
ngtgtccagg cggaacagca gagcccaggt cccgcggcct atacggtgcc ctcgctcttg     660
ggtccgcgcg tcatcggcaa agtctccgcc ccaacttgct ccatctacgg ccgcagagcg     720
gctggcagtt tcttcgagga cctcagcaag gtcgtgagtc caggggtcta caagtcccgg     780
gccccccagt tcacgattct ggcgcggact tcgctccccc aagacaacac tcggaagcca     840
gggcccgcgg cctacaacgt ggatcagcac cggaagcccc gcggctggag tttcgggatc     900
cggcactcgg actacctggc cccgctggtg accgacgcgg acaactgacc cgccaggcgg     960
gagcggcccc acacgtgttt gcttaaagtc tgcgagtccg catcgtgtcc gcctctctct    1020
ctctctctct gcgcgtcctg gcgcaaggcc tggggtggag ccacggctgg ggccgtgtcc    1080
caactccgaa cccagcgggg cggggcccga gcgtcgggcg aggccgggac cccagcgctg    1140
cgccgcgtcc gaacgtcgag acccaccga gggcgggagg gggactctcg ggagccacag     1200
acgcccgaga cccacgccgg gcgggaccgg ccagggatca cccccgccga cggccccggg    1260
ccccgacggc ccggaagttc cgcgtgtccg ggggcaccng gggattggcc ggggcgcggc    1320
gtgcaaggct tcccggggc ggcgactgcc gagctccgcc ctccaggcgg ccccacccgc     1380
ctgccgtcct ggggcgccgc cgccccgccg ccggcagtgg accgctgtgc gcgaaccctg    1440
aaccctacgg tcccgacccg cgggcgaggc cgggtacctg gctgggatc cggagcaagc     1500
gggcgagggc agcgccctaa gcaggtacgg gcggggctca agtcgcgagg cggggaagcg    1560
ggaggcagac acgacgagg gcgacacaga cacgggaccg aggggcggac accgagaga      1620
cacgggaaag gggtcgggac aggagcacgt ggctcagaca ccgacgccgg gaggccgcag    1680
accccggacg tgtcaggcat ccccgcaggc ccggagcg                            1718
```

<210> SEQ ID NO 11
<211> LENGTH: 5847
<212> TYPE: DNA
<213> ORGANISM: Homo sapiens
<220> FEATURE:
<221> NAME/KEY: misc_feature
<222> LOCATION: 124, 3346, 5024, 5484, 5650
<223> OTHER INFORMATION: n = c or t
<221> NAME/KEY: misc_feature

```
<222> LOCATION: 439, 1333, 1979, 2151, 2469, 2977, 4784, 5268, 5631,
      5733
<223> OTHER INFORMATION: n = g or a
<221> NAME/KEY: misc_feature
<222> LOCATION: 1045
<223> OTHER INFORMATION: nucleotide at position 1045 is c, or absent
<221> NAME/KEY: misc_feature
<222> LOCATION: 1046
<223> OTHER INFORMATION: nucleotide at position 1046 is t, or absent
<221> NAME/KEY: misc_feature
<222> LOCATION: 2636, 5287
<223> OTHER INFORMATION: n = c or g
<221> NAME/KEY: misc_feature
<222> LOCATION: 3118
<223> OTHER INFORMATION: n = g or t
<221> NAME/KEY: misc_feature
<222> LOCATION: 3257, 4053
<223> OTHER INFORMATION: n = a or c
<221> NAME/KEY: misc_feature
<222> LOCATION: 5440
<223> OTHER INFORMATION: n = t or a

<400> SEQUENCE: 11
gatattcggt acccatatc cggatctcaa atcccaaacc ccgaaccca cggggctttg      60
ataaatcgtg gctcagactc cccactagtc ccaggacccc atctcgggta cccaccaggc     120
tccnacgcag ttctagcccc ccacacctt gatccgcccc gcaggcaggt acttcccgga     180
gcgagcgggg aacgcgacgt accccagtgc gcctcggcac accattgctc cccgaaactg     240
gggtgtccag gcggaacagc agagcccagg tgaggtcaga acggcccatc ccagaactgt     300
gggccttccc actcgagacc ggggaccgcc ctccgggagc tgggaccacc ctgcgcctgt     360
ccgcggagac ccactacccc cgagcccctgc ctcctcccca ggtcccgcgg cctatacggt     420
gccctcgctc ttgggtccnc gcgtcatcgg caaagtctcc gccccaactt gctccatcta     480
cggccgcaga gcggctggca gtttcttcga ggacctcagc aaggtggggg agggccggg      540
gcggacgcag gggtccctg gtccgcggca gtggaggcgg cagccagcac cctctgccct     600
ctcgcagacc ccgggcccct gcgcctatca gtcgtgagt ccaggggtct acaagtcccg     660
ggcccccag ttcacgattc tggcgcggac ttcgctcccc caagacaaca ctcggaagcc     720
aggggcccgcg gcctacaacg tggatcaggt ggcctggagc ccagggtcaa gggtcagagt     780
caggagagtg gggagggcct gaggtcggag tgatgggatc agagtccccg ggggtccagg     840
ggtcccggcg cggagaggat gccggcccgg cgaggtcagc ggtgtctccg ggcccgcagc     900
accggaagcc ccgcggctgg agtttcggga tccggcactc ggactacctg gccccgctgg     960
tgaccgacgc ggacaactga cccgccaggc gggagcggcc ccacacgtgt ttgcttaaag    1020
tctgcgagtc cgcatcgtgt ccgcnnctct ctctctctct ctctgcgcgt cctgcgcaa     1080
ggcctgggt ggagccacgg ctgggccgt gtcccaactc cgaacccagc ggggcggggc     1140
ccgagcgtcg ggcgaggccg ggaccccagc gctgcgccgc gtccgaacgt cgagacccca    1200
ccgagggcgg gaggggact ctcgggagcc acagacgccc gagacccacg ccgggcggga    1260
ccggccaggg atcaccccg ccgacggccc cgggccccga cggccggaa gttccgcgtg    1320
tccgggggca ccngggatt ggccggggcg cggcgtgcaa ggcttcccgg gggcggcgac    1380
tgccgagctc cgcctccag gcggcccac ccgcctgccg tcctgggcg ccgccgcccc    1440
gccgccggca gtggaccgct gtgcgcgaac cctgaaccct acggtcccga cccgcgggcg    1500
aggccgggta cctgggctgg gatcggagc aagcggcga gggcagcgcc ctaagcaggt    1560
acgggcgggg ctcaagtcgc gaggcgggga agcgggaggc agacacggac gagggcgaca    1620
cagacacggg accgaggggc ggacaccgga gagacacggg aaagggtcg ggacaggagc    1680
```

-continued

```
acgtggctca gacaccgacg ccgggaggcc gcagaccccg gacgtgtcag gcatccccgc    1740
aggcccggag cgatggcagc cttgatgacc ccgggaaccg gggccccacc cgcgcctggt    1800
gacttctccg gggaagggag ccagggactt cccgacccctt cgccagagcc caagcagctc   1860
ccggagctga tccgcatgaa gcgagacgga ggccgcctga gcgaagcgga catcaggggc    1920
ttcgtggccg ctgtggtgaa tgggagcgcg cagggcgcac agatcggtgc gtggggagng    1980
ttgggcgttc ctgaccccga ctgggaggtc agcccgagag actttgggtc cctgggggtg    2040
cgacggtgcc ccactaccag caccggcccc agggtgcccc accgctgtgg gctgccaccc    2100
tcacgcgtac ccccacatac caggggccat gctgatggcc atccgacttc ngggcatgga    2160
tctggaggag acctcggtgc tgacccaggc cctggctcag tcgggacagc agctggagtg    2220
gccagaggcc tggcgccagc agcttgtgga caagcattcc acaggggtg tgggtgacaa    2280
ggtcagcctg gtcctcgcac ctgccctggc ggcatgtggc tgcaaggtta gaaaccacct    2340
cctttccaga cgggagccta taccgcacat gcagcaacca gtccatccac aggcagctcc    2400
caacctcaag cctggcccaa agcctccaag accctaccaa ggcttctccc caccctgctc    2460
cccagcacng ttctccccac cccgttcccc agcacagcgc ttggggcccc tctggctcca    2520
gaccaggccc cttggagcag gaaaaagatc cactgatgga attcagaccc ctttccccctt   2580
gggtccccag acagctcccc caagggagga gctgaggact cccctccctc tgcccnaagc    2640
cttgtttccc caaggagagg taccaacctc ctccccctact gacacttctc aaccaagaaa    2700
acttcctttc cattccctca ccagctgggc accctatag ctgcttaaat actttccaaa    2760
tccagctgca ctcctagcca gggaaggtga agggatgcac agaggtgggg gagggtact    2820
gtgcagggta ctcagcatcc ctgaccacca ggtgccaatg atcagcggac gtggtctggg    2880
gcacacagga ggcaccttgg ataagctgga gtctattcct ggattcaatg tcatccagag    2940
cccagagcag gtacggggcg ccacggatca gtcattnatc caggttgatg atccagaccc    3000
tggccagaat cactaaaaga tcactggtgg atcattaggg tcactaatga aacactggt    3060
caaggttact catgagtcac tgggcctggg ccgaaatcat cagtggaact ttgattanga    3120
tcataaaatg ggaagttggt caaaatcaca gatggctggc ggggcacggt ggctcacacc    3180
tgtagtccta gcacttgggg aggccgaaga gggcagatcc cttgaaccca ggagttcaaa    3240
accagcctgg ataacanggc aaaacccccat ctctacaaaa tagttcgctg cgtgtggtgg    3300
tgcacgcatg tggttccagc tactcaggag gctgaggcag gaggancact tgagcctggg    3360
aggtctaggc tgcagtgagc cgggacgatg ccactgcact ccagcctggg caacagagtg    3420
agaccctgtc ccagcactct gggaggcaga ggagcccagt tggagatcag cctgggtaat    3480
atagtgaaac ttgatctcta caaaaaaag aagaaaaaa aaagccgcgt gtggtggtgc    3540
gcacctgtag tcccagctac tgggaagctg aggtgggagg atcacttaag cccaggaggc    3600
agaggtcaca atgagccgaa attgtgccaa ctgcactcca gcctgggcaa cagaggaaga    3660
ctcttcacag aaaaaaaaaa aaaaaaaag ctgctaagtc atttaccata agtcactgag    3720
aacagggat gtctgaccag atgcaagtgc tgctggacca ggcgggctgc tgtatcgtgg    3780
gtcagagtga gcagctggtt cctgcggacg gaatcctata tgcagccaga gatgtgacag    3840
ccaccgtgga cagcctgcca ctcatcacag gtgacctgac tccatggcct gcttctgcat    3900
gttcacaggc tcctgacctc caaactcaag tcaaggcct ctcgttagga gttacccgtc    3960
acctgaccgt gtgccccct accccatca caagatgcct gaccaccacc atgtgggtgg    4020
```

-continued

| | |
|---|---|
| cctgatactc aacccaccag gtgctgccac ccncataata agggacttga ccctcaatgc | 4080 |
| tcagggcccc tgaccccaaa gtcggcatcc ccgaactctc ccaagaagct ccaggttctc | 4140 |
| cattgtctcc aacctcctct gcctcccca aagcctccat tctcagtaag aaactcgtgg | 4200 |
| agggctgtc cgctctggtg gtggacgtta agttcggagg ggccgccgtc ttccccaacc | 4260 |
| aggagcaggc ccgggagctg gcaaagacgc tggtgagcgg tgtggccttt ccctgggcaa | 4320 |
| gcgtcttgat gcgggcccag cctacccttc acccctcccg tccccactgc ctccctccac | 4380 |
| tcagcagtcc tgcctaaccc cagtcccacc ctcttctgcc cgaagtccct ccctccttca | 4440 |
| cggcttccta acctgctgtg actttagagg tcaaggctgg cccggcctgg acctggggaa | 4500 |
| gccctctgtg gggttcctgc cccagaccaa gtacaagttc ctcctggccc catggcgagg | 4560 |
| tgtcgcactt cactcgtgtc tcttccccac cccaatcctt ccctgacttc atgctggggg | 4620 |
| gctggcaacc caccctgcag cagggctgg agttcgacca agaaccggct gcagaaggcc | 4680 |
| ccgccatggg gggtccacgc tgagcctcct ctccgcaggt tggcgtggga gccagcctag | 4740 |
| ggcttcgggt cgcggcagcg ctgaccgcca tggacaagcc cctngtcgc tgcgtgggcc | 4800 |
| acgccctgga ggtggaggag gcgctgctct gcatggacgc cgcaggcccg ccagacttaa | 4860 |
| gggacctggt caccacgctc ggtgaggggg acggggtgta ggggagcgga ggcggcgggg | 4920 |
| ggtgcttccc gctgggccg ccccgacccg gccgcgccta agacccgtcc ccgcccgcag | 4980 |
| ggggcgccct gctctggctc agcggacacg cggggactca ggcncagggc gctgcccggg | 5040 |
| tggccgcggc gctggacgac ggctcggccc ttggccgctt cgagcggatg ctggcggcgc | 5100 |
| agggcgtgga tcccggtctg acccgagccc tgtgctcggg aagtcccgca gaacgccggc | 5160 |
| agctgctgcc tcgcgcccgg gagcaggagg agctgctggc cccgcagat ggtgagcgtc | 5220 |
| gggggagtcc ccgtccttcc gcctccgcca tcccctccc ttcccgangc ccgcccctt | 5280 |
| cccgagnccg cgcctctcag cccctctccc cgcaggcacc gtggagctgg tccgggcgct | 5340 |
| gccgctggcg ctggtgctgc acgagctcgg ggccgggcgc agccgcgctg gggagccgct | 5400 |
| ccgcctgggg gtgggcgcag agctgctggt cgacgtgggn cagaggctgc gccgtggtga | 5460 |
| gcgccgcccc cgccctgctg gccncgcacc ccgcccagc tccggccgcg cggcctctaa | 5520 |
| cagcccctcg ctctgcaggg acccctggc tccgcgtgca ccgggacggc cccgcgctca | 5580 |
| gcggcccgca gagccgcgcc ctgcaggagg cgctcgtact ctccgaccgc ncgccattcg | 5640 |
| ccgcccctn gccccttcgca gagctcgttc tgccgccgca gcaataaagc tcctttgccg | 5700 |
| cgaaaccttg tcagtgcttg ggcgggagcg ganggatcca gggctgcgga ggcgggggcc | 5760 |
| gtctcgatga acacgtgacc cccggcgggc tccgccttcc gcgcacgcgc tgagagcctg | 5820 |
| tcagcggctg cgcccgtgtg cgcatgc | 5847 |

<210> SEQ ID NO 12
<211> LENGTH: 2158
<212> TYPE: DNA
<213> ORGANISM: Homo sapiens
<220> FEATURE:
<221> NAME/KEY: misc_feature
<222> LOCATION: 802, 1900
<223> OTHER INFORMATION: n = c or t
<221> NAME/KEY: misc_feature
<222> LOCATION: 1747
<223> OTHER INFORMATION: n = t or g

<400> SEQUENCE: 12
gcgcggcata acgacccagg tcgcggcgcg gcggggcttg agcgcgtggc cggtgccgca        60

-continued

```
ggagccgagc atggagtacc aggatgccgt gcgcatgctc aatacccctgc agaccaatgc      120 cggctacctg gagcaggtga agcgccagcg gggtgaccct cagacacagt tggaagccat      180
ggaactgtac ctggcacgga gtgggctgca gtgggaggac ttggaccggc tgaacatcat      240
ccacgtcact gggacgaagg ggaagggctc cacctgtgcc ttcacggaat gtatcctccg      300
aagctatggc ctgaagacgg gattctttag ctctccccac ctggtgcagg ttcgggagcg      360
gatccgcatc aatgggcagc ccatcagtcc tgagctcttc accaagtact tctggcgcct      420
ctaccaccgg ctggaggaga ccaaggatgg cagctgtgtc tccatgcccc cctacttccg      480
cttcctgaca ctcatggcct ccacgtcttt cctccaagag aaggtggacc tggcagtggt      540
ggaggtgggc attggcgggg cttatgactg caccaacatc atcaggaagc tgtggtgtg      600 cggagtctcc tctcttggca tcgaccacac cagcctcctg ggggatacgg tggagaagat      660
cgcatggcag aaaggggca tctttaagca aggtgtccct gccttcactg tgctccaacc      720
tgaaggtccc ctggcagtgc tgagggaccg agcccagcag atctcatgtc ctctatacct      780
gtgtccgatg ctggaggccc tngaggaagg ggggccgccg ctgaccctgg gcctggaggg      840
ggagcaccag cggtccaacg ccgccttggc cttgcagctg gcccactgct ggctgcagcg      900
gcaggaccgc catggtgctg gggagccaaa ggcatccagg ccagggctcc tgtggcagct      960 gccctggca cctgtgttcc agcccacatc ccacatgcgg ctcgggcttc ggaacacgga     1020
gtggccgggc cggacgcagg tgctgcggcg cgggcccctc acctggtacc tggacggtgc     1080
gcacaccgcc agcagcgcgc aggcctgcgt gcgctggttc cgccaggcgc tgcagggccg     1140
cgagaggccg agcggtggcc ccgaggttcg agtcttgctc ttcaatgcta ccggggaccg     1200
ggacccggcg gccctgctga gctgctgca gccctgccag tttgactatg ccgtcttctg     1260
ccctaacctg acagaggtgt catccacagg caacgcagac caacagaact tcacagtgac     1320
actgaccagg tcctgctcc gctgcctgga acaccagcag cactggaacc acctggacga     1380
agagcaggcc agcccggacc tctggagtgc cccagccca gagcccggtg ggtccgcatc     1440
cctgcttctg gcgcccacc caccccacac ctgcagtgcc agctccctcg tcttcagctg     1500
catttcacat gccttgcaat ggatcagcca aggccgagac ccatcttcc agccacctag     1560 tcccccaaag ggcctcctca cccacccctgt ggctcacagt ggggccagca tactccgtga     1620
ggctgctgcc atccatgtgc tagtcactgg cagcctgcac ctggtgggtg gtgtcctgaa     1680
gctgctggag cccgcactgt cccagtagcc aaggcccggg gttggaggtg ggagcttccc     1740
acacctncct gcgttctccc catgaactta catactaggt gccttttgtt tttggctttc     1800
ctggttctgt ctagactggc ctaggggcca gggctttggg atgggaggcc gggagaggat     1860 gtcttttta aggctctgtg ccttggtctc tccttcctcn tggctgagat agcagagggg     1920
ctccccgggt ctctcactgt tgcagtggcc tggccgttca gcctgtctcc cccaacaccc     1980
cgcctgcctc ctggctcagg cccagcttat tgtgtgcgct gcctggccag gccctgggtc     2040
ttgccatgtg ctggtggta gatttcctcc tcccagtgcc ttctgggaag ggagagggcc     2100
tctgcctggg acactgcggg acagagggtg gctggagtga attaaagcct ttgtttttt     2158
```

<210> SEQ ID NO 13
<211> LENGTH: 2630
<212> TYPE: DNA
<213> ORGANISM: Homo sapiens
<220> FEATURE:
<221> NAME/KEY: misc_feature
<222> LOCATION: 1424
<223> OTHER INFORMATION: n = c or a
<221> NAME/KEY: misc_feature
<222> LOCATION: 1649, 2554
<223> OTHER INFORMATION: n = a or g

<400> SEQUENCE: 13

| | | | | | | |
|---|---|---|---|---|---|---|
| ctgattggta | tgggactgtt | ggagcccata | gaatgtgcaa | gaccagcctg | ggtgaggagg | 60 |
| ctgtcttagt | tgagaccaac | gtggtgaata | gggtgagcca | ggtgcagagg | cctgagata | 120 |
| gaagatgggg | aggactgggg | ggctacagat | agtccggggg | gatgggcac | caggaacaaa | 180 |
| ccgagggaca | caggagagat | gaggcacgga | ggccagtagc | atcagtccct | gcagggtggg | 240 |
| ggaaggccag | gacgctcggg | aagggagtcc | tgatgacccc | agctgtcccg | gcagctctcc | 300 |
| ccacctggtg | caggttcggg | agcggatccg | catcaatggg | cagcccatca | gtcctgagct | 360 |
| cttcaccaag | tacttctggc | gcctctacca | ccggctggag | gagaccaagg | tgccgcatgc | 420 |
| aggagggctg | gcgggtgggt | atggttgggg | gtgctacgtg | ttccagcacc | ccatctcccc | 480 |
| agagaagggg | ctgcatggct | ctgggccctg | acatgtccct | gtgccacagg | atggcagctg | 540 |
| tgtctccatg | cccccctact | tccgcttcct | gacactcatg | gccttccacg | tcttcctcca | 600 |
| agagaaggtg | tgtgccctct | ccctagaacc | ctgcatctga | ggccttggga | acgggaacct | 660 |
| cagcaggcct | gggggctccc | tgcttccatg | cggcctctgg | gcaccctcat | atccctgcc | 720 |
| atgccctctg | gtctttgaca | ggtggacctg | gcagtggtgg | aggtgggcat | tggcggggct | 780 |
| tatgactgca | ccaacatcat | caggtgagcg | cagttgcttg | ggacgagggg | tggcagccag | 840 |
| gagcacagcc | tcacctgcgc | ctggtggctc | agggcaggcc | tcatgccctt | tcctccccct | 900 |
| gcaggaagcc | tgtggtgtgc | ggagtctcct | ctcttggcat | cgaccacacc | agcctcctgg | 960 |
| gggatacggt | ggagaagatc | gcatggcaga | aaggggggcat | ctttaaggtg | accaggcaga | 1020 |
| ctgggggaag | ggagagacat | ggaaggcctg | ggagtctacg | ttttcatcct | ggcttcactg | 1080 |
| tgtgactgga | acaagttgag | tctcctctcc | agactatttc | cccattgaaa | cgtgagggat | 1140 |
| ggctgggcat | ggtggcttat | atgcttgcaa | tcccagcatt | tcaggaggtc | gaggtgagag | 1200 |
| gatcacctga | gatccggagt | ttgagaccag | cctgaccaat | atgggaaac | tctgtctcta | 1260 |
| ctaaaaatac | aaaaattagc | caggtgtggt | ggtgtacgcc | tgtagttcca | gctacttggg | 1320 |
| agactgaggc | aggagaatca | ctcgaacccg | ggaggcagac | gttgcagtga | gccgagattg | 1380 |
| cgccacagca | ctccagcctg | ggtgacagag | tgagacttca | tctngaaaaa | gaaaagaaaa | 1440 |
| gaaacatgag | ggatgagaga | cagtggtagc | ccagacccag | ggatgtgggg | gccagagata | 1500 |
| ggagtgtgga | ggatgctagg | tagccctttc | tctctccttc | ttccctccac | agcaaggtgt | 1560 |
| ccctgccttc | actgtgctcc | aacctgaagg | tccctggca | gtgctgaggg | accgagccca | 1620 |
| gcagatctca | gtaagtctga | ttggaatgng | gcagcggcag | ggtgggtttg | tgtccctcct | 1680 |
| gtttgaggag | gcactgcatc | ctctggggcc | tcagtttgcc | catctgtgca | gtgaggacgc | 1740 |
| tgggccagct | gccaggcctg | ctggaacaca | tctcagttct | gggagcaggg | cttggtggct | 1800 |
| gggggagggg | agagatgcaa | gggctgacgt | ggtcagggag | ggcctctgct | gacccgctcc | 1860 |
| tgcctgtctc | ccctagtgtc | ctctatacct | gtgtccgatg | ctggaggccc | tcgaggaagg | 1920 |
| ggggccgccg | ctgacccctgg | gcctggaggg | ggagcaccag | cggtccaacg | ccgccttggc | 1980 |
| cttgcagctg | gcccactgct | ggctgcagcg | gcaggaccgc | catggtgagt | gggcagctga | 2040 |
| gtgggcaggc | aggtgggtgg | cacctgtgga | gcctgcctag | gagggtcccg | gacacacttg | 2100 |
| gtctcacaca | ccccgcaggt | gctggggagc | caaaggcatc | caggccaggg | ctcctgtggc | 2160 |
| agctgcccct | ggcacctgtg | ttccagccca | catcccacat | gcggctcggt | gagttagacc | 2220 |

| | | | | |
|---|---|---|---|---|
| ttcctgccca | gctgggacca | ctgcgtgtgt | ctgtgcccct | tcagattttt tttttttttt | 2280 |
| ttttggtttt | ctgtttggga | gataagagac | aatttgaagt | ggtgcttaag agaaaggact | 2340 |
| ctgatgtcag | caaacctccc | tgaccttgag | ctcatgaact | ctttctgagc ctgtcttctc | 2400 |
| atctgccaaa | gtagatgatg | ataggagcca | ctgccacggg | ctgtggtggg gattcgctga | 2460 |
| ggtgacatca | ctaaggtgct | gagtgcagag | cctggccaat | gtgggataaa gtgccagcca | 2520 |
| gtggtagctg | ctgtcactgt | cactatcatc | atcntcagac | cctgaggttc tggaggatgg | 2580 |
| tgatccagtc | atctgcttct | tgcctccccc | aaagctttca | gcacccagca | 2630 |

<210> SEQ ID NO 14
<211> LENGTH: 2912
<212> TYPE: DNA
<213> ORGANISM: Homo sapiens
<220> FEATURE:
<221> NAME/KEY: misc_feature
<222> LOCATION: 263, 1037, 1139, 1955, 2017, 2037, 2189, 2309
<223> OTHER INFORMATION: n = a or g
<221> NAME/KEY: misc_feature
<222> LOCATION: 266
<223> OTHER INFORMATION: n = g or t
<221> NAME/KEY: misc_feature
<222> LOCATION: 527
<223> OTHER INFORMATION: n = c or g
<221> NAME/KEY: misc_feature
<222> LOCATION: 1217, 1647, 2282
<223> OTHER INFORMATION: n = c or t

<400> SEQUENCE: 14

| | | | | |
|---|---|---|---|---|
| ggccctgcgt | ccagtctctt | gattattttt | atgcagtcat | taaactatat acatgcatat | 60 |
| gtatagagaa | agtttcaatg | actaaaaata | aggaaaccaa | gaaagaactt ctctatctgc | 120 |
| catggggcca | gggtcgggc | accccagcag | tgtgtgaaga | gcagaagtcc agccaatgac | 180 |
| agactcttcc | caaacatca | cttgcttatt | tcgaaatcaa | acaatttctc ataaatattt | 240 |
| tctcccaatg | ctgggaagag | ggnganggga | aggaggtacg | gaaactccat caatcatttg | 300 |
| aagggctgcc | ttttatcaga | ctgattttcc | gtagtgggtt | gtttgcagct tcctcctccc | 360 |
| cagttctggg | cctcagctgt | caaaaggatt | tcaccatgca | acttttcat gctagcagtt | 420 |
| ggggccaaga | agctaataga | tgggaaaaag | ctctgaaaac | tccaggacga caaataggtg | 480 |
| tcctcctcac | agaaaaggat | tactgcccca | ccatcccag | gtggcntca aatccgttct | 540 |
| ctaaacggca | gcagctgttt | agaggtgtcc | accaggtgtc | cgcagctttg tcatcctatc | 600 |
| cctgttcggg | gcagagactg | agggctgctg | acccggaccg | gctattttgg gacgtgctgc | 660 |
| gggggggcctt | gggaggttgg | tgacgaaagg | agtgcgtgcc | cgctaaggga ggggacgccc | 720 |
| cggagcgtac | actcataaac | ctggtcccga | ggcctgcccc | tcaccaggat ggtgcacgcg | 780 |
| gaaggggcgg | cttttagtg | gcgcaagggg | gctggtcggt | ggtagtttgg ggcggtgctg | 840 |
| attgatggcg | ggcggggcgg | ggcggtgctg | attggcgggg | gggcggggt gaggcgacgc | 900 |
| tgcgctgatt | ggctggggc | ggggcgggc | gtctcccgcc | cgggcctaga gcgctgccgg | 960 |
| gggcgccggg | actatgtcgc | gggcgcggag | ccacctgcgc | gccgctctat tcctggcagc | 1020 |
| ggcgtctgcg | cgcggcntaa | cgacccaggt | cgcggcgcgg | cggggcttga gcgcgtggcc | 1080 |
| ggtgccgcag | gagccgagca | tggagtacca | ggtatcaggc | gggccagcgg gccagcggnc | 1140 |
| ctgggcgcga | cgacacgtgg | gcctgcgctg | agccgcagaa | catccgggct ccgctagccg | 1200 |
| agagggtatc | gggagcnctg | gactgggga | ctcgggggc | ggaacatcct ggaggctggg | 1260 |
| ggtggggaca | gggaccagga | agttgggccc | gggccgccgg | ggctgggaat tcggagacta | 1320 |

-continued

```
tagcgtcccc gccccgggtt gggaagtggg aagtggcaca ggagctagga tccagaagcc    1380
cagaggctca gcggtgcttc tggagttcca gtgatcccgg agtctgaacc ggcagtgaga    1440
gtggggaaag agggtaggga agagactcag gaattcaggc ttgaaagatc caggagtatt    1500
gatctggggg tgggctgtcc aggattcaga agattgggga tccaagtgcc tggatttggg    1560
ggagaggcag gaatcagggg tagtggaggg ccccagaacc tggaaaatag aaaatgtccg    1620
cgggcgctgt gtcaagagcc ggttgcncta gaccagaccc tgatgccagt gaggcgggtg    1680
gcactggttt gatgagggtg gagcctccaa ccagccttga ggtcctgagg gtgggaggca    1740
cggaatatga ggcctaaggg gaatgaaata gcaccccac tcccacttcc attgtgaacc     1800
ctcctgaagc cgtacctacc tgccttcctg gctgagtgac ccctggcaca ccctcctcc    1860 ctctgagttg ctcctctgtg ggttggaatg tggaacccca gagtcatgag ggttggggtg    1920
gagcttcggg gaactccaga attcgaatac cccanccttc tgtagttctg gccccgctct    1980
ggcagggagc aatatagcaa tggaccccat tggagganaat gagggcaaag gcccagnagt    2040
gaagtcgggg gagcctgggc aggaagcaag gctagcccgt tagtcatgcc accttctttg    2100
tgtagcactc cctgggtggg gctgaactgc cccagactcc cattttttgcc agagctggaa   2160 agatgccata ctctctgttg cttaacctnc aggctaggct aacagtgctg gcatggcagg    2220
cgggcctggt actggccttg ttgccctggc ttggccactg gtctgctggc tgtctctgtg    2280
cntgtggacc ctgagtgagc cttaacctnc tatctgggca ctgtggttgc caggatgccg    2340
tgcgcatgct caatacccctg cagaccaatg ccggctacct ggagcaggtg aagcgccagc   2400
ggggtgaccc tcagacacag ttggaagcca tggaactgta cctggcacgg agtgggctgc    2460
aggtaaggta gagagggcct gtgaccacct cccaccccca tttgtgattc ccgtagctga    2520
ggcagggacc ttgtctgtct gtcccaggtg gaggacttgg accggctgaa catcatccac    2580
gtcactggga cgaaggggaa ggtgaggggc aggaccctgg ggtaggggt ctattaagtg    2640 gctggtggag tagagcctgc ccagacaatc ccttttcttt caagggctcc acctgtgcct    2700
tcacggaatg tatcctccga agctatggcc tgaagacggg attctttagg tactggcttg    2760
tggggggatg tggtgtctgt gtcccaatgg accctggggg gctatggaac cagccagtgc    2820
ttcaggacca gggtcacccc caggaggtca gctgcatgtc tctctgccca gtgtttattc    2880
attcaataaa cattcagtta gcacttacca ta                                  2912
```

<210> SEQ ID NO 15
<211> LENGTH: 2196
<212> TYPE: DNA
<213> ORGANISM: Artificial Sequence
<220> FEATURE:
<223> OTHER INFORMATION: Synthetic construct
<221> NAME/KEY: misc_feature
<222> LOCATION: 1784
<223> OTHER INFORMATION: n = a or g
<221> NAME/KEY: misc_feature
<222> LOCATION: 464
<223> OTHER INFORMATION: n = g or t
<221> NAME/KEY: misc_feature
<222> LOCATION: 120, 519, 668, 1059, 1308
<223> OTHER INFORMATION: n = c or t
<221> NAME/KEY: misc_feature
<222> LOCATION: 1289
<223> OTHER INFORMATION: n = c or a

<400> SEQUENCE: 15

```
aattccggag ccatggtgaa cgaagccaga ggaaacagca gcctcaaccc ctgcttggag      60
```

-continued

```
ggcagtgcca gcagtggcag tgagagctcc aaagatagtt cgagatgttc caccccgggn    120
ctggaccctg agcggcatga gagactccgg gagaagatga ggcggcgatt ggaatctggt    180
gacaagtggt tctccctgga attcttccct cctcgaactg ctgagggagc tgtcaatctc    240
atctcaaggt ttgaccggat ggcagcaggt ggcccctct acatagacgt gacctggcac     300
ccagcaggtg accctggctc agacaaggag acctcctcca tgatgatcgc cagcaccgcc    360
gtgaactact gtggcctgga gaccatcctg cacatgacct gctgccgtca gcgcctggag    420
gagatcacgg gccatctgca caaagctaag cagctgggcc tgangaacat catggcgctg    480
cggggagacc caataggtga ccagtgggaa gaggaggang gaggcttcaa ctacgcagtg    540
gacctggtga agcacatccg aagtgagttt ggtgactact ttgacatctg tgtggcaggt    600
taccccaaag gccaccccga agcagggagc tttgaggctg acctgaagca cttgaaggag    660
aaggtgtntg cgggagccga tttcatcatc acgcagcttt tctttgaggc tgacacattc    720
ttccgctttg tgaaggcatg caccgacatg ggcatcactt gccccatcgt ccccgggatc    780
tttcccatcc agggctacca ctcccttcgg cagcttgtga agctgtccaa gctggaggtg    840
ccacaggaga tcaaggacgt gattgagcca atcaaagaca acgatgctgc catccgcaac    900
tatggcatcg agctggccgt gagcctgtgc caggagcttc tggccagtgg cttggtgcca    960
ggcctccact tctacaccct caaccgcgag atggctacca cagaggtgct gaagcgcctg    1020
gggatgtgga ctgaggaccc caggcgtccc ctaccctgng ctctcagtgc ccaccccaag    1080
cgccgagagg aagatgtacg tcccatcttc tgggcctcca gaccaaagag ttacatctac    1140
cgtacccagg agtgggacga gttccctaac ggccgctggg gcaattcctc ttcccctgcc    1200
tttggggagc tgaaggacta ctacctcttc tacctgaaga gcaagtcccc caaggaggag    1260
ctgctgaaga tgtgggggga ggagctganc agtgaagcaa gtgtcttnga agtctttgtt    1320
ctttacctct cgggagaacc aaaccggaat ggtcacaaag tgacttgcct gccctggaac    1380
gatgagcccc tggcggctga gaccagcctg ctgaaggagg agctgctgcg ggtgaaccgc    1440
cagggcatcc tcaccatcaa ctcacagccc aacatcaacg ggaagccgtc ctccgacccc    1500
atcgtgggct ggggccccag cggggctat gtcttccaga aggcctactt agagtttttc     1560
acttcccgcg agacagcgga agcacttctg caagtgctga agaagtacga gctccgggtt    1620
aattaccacc ttgtcaatgt gaagggtgaa acatcacca atgcccctga actgcagccg     1680
aatgctgtca cttggggcat cttccctggg cgagagatca tccagcccac cgtagtggat    1740
cccgtcagct tcatgttctg gaaggacgag gcctttgccc tgtngattga gcggtgggga    1800
aagctgtatg aggaggagtc cccgtcccgc accatcatcc agtacatcca cgacaactac    1860
ttcctggtca acctggtgga caatgacttc ccactggaca actgcctctg gcaggtggtg    1920
gaagacacat tggagcttct caacaggccc acccagaatg cgagagaaac ggaggctcca    1980
tgaccctgcg tcctgacgcc ctgcgttgga gccactcctg tcccgccttc ctcctccaca    2040
gtgctgcttc tcttgggaac tccactctcc ttcgtgtctc tcccacccccg gcctccactc    2100 ccccacctga caatggcagc tagactggag tgaggcttcc aggctcttcc tggacctgag    2160
tcggccccac atgggaacct agtactctct gctcta                              2196
```

<210> SEQ ID NO 16
<211> LENGTH: 1137
<212> TYPE: DNA
<213> ORGANISM: Homo sapiens
<220> FEATURE:
<221> NAME/KEY: misc_feature -continued

```
<222> LOCATION: 575, 648
<223> OTHER INFORMATION: n = t or c
<221> NAME/KEY: misc_feature
<222> LOCATION: 771
<223> OTHER INFORMATION: n = g or c
<221> NAME/KEY: misc_feature
<222> LOCATION: 883
<223> OTHER INFORMATION: n = g or a
<221> NAME/KEY: misc_feature
<222> LOCATION: 942
<223> OTHER INFORMATION: nucleotide at position 942 is c, or absent
<221> NAME/KEY: misc_feature
<222> LOCATION: 1052
<223> OTHER INFORMATION: n = a or c

<400> SEQUENCE: 16
gaattcaaac catggtttac taaactccaa agctggagcc cttctacagt ctcaggatct      60
agaacaggga ttattactat ctctgctgtt gacatgagga aactgtggtt cagggaggtc     120
aagtgacctg ccaaagcttg tacacatgga aagtagtaga accaggatgc aaacacattt     180
ctttaccacc aacaccaata tctattttgc caacaaaaca atgaggggc ctgagtaaat      240 aatctcaacg gttaactcca ccctccaatt gagatacttt tttttttttt ttttttttga     300
gacagggtct ggctctctgt cacccaggct ggaatgcagt ggtgccctca gcttccaag      360 tagctaggac tacaggccac atgccaccat gcccagctaa ttttttgtatt ttttgtagaa    420 acagggtttt gccatattgc caaggctgtt ctcaaactcc tgggctcaag cagtcctcct     480
gcctcagcct cctaaagtaa gagaagttgg aaggaaaatg ggtgaaaata aagaagttct     540
cagttatact gcagcttgtt catgcctcct gcctngggat gccgcagtgg ctgccccagc     600 cctgccttt cagcctcagc ccttccctca gtgaaggaga gaaaaagnga tttaacaaag      660
tgaggactgt cagcccttgg accttggacc tttgagatct catgacccac ccctcagtgt     720
gtccaccagt gagagtggtt cctaagggag agtgtgaagc acacgtggca ntgtcttaca     780
ccacacctgc tgagtccaaa ccatgggagg ctcctctcct agaccctgca tcctgaaagc     840
tgcgtacctg agagctgcgg tctggctgca gggacacacc canggggagg agctgcaatc     900
gtgtctgggg ccccagccag gctggccgga gctcctgttt cncgctgctc tgctgcctgc     960
ccggggtacc aacatggccc agaagcgtcc tgcctgcacc ctgaagcctg agtgtgtcca    1020
gcagctgctg gtttgctccc aggaggccaa gnagtcagcc tactgcccct acagtcactt    1080
tcctgtgggg gctgccctgc tcacccagga ggggagaatc ttcaaaggta aaggtgg       1137
```